US012661392B2

(12) United States Patent
Barbour et al.

(10) Patent No.: US 12,661,392 B2
(45) Date of Patent: Jun. 23, 2026

(54) MULTIEPITOPE VACCINE FOR THE TREATMENT OF ALZHEIMER'S DISEASE

(71) Applicant: OTHAIR PROTHENA LIMITED, Dublin (IE)

(72) Inventors: Robin Barbour, Walnut Creek, CA (US); Gene Kinney, Boca Raton, FL (US); Wagner Zago, San Carlos, CA (US)

(73) Assignee: OTHAIR PROTHENA LIMITED, Dublin (IE)

( * ) Notice: Subject to any disclaimer, the term of this patent is extended or adjusted under 35 U.S.C. 154(b) by 565 days.

(21) Appl. No.: 18/020,034

(22) PCT Filed: Aug. 6, 2021

(86) PCT No.: PCT/US2021/045062
§ 371 (c)(1),
(2) Date: Feb. 6, 2023

(87) PCT Pub. No.: WO2022/032166
PCT Pub. Date: Feb. 10, 2022

(65) Prior Publication Data
US 2025/0186567 A1     Jun. 12, 2025

Related U.S. Application Data

(60) Provisional application No. 63/062,919, filed on Aug. 7, 2020.

(51) Int. Cl.
*A61K 39/00*          (2006.01)
*A61P 25/28*          (2006.01)
(Continued)

(52) U.S. Cl.
CPC .......... *A61K 39/0007* (2013.01); *A61P 25/28* (2018.01); *A61P 37/04* (2018.01);
(Continued)

(58) Field of Classification Search
None
See application file for complete search history.

(56) References Cited

U.S. PATENT DOCUMENTS

| | | | |
|---|---|---|---|
| 5,057,540 | A | 10/1991 | Kensil |
| 5,208,036 | A | 5/1993 | Eppstein |

(Continued)

FOREIGN PATENT DOCUMENTS

| | | | |
|---|---|---|---|
| CN | 109022460 A | 12/2018 | |
| CN | 110684122 A | 3/2021 | |

(Continued)

OTHER PUBLICATIONS

Novak et al., "AADvac1, an Active Immunotherapy for Alzheimer's Disease and Non Alzheimer Tauopathies: An Overview of Preclinical and Clinical Development." J. Prev. Alzheimers Dis 61(1):63-69 (2018).

(Continued)

*Primary Examiner* — Daniel C Gamett
(74) *Attorney, Agent, or Firm* — MCDONNELL BOEHNEN HULBERT & BERGHOFF LLP

(57) ABSTRACT

The disclosure provides peptide compositions and immunotherapy compositions comprising an amyloid-beta (Aβ, Abeta) peptide, a tau peptide, and an alpha-synuclein peptide. The disclosure also provides methods of treating or effecting prophylaxis of Alzheimer's disease or other diseases with beta-amyloid deposition in a subject, including methods of clearing deposits, inhibiting or reducing aggregation of Aβ and tau and an alpha-synuclein, blocking the uptake by neurons, clearing amyloid, and inhibiting propagation of tau seeds and an alpha-synuclein synucleinopathies in a subject having or at risk of developing Alzheimer's disease or other diseases containing tau and amyloid-beta and an alpha-synuclein accumulations. The methods include administering to such patients the compositions comprising (Continued)

an amyloid-beta (Aβ) peptide and a tau peptide and an alpha-synuclein peptide.

39 Claims, 9 Drawing Sheets

Specification includes a Sequence Listing.

(51) Int. Cl.
  *A61P 37/04* (2006.01)
  *C07K 14/47* (2006.01)
(52) U.S. Cl.
  CPC .... *C07K 14/4711* (2013.01); *A61K 2039/545* (2013.01); *A61K 2039/55555* (2013.01); *A61K 2039/55566* (2013.01); *A61K 2039/55572* (2013.01); *A61K 2039/55577* (2013.01); *A61K 2039/6037* (2013.01); *A61K 2039/645* (2013.01); *C07K 2319/40* (2013.01)

(56) References Cited

U.S. PATENT DOCUMENTS

| | | | |
|---|---|---|---|
| 5,264,618 | A | 11/1993 | Felgner |
| 5,279,833 | A | 1/1994 | Rose |
| 5,283,185 | A | 2/1994 | Epand |
| 5,643,576 | A | 7/1997 | Johnston |
| 5,736,142 | A | 4/1998 | Sette |
| 5,840,838 | A | 11/1998 | Hensley |
| 7,632,816 | B2 | 12/2009 | Wisniewski |
| 8,034,348 | B2 | 10/2011 | Schenk |
| 8,906,367 | B2 | 12/2014 | Nitsch |
| 10,501,531 | B2 | 12/2019 | Seubert |
| 10,562,973 | B2 | 2/2020 | Barbour |
| 2003/0175290 | A1 | 9/2003 | Renner |
| 2006/0135403 | A1 | 6/2006 | Gervais et al. |
| 2008/0300204 | A1 | 12/2008 | Federoff |
| 2010/0202968 | A1 | 8/2010 | Nitsch |
| 2011/0097351 | A1 | 4/2011 | Mandler |
| 2014/0294839 | A1 | 10/2014 | Kuret |
| 2015/0232524 | A1 | 8/2015 | Agadjanyan et al. |
| 2016/0318975 | A1 | 11/2016 | Baileykobayashi |
| 2017/0239349 | A1 | 8/2017 | Agadjanyan |
| 2018/0327436 | A1 | 11/2018 | Gin |
| 2019/0330314 | A1 | 10/2019 | Barbour |
| 2019/0330316 | A1 | 10/2019 | Barbour |

FOREIGN PATENT DOCUMENTS

| | | | |
|---|---|---|---|
| EP | 3067066 | B1 | 3/2019 |
| GB | 2220211 | A | 1/1990 |
| WO | 1994012629 | A1 | 6/1994 |
| WO | 1995007707 | A1 | 3/1995 |
| WO | 1996034625 | A1 | 11/1996 |
| WO | 1998040100 | A1 | 9/1998 |
| WO | 2004044195 | A2 | 5/2004 |
| WO | 2006121656 | A2 | 11/2006 |
| WO | 2008084402 | A2 | 7/2008 |
| WO | 2008084483 | A1 | 7/2008 |
| WO | 2008103472 | A2 | 8/2008 |
| WO | 2011013034 | A1 | 2/2011 |
| WO | 2013020723 | A1 | 2/2013 |
| WO | 2013041962 | A1 | 3/2013 |
| WO | 2014031697 | A2 | 2/2014 |
| WO | 2014058924 | A2 | 4/2014 |
| WO | 2014078656 | A1 | 5/2014 |
| WO | 2014165271 | A2 | 10/2014 |
| WO | 2015165961 | A1 | 11/2015 |
| WO | 2017191559 | A1 | 11/2017 |
| WO | 2017191560 | A1 | 11/2017 |
| WO | 2017191561 | A1 | 11/2017 |
| WO | 2018151821 | A1 | 8/2018 |
| WO | 2018191598 | A1 | 10/2018 |
| WO | 2018200656 | A1 | 11/2018 |
| WO | 2018204546 | A2 | 11/2018 |
| WO | 2018232369 | A1 | 12/2018 |
| WO | 2019070480 | A1 | 4/2019 |
| WO | 2019070813 | A2 | 4/2019 |
| WO | 2019079160 | A1 | 4/2019 |
| WO | 2019084118 | A2 | 5/2019 |
| WO | 2019166832 | A1 | 9/2019 |
| WO | 2019226941 | A1 | 11/2019 |
| WO | 2020120644 | A1 | 6/2020 |

OTHER PUBLICATIONS

Alexander, et al. (1994). "Development of high potency universal DR-restricted helper epitopes by modification of high affinity DR-blocking peptides." Immunity 1(9), 751-761.

Beissert, et al. (2020). "A trans-amplifying RNA vaccine strategy for induction of potent protective immunity." Mol. Ther. 28(1), 119-128.

Bett, et al. (1993). "Packaging capacity and stability of human adenovirus type 5 vectors." J. Virol. 67(10), 5911-5921.

Boris-Lawrie and Temin. (1993). "Recent advances in retrovirus vector technology." Curr. Opin. Genet. Develop. 3(1), 102-109.

Chen, et al. (2013). "Fusion Protein Linkers: Property, Design and Functionality." Adv. Drug Deliv. Rev. 65(10), 1357-1369.

Cunningham, et al. (2016). "Efficacy of the Herpes Zoster Subunit Vaccine in Adults 70 Years of Age or Older." N. Engl. J. Med. 375(11), 1019-1032.

Dubensky, et al. (1996). "Sindbis virus DNA-based expression vectors: utility for in vitro and in vivo gene transfer." J. Virol. 70(1), 508-519.

GenBank ID: BC108275.1. Homo sapiens synuclein, alpha. Submitted Nov. 3, 2005.

Gilman, et al. (2005). "Clinical effects of Abeta immunization (AN1792) in patients with AD in an interrupted trial." Neurology 64(9), 1553-1562.

Hull, et al. (2017). "Long-term extensions of randomized vaccination trials of ACC-001 and QS-21 in mild to moderate Alzheimer's disease." Curr. Alzheimer Res. 14(7), 696-708.

Jansen, et al. (1982). "Immunotoxins: Hybrid Molecules Combining High Specificity and Potent Cytotoxicity" Immunol. Rev. 62(1), 185-216.

McGee, et al. (1997). "The encapsulation of a model protein in poly (D,L lactide-co-glycolide) microparticles of various sizes: an evaluation of process reproducibility." J. Microencapsul. 14(2), 197-210.

NCT00960531. (2009-2013). "A Long Term Extension Study Evaluating ACC-001 With QS-21 in Subjects With Mild to Moderate Alzheimer's Disease." <https://clinicaltrials.gov/study/NCT00960531>.

Ohe, et al. (1995). "Construction of a novel bovine papillomavirus vector without detectable transforming activity suitable for gene transfer." Hum. Gene Ther. 6(3), 325-333.

Powilleit, et al. (2007). "Exploiting the Yeast L-A Viral Capsid for the In Vivo Assembly of Chimeric VLPs as Platform in Vaccine Development and Foreign Protein Expression." PLoS ONE 2(5), e415.

Stoute, et al. (1997). "A preliminary evaluation of a recombinant circumsporozite protein vaccine against Plasmodium falciparum malaria." N. Engl. J. Med. 336(2), 86-91.

Strejan, et al. (1984). "Suppression of chronic-relapsing experimental allergic encephalomyelitis in strain-13 guinea pigs by administration of liposome-associated myelin basic protein." J. Neuroimmunol. 7, 27-41.

Wald, et al. (2011). "Safety and immunogenicity of long HSV-2 peptides complexed with rhHsc70 in HSV-2 seropositive persons." Vaccine 29(47), 8520-8529.

Xiao and Brandsma. (1996). "High efficiency, long-term clinical expression of cottontail rabbit papillomavirus (CRPV) DNA in rabbit skin following particle-mediated DNA transfer." Nucleic Acids Res. 24(13), 2620-2622.

Zago, et al. (2012). "Neutralization of Soluble, Synaptotoxic Amyloid B Species by Antibodies is Epitope Specific." J. Neurosci. 32(8), 2696-2702.

(56) References Cited

OTHER PUBLICATIONS

Zhou et al. (1994). "Adeno-associated virus 2-mediated high efficiency gene transfer into immature and mature subsets of hematopoietic progenitor cells in human umbilical cord blood." J. Exp. Med. 179(6), 1867-1875.

International Search Report for PCT/US2021/033222; mailed on Nov. 4, 2021, pp. 1-5.

Inaba et al. "Molecular Encapsulation Inside Microtubules Based on Tau-Derived Peptides" Chem. Eur. J. 24:14958-67 (2018).

Morris et al. "Tau post-translational modifications in wild-type and human amyloid precursor protein transgenic mice" Nat. Neurosci. 18(8): 1183-89 (2015).

Chan et al., "Enhancement of Tetravalent Immune Responses to Highly Conserved Epitopes of A Dengue Peptide Vaccine Conjugated to Polystyrene Nanoparticles." Vaccines (Basel), 8(3):417, 2020.

Chen et al., "Triggered Immune Response Induced by Antigenic Epitopes Covalently Linked with Immunoadjuvant-Pulsed Dendritic Cells as a Promising Cancer Vaccine" J. Immunol. 2020.

Ghaffari-Nazari et al., "Improving Multi-Epitope Long Peptide Vaccine Potency by Using a Strategy that Enhances CD4+ T Help in BALB/c Mice" PLoS One, 2015.

Ulrich et al., "Induction of an antigen-specific CTL response by a conformationally biased agonist of human C5a anaphylatoxin as a molecular adjuvant" J. Immunol. 164(10):5492-8, 2000.

SEQUENCE LISTING

```
<160> NUMBER OF SEQ ID NOS: 1065

<210> SEQ ID NO 1
<211> LENGTH: 42
<212> TYPE: PRT
<213> ORGANISM: Artificial Sequence
<220> FEATURE:
<223> OTHER INFORMATION: Synthetic peptide

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30
```

-continued

```
Gly Leu Met Val Gly Gly Val Val Ile Ala
        35                  40

<210> SEQ ID NO 2
<211> LENGTH: 441
<212> TYPE: PRT
<213> ORGANISM: Artificial Sequence
<220> FEATURE:
<223> OTHER INFORMATION: Synthetic peptide

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350
```

-continued

```
Lys Ile Gly Ser Leu Asp Asn Ile Thr His Val Pro Gly Gly Asn
        355                 360             365

Lys Lys Ile Glu Thr His Lys Leu Thr Phe Arg Glu Asn Ala Lys Ala
    370                 375             380

Lys Thr Asp His Gly Ala Glu Ile Val Tyr Lys Ser Pro Val Val Ser
385                 390             395                 400

Gly Asp Thr Ser Pro Arg His Leu Ser Asn Val Ser Ser Thr Gly Ser
                405             410             415

Ile Asp Met Val Asp Ser Pro Gln Leu Ala Thr Leu Ala Asp Glu Val
            420             425             430

Ser Ala Ser Leu Ala Lys Gln Gly Leu
        435             440
```

```
<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Asp Ala Glu Phe Arg His Asp Ser Gly Tyr
1               5               10
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Asp Ala Glu Phe Arg His Asp Ser Gly
1               5
```

```
<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

Asp Ala Glu Phe Arg His Asp Ser
1               5
```

```
<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Asp Ala Glu Phe Arg His Asp
1               5
```

```
<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7
```

```
Asp Ala Glu Phe Arg His
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide

<400> SEQUENCE: 8

Asp Ala Glu Phe Arg
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic peptide

<400> SEQUENCE: 9

Asp Ala Glu Phe
1

<210> SEQ ID NO 10
<211> LENGTH: 3
<212> TYPE: PRT
<213> ORGANISM: Artificial Sequence
<220> FEATURE:
<223> OTHER INFORMATION: Synthetic peptide

<400> SEQUENCE: 10

Asp Ala Glu
1

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide

<400> SEQUENCE: 11

Ala Glu Phe Arg His Asp Ser Gly Tyr
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Ala Glu Phe Arg His Asp Ser Gly
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13
```

```
Ala Glu Phe Arg His Asp Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Ala Glu Phe Arg His Asp
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic peptide

<400> SEQUENCE: 15

Ala Glu Phe Arg His
1               5

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

<400> SEQUENCE: 16

Ala Glu Phe Arg
1

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide

<400> SEQUENCE: 17

Ala Glu Phe
1

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Glu Phe Arg His Asp Ser Gly Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Glu Phe Arg His Asp Ser Gly
```

```
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Glu Phe Arg His Asp Ser
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Glu Phe Arg His Asp
1               5

<210> SEQ ID NO 22
<211> LENGTH: 4
<212> TYPE: PRT
<213> ORGANISM: Artificial Sequence
<220> FEATURE:
<223> OTHER INFORMATION: Synthetic peptide

<400> SEQUENCE: 22

Glu Phe Arg His
1

<210> SEQ ID NO 23
<211> LENGTH: 3
<212> TYPE: PRT
<213> ORGANISM: Artificial Sequence
<220> FEATURE:
<223> OTHER INFORMATION: Synthetic peptide

<400> SEQUENCE: 23

Glu Phe Arg
1

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Phe Arg His Asp Ser Gly Tyr
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Phe Arg His Asp Ser Gly
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: Synthetic peptide

<400> SEQUENCE: 26

Phe Arg His Asp Ser
1               5

<210> SEQ ID NO 27
<211> LENGTH: 4
<212> TYPE: PRT
<213> ORGANISM: Artificial Sequence
<220> FEATURE:
<223> OTHER INFORMATION: Synthetic peptide

<400> SEQUENCE: 27

Phe Arg His Asp
1

<210> SEQ ID NO 28
<211> LENGTH: 3
<212> TYPE: PRT
<213> ORGANISM: Artificial Sequence
<220> FEATURE:
<223> OTHER INFORMATION: Synthetic peptide

<400> SEQUENCE: 28

Phe Arg His
1

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Arg His Asp Ser Gly Tyr
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide

<400> SEQUENCE: 30

Arg His Asp Ser Gly
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide

<400> SEQUENCE: 31

Arg His Asp Ser
1
```

```
<210> SEQ ID NO 32
<211> LENGTH: 3
<212> TYPE: PRT
<213> ORGANISM: Artificial Sequence
<220> FEATURE:
<223> OTHER INFORMATION: Synthetic peptide

<400> SEQUENCE: 32

Arg His Asp
1

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

His Asp Ser Gly Tyr
1               5

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

His Asp Ser Gly
1

<210> SEQ ID NO 35
<211> LENGTH: 3
<212> TYPE: PRT
<213> ORGANISM: Artificial Sequence
<220> FEATURE:
<223> OTHER INFORMATION: Synthetic peptide

<400> SEQUENCE: 35

His Asp Ser
1

<210> SEQ ID NO 36
<211> LENGTH: 4
<212> TYPE: PRT
<213> ORGANISM: Artificial Sequence
<220> FEATURE:
<223> OTHER INFORMATION: Synthetic peptide

<400> SEQUENCE: 36

Asp Ser Gly Tyr
1

<210> SEQ ID NO 37
<211> LENGTH: 3
<212> TYPE: PRT
<213> ORGANISM: Artificial Sequence
<220> FEATURE:
<223> OTHER INFORMATION: Synthetic peptide

<400> SEQUENCE: 37

Asp Ser Gly
1
```

<210> SEQ ID NO 38
<211> LENGTH: 3
<212> TYPE: PRT
<213> ORGANISM: Artificial Sequence
<220> FEATURE:
<223> OTHER INFORMATION: Synthetic peptide

<400> SEQUENCE: 38

Ser Gly Tyr
1

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

Gln Ile Val Tyr Lys Pro Val
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide

<400> SEQUENCE: 40

Gln Ile Val Tyr Lys Pro
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Gln Ile Val Tyr Lys Ser Val
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Glu Ile Val Tyr Lys Ser Val
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Glu Ile Val Tyr Lys Ser Pro
1               5

<210> SEQ ID NO 44

-continued

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Glu Ile Val Tyr Lys Pro Val
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Ile Val Tyr Lys Ser Pro Val
1               5

<210> SEQ ID NO 46
<211> LENGTH: 4
<212> TYPE: PRT
<213> ORGANISM: Artificial Sequence
<220> FEATURE:
<223> OTHER INFORMATION: Synthetic peptide

<400> SEQUENCE: 46

Ile Val Tyr Lys
1

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Cys Asn Ile Lys His Val Pro
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide

<400> SEQUENCE: 48

Asn Ile Lys His Val Pro
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide

<400> SEQUENCE: 49

His Val Pro Gly Gly Gly
1               5

<210> SEQ ID NO 50
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 50

His Val Pro Gly Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide

<400> SEQUENCE: 51

His Lys Pro Gly Gly Gly
1               5

<210> SEQ ID NO 52
<211> LENGTH: 5
<212> TYPE: PRT
<213> ORGANISM: Artificial Sequence
<220> FEATURE:
<223> OTHER INFORMATION: Synthetic peptide

<400> SEQUENCE: 52

His Lys Pro Gly Gly
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Lys His Val Pro Gly Gly Gly
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide

<400> SEQUENCE: 54

Lys His Val Pro Gly Gly
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic peptide

<400> SEQUENCE: 55

His Gln Pro Gly Gly Gly
1               5

<210> SEQ ID NO 56
<211> LENGTH: 5
<212> TYPE: PRT
```

-continued

<213> ORGANISM: Artificial Sequence
<220> FEATURE:
<223> OTHER INFORMATION: Synthetic peptide

<400> SEQUENCE: 56

His Gln Pro Gly Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Asn Ile Lys His Val Pro Gly
1               5

<210> SEQ ID NO 58
<211> LENGTH: 140
<212> TYPE: PRT
<213> ORGANISM: Artificial Sequence
<220> FEATURE:
<223> OTHER INFORMATION: Synthetic peptide

<400> SEQUENCE: 58

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
        50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 59
<211> LENGTH: 10
<212> TYPE: PRT
<213> ORGANISM: Artificial Sequence
<220> FEATURE:
<223> OTHER INFORMATION: Synthetic peptide

<400> SEQUENCE: 59

Val Asp Pro Asp Asn Glu Ala Tyr Glu Met
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Val Asp Pro Asp Asn Glu Ala Tyr Glu
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic peptide

<400> SEQUENCE: 61

Val Asp Pro Asp Asn Glu Ala Tyr
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Val Asp Pro Asp Asn Glu Ala
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic peptide

<400> SEQUENCE: 63

Val Asp Pro Asp Asn Glu
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic peptide

<400> SEQUENCE: 64

Val Asp Pro Asp Asn
1               5

<210> SEQ ID NO 65
<211> LENGTH: 4
<212> TYPE: PRT
<213> ORGANISM: Artificial Sequence
<220> FEATURE:
<223> OTHER INFORMATION: Synthetic peptide

<400> SEQUENCE: 65

Val Asp Pro Asp
1

<210> SEQ ID NO 66
<211> LENGTH: 3
<212> TYPE: PRT
<213> ORGANISM: Artificial Sequence
<220> FEATURE:
<223> OTHER INFORMATION: Synthetic peptide

<400> SEQUENCE: 66

Val Asp Pro
1

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Asp Pro Asp Asn Glu Ala Tyr Glu Met
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic peptide

<400> SEQUENCE: 68

Asp Pro Asp Asn Glu Ala Tyr Glu
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic peptide

<400> SEQUENCE: 69

Asp Pro Asp Asn Glu Ala Tyr
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (17)..(18)
<223> OTHER INFORMATION: Xaa Xaa can be GG or AA or KK or SS

<400> SEQUENCE: 70

Asp Pro Asp Asn Glu Ala
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic peptide

<400> SEQUENCE: 71

Asp Pro Asp Asn Glu
1               5

<210> SEQ ID NO 72
<211> LENGTH: 4
<212> TYPE: PRT
<213> ORGANISM: Artificial Sequence

```
<220> FEATURE:
<223> OTHER INFORMATION: Synthetic peptide

<400> SEQUENCE: 72

Asp Pro Asp Asn
1

<210> SEQ ID NO 73
<211> LENGTH: 3
<212> TYPE: PRT
<213> ORGANISM: Artificial Sequence
<220> FEATURE:
<223> OTHER INFORMATION: Synthetic peptide

<400> SEQUENCE: 73

Asp Pro Asp
1

<210> SEQ ID NO 74
<211> LENGTH: 8
<212> TYPE: PRT
<213> ORGANISM: Artificial Sequence
<220> FEATURE:
<223> OTHER INFORMATION: Synthetic peptide

<400> SEQUENCE: 74

Pro Asp Asn Glu Ala Tyr Glu Met
1               5

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide

<400> SEQUENCE: 75

Pro Asp Asn Glu Ala Tyr Glu
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic peptide

<400> SEQUENCE: 76

Pro Asp Asn Glu Ala Tyr
1               5

<210> SEQ ID NO 77
<211> LENGTH: 5
<212> TYPE: PRT
<213> ORGANISM: Artificial Sequence
<220> FEATURE:
<223> OTHER INFORMATION: Synthetic peptide

<400> SEQUENCE: 77

Pro Asp Asn Glu Ala
1               5

<210> SEQ ID NO 78
<211> LENGTH: 4
<212> TYPE: PRT
<213> ORGANISM: Artificial Sequence
<220> FEATURE:
```

<223> OTHER INFORMATION: Synthetic peptide

<400> SEQUENCE: 78

Pro Asp Asn Glu
1

<210> SEQ ID NO 79
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (17)..(18)
<223> OTHER INFORMATION: Xaa Xaa can be GG or AA or KK or SS

<400> SEQUENCE: 79

Pro Asp Asn
1

<210> SEQ ID NO 80
<211> LENGTH: 7
<212> TYPE: PRT
<213> ORGANISM: Artificial Sequence
<220> FEATURE:
<223> OTHER INFORMATION: Synthetic peptide

<400> SEQUENCE: 80

Asp Asn Glu Ala Tyr Glu Met
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic peptide

<400> SEQUENCE: 81

Asp Asn Glu Ala Tyr Glu
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic peptide

<400> SEQUENCE: 82

Asp Asn Glu Ala Tyr
1               5

<210> SEQ ID NO 83
<211> LENGTH: 4
<212> TYPE: PRT
<213> ORGANISM: Artificial Sequence
<220> FEATURE:
<223> OTHER INFORMATION: Synthetic peptide

<400> SEQUENCE: 83

Asp Asn Glu Ala
1

<210> SEQ ID NO 84
<211> LENGTH: 3

```
<212> TYPE: PRT
<213> ORGANISM: Artificial Sequence
<220> FEATURE:
<223> OTHER INFORMATION: Synthetic peptide

<400> SEQUENCE: 84

Asp Asn Glu
1

<210> SEQ ID NO 85
<211> LENGTH: 6
<212> TYPE: PRT
<213> ORGANISM: Artificial Sequence
<220> FEATURE:
<223> OTHER INFORMATION: Synthetic peptide

<400> SEQUENCE: 85

Asn Glu Ala Tyr Glu Met
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic peptide

<400> SEQUENCE: 86

Asn Glu Ala Tyr Glu
1               5

<210> SEQ ID NO 87
<211> LENGTH: 4
<212> TYPE: PRT
<213> ORGANISM: Artificial Sequence
<220> FEATURE:
<223> OTHER INFORMATION: Synthetic peptide

<400> SEQUENCE: 87

Asn Glu Ala Tyr
1

<210> SEQ ID NO 88
<211> LENGTH: 3
<212> TYPE: PRT
<213> ORGANISM: Artificial Sequence
<220> FEATURE:
<223> OTHER INFORMATION: Synthetic peptide

<400> SEQUENCE: 88

Asn Glu Ala
1

<210> SEQ ID NO 89
<211> LENGTH: 5
<212> TYPE: PRT
<213> ORGANISM: Artificial Sequence
<220> FEATURE:
<223> OTHER INFORMATION: Synthetic peptide

<400> SEQUENCE: 89

Glu Ala Tyr Glu Met
1               5

<210> SEQ ID NO 90
<211> LENGTH: 4
<212> TYPE: PRT
```

-continued

```
<213> ORGANISM: Artificial Sequence
<220> FEATURE:
<223> OTHER INFORMATION: Synthetic peptide

<400> SEQUENCE: 90

Glu Ala Tyr Glu
1

<210> SEQ ID NO 91
<211> LENGTH: 3
<212> TYPE: PRT
<213> ORGANISM: Artificial Sequence
<220> FEATURE:
<223> OTHER INFORMATION: Synthetic peptide

<400> SEQUENCE: 91

Glu Ala Tyr
1

<210> SEQ ID NO 92
<211> LENGTH: 4
<212> TYPE: PRT
<213> ORGANISM: Artificial Sequence
<220> FEATURE:
<223> OTHER INFORMATION: Synthetic peptide

<400> SEQUENCE: 92

Ala Tyr Glu Met
1

<210> SEQ ID NO 93
<211> LENGTH: 3
<212> TYPE: PRT
<213> ORGANISM: Artificial Sequence
<220> FEATURE:
<223> OTHER INFORMATION: Synthetic peptide

<400> SEQUENCE: 93

Ala Tyr Glu
1

<210> SEQ ID NO 94
<211> LENGTH: 3
<212> TYPE: PRT
<213> ORGANISM: Artificial Sequence
<220> FEATURE:
<223> OTHER INFORMATION: Synthetic peptide

<400> SEQUENCE: 94

Tyr Glu Met
1

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Ala Thr Gly Phe Val Lys Lys Asp Gln Leu
1               5                   10

<210> SEQ ID NO 96
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 96

Ala Thr Gly Phe Val Lys Lys Asp Gln
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic peptide

<400> SEQUENCE: 97

Ala Thr Gly Phe Val Lys Lys Asp
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Ala Thr Gly Phe Val Lys Lys
1               5

<210> SEQ ID NO 99
<211> LENGTH: 6
<212> TYPE: PRT
<213> ORGANISM: Artificial Sequence
<220> FEATURE:
<223> OTHER INFORMATION: Synthetic peptide

<400> SEQUENCE: 99

Ala Thr Gly Phe Val Lys
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic peptide

<400> SEQUENCE: 100

Ala Thr Gly Phe Val
1               5

<210> SEQ ID NO 101
<211> LENGTH: 4
<212> TYPE: PRT
<213> ORGANISM: Artificial Sequence
<220> FEATURE:
<223> OTHER INFORMATION: Synthetic peptide

<400> SEQUENCE: 101

Ala Thr Gly Phe
1

<210> SEQ ID NO 102
<211> LENGTH: 3
<212> TYPE: PRT
<213> ORGANISM: Artificial Sequence
<220> FEATURE:
```

<223> OTHER INFORMATION: Synthetic peptide

<400> SEQUENCE: 102

Ala Thr Gly
1

<210> SEQ ID NO 103
<211> LENGTH: 9
<212> TYPE: PRT
<213> ORGANISM: Artificial Sequence
<220> FEATURE:
<223> OTHER INFORMATION: Synthetic peptide

<400> SEQUENCE: 103

Thr Gly Phe Val Lys Lys Asp Gln Leu
1               5

<210> SEQ ID NO 104
<211> LENGTH: 8
<212> TYPE: PRT
<213> ORGANISM: Artificial Sequence
<220> FEATURE:
<223> OTHER INFORMATION: Synthetic peptide

<400> SEQUENCE: 104

Thr Gly Phe Val Lys Lys Asp Gln
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Thr Gly Phe Val Lys Lys Asp
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic peptide

<400> SEQUENCE: 106

Thr Gly Phe Val Lys Lys
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic peptide

<400> SEQUENCE: 107

Thr Gly Phe Val Lys
1               5

<210> SEQ ID NO 108
<211> LENGTH: 4
<212> TYPE: PRT
<213> ORGANISM: Artificial Sequence
<220> FEATURE:
<223> OTHER INFORMATION: Synthetic peptide

<400> SEQUENCE: 108

Thr Gly Phe Val
1

<210> SEQ ID NO 109
<211> LENGTH: 3
<212> TYPE: PRT
<213> ORGANISM: Artificial Sequence
<220> FEATURE:
<223> OTHER INFORMATION: Synthetic peptide

<400> SEQUENCE: 109

Thr Gly Phe
1

<210> SEQ ID NO 110
<211> LENGTH: 8
<212> TYPE: PRT
<213> ORGANISM: Artificial Sequence
<220> FEATURE:
<223> OTHER INFORMATION: Synthetic peptide

<400> SEQUENCE: 110

Gly Phe Val Lys Lys Asp Gln Leu
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 111

Gly Phe Val Lys Lys Asp Gln
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic peptide

<400> SEQUENCE: 112

Gly Phe Val Lys Lys Asp
1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic peptide

<400> SEQUENCE: 113

Gly Phe Val Lys Lys
1               5

<210> SEQ ID NO 114
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 114

Gly Phe Val Lys
1

<210> SEQ ID NO 115
<211> LENGTH: 3
<212> TYPE: PRT
<213> ORGANISM: Artificial Sequence
<220> FEATURE:
<223> OTHER INFORMATION: Synthetic peptide

<400> SEQUENCE: 115

Gly Phe Val
1

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 116

Phe Val Lys Lys Asp Gln Leu
1               5

<210> SEQ ID NO 117
<211> LENGTH: 6
<212> TYPE: PRT
<213> ORGANISM: Artificial Sequence
<220> FEATURE:
<223> OTHER INFORMATION: Synthetic peptide

<400> SEQUENCE: 117

Phe Val Lys Lys Asp Gln
1               5

<210> SEQ ID NO 118
<211> LENGTH: 5
<212> TYPE: PRT
<213> ORGANISM: Artificial Sequence
<220> FEATURE:
<223> OTHER INFORMATION: Synthetic peptide

<400> SEQUENCE: 118

Phe Val Lys Lys Asp
1               5

<210> SEQ ID NO 119
<211> LENGTH: 4
<212> TYPE: PRT
<213> ORGANISM: Artificial Sequence
<220> FEATURE:
<223> OTHER INFORMATION: Synthetic peptide

<400> SEQUENCE: 119

Phe Val Lys Lys
1

<210> SEQ ID NO 120
<211> LENGTH: 3
<212> TYPE: PRT
<213> ORGANISM: Artificial Sequence
<220> FEATURE:
<223> OTHER INFORMATION: Synthetic peptide

<400> SEQUENCE: 120
```

Phe Val Lys
1

<210> SEQ ID NO 121
<211> LENGTH: 6
<212> TYPE: PRT
<213> ORGANISM: Artificial Sequence
<220> FEATURE:
<223> OTHER INFORMATION: Synthetic peptide

<400> SEQUENCE: 121

Val Lys Lys Asp Gln Leu
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic peptide

<400> SEQUENCE: 122

Val Lys Lys Asp Gln
1               5

<210> SEQ ID NO 123
<211> LENGTH: 4
<212> TYPE: PRT
<213> ORGANISM: Artificial Sequence
<220> FEATURE:
<223> OTHER INFORMATION: Synthetic peptide

<400> SEQUENCE: 123

Val Lys Lys Asp
1

<210> SEQ ID NO 124
<211> LENGTH: 3
<212> TYPE: PRT
<213> ORGANISM: Artificial Sequence
<220> FEATURE:
<223> OTHER INFORMATION: Synthetic peptide

<400> SEQUENCE: 124

Val Lys Lys
1

<210> SEQ ID NO 125
<211> LENGTH: 5
<212> TYPE: PRT
<213> ORGANISM: Artificial Sequence
<220> FEATURE:
<223> OTHER INFORMATION: Synthetic peptide

<400> SEQUENCE: 125

Lys Lys Asp Gln Leu
1               5

<210> SEQ ID NO 126
<211> LENGTH: 4
<212> TYPE: PRT
<213> ORGANISM: Artificial Sequence
<220> FEATURE:
<223> OTHER INFORMATION: Synthetic peptide

<400> SEQUENCE: 126

-continued

```
Lys Lys Asp Gln
1

<210> SEQ ID NO 127
<211> LENGTH: 3
<212> TYPE: PRT
<213> ORGANISM: Artificial Sequence
<220> FEATURE:
<223> OTHER INFORMATION: Synthetic peptide

<400> SEQUENCE: 127

Lys Lys Asp
1

<210> SEQ ID NO 128
<211> LENGTH: 4
<212> TYPE: PRT
<213> ORGANISM: Artificial Sequence
<220> FEATURE:
<223> OTHER INFORMATION: Synthetic peptide

<400> SEQUENCE: 128

Lys Asp Gln Leu
1

<210> SEQ ID NO 129
<211> LENGTH: 3
<212> TYPE: PRT
<213> ORGANISM: Artificial Sequence
<220> FEATURE:
<223> OTHER INFORMATION: Synthetic peptide

<400> SEQUENCE: 129

Lys Asp Gln
1

<210> SEQ ID NO 130
<211> LENGTH: 28
<212> TYPE: PRT
<213> ORGANISM: Artificial Sequence
<220> FEATURE:
<223> OTHER INFORMATION: Synthetic peptide

<400> SEQUENCE: 130

Asp Ala Glu Phe Arg His Asp Arg Arg Pro Asp Asn Glu Ala Tyr Glu
1               5                   10                  15

Arg Arg Gln Ile Val Tyr Lys Pro Val Lys Lys Cys
            20                  25

<210> SEQ ID NO 131
<211> LENGTH: 28
<212> TYPE: PRT
<213> ORGANISM: Artificial Sequence
<220> FEATURE:
<223> OTHER INFORMATION: Synthetic peptide

<400> SEQUENCE: 131

Asp Ala Glu Phe Arg His Asp Arg Arg Gln Ile Val Tyr Lys Pro Val
1               5                   10                  15

Arg Arg Pro Asp Asn Glu Ala Tyr Glu Lys Lys Cys
            20                  25

<210> SEQ ID NO 132
<211> LENGTH: 28
<212> TYPE: PRT
<213> ORGANISM: Artificial Sequence
```

-continued

```
<220> FEATURE:
<223> OTHER INFORMATION: Synthetic peptide

<400> SEQUENCE: 132

Asp Ala Glu Phe Arg His Asp Arg Arg Pro Asp Asn Glu Ala Tyr Glu
1               5                   10                  15

Arg Arg Asn Ile Lys His Val Pro Gly Lys Lys Cys
            20                  25

<210> SEQ ID NO 133
<211> LENGTH: 28
<212> TYPE: PRT
<213> ORGANISM: Artificial Sequence
<220> FEATURE:
<223> OTHER INFORMATION: Synthetic peptide

<400> SEQUENCE: 133

Asp Ala Glu Phe Arg His Asp Arg Arg Asn Ile Lys His Val Pro Gly
1               5                   10                  15

Arg Arg Pro Asp Asn Glu Ala Tyr Glu Lys Lys Cys
            20                  25

<210> SEQ ID NO 134
<211> LENGTH: 36
<212> TYPE: PRT
<213> ORGANISM: Artificial Sequence
<220> FEATURE:
<223> OTHER INFORMATION: Synthetic peptide

<400> SEQUENCE: 134

Asp Ala Glu Phe Arg His Asp Arg Arg Gln Ile Val Tyr Lys Pro Val
1               5                   10                  15

Arg Arg Pro Asp Asn Glu Ala Tyr Glu Arg Arg Asn Ile Lys His Val
            20                  25                  30

Pro Gly Gly Cys
        35

<210> SEQ ID NO 135
<211> LENGTH: 37
<212> TYPE: PRT
<213> ORGANISM: Artificial Sequence
<220> FEATURE:
<223> OTHER INFORMATION: Synthetic peptide

<400> SEQUENCE: 135

Asp Ala Glu Phe Arg His Asp Arg Arg Asp Pro Asp Asn Glu Ala Tyr
1               5                   10                  15

Arg Arg Asn Ile Lys His Val Pro Gly Arg Arg Gln Ile Val Tyr Lys
            20                  25                  30

Pro Val Gly Gly Cys
        35

<210> SEQ ID NO 136
<211> LENGTH: 36
<212> TYPE: PRT
<213> ORGANISM: Artificial Sequence
<220> FEATURE:
<223> OTHER INFORMATION: Synthetic peptide

<400> SEQUENCE: 136

Glu Phe Arg His Asp Ser Gly Arg Arg Gln Ile Val Tyr Lys Pro Val
1               5                   10                  15

Arg Arg Pro Asp Asn Glu Ala Tyr Glu Arg Arg Asn Ile Lys His Val
```

-continued

```
                20                  25                  30

Pro Gly Gly Cys
        35

<210> SEQ ID NO 137
<211> LENGTH: 37
<212> TYPE: PRT
<213> ORGANISM: Artificial Sequence
<220> FEATURE:
<223> OTHER INFORMATION: Synthetic peptide

<400> SEQUENCE: 137

Glu Phe Arg His Asp Ser Gly Arg Arg Asp Pro Asp Asn Glu Ala Tyr
1               5                  10                  15

Arg Arg Asn Ile Lys His Val Pro Gly Arg Arg Gln Ile Val Tyr Lys
                20                  25                  30

Pro Val Gly Gly Cys
        35

<210> SEQ ID NO 138
<211> LENGTH: 4
<212> TYPE: PRT
<213> ORGANISM: Artificial Sequence
<220> FEATURE:
<223> OTHER INFORMATION: Synthetic peptide

<400> SEQUENCE: 138

Arg Val Arg Arg
1

<210> SEQ ID NO 139
<211> LENGTH: 4
<212> TYPE: PRT
<213> ORGANISM: Artificial Sequence
<220> FEATURE:
<223> OTHER INFORMATION: Synthetic peptide

<400> SEQUENCE: 139

Gly Ala Gly Ala
1

<210> SEQ ID NO 140
<211> LENGTH: 4
<212> TYPE: PRT
<213> ORGANISM: Artificial Sequence
<220> FEATURE:
<223> OTHER INFORMATION: Synthetic peptide

<400> SEQUENCE: 140

Ala Gly Ala Gly
1

<210> SEQ ID NO 141
<211> LENGTH: 4
<212> TYPE: PRT
<213> ORGANISM: Artificial Sequence
<220> FEATURE:
<223> OTHER INFORMATION: Synthetic peptide

<400> SEQUENCE: 141

Lys Gly Lys Gly
1

<210> SEQ ID NO 142
<211> LENGTH: 9
```

```
<212> TYPE: PRT
<213> ORGANISM: Artificial Sequence
<220> FEATURE:
<223> OTHER INFORMATION: Synthetic peptide

<400> SEQUENCE: 142

Ala Glu Phe Arg His Asp Ser Gly Cys
1               5

<210> SEQ ID NO 143
<211> LENGTH: 8
<212> TYPE: PRT
<213> ORGANISM: Artificial Sequence
<220> FEATURE:
<223> OTHER INFORMATION: Synthetic peptide

<400> SEQUENCE: 143

Asp Ala Glu Phe Arg His Asp Cys
1               5

<210> SEQ ID NO 144
<211> LENGTH: 8
<212> TYPE: PRT
<213> ORGANISM: Artificial Sequence
<220> FEATURE:
<223> OTHER INFORMATION: Synthetic peptide

<400> SEQUENCE: 144

Cys Pro Asp Asn Glu Ala Tyr Glu
1               5

<210> SEQ ID NO 145
<211> LENGTH: 8
<212> TYPE: PRT
<213> ORGANISM: Artificial Sequence
<220> FEATURE:
<223> OTHER INFORMATION: Synthetic peptide

<400> SEQUENCE: 145

Asp Pro Asp Asn Glu Ala Tyr Cys
1               5

<210> SEQ ID NO 146
<211> LENGTH: 6
<212> TYPE: PRT
<213> ORGANISM: Artificial Sequence
<220> FEATURE:
<223> OTHER INFORMATION: Synthetic peptide

<400> SEQUENCE: 146

Val Gln Ile Ile Asn Lys
1               5

<210> SEQ ID NO 147
<211> LENGTH: 7
<212> TYPE: PRT
<213> ORGANISM: Artificial Sequence
<220> FEATURE:
<223> OTHER INFORMATION: Synthetic peptide

<400> SEQUENCE: 147

Val Gln Ile Ile Asn Lys Lys
1               5

<210> SEQ ID NO 148
<211> LENGTH: 8
<212> TYPE: PRT
```

```
<213> ORGANISM: Artificial Sequence
<220> FEATURE:
<223> OTHER INFORMATION: Synthetic peptide

<400> SEQUENCE: 148

Val Gln Ile Ile Asn Lys Lys Leu
1               5

<210> SEQ ID NO 149
<211> LENGTH: 5
<212> TYPE: PRT
<213> ORGANISM: Artificial Sequence
<220> FEATURE:
<223> OTHER INFORMATION: Synthetic peptide

<400> SEQUENCE: 149

Gln Ile Ile Asn Lys
1               5

<210> SEQ ID NO 150
<211> LENGTH: 6
<212> TYPE: PRT
<213> ORGANISM: Artificial Sequence
<220> FEATURE:
<223> OTHER INFORMATION: Synthetic peptide

<400> SEQUENCE: 150

Gln Ile Ile Asn Lys Lys
1               5

<210> SEQ ID NO 151
<211> LENGTH: 7
<212> TYPE: PRT
<213> ORGANISM: Artificial Sequence
<220> FEATURE:
<223> OTHER INFORMATION: Synthetic peptide

<400> SEQUENCE: 151

Gln Ile Ile Asn Lys Lys Leu
1               5

<210> SEQ ID NO 152
<211> LENGTH: 9
<212> TYPE: PRT
<213> ORGANISM: Artificial Sequence
<220> FEATURE:
<223> OTHER INFORMATION: Synthetic peptide

<400> SEQUENCE: 152

Glu Ala Ala Gly His Val Thr Gln Cys
1               5

<210> SEQ ID NO 153
<211> LENGTH: 10
<212> TYPE: PRT
<213> ORGANISM: Artificial Sequence
<220> FEATURE:
<223> OTHER INFORMATION: Synthetic peptide

<400> SEQUENCE: 153

Glu Ala Ala Gly His Val Thr Gln Ala Arg
1               5                   10

<210> SEQ ID NO 154
<211> LENGTH: 9
<212> TYPE: PRT
<213> ORGANISM: Artificial Sequence
```

```
<220> FEATURE:
<223> OTHER INFORMATION: Synthetic peptide

<400> SEQUENCE: 154

Ala Ala Gly His Val Thr Gln Ala Cys
1               5

<210> SEQ ID NO 155
<211> LENGTH: 9
<212> TYPE: PRT
<213> ORGANISM: Artificial Sequence
<220> FEATURE:
<223> OTHER INFORMATION: Synthetic peptide

<400> SEQUENCE: 155

Ala Gly His Val Thr Gln Ala Arg Cys
1               5

<210> SEQ ID NO 156
<211> LENGTH: 8
<212> TYPE: PRT
<213> ORGANISM: Artificial Sequence
<220> FEATURE:
<223> OTHER INFORMATION: Synthetic peptide

<400> SEQUENCE: 156

Ala Gly His Val Thr Gln Ala Arg
1               5

<210> SEQ ID NO 157
<211> LENGTH: 7
<212> TYPE: PRT
<213> ORGANISM: Artificial Sequence
<220> FEATURE:
<223> OTHER INFORMATION: Synthetic peptide

<400> SEQUENCE: 157

Gly Tyr Thr Met His Gln Asp
1               5

<210> SEQ ID NO 158
<211> LENGTH: 8
<212> TYPE: PRT
<213> ORGANISM: Artificial Sequence
<220> FEATURE:
<223> OTHER INFORMATION: Synthetic peptide

<400> SEQUENCE: 158

Gln Gly Gly Tyr Thr Met His Cys
1               5

<210> SEQ ID NO 159
<211> LENGTH: 9
<212> TYPE: PRT
<213> ORGANISM: Artificial Sequence
<220> FEATURE:
<223> OTHER INFORMATION: Synthetic peptide

<400> SEQUENCE: 159

Gln Gly Gly Tyr Thr Met His Gln Asp
1               5

<210> SEQ ID NO 160
<211> LENGTH: 8
<212> TYPE: PRT
<213> ORGANISM: Artificial Sequence
<220> FEATURE:
```

-continued

```
<223> OTHER INFORMATION: Synthetic peptide

<400> SEQUENCE: 160

Gly Gly Tyr Thr Met His Gln Cys
1               5

<210> SEQ ID NO 161
<211> LENGTH: 10
<212> TYPE: PRT
<213> ORGANISM: Artificial Sequence
<220> FEATURE:
<223> OTHER INFORMATION: Synthetic peptide

<400> SEQUENCE: 161

Val Pro Gly Gly Gly Ser Val Gln Ile Val
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Synthetic peptide

<400> SEQUENCE: 162

Pro Gly Gly Gly Ser Val Gln Ile Val
1               5

<210> SEQ ID NO 163
<211> LENGTH: 8
<212> TYPE: PRT
<213> ORGANISM: Artificial Sequence
<220> FEATURE:
<223> OTHER INFORMATION: Synthetic peptide

<400> SEQUENCE: 163

Gly Gly Gly Ser Val Gln Ile Val
1               5

<210> SEQ ID NO 164
<211> LENGTH: 7
<212> TYPE: PRT
<213> ORGANISM: Artificial Sequence
<220> FEATURE:
<223> OTHER INFORMATION: Synthetic peptide

<400> SEQUENCE: 164

Gly Gly Ser Val Gln Ile Val
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic peptide

<400> SEQUENCE: 165

Gly Ser Val Gln Ile Val
1               5

<210> SEQ ID NO 166
<211> LENGTH: 5
<212> TYPE: PRT
<213> ORGANISM: Artificial Sequence
<220> FEATURE:
<223> OTHER INFORMATION: Synthetic peptide
```

-continued

<400> SEQUENCE: 166

Ser Val Gln Ile Val
1               5

<210> SEQ ID NO 167
<211> LENGTH: 4
<212> TYPE: PRT
<213> ORGANISM: Artificial Sequence
<220> FEATURE:
<223> OTHER INFORMATION: Synthetic peptide

<400> SEQUENCE: 167

Val Gln Ile Val
1

<210> SEQ ID NO 168
<211> LENGTH: 3
<212> TYPE: PRT
<213> ORGANISM: Artificial Sequence
<220> FEATURE:
<223> OTHER INFORMATION: Synthetic peptide

<400> SEQUENCE: 168

Gln Ile Val
1

<210> SEQ ID NO 169
<211> LENGTH: 10
<212> TYPE: PRT
<213> ORGANISM: Artificial Sequence
<220> FEATURE:
<223> OTHER INFORMATION: Synthetic peptide

<400> SEQUENCE: 169

Pro Gly Gly Gly Ser Val Gln Ile Val Tyr
1               5                   10

<210> SEQ ID NO 170
<211> LENGTH: 9
<212> TYPE: PRT
<213> ORGANISM: Artificial Sequence
<220> FEATURE:
<223> OTHER INFORMATION: Synthetic peptide

<400> SEQUENCE: 170

Gly Gly Gly Ser Val Gln Ile Val Tyr
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic peptide

<400> SEQUENCE: 171

Gly Gly Ser Val Gln Ile Val Tyr
1               5

<210> SEQ ID NO 172
<211> LENGTH: 7
<212> TYPE: PRT
<213> ORGANISM: Artificial Sequence
<220> FEATURE:
<223> OTHER INFORMATION: Synthetic peptide -continued

```
<400> SEQUENCE: 172

Gly Ser Val Gln Ile Val Tyr
1               5

<210> SEQ ID NO 173
<211> LENGTH: 6
<212> TYPE: PRT
<213> ORGANISM: Artificial Sequence
<220> FEATURE:
<223> OTHER INFORMATION: Synthetic peptide

<400> SEQUENCE: 173

Ser Val Gln Ile Val Tyr
1               5

<210> SEQ ID NO 174
<211> LENGTH: 5
<212> TYPE: PRT
<213> ORGANISM: Artificial Sequence
<220> FEATURE:
<223> OTHER INFORMATION: Synthetic peptide

<400> SEQUENCE: 174

Val Gln Ile Val Tyr
1               5

<210> SEQ ID NO 175
<211> LENGTH: 4
<212> TYPE: PRT
<213> ORGANISM: Artificial Sequence
<220> FEATURE:
<223> OTHER INFORMATION: Synthetic peptide

<400> SEQUENCE: 175

Gln Ile Val Tyr
1

<210> SEQ ID NO 176
<211> LENGTH: 3
<212> TYPE: PRT
<213> ORGANISM: Artificial Sequence
<220> FEATURE:
<223> OTHER INFORMATION: Synthetic peptide

<400> SEQUENCE: 176

Ile Val Tyr
1

<210> SEQ ID NO 177
<211> LENGTH: 10
<212> TYPE: PRT
<213> ORGANISM: Artificial Sequence
<220> FEATURE:
<223> OTHER INFORMATION: Synthetic peptide

<400> SEQUENCE: 177

Gly Gly Gly Ser Val Gln Ile Val Tyr Lys
1               5                   10

<210> SEQ ID NO 178
<211> LENGTH: 9
<212> TYPE: PRT
<213> ORGANISM: Artificial Sequence
<220> FEATURE:
<223> OTHER INFORMATION: Synthetic peptide

<400> SEQUENCE: 178
```

-continued

```
Gly Gly Ser Val Gln Ile Val Tyr Lys
1               5

<210> SEQ ID NO 179
<211> LENGTH: 8
<212> TYPE: PRT
<213> ORGANISM: Artificial Sequence
<220> FEATURE:
<223> OTHER INFORMATION: Synthetic peptide

<400> SEQUENCE: 179

Gly Ser Val Gln Ile Val Tyr Lys
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic peptide

<400> SEQUENCE: 180

Ser Val Gln Ile Val Tyr Lys
1               5

<210> SEQ ID NO 181
<211> LENGTH: 6
<212> TYPE: PRT
<213> ORGANISM: Artificial Sequence
<220> FEATURE:
<223> OTHER INFORMATION: Synthetic peptide

<400> SEQUENCE: 181

Val Gln Ile Val Tyr Lys
1               5

<210> SEQ ID NO 182
<211> LENGTH: 5
<212> TYPE: PRT
<213> ORGANISM: Artificial Sequence
<220> FEATURE:
<223> OTHER INFORMATION: Synthetic peptide

<400> SEQUENCE: 182

Gln Ile Val Tyr Lys
1               5

<210> SEQ ID NO 183
<211> LENGTH: 3
<212> TYPE: PRT
<213> ORGANISM: Artificial Sequence
<220> FEATURE:
<223> OTHER INFORMATION: Synthetic peptide

<400> SEQUENCE: 183

Val Tyr Lys
1

<210> SEQ ID NO 184
<211> LENGTH: 10
<212> TYPE: PRT
<213> ORGANISM: Artificial Sequence
<220> FEATURE:
<223> OTHER INFORMATION: Synthetic peptide

<400> SEQUENCE: 184
```

```
Gly Gly Ser Val Gln Ile Val Tyr Lys Pro
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Synthetic peptide

<400> SEQUENCE: 185

Gly Ser Val Gln Ile Val Tyr Lys Pro
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic peptide

<400> SEQUENCE: 186

Ser Val Gln Ile Val Tyr Lys Pro
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic peptide

<400> SEQUENCE: 187

Val Gln Ile Val Tyr Lys Pro
1               5

<210> SEQ ID NO 188
<211> LENGTH: 5
<212> TYPE: PRT
<213> ORGANISM: Artificial Sequence
<220> FEATURE:
<223> OTHER INFORMATION: Synthetic peptide

<400> SEQUENCE: 188

Ile Val Tyr Lys Pro
1               5

<210> SEQ ID NO 189
<211> LENGTH: 4
<212> TYPE: PRT
<213> ORGANISM: Artificial Sequence
<220> FEATURE:
<223> OTHER INFORMATION: Synthetic peptide

<400> SEQUENCE: 189

Val Tyr Lys Pro
1

<210> SEQ ID NO 190
<211> LENGTH: 3
<212> TYPE: PRT
<213> ORGANISM: Artificial Sequence
<220> FEATURE:
<223> OTHER INFORMATION: Synthetic peptide

<400> SEQUENCE: 190

Tyr Lys Pro
```

1

```
<210> SEQ ID NO 191
<211> LENGTH: 10
<212> TYPE: PRT
<213> ORGANISM: Artificial Sequence
<220> FEATURE:
<223> OTHER INFORMATION: Synthetic peptide

<400> SEQUENCE: 191

Gly Ser Val Gln Ile Val Tyr Lys Pro Val
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Synthetic peptide

<400> SEQUENCE: 192

Ser Val Gln Ile Val Tyr Lys Pro Val
1               5

<210> SEQ ID NO 193
<211> LENGTH: 8
<212> TYPE: PRT
<213> ORGANISM: Artificial Sequence
<220> FEATURE:
<223> OTHER INFORMATION: Synthetic peptide

<400> SEQUENCE: 193

Val Gln Ile Val Tyr Lys Pro Val
1               5

<210> SEQ ID NO 194
<211> LENGTH: 6
<212> TYPE: PRT
<213> ORGANISM: Artificial Sequence
<220> FEATURE:
<223> OTHER INFORMATION: Synthetic peptide

<400> SEQUENCE: 194

Ile Val Tyr Lys Pro Val
1               5

<210> SEQ ID NO 195
<211> LENGTH: 5
<212> TYPE: PRT
<213> ORGANISM: Artificial Sequence
<220> FEATURE:
<223> OTHER INFORMATION: Synthetic peptide

<400> SEQUENCE: 195

Val Tyr Lys Pro Val
1               5

<210> SEQ ID NO 196
<211> LENGTH: 4
<212> TYPE: PRT
<213> ORGANISM: Artificial Sequence
<220> FEATURE:
<223> OTHER INFORMATION: Synthetic peptide

<400> SEQUENCE: 196

Tyr Lys Pro Val
1
```

```
<210> SEQ ID NO 197
<211> LENGTH: 3
<212> TYPE: PRT
<213> ORGANISM: Artificial Sequence
<220> FEATURE:
<223> OTHER INFORMATION: Synthetic peptide

<400> SEQUENCE: 197

Lys Pro Val
1

<210> SEQ ID NO 198
<211> LENGTH: 10
<212> TYPE: PRT
<213> ORGANISM: Artificial Sequence
<220> FEATURE:
<223> OTHER INFORMATION: Synthetic peptide

<400> SEQUENCE: 198

Ser Val Gln Ile Val Tyr Lys Pro Val Asp
1               5                   10

<210> SEQ ID NO 199
<211> LENGTH: 9
<212> TYPE: PRT
<213> ORGANISM: Artificial Sequence
<220> FEATURE:
<223> OTHER INFORMATION: Synthetic peptide

<400> SEQUENCE: 199

Val Gln Ile Val Tyr Lys Pro Val Asp
1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic peptide

<400> SEQUENCE: 200

Gln Ile Val Tyr Lys Pro Val Asp
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic peptide

<400> SEQUENCE: 201

Ile Val Tyr Lys Pro Val Asp
1               5

<210> SEQ ID NO 202

<400> SEQUENCE: 202

000

<210> SEQ ID NO 203
<211> LENGTH: 6
<212> TYPE: PRT
<213> ORGANISM: Artificial Sequence
<220> FEATURE:
```

-continued

```
<223> OTHER INFORMATION: Synthetic peptide

<400> SEQUENCE: 203

Val Tyr Lys Pro Val Asp
1               5

<210> SEQ ID NO 204
<211> LENGTH: 5
<212> TYPE: PRT
<213> ORGANISM: Artificial Sequence
<220> FEATURE:
<223> OTHER INFORMATION: Synthetic peptide

<400> SEQUENCE: 204

Tyr Lys Pro Val Asp
1               5

<210> SEQ ID NO 205
<211> LENGTH: 4
<212> TYPE: PRT
<213> ORGANISM: Artificial Sequence
<220> FEATURE:
<223> OTHER INFORMATION: Synthetic peptide

<400> SEQUENCE: 205

Lys Pro Val Asp
1

<210> SEQ ID NO 206
<211> LENGTH: 3
<212> TYPE: PRT
<213> ORGANISM: Artificial Sequence
<220> FEATURE:
<223> OTHER INFORMATION: Synthetic peptide

<400> SEQUENCE: 206

Pro Val Asp
1

<210> SEQ ID NO 207
<211> LENGTH: 10
<212> TYPE: PRT
<213> ORGANISM: Artificial Sequence
<220> FEATURE:
<223> OTHER INFORMATION: Synthetic peptide

<400> SEQUENCE: 207

Val Gln Ile Val Tyr Lys Pro Val Asp Leu
1               5                   10

<210> SEQ ID NO 208
<211> LENGTH: 9
<212> TYPE: PRT
<213> ORGANISM: Artificial Sequence
<220> FEATURE:
<223> OTHER INFORMATION: Synthetic peptide

<400> SEQUENCE: 208

Gln Ile Val Tyr Lys Pro Val Asp Leu
1               5

<210> SEQ ID NO 209
<211> LENGTH: 8
<212> TYPE: PRT
<213> ORGANISM: Artificial Sequence
<220> FEATURE:
<223> OTHER INFORMATION: Synthetic peptide
```

<400> SEQUENCE: 209

Ile Val Tyr Lys Pro Val Asp Leu
1               5

<210> SEQ ID NO 210
<211> LENGTH: 7
<212> TYPE: PRT
<213> ORGANISM: Artificial Sequence
<220> FEATURE:
<223> OTHER INFORMATION: Synthetic peptide

<400> SEQUENCE: 210

Val Tyr Lys Pro Val Asp Leu
1               5

<210> SEQ ID NO 211
<211> LENGTH: 6
<212> TYPE: PRT
<213> ORGANISM: Artificial Sequence
<220> FEATURE:
<223> OTHER INFORMATION: Synthetic peptide

<400> SEQUENCE: 211

Tyr Lys Pro Val Asp Leu
1               5

<210> SEQ ID NO 212
<211> LENGTH: 5
<212> TYPE: PRT
<213> ORGANISM: Artificial Sequence
<220> FEATURE:
<223> OTHER INFORMATION: Synthetic peptide

<400> SEQUENCE: 212

Lys Pro Val Asp Leu
1               5

<210> SEQ ID NO 213
<211> LENGTH: 4
<212> TYPE: PRT
<213> ORGANISM: Artificial Sequence
<220> FEATURE:
<223> OTHER INFORMATION: Synthetic peptide

<400> SEQUENCE: 213

Pro Val Asp Leu
1

<210> SEQ ID NO 214
<211> LENGTH: 3
<212> TYPE: PRT
<213> ORGANISM: Artificial Sequence
<220> FEATURE:
<223> OTHER INFORMATION: Synthetic peptide

<400> SEQUENCE: 214

Val Asp Leu
1

<210> SEQ ID NO 215
<211> LENGTH: 10
<212> TYPE: PRT
<213> ORGANISM: Artificial Sequence
<220> FEATURE:
<223> OTHER INFORMATION: Synthetic peptide -continued

```
<400> SEQUENCE: 215

Gln Ile Val Tyr Lys Pro Val Asp Leu Ser
1               5                   10

<210> SEQ ID NO 216
<211> LENGTH: 9
<212> TYPE: PRT
<213> ORGANISM: Artificial Sequence
<220> FEATURE:
<223> OTHER INFORMATION: Synthetic peptide

<400> SEQUENCE: 216

Ile Val Tyr Lys Pro Val Asp Leu Ser
1               5

<210> SEQ ID NO 217
<211> LENGTH: 8
<212> TYPE: PRT
<213> ORGANISM: Artificial Sequence
<220> FEATURE:
<223> OTHER INFORMATION: Synthetic peptide

<400> SEQUENCE: 217

Val Tyr Lys Pro Val Asp Leu Ser
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic peptide

<400> SEQUENCE: 218

Tyr Lys Pro Val Asp Leu Ser
1               5

<210> SEQ ID NO 219
<211> LENGTH: 6
<212> TYPE: PRT
<213> ORGANISM: Artificial Sequence
<220> FEATURE:
<223> OTHER INFORMATION: Synthetic peptide

<400> SEQUENCE: 219

Lys Pro Val Asp Leu Ser
1               5

<210> SEQ ID NO 220
<211> LENGTH: 5
<212> TYPE: PRT
<213> ORGANISM: Artificial Sequence
<220> FEATURE:
<223> OTHER INFORMATION: Synthetic peptide

<400> SEQUENCE: 220

Pro Val Asp Leu Ser
1               5

<210> SEQ ID NO 221
<211> LENGTH: 4
<212> TYPE: PRT
<213> ORGANISM: Artificial Sequence
<220> FEATURE:
<223> OTHER INFORMATION: Synthetic peptide

<400> SEQUENCE: 221
```

-continued

Val Asp Leu Ser
1

<210> SEQ ID NO 222
<211> LENGTH: 3
<212> TYPE: PRT
<213> ORGANISM: Artificial Sequence
<220> FEATURE:
<223> OTHER INFORMATION: Synthetic peptide

<400> SEQUENCE: 222

Asp Leu Ser
1

<210> SEQ ID NO 223
<211> LENGTH: 10
<212> TYPE: PRT
<213> ORGANISM: Artificial Sequence
<220> FEATURE:
<223> OTHER INFORMATION: Synthetic peptide

<400> SEQUENCE: 223

Ile Val Tyr Lys Pro Val Asp Leu Ser Lys
1               5                   10

<210> SEQ ID NO 224
<211> LENGTH: 9
<212> TYPE: PRT
<213> ORGANISM: Artificial Sequence
<220> FEATURE:
<223> OTHER INFORMATION: Synthetic peptide

<400> SEQUENCE: 224

Val Tyr Lys Pro Val Asp Leu Ser Lys
1               5

<210> SEQ ID NO 225
<211> LENGTH: 8
<212> TYPE: PRT
<213> ORGANISM: Artificial Sequence
<220> FEATURE:
<223> OTHER INFORMATION: Synthetic peptide

<400> SEQUENCE: 225

Tyr Lys Pro Val Asp Leu Ser Lys
1               5

<210> SEQ ID NO 226
<211> LENGTH: 7
<212> TYPE: PRT
<213> ORGANISM: Artificial Sequence
<220> FEATURE:
<223> OTHER INFORMATION: Synthetic peptide

<400> SEQUENCE: 226

Lys Pro Val Asp Leu Ser Lys
1               5

<210> SEQ ID NO 227
<211> LENGTH: 6
<212> TYPE: PRT
<213> ORGANISM: Artificial Sequence
<220> FEATURE:
<223> OTHER INFORMATION: Synthetic peptide

<400> SEQUENCE: 227

```
Pro Val Asp Leu Ser Lys
1               5

<210> SEQ ID NO 228
<211> LENGTH: 5
<212> TYPE: PRT
<213> ORGANISM: Artificial Sequence
<220> FEATURE:
<223> OTHER INFORMATION: Synthetic peptide

<400> SEQUENCE: 228

Val Asp Leu Ser Lys
1               5

<210> SEQ ID NO 229
<211> LENGTH: 4
<212> TYPE: PRT
<213> ORGANISM: Artificial Sequence
<220> FEATURE:
<223> OTHER INFORMATION: Synthetic peptide

<400> SEQUENCE: 229

Asp Leu Ser Lys
1

<210> SEQ ID NO 230
<211> LENGTH: 3
<212> TYPE: PRT
<213> ORGANISM: Artificial Sequence
<220> FEATURE:
<223> OTHER INFORMATION: Synthetic peptide

<400> SEQUENCE: 230

Leu Ser Lys
1

<210> SEQ ID NO 231
<211> LENGTH: 10
<212> TYPE: PRT
<213> ORGANISM: Artificial Sequence
<220> FEATURE:
<223> OTHER INFORMATION: Synthetic peptide

<400> SEQUENCE: 231

Val Tyr Lys Pro Val Asp Leu Ser Lys Val
1               5                   10

<210> SEQ ID NO 232
<211> LENGTH: 9
<212> TYPE: PRT
<213> ORGANISM: Artificial Sequence
<220> FEATURE:
<223> OTHER INFORMATION: Synthetic peptide

<400> SEQUENCE: 232

Tyr Lys Pro Val Asp Leu Ser Lys Val
1               5

<210> SEQ ID NO 233
<211> LENGTH: 8
<212> TYPE: PRT
<213> ORGANISM: Artificial Sequence
<220> FEATURE:
<223> OTHER INFORMATION: Synthetic peptide

<400> SEQUENCE: 233

Lys Pro Val Asp Leu Ser Lys Val
```

-continued

```
1               5

<210> SEQ ID NO 234
<211> LENGTH: 7
<212> TYPE: PRT
<213> ORGANISM: Artificial Sequence
<220> FEATURE:
<223> OTHER INFORMATION: Synthetic peptide

<400> SEQUENCE: 234

Pro Val Asp Leu Ser Lys Val
1               5

<210> SEQ ID NO 235
<211> LENGTH: 6
<212> TYPE: PRT
<213> ORGANISM: Artificial Sequence
<220> FEATURE:
<223> OTHER INFORMATION: Synthetic peptide

<400> SEQUENCE: 235

Val Asp Leu Ser Lys Val
1               5

<210> SEQ ID NO 236
<211> LENGTH: 5
<212> TYPE: PRT
<213> ORGANISM: Artificial Sequence
<220> FEATURE:
<223> OTHER INFORMATION: Synthetic peptide

<400> SEQUENCE: 236

Asp Leu Ser Lys Val
1               5

<210> SEQ ID NO 237
<211> LENGTH: 4
<212> TYPE: PRT
<213> ORGANISM: Artificial Sequence
<220> FEATURE:
<223> OTHER INFORMATION: Synthetic peptide

<400> SEQUENCE: 237

Leu Ser Lys Val
1

<210> SEQ ID NO 238
<211> LENGTH: 3
<212> TYPE: PRT
<213> ORGANISM: Artificial Sequence
<220> FEATURE:
<223> OTHER INFORMATION: Synthetic peptide

<400> SEQUENCE: 238

Ser Lys Val
1

<210> SEQ ID NO 239
<211> LENGTH: 10
<212> TYPE: PRT
<213> ORGANISM: Artificial Sequence
<220> FEATURE:
<223> OTHER INFORMATION: Synthetic peptide

<400> SEQUENCE: 239

Tyr Lys Pro Val Asp Leu Ser Lys Val Thr
1               5                   10
```

```
<210> SEQ ID NO 240
<211> LENGTH: 9
<212> TYPE: PRT
<213> ORGANISM: Artificial Sequence
<220> FEATURE:
<223> OTHER INFORMATION: Synthetic peptide

<400> SEQUENCE: 240

Lys Pro Val Asp Leu Ser Lys Val Thr
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic peptide

<400> SEQUENCE: 241

Pro Val Asp Leu Ser Lys Val Thr
1               5

<210> SEQ ID NO 242
<211> LENGTH: 7
<212> TYPE: PRT
<213> ORGANISM: Artificial Sequence
<220> FEATURE:
<223> OTHER INFORMATION: Synthetic peptide

<400> SEQUENCE: 242

Val Asp Leu Ser Lys Val Thr
1               5

<210> SEQ ID NO 243
<211> LENGTH: 10
<212> TYPE: PRT
<213> ORGANISM: Artificial Sequence
<220> FEATURE:
<223> OTHER INFORMATION: Synthetic peptide

<400> SEQUENCE: 243

Ala Lys Thr Asp His Gly Ala Glu Ile Val
1               5                   10

<210> SEQ ID NO 244
<211> LENGTH: 9
<212> TYPE: PRT
<213> ORGANISM: Artificial Sequence
<220> FEATURE:
<223> OTHER INFORMATION: Synthetic peptide

<400> SEQUENCE: 244

Lys Thr Asp His Gly Ala Glu Ile Val
1               5

<210> SEQ ID NO 245
<211> LENGTH: 8
<212> TYPE: PRT
<213> ORGANISM: Artificial Sequence
<220> FEATURE:
<223> OTHER INFORMATION: Synthetic peptide

<400> SEQUENCE: 245

Thr Asp His Gly Ala Glu Ile Val
1               5
```

```
<210> SEQ ID NO 246
<211> LENGTH: 7
<212> TYPE: PRT
<213> ORGANISM: Artificial Sequence
<220> FEATURE:
<223> OTHER INFORMATION: Synthetic peptide

<400> SEQUENCE: 246

Asp His Gly Ala Glu Ile Val
1               5

<210> SEQ ID NO 247
<211> LENGTH: 6
<212> TYPE: PRT
<213> ORGANISM: Artificial Sequence
<220> FEATURE:
<223> OTHER INFORMATION: Synthetic peptide

<400> SEQUENCE: 247

His Gly Ala Glu Ile Val
1               5

<210> SEQ ID NO 248
<211> LENGTH: 5
<212> TYPE: PRT
<213> ORGANISM: Artificial Sequence
<220> FEATURE:
<223> OTHER INFORMATION: Synthetic peptide

<400> SEQUENCE: 248

Gly Ala Glu Ile Val
1               5

<210> SEQ ID NO 249
<211> LENGTH: 4
<212> TYPE: PRT
<213> ORGANISM: Artificial Sequence
<220> FEATURE:
<223> OTHER INFORMATION: Synthetic peptide

<400> SEQUENCE: 249

Ala Glu Ile Val
1

<210> SEQ ID NO 250
<211> LENGTH: 3
<212> TYPE: PRT
<213> ORGANISM: Artificial Sequence
<220> FEATURE:
<223> OTHER INFORMATION: Synthetic peptide

<400> SEQUENCE: 250

Glu Ile Val
1

<210> SEQ ID NO 251
<211> LENGTH: 10
<212> TYPE: PRT
<213> ORGANISM: Artificial Sequence
<220> FEATURE:
<223> OTHER INFORMATION: Synthetic peptide

<400> SEQUENCE: 251

Lys Thr Asp His Gly Ala Glu Ile Val Tyr
1               5                   10
```

<210> SEQ ID NO 252
<211> LENGTH: 9
<212> TYPE: PRT
<213> ORGANISM: Artificial Sequence
<220> FEATURE:
<223> OTHER INFORMATION: Synthetic peptide

<400> SEQUENCE: 252

Thr Asp His Gly Ala Glu Ile Val Tyr
1               5

<210> SEQ ID NO 253
<211> LENGTH: 8
<212> TYPE: PRT
<213> ORGANISM: Artificial Sequence
<220> FEATURE:
<223> OTHER INFORMATION: Synthetic peptide

<400> SEQUENCE: 253

Asp His Gly Ala Glu Ile Val Tyr
1               5

<210> SEQ ID NO 254
<211> LENGTH: 7
<212> TYPE: PRT
<213> ORGANISM: Artificial Sequence
<220> FEATURE:
<223> OTHER INFORMATION: Synthetic peptide

<400> SEQUENCE: 254

His Gly Ala Glu Ile Val Tyr
1               5

<210> SEQ ID NO 255
<211> LENGTH: 6
<212> TYPE: PRT
<213> ORGANISM: Artificial Sequence
<220> FEATURE:
<223> OTHER INFORMATION: Synthetic peptide

<400> SEQUENCE: 255

Gly Ala Glu Ile Val Tyr
1               5

<210> SEQ ID NO 256
<211> LENGTH: 5
<212> TYPE: PRT
<213> ORGANISM: Artificial Sequence
<220> FEATURE:
<223> OTHER INFORMATION: Synthetic peptide

<400> SEQUENCE: 256

Ala Glu Ile Val Tyr
1               5

<210> SEQ ID NO 257
<211> LENGTH: 4
<212> TYPE: PRT
<213> ORGANISM: Artificial Sequence
<220> FEATURE:
<223> OTHER INFORMATION: Synthetic peptide

<400> SEQUENCE: 257

Glu Ile Val Tyr
1

<210> SEQ ID NO 258

-continued

```
<211> LENGTH: 3
<212> TYPE: PRT
<213> ORGANISM: Artificial Sequence
<220> FEATURE:
<223> OTHER INFORMATION: Synthetic peptide

<400> SEQUENCE: 258

Ile Val Tyr
1

<210> SEQ ID NO 259
<211> LENGTH: 10
<212> TYPE: PRT
<213> ORGANISM: Artificial Sequence
<220> FEATURE:
<223> OTHER INFORMATION: Synthetic peptide

<400> SEQUENCE: 259

Thr Asp His Gly Ala Glu Ile Val Tyr Lys
1               5                   10

<210> SEQ ID NO 260
<211> LENGTH: 9
<212> TYPE: PRT
<213> ORGANISM: Artificial Sequence
<220> FEATURE:
<223> OTHER INFORMATION: Synthetic peptide

<400> SEQUENCE: 260

Asp His Gly Ala Glu Ile Val Tyr Lys
1               5

<210> SEQ ID NO 261
<211> LENGTH: 8
<212> TYPE: PRT
<213> ORGANISM: Artificial Sequence
<220> FEATURE:
<223> OTHER INFORMATION: Synthetic peptide

<400> SEQUENCE: 261

His Gly Ala Glu Ile Val Tyr Lys
1               5

<210> SEQ ID NO 262
<211> LENGTH: 7
<212> TYPE: PRT
<213> ORGANISM: Artificial Sequence
<220> FEATURE:
<223> OTHER INFORMATION: Synthetic peptide

<400> SEQUENCE: 262

Gly Ala Glu Ile Val Tyr Lys
1               5

<210> SEQ ID NO 263
<211> LENGTH: 6
<212> TYPE: PRT
<213> ORGANISM: Artificial Sequence
<220> FEATURE:
<223> OTHER INFORMATION: Synthetic peptide

<400> SEQUENCE: 263

Ala Glu Ile Val Tyr Lys
1               5

<210> SEQ ID NO 264
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 264

Glu Ile Val Tyr Lys
1               5

<210> SEQ ID NO 265
<211> LENGTH: 4
<212> TYPE: PRT
<213> ORGANISM: Artificial Sequence
<220> FEATURE:
<223> OTHER INFORMATION: Synthetic peptide

<400> SEQUENCE: 265

Ile Val Tyr Lys
1

<210> SEQ ID NO 266
<211> LENGTH: 10
<212> TYPE: PRT
<213> ORGANISM: Artificial Sequence
<220> FEATURE:
<223> OTHER INFORMATION: Synthetic peptide

<400> SEQUENCE: 266

Asp His Gly Ala Glu Ile Val Tyr Lys Ser
1               5                   10

<210> SEQ ID NO 267
<211> LENGTH: 9
<212> TYPE: PRT
<213> ORGANISM: Artificial Sequence
<220> FEATURE:
<223> OTHER INFORMATION: Synthetic peptide

<400> SEQUENCE: 267

His Gly Ala Glu Ile Val Tyr Lys Ser
1               5

<210> SEQ ID NO 268
<211> LENGTH: 8
<212> TYPE: PRT
<213> ORGANISM: Artificial Sequence
<220> FEATURE:
<223> OTHER INFORMATION: Synthetic peptide

<400> SEQUENCE: 268

Gly Ala Glu Ile Val Tyr Lys Ser
1               5

<210> SEQ ID NO 269
<211> LENGTH: 7
<212> TYPE: PRT
<213> ORGANISM: Artificial Sequence
<220> FEATURE:
<223> OTHER INFORMATION: Synthetic peptide

<400> SEQUENCE: 269

Ala Glu Ile Val Tyr Lys Ser
1               5

<210> SEQ ID NO 270
<211> LENGTH: 6
<212> TYPE: PRT
```

-continued

<213> ORGANISM: Artificial Sequence
<220> FEATURE:
<223> OTHER INFORMATION: Synthetic peptide

<400> SEQUENCE: 270

Glu Ile Val Tyr Lys Ser
1               5

<210> SEQ ID NO 271
<211> LENGTH: 5
<212> TYPE: PRT
<213> ORGANISM: Artificial Sequence
<220> FEATURE:
<223> OTHER INFORMATION: Synthetic peptide

<400> SEQUENCE: 271

Ile Val Tyr Lys Ser
1               5

<210> SEQ ID NO 272
<211> LENGTH: 4
<212> TYPE: PRT
<213> ORGANISM: Artificial Sequence
<220> FEATURE:
<223> OTHER INFORMATION: Synthetic peptide

<400> SEQUENCE: 272

Val Tyr Lys Ser
1

<210> SEQ ID NO 273
<211> LENGTH: 3
<212> TYPE: PRT
<213> ORGANISM: Artificial Sequence
<220> FEATURE:
<223> OTHER INFORMATION: Synthetic peptide

<400> SEQUENCE: 273

Tyr Lys Ser
1

<210> SEQ ID NO 274
<211> LENGTH: 10
<212> TYPE: PRT
<213> ORGANISM: Artificial Sequence
<220> FEATURE:
<223> OTHER INFORMATION: Synthetic peptide

<400> SEQUENCE: 274

His Gly Ala Glu Ile Val Tyr Lys Ser Pro
1               5                   10

<210> SEQ ID NO 275
<211> LENGTH: 9
<212> TYPE: PRT
<213> ORGANISM: Artificial Sequence
<220> FEATURE:
<223> OTHER INFORMATION: Synthetic peptide

<400> SEQUENCE: 275

Gly Ala Glu Ile Val Tyr Lys Ser Pro
1               5

<210> SEQ ID NO 276
<211> LENGTH: 8
<212> TYPE: PRT
<213> ORGANISM: Artificial Sequence

```
<220> FEATURE:
<223> OTHER INFORMATION: Synthetic peptide

<400> SEQUENCE: 276

Ala Glu Ile Val Tyr Lys Ser Pro
1               5

<210> SEQ ID NO 277
<211> LENGTH: 7
<212> TYPE: PRT
<213> ORGANISM: Artificial Sequence
<220> FEATURE:
<223> OTHER INFORMATION: Synthetic peptide

<400> SEQUENCE: 277

Glu Ile Val Tyr Lys Ser Pro
1               5

<210> SEQ ID NO 278
<211> LENGTH: 6
<212> TYPE: PRT
<213> ORGANISM: Artificial Sequence
<220> FEATURE:
<223> OTHER INFORMATION: Synthetic peptide

<400> SEQUENCE: 278

Ile Val Tyr Lys Ser Pro
1               5

<210> SEQ ID NO 279
<211> LENGTH: 5
<212> TYPE: PRT
<213> ORGANISM: Artificial Sequence
<220> FEATURE:
<223> OTHER INFORMATION: Synthetic peptide

<400> SEQUENCE: 279

Val Tyr Lys Ser Pro
1               5

<210> SEQ ID NO 280
<211> LENGTH: 4
<212> TYPE: PRT
<213> ORGANISM: Artificial Sequence
<220> FEATURE:
<223> OTHER INFORMATION: Synthetic peptide

<400> SEQUENCE: 280

Tyr Lys Ser Pro
1

<210> SEQ ID NO 281
<211> LENGTH: 3
<212> TYPE: PRT
<213> ORGANISM: Artificial Sequence
<220> FEATURE:
<223> OTHER INFORMATION: Synthetic peptide

<400> SEQUENCE: 281

Lys Ser Pro
1

<210> SEQ ID NO 282
<211> LENGTH: 10
<212> TYPE: PRT
<213> ORGANISM: Artificial Sequence
<220> FEATURE:
```

<223> OTHER INFORMATION: Synthetic peptide

<400> SEQUENCE: 282

Gly Ala Glu Ile Val Tyr Lys Ser Pro Val
1               5                   10

<210> SEQ ID NO 283
<211> LENGTH: 9
<212> TYPE: PRT
<213> ORGANISM: Artificial Sequence
<220> FEATURE:
<223> OTHER INFORMATION: Synthetic peptide

<400> SEQUENCE: 283

Ala Glu Ile Val Tyr Lys Ser Pro Val
1               5

<210> SEQ ID NO 284
<211> LENGTH: 8
<212> TYPE: PRT
<213> ORGANISM: Artificial Sequence
<220> FEATURE:
<223> OTHER INFORMATION: Synthetic peptide

<400> SEQUENCE: 284

Glu Ile Val Tyr Lys Ser Pro Val
1               5

<210> SEQ ID NO 285
<211> LENGTH: 7
<212> TYPE: PRT
<213> ORGANISM: Artificial Sequence
<220> FEATURE:
<223> OTHER INFORMATION: Synthetic peptide

<400> SEQUENCE: 285

Ile Val Tyr Lys Ser Pro Val
1               5

<210> SEQ ID NO 286
<211> LENGTH: 6
<212> TYPE: PRT
<213> ORGANISM: Artificial Sequence
<220> FEATURE:
<223> OTHER INFORMATION: Synthetic peptide

<400> SEQUENCE: 286

Val Tyr Lys Ser Pro Val
1               5

<210> SEQ ID NO 287
<211> LENGTH: 5
<212> TYPE: PRT
<213> ORGANISM: Artificial Sequence
<220> FEATURE:
<223> OTHER INFORMATION: Synthetic peptide

<400> SEQUENCE: 287

Tyr Lys Ser Pro Val
1               5

<210> SEQ ID NO 288
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 288

Lys Ser Pro Val
1

<210> SEQ ID NO 289
<211> LENGTH: 3
<212> TYPE: PRT
<213> ORGANISM: Artificial Sequence
<220> FEATURE:
<223> OTHER INFORMATION: Synthetic peptide

<400> SEQUENCE: 289

Ser Pro Val
1

<210> SEQ ID NO 290
<211> LENGTH: 10
<212> TYPE: PRT
<213> ORGANISM: Artificial Sequence
<220> FEATURE:
<223> OTHER INFORMATION: Synthetic peptide

<400> SEQUENCE: 290

Ala Glu Ile Val Tyr Lys Ser Pro Val Val
1               5                   10

<210> SEQ ID NO 291
<211> LENGTH: 9
<212> TYPE: PRT
<213> ORGANISM: Artificial Sequence
<220> FEATURE:
<223> OTHER INFORMATION: Synthetic peptide

<400> SEQUENCE: 291

Glu Ile Val Tyr Lys Ser Pro Val Val
1               5

<210> SEQ ID NO 292
<211> LENGTH: 8
<212> TYPE: PRT
<213> ORGANISM: Artificial Sequence
<220> FEATURE:
<223> OTHER INFORMATION: Synthetic peptide

<400> SEQUENCE: 292

Ile Val Tyr Lys Ser Pro Val Val
1               5

<210> SEQ ID NO 293
<211> LENGTH: 7
<212> TYPE: PRT
<213> ORGANISM: Artificial Sequence
<220> FEATURE:
<223> OTHER INFORMATION: Synthetic peptide

<400> SEQUENCE: 293

Val Tyr Lys Ser Pro Val Val
1               5

<210> SEQ ID NO 294
<211> LENGTH: 6
<212> TYPE: PRT
<213> ORGANISM: Artificial Sequence
<220> FEATURE:
<223> OTHER INFORMATION: Synthetic peptide
```

-continued

<400> SEQUENCE: 294

Tyr Lys Ser Pro Val Val
1               5

<210> SEQ ID NO 295
<211> LENGTH: 5
<212> TYPE: PRT
<213> ORGANISM: Artificial Sequence
<220> FEATURE:
<223> OTHER INFORMATION: Synthetic peptide

<400> SEQUENCE: 295

Lys Ser Pro Val Val
1               5

<210> SEQ ID NO 296
<211> LENGTH: 4
<212> TYPE: PRT
<213> ORGANISM: Artificial Sequence
<220> FEATURE:
<223> OTHER INFORMATION: Synthetic peptide

<400> SEQUENCE: 296

Ser Pro Val Val
1

<210> SEQ ID NO 297
<211> LENGTH: 3
<212> TYPE: PRT
<213> ORGANISM: Artificial Sequence
<220> FEATURE:
<223> OTHER INFORMATION: Synthetic peptide

<400> SEQUENCE: 297

Pro Val Val
1

<210> SEQ ID NO 298
<211> LENGTH: 10
<212> TYPE: PRT
<213> ORGANISM: Artificial Sequence
<220> FEATURE:
<223> OTHER INFORMATION: Synthetic peptide

<400> SEQUENCE: 298

Glu Ile Val Tyr Lys Ser Pro Val Val Ser
1               5                   10

<210> SEQ ID NO 299
<211> LENGTH: 9
<212> TYPE: PRT
<213> ORGANISM: Artificial Sequence
<220> FEATURE:
<223> OTHER INFORMATION: Synthetic peptide

<400> SEQUENCE: 299

Ile Val Tyr Lys Ser Pro Val Val Ser
1               5

<210> SEQ ID NO 300
<211> LENGTH: 8
<212> TYPE: PRT
<213> ORGANISM: Artificial Sequence
<220> FEATURE:
<223> OTHER INFORMATION: Synthetic peptide

<400> SEQUENCE: 300

```
Val Tyr Lys Ser Pro Val Val Ser
1               5

<210> SEQ ID NO 301
<211> LENGTH: 7
<212> TYPE: PRT
<213> ORGANISM: Artificial Sequence
<220> FEATURE:
<223> OTHER INFORMATION: Synthetic peptide

<400> SEQUENCE: 301

Tyr Lys Ser Pro Val Val Ser
1               5

<210> SEQ ID NO 302
<211> LENGTH: 6
<212> TYPE: PRT
<213> ORGANISM: Artificial Sequence
<220> FEATURE:
<223> OTHER INFORMATION: Synthetic peptide

<400> SEQUENCE: 302

Lys Ser Pro Val Val Ser
1               5

<210> SEQ ID NO 303
<211> LENGTH: 5
<212> TYPE: PRT
<213> ORGANISM: Artificial Sequence
<220> FEATURE:
<223> OTHER INFORMATION: Synthetic peptide

<400> SEQUENCE: 303

Ser Pro Val Val Ser
1               5

<210> SEQ ID NO 304
<211> LENGTH: 4
<212> TYPE: PRT
<213> ORGANISM: Artificial Sequence
<220> FEATURE:
<223> OTHER INFORMATION: Synthetic peptide

<400> SEQUENCE: 304

Pro Val Val Ser
1

<210> SEQ ID NO 305
<211> LENGTH: 3
<212> TYPE: PRT
<213> ORGANISM: Artificial Sequence
<220> FEATURE:
<223> OTHER INFORMATION: Synthetic peptide

<400> SEQUENCE: 305

Val Val Ser
1

<210> SEQ ID NO 306
<211> LENGTH: 10
<212> TYPE: PRT
<213> ORGANISM: Artificial Sequence
<220> FEATURE:
<223> OTHER INFORMATION: Synthetic peptide

<400> SEQUENCE: 306
```

```
Ile Val Tyr Lys Ser Pro Val Val Ser Gly
1               5                   10

<210> SEQ ID NO 307
<211> LENGTH: 9
<212> TYPE: PRT
<213> ORGANISM: Artificial Sequence
<220> FEATURE:
<223> OTHER INFORMATION: Synthetic peptide

<400> SEQUENCE: 307

Val Tyr Lys Ser Pro Val Val Ser Gly
1               5

<210> SEQ ID NO 308
<211> LENGTH: 8
<212> TYPE: PRT
<213> ORGANISM: Artificial Sequence
<220> FEATURE:
<223> OTHER INFORMATION: Synthetic peptide

<400> SEQUENCE: 308

Tyr Lys Ser Pro Val Val Ser Gly
1               5

<210> SEQ ID NO 309
<211> LENGTH: 7
<212> TYPE: PRT
<213> ORGANISM: Artificial Sequence
<220> FEATURE:
<223> OTHER INFORMATION: Synthetic peptide

<400> SEQUENCE: 309

Lys Ser Pro Val Val Ser Gly
1               5

<210> SEQ ID NO 310
<211> LENGTH: 6
<212> TYPE: PRT
<213> ORGANISM: Artificial Sequence
<220> FEATURE:
<223> OTHER INFORMATION: Synthetic peptide

<400> SEQUENCE: 310

Ser Pro Val Val Ser Gly
1               5

<210> SEQ ID NO 311
<211> LENGTH: 5
<212> TYPE: PRT
<213> ORGANISM: Artificial Sequence
<220> FEATURE:
<223> OTHER INFORMATION: Synthetic peptide

<400> SEQUENCE: 311

Pro Val Val Ser Gly
1               5

<210> SEQ ID NO 312
<211> LENGTH: 4
<212> TYPE: PRT
<213> ORGANISM: Artificial Sequence
<220> FEATURE:
<223> OTHER INFORMATION: Synthetic peptide

<400> SEQUENCE: 312

Val Val Ser Gly
```

1

```
<210> SEQ ID NO 313
<211> LENGTH: 3
<212> TYPE: PRT
<213> ORGANISM: Artificial Sequence
<220> FEATURE:
<223> OTHER INFORMATION: Synthetic peptide

<400> SEQUENCE: 313

Val Ser Gly
1

<210> SEQ ID NO 314
<211> LENGTH: 10
<212> TYPE: PRT
<213> ORGANISM: Artificial Sequence
<220> FEATURE:
<223> OTHER INFORMATION: Synthetic peptide

<400> SEQUENCE: 314

Val Tyr Lys Ser Pro Val Val Ser Gly Asp
1               5                   10

<210> SEQ ID NO 315
<211> LENGTH: 9
<212> TYPE: PRT
<213> ORGANISM: Artificial Sequence
<220> FEATURE:
<223> OTHER INFORMATION: Synthetic peptide

<400> SEQUENCE: 315

Tyr Lys Ser Pro Val Val Ser Gly Asp
1               5

<210> SEQ ID NO 316
<211> LENGTH: 8
<212> TYPE: PRT
<213> ORGANISM: Artificial Sequence
<220> FEATURE:
<223> OTHER INFORMATION: Synthetic peptide

<400> SEQUENCE: 316

Lys Ser Pro Val Val Ser Gly Asp
1               5

<210> SEQ ID NO 317
<211> LENGTH: 7
<212> TYPE: PRT
<213> ORGANISM: Artificial Sequence
<220> FEATURE:
<223> OTHER INFORMATION: Synthetic peptide

<400> SEQUENCE: 317

Ser Pro Val Val Ser Gly Asp
1               5

<210> SEQ ID NO 318
<211> LENGTH: 6
<212> TYPE: PRT
<213> ORGANISM: Artificial Sequence
<220> FEATURE:
<223> OTHER INFORMATION: Synthetic peptide

<400> SEQUENCE: 318

Pro Val Val Ser Gly Asp
1               5
```

-continued

```
<210> SEQ ID NO 319
<211> LENGTH: 5
<212> TYPE: PRT
<213> ORGANISM: Artificial Sequence
<220> FEATURE:
<223> OTHER INFORMATION: Synthetic peptide

<400> SEQUENCE: 319

Val Val Ser Gly Asp
1               5

<210> SEQ ID NO 320
<211> LENGTH: 4
<212> TYPE: PRT
<213> ORGANISM: Artificial Sequence
<220> FEATURE:
<223> OTHER INFORMATION: Synthetic peptide

<400> SEQUENCE: 320

Val Ser Gly Asp
1

<210> SEQ ID NO 321
<211> LENGTH: 3
<212> TYPE: PRT
<213> ORGANISM: Artificial Sequence
<220> FEATURE:
<223> OTHER INFORMATION: Synthetic peptide

<400> SEQUENCE: 321

Ser Gly Asp
1

<210> SEQ ID NO 322
<211> LENGTH: 10
<212> TYPE: PRT
<213> ORGANISM: Artificial Sequence
<220> FEATURE:
<223> OTHER INFORMATION: Synthetic peptide

<400> SEQUENCE: 322

Tyr Lys Ser Pro Val Val Ser Gly Asp Thr
1               5                   10

<210> SEQ ID NO 323
<211> LENGTH: 9
<212> TYPE: PRT
<213> ORGANISM: Artificial Sequence
<220> FEATURE:
<223> OTHER INFORMATION: Synthetic peptide

<400> SEQUENCE: 323

Lys Ser Pro Val Val Ser Gly Asp Thr
1               5

<210> SEQ ID NO 324
<211> LENGTH: 8
<212> TYPE: PRT
<213> ORGANISM: Artificial Sequence
<220> FEATURE:
<223> OTHER INFORMATION: Synthetic peptide

<400> SEQUENCE: 324

Ser Pro Val Val Ser Gly Asp Thr
1               5
```

-continued

```
<210> SEQ ID NO 325
<211> LENGTH: 7
<212> TYPE: PRT
<213> ORGANISM: Artificial Sequence
<220> FEATURE:
<223> OTHER INFORMATION: Synthetic peptide

<400> SEQUENCE: 325

Pro Val Val Ser Gly Asp Thr
1               5

<210> SEQ ID NO 326
<211> LENGTH: 6
<212> TYPE: PRT
<213> ORGANISM: Artificial Sequence
<220> FEATURE:
<223> OTHER INFORMATION: Synthetic peptide

<400> SEQUENCE: 326

Val Val Ser Gly Asp Thr
1               5

<210> SEQ ID NO 327
<211> LENGTH: 5
<212> TYPE: PRT
<213> ORGANISM: Artificial Sequence
<220> FEATURE:
<223> OTHER INFORMATION: Synthetic peptide

<400> SEQUENCE: 327

Val Ser Gly Asp Thr
1               5

<210> SEQ ID NO 328
<211> LENGTH: 4
<212> TYPE: PRT
<213> ORGANISM: Artificial Sequence
<220> FEATURE:
<223> OTHER INFORMATION: Synthetic peptide

<400> SEQUENCE: 328

Ser Gly Asp Thr
1

<210> SEQ ID NO 329
<211> LENGTH: 3
<212> TYPE: PRT
<213> ORGANISM: Artificial Sequence
<220> FEATURE:
<223> OTHER INFORMATION: Synthetic peptide

<400> SEQUENCE: 329

Gly Asp Thr
1

<210> SEQ ID NO 330
<211> LENGTH: 10
<212> TYPE: PRT
<213> ORGANISM: Artificial Sequence
<220> FEATURE:
<223> OTHER INFORMATION: Synthetic peptide

<400> SEQUENCE: 330

Lys Ser Pro Val Val Ser Gly Asp Thr Ser
1               5                   10
```

<210> SEQ ID NO 331
<211> LENGTH: 9
<212> TYPE: PRT
<213> ORGANISM: Artificial Sequence
<220> FEATURE:
<223> OTHER INFORMATION: Synthetic peptide

<400> SEQUENCE: 331

Ser Pro Val Val Ser Gly Asp Thr Ser
1               5

<210> SEQ ID NO 332
<211> LENGTH: 8
<212> TYPE: PRT
<213> ORGANISM: Artificial Sequence
<220> FEATURE:
<223> OTHER INFORMATION: Synthetic peptide

<400> SEQUENCE: 332

Pro Val Val Ser Gly Asp Thr Ser
1               5

<210> SEQ ID NO 333
<211> LENGTH: 7
<212> TYPE: PRT
<213> ORGANISM: Artificial Sequence
<220> FEATURE:
<223> OTHER INFORMATION: Synthetic peptide

<400> SEQUENCE: 333

Val Val Ser Gly Asp Thr Ser
1               5

<210> SEQ ID NO 334
<211> LENGTH: 6
<212> TYPE: PRT
<213> ORGANISM: Artificial Sequence
<220> FEATURE:
<223> OTHER INFORMATION: Synthetic peptide

<400> SEQUENCE: 334

Val Ser Gly Asp Thr Ser
1               5

<210> SEQ ID NO 335
<211> LENGTH: 5
<212> TYPE: PRT
<213> ORGANISM: Artificial Sequence
<220> FEATURE:
<223> OTHER INFORMATION: Synthetic peptide

<400> SEQUENCE: 335

Ser Gly Asp Thr Ser
1               5

<210> SEQ ID NO 336
<211> LENGTH: 4
<212> TYPE: PRT
<213> ORGANISM: Artificial Sequence
<220> FEATURE:
<223> OTHER INFORMATION: Synthetic peptide

<400> SEQUENCE: 336

Gly Asp Thr Ser
1

<210> SEQ ID NO 337

```
<211> LENGTH: 3
<212> TYPE: PRT
<213> ORGANISM: Artificial Sequence
<220> FEATURE:
<223> OTHER INFORMATION: Synthetic peptide

<400> SEQUENCE: 337

Asp Thr Ser
1

<210> SEQ ID NO 338
<211> LENGTH: 10
<212> TYPE: PRT
<213> ORGANISM: Artificial Sequence
<220> FEATURE:
<223> OTHER INFORMATION: Synthetic peptide

<400> SEQUENCE: 338

Ser Pro Val Val Ser Gly Asp Thr Ser Pro
1               5                   10

<210> SEQ ID NO 339
<211> LENGTH: 9
<212> TYPE: PRT
<213> ORGANISM: Artificial Sequence
<220> FEATURE:
<223> OTHER INFORMATION: Synthetic peptide

<400> SEQUENCE: 339

Pro Val Val Ser Gly Asp Thr Ser Pro
1               5

<210> SEQ ID NO 340
<211> LENGTH: 8
<212> TYPE: PRT
<213> ORGANISM: Artificial Sequence
<220> FEATURE:
<223> OTHER INFORMATION: Synthetic peptide

<400> SEQUENCE: 340

Val Val Ser Gly Asp Thr Ser Pro
1               5

<210> SEQ ID NO 341
<211> LENGTH: 7
<212> TYPE: PRT
<213> ORGANISM: Artificial Sequence
<220> FEATURE:
<223> OTHER INFORMATION: Synthetic peptide

<400> SEQUENCE: 341

Val Ser Gly Asp Thr Ser Pro
1               5

<210> SEQ ID NO 342
<211> LENGTH: 6
<212> TYPE: PRT
<213> ORGANISM: Artificial Sequence
<220> FEATURE:
<223> OTHER INFORMATION: Synthetic peptide

<400> SEQUENCE: 342

Ser Gly Asp Thr Ser Pro
1               5

<210> SEQ ID NO 343
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 343

Gly Asp Thr Ser Pro
1               5

<210> SEQ ID NO 344
<211> LENGTH: 4
<212> TYPE: PRT
<213> ORGANISM: Artificial Sequence
<220> FEATURE:
<223> OTHER INFORMATION: Synthetic peptide

<400> SEQUENCE: 344

Asp Thr Ser Pro
1

<210> SEQ ID NO 345
<211> LENGTH: 3
<212> TYPE: PRT
<213> ORGANISM: Artificial Sequence
<220> FEATURE:
<223> OTHER INFORMATION: Synthetic peptide

<400> SEQUENCE: 345

Thr Ser Pro
1

<210> SEQ ID NO 346
<211> LENGTH: 10
<212> TYPE: PRT
<213> ORGANISM: Artificial Sequence
<220> FEATURE:
<223> OTHER INFORMATION: Synthetic peptide

<400> SEQUENCE: 346

Pro Val Val Ser Gly Asp Thr Ser Pro Arg
1               5                   10

<210> SEQ ID NO 347
<211> LENGTH: 9
<212> TYPE: PRT
<213> ORGANISM: Artificial Sequence
<220> FEATURE:
<223> OTHER INFORMATION: Synthetic peptide

<400> SEQUENCE: 347

Val Val Ser Gly Asp Thr Ser Pro Arg
1               5

<210> SEQ ID NO 348
<211> LENGTH: 8
<212> TYPE: PRT
<213> ORGANISM: Artificial Sequence
<220> FEATURE:
<223> OTHER INFORMATION: Synthetic peptide

<400> SEQUENCE: 348

Val Ser Gly Asp Thr Ser Pro Arg
1               5

<210> SEQ ID NO 349
<211> LENGTH: 7
<212> TYPE: PRT
```

-continued

```
<213> ORGANISM: Artificial Sequence
<220> FEATURE:
<223> OTHER INFORMATION: Synthetic peptide

<400> SEQUENCE: 349

Ser Gly Asp Thr Ser Pro Arg
1               5

<210> SEQ ID NO 350
<211> LENGTH: 6
<212> TYPE: PRT
<213> ORGANISM: Artificial Sequence
<220> FEATURE:
<223> OTHER INFORMATION: Synthetic peptide

<400> SEQUENCE: 350

Gly Asp Thr Ser Pro Arg
1               5

<210> SEQ ID NO 351
<211> LENGTH: 5
<212> TYPE: PRT
<213> ORGANISM: Artificial Sequence
<220> FEATURE:
<223> OTHER INFORMATION: Synthetic peptide

<400> SEQUENCE: 351

Asp Thr Ser Pro Arg
1               5

<210> SEQ ID NO 352
<211> LENGTH: 4
<212> TYPE: PRT
<213> ORGANISM: Artificial Sequence
<220> FEATURE:
<223> OTHER INFORMATION: Synthetic peptide

<400> SEQUENCE: 352

Thr Ser Pro Arg
1

<210> SEQ ID NO 353
<211> LENGTH: 3
<212> TYPE: PRT
<213> ORGANISM: Artificial Sequence
<220> FEATURE:
<223> OTHER INFORMATION: Synthetic peptide

<400> SEQUENCE: 353

Ser Pro Arg
1

<210> SEQ ID NO 354
<211> LENGTH: 10
<212> TYPE: PRT
<213> ORGANISM: Artificial Sequence
<220> FEATURE:
<223> OTHER INFORMATION: Synthetic peptide

<400> SEQUENCE: 354

His Gln Pro Gly Gly Gly Lys Val Gln Ile
1               5                   10

<210> SEQ ID NO 355
<211> LENGTH: 9
<212> TYPE: PRT
<213> ORGANISM: Artificial Sequence
```

-continued

```
<220> FEATURE:
<223> OTHER INFORMATION: Synthetic peptide

<400> SEQUENCE: 355

Gln Pro Gly Gly Gly Lys Val Gln Ile
1               5

<210> SEQ ID NO 356
<211> LENGTH: 8
<212> TYPE: PRT
<213> ORGANISM: Artificial Sequence
<220> FEATURE:
<223> OTHER INFORMATION: Synthetic peptide

<400> SEQUENCE: 356

Pro Gly Gly Gly Lys Val Gln Ile
1               5

<210> SEQ ID NO 357
<211> LENGTH: 7
<212> TYPE: PRT
<213> ORGANISM: Artificial Sequence
<220> FEATURE:
<223> OTHER INFORMATION: Synthetic peptide

<400> SEQUENCE: 357

Gly Gly Gly Lys Val Gln Ile
1               5

<210> SEQ ID NO 358
<211> LENGTH: 6
<212> TYPE: PRT
<213> ORGANISM: Artificial Sequence
<220> FEATURE:
<223> OTHER INFORMATION: Synthetic peptide

<400> SEQUENCE: 358

Gly Gly Lys Val Gln Ile
1               5

<210> SEQ ID NO 359
<211> LENGTH: 5
<212> TYPE: PRT
<213> ORGANISM: Artificial Sequence
<220> FEATURE:
<223> OTHER INFORMATION: Synthetic peptide

<400> SEQUENCE: 359

Gly Lys Val Gln Ile
1               5

<210> SEQ ID NO 360
<211> LENGTH: 4
<212> TYPE: PRT
<213> ORGANISM: Artificial Sequence
<220> FEATURE:
<223> OTHER INFORMATION: Synthetic peptide

<400> SEQUENCE: 360

Lys Val Gln Ile
1

<210> SEQ ID NO 361
<211> LENGTH: 3
<212> TYPE: PRT
<213> ORGANISM: Artificial Sequence
<220> FEATURE:
```

```
<223> OTHER INFORMATION: Synthetic peptide

<400> SEQUENCE: 361

Val Gln Ile
1

<210> SEQ ID NO 362
<211> LENGTH: 10
<212> TYPE: PRT
<213> ORGANISM: Artificial Sequence
<220> FEATURE:
<223> OTHER INFORMATION: Synthetic peptide

<400> SEQUENCE: 362

Gln Pro Gly Gly Gly Lys Val Gln Ile Ile
1               5                   10

<210> SEQ ID NO 363
<211> LENGTH: 9
<212> TYPE: PRT
<213> ORGANISM: Artificial Sequence
<220> FEATURE:
<223> OTHER INFORMATION: Synthetic peptide

<400> SEQUENCE: 363

Pro Gly Gly Gly Lys Val Gln Ile Ile
1               5

<210> SEQ ID NO 364
<211> LENGTH: 6
<212> TYPE: PRT
<213> ORGANISM: Artificial Sequence
<220> FEATURE:
<223> OTHER INFORMATION: Synthetic peptide

<400> SEQUENCE: 364

Ser Val Asp Leu Ser Lys
1               5

<210> SEQ ID NO 365
<211> LENGTH: 8
<212> TYPE: PRT
<213> ORGANISM: Artificial Sequence
<220> FEATURE:
<223> OTHER INFORMATION: Synthetic peptide

<400> SEQUENCE: 365

Gly Gly Gly Lys Val Gln Ile Ile
1               5

<210> SEQ ID NO 366
<211> LENGTH: 7
<212> TYPE: PRT
<213> ORGANISM: Artificial Sequence
<220> FEATURE:
<223> OTHER INFORMATION: Synthetic peptide

<400> SEQUENCE: 366

Gly Gly Lys Val Gln Ile Ile
1               5

<210> SEQ ID NO 367
<211> LENGTH: 6
<212> TYPE: PRT
<213> ORGANISM: Artificial Sequence
<220> FEATURE:
<223> OTHER INFORMATION: Synthetic peptide
```

-continued

```
<400> SEQUENCE: 367

Gly Lys Val Gln Ile Ile
1               5

<210> SEQ ID NO 368
<211> LENGTH: 5
<212> TYPE: PRT
<213> ORGANISM: Artificial Sequence
<220> FEATURE:
<223> OTHER INFORMATION: Synthetic peptide

<400> SEQUENCE: 368

Lys Val Gln Ile Ile
1               5

<210> SEQ ID NO 369
<211> LENGTH: 4
<212> TYPE: PRT
<213> ORGANISM: Artificial Sequence
<220> FEATURE:
<223> OTHER INFORMATION: Synthetic peptide

<400> SEQUENCE: 369

Val Gln Ile Ile
1

<210> SEQ ID NO 370
<211> LENGTH: 3
<212> TYPE: PRT
<213> ORGANISM: Artificial Sequence
<220> FEATURE:
<223> OTHER INFORMATION: Synthetic peptide

<400> SEQUENCE: 370

Gln Ile Ile
1

<210> SEQ ID NO 371
<211> LENGTH: 10
<212> TYPE: PRT
<213> ORGANISM: Artificial Sequence
<220> FEATURE:
<223> OTHER INFORMATION: Synthetic peptide

<400> SEQUENCE: 371

Pro Gly Gly Gly Lys Val Gln Ile Ile Asn
1               5                   10

<210> SEQ ID NO 372
<211> LENGTH: 9
<212> TYPE: PRT
<213> ORGANISM: Artificial Sequence
<220> FEATURE:
<223> OTHER INFORMATION: Synthetic peptide

<400> SEQUENCE: 372

Gly Gly Gly Lys Val Gln Ile Ile Asn
1               5

<210> SEQ ID NO 373
<211> LENGTH: 8
<212> TYPE: PRT
<213> ORGANISM: Artificial Sequence
<220> FEATURE:
<223> OTHER INFORMATION: Synthetic peptide
```

<400> SEQUENCE: 373

Gly Gly Lys Val Gln Ile Ile Asn
1               5

<210> SEQ ID NO 374
<211> LENGTH: 7
<212> TYPE: PRT
<213> ORGANISM: Artificial Sequence
<220> FEATURE:
<223> OTHER INFORMATION: Synthetic peptide

<400> SEQUENCE: 374

Gly Lys Val Gln Ile Ile Asn
1               5

<210> SEQ ID NO 375
<211> LENGTH: 6
<212> TYPE: PRT
<213> ORGANISM: Artificial Sequence
<220> FEATURE:
<223> OTHER INFORMATION: Synthetic peptide

<400> SEQUENCE: 375

Lys Val Gln Ile Ile Asn
1               5

<210> SEQ ID NO 376
<211> LENGTH: 5
<212> TYPE: PRT
<213> ORGANISM: Artificial Sequence
<220> FEATURE:
<223> OTHER INFORMATION: Synthetic peptide

<400> SEQUENCE: 376

Val Gln Ile Ile Asn
1               5

<210> SEQ ID NO 377
<211> LENGTH: 4
<212> TYPE: PRT
<213> ORGANISM: Artificial Sequence
<220> FEATURE:
<223> OTHER INFORMATION: Synthetic peptide

<400> SEQUENCE: 377

Gln Ile Ile Asn
1

<210> SEQ ID NO 378
<211> LENGTH: 3
<212> TYPE: PRT
<213> ORGANISM: Artificial Sequence
<220> FEATURE:
<223> OTHER INFORMATION: Synthetic peptide

<400> SEQUENCE: 378

Ile Ile Asn
1

<210> SEQ ID NO 379
<211> LENGTH: 10
<212> TYPE: PRT
<213> ORGANISM: Artificial Sequence
<220> FEATURE:
<223> OTHER INFORMATION: Synthetic peptide

<400> SEQUENCE: 379

-continued

```
Gly Gly Gly Lys Val Gln Ile Ile Asn Lys
1               5                   10

<210> SEQ ID NO 380
<211> LENGTH: 9
<212> TYPE: PRT
<213> ORGANISM: Artificial Sequence
<220> FEATURE:
<223> OTHER INFORMATION: Synthetic peptide

<400> SEQUENCE: 380

Gly Gly Lys Val Gln Ile Ile Asn Lys
1               5

<210> SEQ ID NO 381
<211> LENGTH: 8
<212> TYPE: PRT
<213> ORGANISM: Artificial Sequence
<220> FEATURE:
<223> OTHER INFORMATION: Synthetic peptide

<400> SEQUENCE: 381

Gly Lys Val Gln Ile Ile Asn Lys
1               5

<210> SEQ ID NO 382
<211> LENGTH: 7
<212> TYPE: PRT
<213> ORGANISM: Artificial Sequence
<220> FEATURE:
<223> OTHER INFORMATION: Synthetic peptide

<400> SEQUENCE: 382

Lys Val Gln Ile Ile Asn Lys
1               5

<210> SEQ ID NO 383
<211> LENGTH: 4
<212> TYPE: PRT
<213> ORGANISM: Artificial Sequence
<220> FEATURE:
<223> OTHER INFORMATION: Synthetic peptide

<400> SEQUENCE: 383

Ile Ile Asn Lys
1

<210> SEQ ID NO 384
<211> LENGTH: 3
<212> TYPE: PRT
<213> ORGANISM: Artificial Sequence
<220> FEATURE:
<223> OTHER INFORMATION: Synthetic peptide

<400> SEQUENCE: 384

Ile Asn Lys
1

<210> SEQ ID NO 385
<211> LENGTH: 10
<212> TYPE: PRT
<213> ORGANISM: Artificial Sequence
<220> FEATURE:
<223> OTHER INFORMATION: Synthetic peptide

<400> SEQUENCE: 385
```

```
Gly Gly Lys Val Gln Ile Ile Asn Lys Lys
1               5                   10

<210> SEQ ID NO 386
<211> LENGTH: 9
<212> TYPE: PRT
<213> ORGANISM: Artificial Sequence
<220> FEATURE:
<223> OTHER INFORMATION: Synthetic peptide

<400> SEQUENCE: 386

Gly Lys Val Gln Ile Ile Asn Lys Lys
1               5

<210> SEQ ID NO 387
<211> LENGTH: 8
<212> TYPE: PRT
<213> ORGANISM: Artificial Sequence
<220> FEATURE:
<223> OTHER INFORMATION: Synthetic peptide

<400> SEQUENCE: 387

Lys Val Gln Ile Ile Asn Lys Lys
1               5

<210> SEQ ID NO 388
<211> LENGTH: 5
<212> TYPE: PRT
<213> ORGANISM: Artificial Sequence
<220> FEATURE:
<223> OTHER INFORMATION: Synthetic peptide

<400> SEQUENCE: 388

Ile Ile Asn Lys Lys
1               5

<210> SEQ ID NO 389
<211> LENGTH: 4
<212> TYPE: PRT
<213> ORGANISM: Artificial Sequence
<220> FEATURE:
<223> OTHER INFORMATION: Synthetic peptide

<400> SEQUENCE: 389

Ile Asn Lys Lys
1

<210> SEQ ID NO 390
<211> LENGTH: 3
<212> TYPE: PRT
<213> ORGANISM: Artificial Sequence
<220> FEATURE:
<223> OTHER INFORMATION: Synthetic peptide

<400> SEQUENCE: 390

Asn Lys Lys
1

<210> SEQ ID NO 391
<211> LENGTH: 10
<212> TYPE: PRT
<213> ORGANISM: Artificial Sequence
<220> FEATURE:
<223> OTHER INFORMATION: Synthetic peptide

<400> SEQUENCE: 391

Gly Lys Val Gln Ile Ile Asn Lys Lys Leu
```

-continued

```
1               5                  10

<210> SEQ ID NO 392
<211> LENGTH: 9
<212> TYPE: PRT
<213> ORGANISM: Artificial Sequence
<220> FEATURE:
<223> OTHER INFORMATION: Synthetic peptide

<400> SEQUENCE: 392

Lys Val Gln Ile Ile Asn Lys Lys Leu
1               5

<210> SEQ ID NO 393
<211> LENGTH: 6
<212> TYPE: PRT
<213> ORGANISM: Artificial Sequence
<220> FEATURE:
<223> OTHER INFORMATION: Synthetic peptide

<400> SEQUENCE: 393

Ile Ile Asn Lys Lys Leu
1               5

<210> SEQ ID NO 394
<211> LENGTH: 5
<212> TYPE: PRT
<213> ORGANISM: Artificial Sequence
<220> FEATURE:
<223> OTHER INFORMATION: Synthetic peptide

<400> SEQUENCE: 394

Ile Asn Lys Lys Leu
1               5

<210> SEQ ID NO 395
<211> LENGTH: 4
<212> TYPE: PRT
<213> ORGANISM: Artificial Sequence
<220> FEATURE:
<223> OTHER INFORMATION: Synthetic peptide

<400> SEQUENCE: 395

Asn Lys Lys Leu
1

<210> SEQ ID NO 396
<211> LENGTH: 3
<212> TYPE: PRT
<213> ORGANISM: Artificial Sequence
<220> FEATURE:
<223> OTHER INFORMATION: Synthetic peptide

<400> SEQUENCE: 396

Lys Lys Leu
1

<210> SEQ ID NO 397
<211> LENGTH: 10
<212> TYPE: PRT
<213> ORGANISM: Artificial Sequence
<220> FEATURE:
<223> OTHER INFORMATION: Synthetic peptide

<400> SEQUENCE: 397

Lys Val Gln Ile Ile Asn Lys Lys Leu Asp
1               5                  10
```

```
<210> SEQ ID NO 398
<211> LENGTH: 9
<212> TYPE: PRT
<213> ORGANISM: Artificial Sequence
<220> FEATURE:
<223> OTHER INFORMATION: Synthetic peptide

<400> SEQUENCE: 398

Val Gln Ile Ile Asn Lys Lys Leu Asp
1               5

<210> SEQ ID NO 399
<211> LENGTH: 8
<212> TYPE: PRT
<213> ORGANISM: Artificial Sequence
<220> FEATURE:
<223> OTHER INFORMATION: Synthetic peptide

<400> SEQUENCE: 399

Gln Ile Ile Asn Lys Lys Leu Asp
1               5

<210> SEQ ID NO 400
<211> LENGTH: 7
<212> TYPE: PRT
<213> ORGANISM: Artificial Sequence
<220> FEATURE:
<223> OTHER INFORMATION: Synthetic peptide

<400> SEQUENCE: 400

Ile Ile Asn Lys Lys Leu Asp
1               5

<210> SEQ ID NO 401
<211> LENGTH: 6
<212> TYPE: PRT
<213> ORGANISM: Artificial Sequence
<220> FEATURE:
<223> OTHER INFORMATION: Synthetic peptide

<400> SEQUENCE: 401

Ile Asn Lys Lys Leu Asp
1               5

<210> SEQ ID NO 402
<211> LENGTH: 5
<212> TYPE: PRT
<213> ORGANISM: Artificial Sequence
<220> FEATURE:
<223> OTHER INFORMATION: Synthetic peptide

<400> SEQUENCE: 402

Asn Lys Lys Leu Asp
1               5

<210> SEQ ID NO 403
<211> LENGTH: 4
<212> TYPE: PRT
<213> ORGANISM: Artificial Sequence
<220> FEATURE:
<223> OTHER INFORMATION: Synthetic peptide

<400> SEQUENCE: 403

Lys Lys Leu Asp
1
```

<210> SEQ ID NO 404
<211> LENGTH: 3
<212> TYPE: PRT
<213> ORGANISM: Artificial Sequence
<220> FEATURE:
<223> OTHER INFORMATION: Synthetic peptide

<400> SEQUENCE: 404

Lys Leu Asp
1

<210> SEQ ID NO 405
<211> LENGTH: 10
<212> TYPE: PRT
<213> ORGANISM: Artificial Sequence
<220> FEATURE:
<223> OTHER INFORMATION: Synthetic peptide

<400> SEQUENCE: 405

Val Gln Ile Ile Asn Lys Lys Leu Asp Leu
1               5                   10

<210> SEQ ID NO 406
<211> LENGTH: 9
<212> TYPE: PRT
<213> ORGANISM: Artificial Sequence
<220> FEATURE:
<223> OTHER INFORMATION: Synthetic peptide

<400> SEQUENCE: 406

Gln Ile Ile Asn Lys Lys Leu Asp Leu
1               5

<210> SEQ ID NO 407
<211> LENGTH: 8
<212> TYPE: PRT
<213> ORGANISM: Artificial Sequence
<220> FEATURE:
<223> OTHER INFORMATION: Synthetic peptide

<400> SEQUENCE: 407

Ile Ile Asn Lys Lys Leu Asp Leu
1               5

<210> SEQ ID NO 408
<211> LENGTH: 7
<212> TYPE: PRT
<213> ORGANISM: Artificial Sequence
<220> FEATURE:
<223> OTHER INFORMATION: Synthetic peptide

<400> SEQUENCE: 408

Ile Asn Lys Lys Leu Asp Leu
1               5

<210> SEQ ID NO 409
<211> LENGTH: 6
<212> TYPE: PRT
<213> ORGANISM: Artificial Sequence
<220> FEATURE:
<223> OTHER INFORMATION: Synthetic peptide

<400> SEQUENCE: 409

Asn Lys Lys Leu Asp Leu
1               5

<210> SEQ ID NO 410
<211> LENGTH: 5
<212> TYPE: PRT
<213> ORGANISM: Artificial Sequence
<220> FEATURE:
<223> OTHER INFORMATION: Synthetic peptide

<400> SEQUENCE: 410

Lys Lys Leu Asp Leu
1               5

<210> SEQ ID NO 411
<211> LENGTH: 4
<212> TYPE: PRT
<213> ORGANISM: Artificial Sequence
<220> FEATURE:
<223> OTHER INFORMATION: Synthetic peptide

<400> SEQUENCE: 411

Lys Leu Asp Leu
1

<210> SEQ ID NO 412
<211> LENGTH: 3
<212> TYPE: PRT
<213> ORGANISM: Artificial Sequence
<220> FEATURE:
<223> OTHER INFORMATION: Synthetic peptide

<400> SEQUENCE: 412

Leu Asp Leu
1

<210> SEQ ID NO 413
<211> LENGTH: 10
<212> TYPE: PRT
<213> ORGANISM: Artificial Sequence
<220> FEATURE:
<223> OTHER INFORMATION: Synthetic peptide

<400> SEQUENCE: 413

Gln Ile Ile Asn Lys Lys Leu Asp Leu Ser
1               5                   10

<210> SEQ ID NO 414
<211> LENGTH: 9
<212> TYPE: PRT
<213> ORGANISM: Artificial Sequence
<220> FEATURE:
<223> OTHER INFORMATION: Synthetic peptide

<400> SEQUENCE: 414

Ile Ile Asn Lys Lys Leu Asp Leu Ser
1               5

<210> SEQ ID NO 415
<211> LENGTH: 8
<212> TYPE: PRT
<213> ORGANISM: Artificial Sequence
<220> FEATURE:
<223> OTHER INFORMATION: Synthetic peptide

<400> SEQUENCE: 415

Ile Asn Lys Lys Leu Asp Leu Ser
1               5

<210> SEQ ID NO 416

-continued

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 416

Asn Lys Lys Leu Asp Leu Ser
1               5

<210> SEQ ID NO 417
<211> LENGTH: 6
<212> TYPE: PRT
<213> ORGANISM: Artificial Sequence
<220> FEATURE:
<223> OTHER INFORMATION: Synthetic peptide

<400> SEQUENCE: 417

Lys Lys Leu Asp Leu Ser
1               5

<210> SEQ ID NO 418
<211> LENGTH: 5
<212> TYPE: PRT
<213> ORGANISM: Artificial Sequence
<220> FEATURE:
<223> OTHER INFORMATION: Synthetic peptide

<400> SEQUENCE: 418

Lys Leu Asp Leu Ser
1               5

<210> SEQ ID NO 419
<211> LENGTH: 4
<212> TYPE: PRT
<213> ORGANISM: Artificial Sequence
<220> FEATURE:
<223> OTHER INFORMATION: Synthetic peptide

<400> SEQUENCE: 419

Leu Asp Leu Ser
1

<210> SEQ ID NO 420
<211> LENGTH: 10
<212> TYPE: PRT
<213> ORGANISM: Artificial Sequence
<220> FEATURE:
<223> OTHER INFORMATION: Synthetic peptide

<400> SEQUENCE: 420

Ile Ile Asn Lys Lys Leu Asp Leu Ser Asn
1               5                   10

<210> SEQ ID NO 421
<211> LENGTH: 9
<212> TYPE: PRT
<213> ORGANISM: Artificial Sequence
<220> FEATURE:
<223> OTHER INFORMATION: Synthetic peptide

<400> SEQUENCE: 421

Ile Asn Lys Lys Leu Asp Leu Ser Asn
1               5

<210> SEQ ID NO 422
<211> LENGTH: 8
```

-continued

```
<212> TYPE: PRT
<213> ORGANISM: Artificial Sequence
<220> FEATURE:
<223> OTHER INFORMATION: Synthetic peptide

<400> SEQUENCE: 422

Asn Lys Lys Leu Asp Leu Ser Asn
1               5

<210> SEQ ID NO 423
<211> LENGTH: 7
<212> TYPE: PRT
<213> ORGANISM: Artificial Sequence
<220> FEATURE:
<223> OTHER INFORMATION: Synthetic peptide

<400> SEQUENCE: 423

Lys Lys Leu Asp Leu Ser Asn
1               5

<210> SEQ ID NO 424
<211> LENGTH: 6
<212> TYPE: PRT
<213> ORGANISM: Artificial Sequence
<220> FEATURE:
<223> OTHER INFORMATION: Synthetic peptide

<400> SEQUENCE: 424

Lys Leu Asp Leu Ser Asn
1               5

<210> SEQ ID NO 425
<211> LENGTH: 5
<212> TYPE: PRT
<213> ORGANISM: Artificial Sequence
<220> FEATURE:
<223> OTHER INFORMATION: Synthetic peptide

<400> SEQUENCE: 425

Leu Asp Leu Ser Asn
1               5

<210> SEQ ID NO 426
<211> LENGTH: 4
<212> TYPE: PRT
<213> ORGANISM: Artificial Sequence
<220> FEATURE:
<223> OTHER INFORMATION: Synthetic peptide

<400> SEQUENCE: 426

Asp Leu Ser Asn
1

<210> SEQ ID NO 427
<211> LENGTH: 3
<212> TYPE: PRT
<213> ORGANISM: Artificial Sequence
<220> FEATURE:
<223> OTHER INFORMATION: Synthetic peptide

<400> SEQUENCE: 427

Leu Ser Asn
1

<210> SEQ ID NO 428
<211> LENGTH: 10
<212> TYPE: PRT
```

-continued

```
<213> ORGANISM: Artificial Sequence
<220> FEATURE:
<223> OTHER INFORMATION: Synthetic peptide

<400> SEQUENCE: 428

Ile Asn Lys Lys Leu Asp Leu Ser Asn Val
1               5                   10

<210> SEQ ID NO 429
<211> LENGTH: 9
<212> TYPE: PRT
<213> ORGANISM: Artificial Sequence
<220> FEATURE:
<223> OTHER INFORMATION: Synthetic peptide

<400> SEQUENCE: 429

Asn Lys Lys Leu Asp Leu Ser Asn Val
1               5

<210> SEQ ID NO 430
<211> LENGTH: 8
<212> TYPE: PRT
<213> ORGANISM: Artificial Sequence
<220> FEATURE:
<223> OTHER INFORMATION: Synthetic peptide

<400> SEQUENCE: 430

Lys Lys Leu Asp Leu Ser Asn Val
1               5

<210> SEQ ID NO 431
<211> LENGTH: 7
<212> TYPE: PRT
<213> ORGANISM: Artificial Sequence
<220> FEATURE:
<223> OTHER INFORMATION: Synthetic peptide

<400> SEQUENCE: 431

Lys Leu Asp Leu Ser Asn Val
1               5

<210> SEQ ID NO 432
<211> LENGTH: 6
<212> TYPE: PRT
<213> ORGANISM: Artificial Sequence
<220> FEATURE:
<223> OTHER INFORMATION: Synthetic peptide

<400> SEQUENCE: 432

Leu Asp Leu Ser Asn Val
1               5

<210> SEQ ID NO 433
<211> LENGTH: 5
<212> TYPE: PRT
<213> ORGANISM: Artificial Sequence
<220> FEATURE:
<223> OTHER INFORMATION: Synthetic peptide

<400> SEQUENCE: 433

Asp Leu Ser Asn Val
1               5

<210> SEQ ID NO 434
<211> LENGTH: 4
<212> TYPE: PRT
<213> ORGANISM: Artificial Sequence
```

-continued

```
<220> FEATURE:
<223> OTHER INFORMATION: Synthetic peptide

<400> SEQUENCE: 434

Leu Ser Asn Val
1

<210> SEQ ID NO 435
<211> LENGTH: 3
<212> TYPE: PRT
<213> ORGANISM: Artificial Sequence
<220> FEATURE:
<223> OTHER INFORMATION: Synthetic peptide

<400> SEQUENCE: 435

Ser Asn Val
1

<210> SEQ ID NO 436
<211> LENGTH: 10
<212> TYPE: PRT
<213> ORGANISM: Artificial Sequence
<220> FEATURE:
<223> OTHER INFORMATION: Synthetic peptide

<400> SEQUENCE: 436

Asn Lys Lys Leu Asp Leu Ser Asn Val Gln
1               5                   10

<210> SEQ ID NO 437
<211> LENGTH: 9
<212> TYPE: PRT
<213> ORGANISM: Artificial Sequence
<220> FEATURE:
<223> OTHER INFORMATION: Synthetic peptide

<400> SEQUENCE: 437

Lys Lys Leu Asp Leu Ser Asn Val Gln
1               5

<210> SEQ ID NO 438
<211> LENGTH: 8
<212> TYPE: PRT
<213> ORGANISM: Artificial Sequence
<220> FEATURE:
<223> OTHER INFORMATION: Synthetic peptide

<400> SEQUENCE: 438

Lys Leu Asp Leu Ser Asn Val Gln
1               5

<210> SEQ ID NO 439
<211> LENGTH: 7
<212> TYPE: PRT
<213> ORGANISM: Artificial Sequence
<220> FEATURE:
<223> OTHER INFORMATION: Synthetic peptide

<400> SEQUENCE: 439

Leu Asp Leu Ser Asn Val Gln
1               5

<210> SEQ ID NO 440
<211> LENGTH: 6
<212> TYPE: PRT
<213> ORGANISM: Artificial Sequence
<220> FEATURE:
```

```
<223> OTHER INFORMATION: Synthetic peptide

<400> SEQUENCE: 440

Asp Leu Ser Asn Val Gln
1               5

<210> SEQ ID NO 441
<211> LENGTH: 5
<212> TYPE: PRT
<213> ORGANISM: Artificial Sequence
<220> FEATURE:
<223> OTHER INFORMATION: Synthetic peptide

<400> SEQUENCE: 441

Leu Ser Asn Val Gln
1               5

<210> SEQ ID NO 442
<211> LENGTH: 4
<212> TYPE: PRT
<213> ORGANISM: Artificial Sequence
<220> FEATURE:
<223> OTHER INFORMATION: Synthetic peptide

<400> SEQUENCE: 442

Ser Asn Val Gln
1

<210> SEQ ID NO 443
<211> LENGTH: 3
<212> TYPE: PRT
<213> ORGANISM: Artificial Sequence
<220> FEATURE:
<223> OTHER INFORMATION: Synthetic peptide

<400> SEQUENCE: 443

Asn Val Gln
1

<210> SEQ ID NO 444
<211> LENGTH: 10
<212> TYPE: PRT
<213> ORGANISM: Artificial Sequence
<220> FEATURE:
<223> OTHER INFORMATION: Synthetic peptide

<400> SEQUENCE: 444

Lys Lys Leu Asp Leu Ser Asn Val Gln Ser
1               5                   10

<210> SEQ ID NO 445
<211> LENGTH: 9
<212> TYPE: PRT
<213> ORGANISM: Artificial Sequence
<220> FEATURE:
<223> OTHER INFORMATION: Synthetic peptide

<400> SEQUENCE: 445

Lys Leu Asp Leu Ser Asn Val Gln Ser
1               5

<210> SEQ ID NO 446
<211> LENGTH: 8
<212> TYPE: PRT
<213> ORGANISM: Artificial Sequence
<220> FEATURE:
<223> OTHER INFORMATION: Synthetic peptide
```

-continued

```
<400> SEQUENCE: 446

Leu Asp Leu Ser Asn Val Gln Ser
1               5

<210> SEQ ID NO 447
<211> LENGTH: 7
<212> TYPE: PRT
<213> ORGANISM: Artificial Sequence
<220> FEATURE:
<223> OTHER INFORMATION: Synthetic peptide

<400> SEQUENCE: 447

Asp Leu Ser Asn Val Gln Ser
1               5

<210> SEQ ID NO 448
<211> LENGTH: 6
<212> TYPE: PRT
<213> ORGANISM: Artificial Sequence
<220> FEATURE:
<223> OTHER INFORMATION: Synthetic peptide

<400> SEQUENCE: 448

Leu Ser Asn Val Gln Ser
1               5

<210> SEQ ID NO 449
<211> LENGTH: 5
<212> TYPE: PRT
<213> ORGANISM: Artificial Sequence
<220> FEATURE:
<223> OTHER INFORMATION: Synthetic peptide

<400> SEQUENCE: 449

Ser Asn Val Gln Ser
1               5

<210> SEQ ID NO 450
<211> LENGTH: 4
<212> TYPE: PRT
<213> ORGANISM: Artificial Sequence
<220> FEATURE:
<223> OTHER INFORMATION: Synthetic peptide

<400> SEQUENCE: 450

Asn Val Gln Ser
1

<210> SEQ ID NO 451
<211> LENGTH: 3
<212> TYPE: PRT
<213> ORGANISM: Artificial Sequence
<220> FEATURE:
<223> OTHER INFORMATION: Synthetic peptide

<400> SEQUENCE: 451

Val Gln Ser
1

<210> SEQ ID NO 452
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 452

Ser Lys Cys Gly Ser Lys Asp Asn Ile Lys
1               5                   10

<210> SEQ ID NO 453
<211> LENGTH: 9
<212> TYPE: PRT
<213> ORGANISM: Artificial Sequence
<220> FEATURE:
<223> OTHER INFORMATION: Synthetic peptide

<400> SEQUENCE: 453

Lys Cys Gly Ser Lys Asp Asn Ile Lys
1               5

<210> SEQ ID NO 454
<211> LENGTH: 8
<212> TYPE: PRT
<213> ORGANISM: Artificial Sequence
<220> FEATURE:
<223> OTHER INFORMATION: Synthetic peptide

<400> SEQUENCE: 454

Cys Gly Ser Lys Asp Asn Ile Lys
1               5

<210> SEQ ID NO 455
<211> LENGTH: 7
<212> TYPE: PRT
<213> ORGANISM: Artificial Sequence
<220> FEATURE:
<223> OTHER INFORMATION: Synthetic peptide

<400> SEQUENCE: 455

Gly Ser Lys Asp Asn Ile Lys
1               5

<210> SEQ ID NO 456
<211> LENGTH: 6
<212> TYPE: PRT
<213> ORGANISM: Artificial Sequence
<220> FEATURE:
<223> OTHER INFORMATION: Synthetic peptide

<400> SEQUENCE: 456

Ser Lys Asp Asn Ile Lys
1               5

<210> SEQ ID NO 457
<211> LENGTH: 5
<212> TYPE: PRT
<213> ORGANISM: Artificial Sequence
<220> FEATURE:
<223> OTHER INFORMATION: Synthetic peptide

<400> SEQUENCE: 457

Lys Asp Asn Ile Lys
1               5

<210> SEQ ID NO 458
<211> LENGTH: 4
<212> TYPE: PRT
<213> ORGANISM: Artificial Sequence
<220> FEATURE:
<223> OTHER INFORMATION: Synthetic peptide

<400> SEQUENCE: 458

Asp Asn Ile Lys
1

<210> SEQ ID NO 459
<211> LENGTH: 3
<212> TYPE: PRT
<213> ORGANISM: Artificial Sequence
<220> FEATURE:
<223> OTHER INFORMATION: Synthetic peptide

<400> SEQUENCE: 459

Asn Ile Lys
1

<210> SEQ ID NO 460
<211> LENGTH: 10
<212> TYPE: PRT
<213> ORGANISM: Artificial Sequence
<220> FEATURE:
<223> OTHER INFORMATION: Synthetic peptide

<400> SEQUENCE: 460

Lys Cys Gly Ser Lys Asp Asn Ile Lys His
1               5                   10

<210> SEQ ID NO 461
<211> LENGTH: 9
<212> TYPE: PRT
<213> ORGANISM: Artificial Sequence
<220> FEATURE:
<223> OTHER INFORMATION: Synthetic peptide

<400> SEQUENCE: 461

Cys Gly Ser Lys Asp Asn Ile Lys His
1               5

<210> SEQ ID NO 462
<211> LENGTH: 8
<212> TYPE: PRT
<213> ORGANISM: Artificial Sequence
<220> FEATURE:
<223> OTHER INFORMATION: Synthetic peptide

<400> SEQUENCE: 462

Gly Ser Lys Asp Asn Ile Lys His
1               5

<210> SEQ ID NO 463
<211> LENGTH: 7
<212> TYPE: PRT
<213> ORGANISM: Artificial Sequence
<220> FEATURE:
<223> OTHER INFORMATION: Synthetic peptide

<400> SEQUENCE: 463

Ser Lys Asp Asn Ile Lys His
1               5

<210> SEQ ID NO 464
<211> LENGTH: 6
<212> TYPE: PRT
<213> ORGANISM: Artificial Sequence
<220> FEATURE:
<223> OTHER INFORMATION: Synthetic peptide

<400> SEQUENCE: 464

```
Lys Asp Asn Ile Lys His
1               5

<210> SEQ ID NO 465
<211> LENGTH: 5
<212> TYPE: PRT
<213> ORGANISM: Artificial Sequence
<220> FEATURE:
<223> OTHER INFORMATION: Synthetic peptide

<400> SEQUENCE: 465

Asp Asn Ile Lys His
1               5

<210> SEQ ID NO 466
<211> LENGTH: 4
<212> TYPE: PRT
<213> ORGANISM: Artificial Sequence
<220> FEATURE:
<223> OTHER INFORMATION: Synthetic peptide

<400> SEQUENCE: 466

Asn Ile Lys His
1

<210> SEQ ID NO 467
<211> LENGTH: 3
<212> TYPE: PRT
<213> ORGANISM: Artificial Sequence
<220> FEATURE:
<223> OTHER INFORMATION: Synthetic peptide

<400> SEQUENCE: 467

Ile Lys His
1

<210> SEQ ID NO 468
<211> LENGTH: 10
<212> TYPE: PRT
<213> ORGANISM: Artificial Sequence
<220> FEATURE:
<223> OTHER INFORMATION: Synthetic peptide

<400> SEQUENCE: 468

Cys Gly Ser Lys Asp Asn Ile Lys His Val
1               5                   10

<210> SEQ ID NO 469
<211> LENGTH: 9
<212> TYPE: PRT
<213> ORGANISM: Artificial Sequence
<220> FEATURE:
<223> OTHER INFORMATION: Synthetic peptide

<400> SEQUENCE: 469

Gly Ser Lys Asp Asn Ile Lys His Val
1               5

<210> SEQ ID NO 470
<211> LENGTH: 8
<212> TYPE: PRT
<213> ORGANISM: Artificial Sequence
<220> FEATURE:
<223> OTHER INFORMATION: Synthetic peptide

<400> SEQUENCE: 470

Ser Lys Asp Asn Ile Lys His Val
```

-continued

```
1               5

<210> SEQ ID NO 471
<211> LENGTH: 7
<212> TYPE: PRT
<213> ORGANISM: Artificial Sequence
<220> FEATURE:
<223> OTHER INFORMATION: Synthetic peptide

<400> SEQUENCE: 471

Lys Asp Asn Ile Lys His Val
1               5

<210> SEQ ID NO 472
<211> LENGTH: 6
<212> TYPE: PRT
<213> ORGANISM: Artificial Sequence
<220> FEATURE:
<223> OTHER INFORMATION: Synthetic peptide

<400> SEQUENCE: 472

Asp Asn Ile Lys His Val
1               5

<210> SEQ ID NO 473
<211> LENGTH: 5
<212> TYPE: PRT
<213> ORGANISM: Artificial Sequence
<220> FEATURE:
<223> OTHER INFORMATION: Synthetic peptide

<400> SEQUENCE: 473

Asn Ile Lys His Val
1               5

<210> SEQ ID NO 474
<211> LENGTH: 4
<212> TYPE: PRT
<213> ORGANISM: Artificial Sequence
<220> FEATURE:
<223> OTHER INFORMATION: Synthetic peptide

<400> SEQUENCE: 474

Ile Lys His Val
1

<210> SEQ ID NO 475
<211> LENGTH: 3
<212> TYPE: PRT
<213> ORGANISM: Artificial Sequence
<220> FEATURE:
<223> OTHER INFORMATION: Synthetic peptide

<400> SEQUENCE: 475

Lys His Val
1

<210> SEQ ID NO 476
<211> LENGTH: 10
<212> TYPE: PRT
<213> ORGANISM: Artificial Sequence
<220> FEATURE:
<223> OTHER INFORMATION: Synthetic peptide

<400> SEQUENCE: 476

Gly Ser Lys Asp Asn Ile Lys His Val Pro
1               5                   10
```

```
<210> SEQ ID NO 477
<211> LENGTH: 9
<212> TYPE: PRT
<213> ORGANISM: Artificial Sequence
<220> FEATURE:
<223> OTHER INFORMATION: Synthetic peptide

<400> SEQUENCE: 477

Ser Lys Asp Asn Ile Lys His Val Pro
1               5

<210> SEQ ID NO 478
<211> LENGTH: 8
<212> TYPE: PRT
<213> ORGANISM: Artificial Sequence
<220> FEATURE:
<223> OTHER INFORMATION: Synthetic peptide

<400> SEQUENCE: 478

Lys Asp Asn Ile Lys His Val Pro
1               5

<210> SEQ ID NO 479
<211> LENGTH: 7
<212> TYPE: PRT
<213> ORGANISM: Artificial Sequence
<220> FEATURE:
<223> OTHER INFORMATION: Synthetic peptide

<400> SEQUENCE: 479

Asp Asn Ile Lys His Val Pro
1               5

<210> SEQ ID NO 480
<211> LENGTH: 5
<212> TYPE: PRT
<213> ORGANISM: Artificial Sequence
<220> FEATURE:
<223> OTHER INFORMATION: Synthetic peptide

<400> SEQUENCE: 480

Ile Lys His Val Pro
1               5

<210> SEQ ID NO 481
<211> LENGTH: 4
<212> TYPE: PRT
<213> ORGANISM: Artificial Sequence
<220> FEATURE:
<223> OTHER INFORMATION: Synthetic peptide

<400> SEQUENCE: 481

Lys His Val Pro
1

<210> SEQ ID NO 482
<211> LENGTH: 3
<212> TYPE: PRT
<213> ORGANISM: Artificial Sequence
<220> FEATURE:
<223> OTHER INFORMATION: Synthetic peptide

<400> SEQUENCE: 482

His Val Pro
1
```

-continued

```
<210> SEQ ID NO 483
<211> LENGTH: 10
<212> TYPE: PRT
<213> ORGANISM: Artificial Sequence
<220> FEATURE:
<223> OTHER INFORMATION: Synthetic peptide

<400> SEQUENCE: 483

Ser Lys Asp Asn Ile Lys His Val Pro Gly
1               5                   10

<210> SEQ ID NO 484
<211> LENGTH: 9
<212> TYPE: PRT
<213> ORGANISM: Artificial Sequence
<220> FEATURE:
<223> OTHER INFORMATION: Synthetic peptide

<400> SEQUENCE: 484

Lys Asp Asn Ile Lys His Val Pro Gly
1               5

<210> SEQ ID NO 485
<211> LENGTH: 8
<212> TYPE: PRT
<213> ORGANISM: Artificial Sequence
<220> FEATURE:
<223> OTHER INFORMATION: Synthetic peptide

<400> SEQUENCE: 485

Asp Asn Ile Lys His Val Pro Gly
1               5

<210> SEQ ID NO 486
<211> LENGTH: 7
<212> TYPE: PRT
<213> ORGANISM: Artificial Sequence
<220> FEATURE:
<223> OTHER INFORMATION: Synthetic peptide

<400> SEQUENCE: 486

Asn Ile Lys His Val Pro Gly
1               5

<210> SEQ ID NO 487
<211> LENGTH: 6
<212> TYPE: PRT
<213> ORGANISM: Artificial Sequence
<220> FEATURE:
<223> OTHER INFORMATION: Synthetic peptide

<400> SEQUENCE: 487

Ile Lys His Val Pro Gly
1               5

<210> SEQ ID NO 488
<211> LENGTH: 5
<212> TYPE: PRT
<213> ORGANISM: Artificial Sequence
<220> FEATURE:
<223> OTHER INFORMATION: Synthetic peptide

<400> SEQUENCE: 488

Lys His Val Pro Gly
1               5
```

```
<210> SEQ ID NO 489
<211> LENGTH: 4
<212> TYPE: PRT
<213> ORGANISM: Artificial Sequence
<220> FEATURE:
<223> OTHER INFORMATION: Synthetic peptide

<400> SEQUENCE: 489

His Val Pro Gly
1

<210> SEQ ID NO 490
<211> LENGTH: 3
<212> TYPE: PRT
<213> ORGANISM: Artificial Sequence
<220> FEATURE:
<223> OTHER INFORMATION: Synthetic peptide

<400> SEQUENCE: 490

Val Pro Gly
1

<210> SEQ ID NO 491
<211> LENGTH: 10
<212> TYPE: PRT
<213> ORGANISM: Artificial Sequence
<220> FEATURE:
<223> OTHER INFORMATION: Synthetic peptide

<400> SEQUENCE: 491

Lys Asp Asn Ile Lys His Val Pro Gly Gly
1               5                   10

<210> SEQ ID NO 492
<211> LENGTH: 9
<212> TYPE: PRT
<213> ORGANISM: Artificial Sequence
<220> FEATURE:
<223> OTHER INFORMATION: Synthetic peptide

<400> SEQUENCE: 492

Asp Asn Ile Lys His Val Pro Gly Gly
1               5

<210> SEQ ID NO 493
<211> LENGTH: 8
<212> TYPE: PRT
<213> ORGANISM: Artificial Sequence
<220> FEATURE:
<223> OTHER INFORMATION: Synthetic peptide

<400> SEQUENCE: 493

Asn Ile Lys His Val Pro Gly Gly
1               5

<210> SEQ ID NO 494
<211> LENGTH: 7
<212> TYPE: PRT
<213> ORGANISM: Artificial Sequence
<220> FEATURE:
<223> OTHER INFORMATION: Synthetic peptide

<400> SEQUENCE: 494

Ile Lys His Val Pro Gly Gly
1               5

<210> SEQ ID NO 495
```

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 495

Lys His Val Pro Gly Gly
1               5

<210> SEQ ID NO 496
<211> LENGTH: 4
<212> TYPE: PRT
<213> ORGANISM: Artificial Sequence
<220> FEATURE:
<223> OTHER INFORMATION: Synthetic peptide

<400> SEQUENCE: 496

Val Pro Gly Gly
1

<210> SEQ ID NO 497
<211> LENGTH: 3
<212> TYPE: PRT
<213> ORGANISM: Artificial Sequence
<220> FEATURE:
<223> OTHER INFORMATION: Synthetic peptide

<400> SEQUENCE: 497

Pro Gly Gly
1

<210> SEQ ID NO 498
<211> LENGTH: 10
<212> TYPE: PRT
<213> ORGANISM: Artificial Sequence
<220> FEATURE:
<223> OTHER INFORMATION: Synthetic peptide

<400> SEQUENCE: 498

Asp Asn Ile Lys His Val Pro Gly Gly Gly
1               5                   10

<210> SEQ ID NO 499
<211> LENGTH: 9
<212> TYPE: PRT
<213> ORGANISM: Artificial Sequence
<220> FEATURE:
<223> OTHER INFORMATION: Synthetic peptide

<400> SEQUENCE: 499

Asn Ile Lys His Val Pro Gly Gly Gly
1               5

<210> SEQ ID NO 500
<211> LENGTH: 8
<212> TYPE: PRT
<213> ORGANISM: Artificial Sequence
<220> FEATURE:
<223> OTHER INFORMATION: Synthetic peptide

<400> SEQUENCE: 500

Ile Lys His Val Pro Gly Gly Gly
1               5

<210> SEQ ID NO 501
<211> LENGTH: 5
```

-continued

```
<212> TYPE: PRT
<213> ORGANISM: Artificial Sequence
<220> FEATURE:
<223> OTHER INFORMATION: Synthetic peptide

<400> SEQUENCE: 501

Val Pro Gly Gly Gly
1               5

<210> SEQ ID NO 502
<211> LENGTH: 4
<212> TYPE: PRT
<213> ORGANISM: Artificial Sequence
<220> FEATURE:
<223> OTHER INFORMATION: Synthetic peptide

<400> SEQUENCE: 502

Pro Gly Gly Gly
1

<210> SEQ ID NO 503
<211> LENGTH: 3
<212> TYPE: PRT
<213> ORGANISM: Artificial Sequence
<220> FEATURE:
<223> OTHER INFORMATION: Synthetic peptide

<400> SEQUENCE: 503

Gly Gly Gly
1

<210> SEQ ID NO 504
<211> LENGTH: 10
<212> TYPE: PRT
<213> ORGANISM: Artificial Sequence
<220> FEATURE:
<223> OTHER INFORMATION: Synthetic peptide

<400> SEQUENCE: 504

Asn Ile Lys His Val Pro Gly Gly Gly Ser
1               5                   10

<210> SEQ ID NO 505
<211> LENGTH: 9
<212> TYPE: PRT
<213> ORGANISM: Artificial Sequence
<220> FEATURE:
<223> OTHER INFORMATION: Synthetic peptide

<400> SEQUENCE: 505

Ile Lys His Val Pro Gly Gly Gly Ser
1               5

<210> SEQ ID NO 506
<211> LENGTH: 8
<212> TYPE: PRT
<213> ORGANISM: Artificial Sequence
<220> FEATURE:
<223> OTHER INFORMATION: Synthetic peptide

<400> SEQUENCE: 506

Lys His Val Pro Gly Gly Gly Ser
1               5

<210> SEQ ID NO 507
<211> LENGTH: 7
<212> TYPE: PRT
```

<213> ORGANISM: Artificial Sequence
<220> FEATURE:
<223> OTHER INFORMATION: Synthetic peptide

<400> SEQUENCE: 507

His Val Pro Gly Gly Gly Ser
1               5

<210> SEQ ID NO 508
<211> LENGTH: 6
<212> TYPE: PRT
<213> ORGANISM: Artificial Sequence
<220> FEATURE:
<223> OTHER INFORMATION: Synthetic peptide

<400> SEQUENCE: 508

Val Pro Gly Gly Gly Ser
1               5

<210> SEQ ID NO 509
<211> LENGTH: 5
<212> TYPE: PRT
<213> ORGANISM: Artificial Sequence
<220> FEATURE:
<223> OTHER INFORMATION: Synthetic peptide

<400> SEQUENCE: 509

Pro Gly Gly Gly Ser
1               5

<210> SEQ ID NO 510
<211> LENGTH: 4
<212> TYPE: PRT
<213> ORGANISM: Artificial Sequence
<220> FEATURE:
<223> OTHER INFORMATION: Synthetic peptide

<400> SEQUENCE: 510

Gly Gly Gly Ser
1

<210> SEQ ID NO 511
<211> LENGTH: 3
<212> TYPE: PRT
<213> ORGANISM: Artificial Sequence
<220> FEATURE:
<223> OTHER INFORMATION: Synthetic peptide

<400> SEQUENCE: 511

Gly Gly Ser
1

<210> SEQ ID NO 512
<211> LENGTH: 10
<212> TYPE: PRT
<213> ORGANISM: Artificial Sequence
<220> FEATURE:
<223> OTHER INFORMATION: Synthetic peptide

<400> SEQUENCE: 512

Ile Lys His Val Pro Gly Gly Gly Ser Val
1               5                   10

<210> SEQ ID NO 513
<211> LENGTH: 9
<212> TYPE: PRT
<213> ORGANISM: Artificial Sequence

```
<220> FEATURE:
<223> OTHER INFORMATION: Synthetic peptide

<400> SEQUENCE: 513

Lys His Val Pro Gly Gly Gly Ser Val
1               5

<210> SEQ ID NO 514
<211> LENGTH: 8
<212> TYPE: PRT
<213> ORGANISM: Artificial Sequence
<220> FEATURE:
<223> OTHER INFORMATION: Synthetic peptide

<400> SEQUENCE: 514

His Val Pro Gly Gly Gly Ser Val
1               5

<210> SEQ ID NO 515
<211> LENGTH: 7
<212> TYPE: PRT
<213> ORGANISM: Artificial Sequence
<220> FEATURE:
<223> OTHER INFORMATION: Synthetic peptide

<400> SEQUENCE: 515

Val Pro Gly Gly Gly Ser Val
1               5

<210> SEQ ID NO 516
<211> LENGTH: 6
<212> TYPE: PRT
<213> ORGANISM: Artificial Sequence
<220> FEATURE:
<223> OTHER INFORMATION: Synthetic peptide

<400> SEQUENCE: 516

Pro Gly Gly Gly Ser Val
1               5

<210> SEQ ID NO 517
<211> LENGTH: 5
<212> TYPE: PRT
<213> ORGANISM: Artificial Sequence
<220> FEATURE:
<223> OTHER INFORMATION: Synthetic peptide

<400> SEQUENCE: 517

Gly Gly Gly Ser Val
1               5

<210> SEQ ID NO 518
<211> LENGTH: 4
<212> TYPE: PRT
<213> ORGANISM: Artificial Sequence
<220> FEATURE:
<223> OTHER INFORMATION: Synthetic peptide

<400> SEQUENCE: 518

Gly Gly Ser Val
1

<210> SEQ ID NO 519
<211> LENGTH: 3
<212> TYPE: PRT
<213> ORGANISM: Artificial Sequence
<220> FEATURE:
```

```
<223> OTHER INFORMATION: Synthetic peptide

<400> SEQUENCE: 519

Gly Ser Val
1

<210> SEQ ID NO 520
<211> LENGTH: 10
<212> TYPE: PRT
<213> ORGANISM: Artificial Sequence
<220> FEATURE:
<223> OTHER INFORMATION: Synthetic peptide

<400> SEQUENCE: 520

Lys His Val Pro Gly Gly Gly Ser Val Gln
1               5                   10

<210> SEQ ID NO 521
<211> LENGTH: 9
<212> TYPE: PRT
<213> ORGANISM: Artificial Sequence
<220> FEATURE:
<223> OTHER INFORMATION: Synthetic peptide

<400> SEQUENCE: 521

His Val Pro Gly Gly Gly Ser Val Gln
1               5

<210> SEQ ID NO 522
<211> LENGTH: 8
<212> TYPE: PRT
<213> ORGANISM: Artificial Sequence
<220> FEATURE:
<223> OTHER INFORMATION: Synthetic peptide

<400> SEQUENCE: 522

Val Pro Gly Gly Gly Ser Val Gln
1               5

<210> SEQ ID NO 523
<211> LENGTH: 7
<212> TYPE: PRT
<213> ORGANISM: Artificial Sequence
<220> FEATURE:
<223> OTHER INFORMATION: Synthetic peptide

<400> SEQUENCE: 523

Pro Gly Gly Gly Ser Val Gln
1               5

<210> SEQ ID NO 524
<211> LENGTH: 6
<212> TYPE: PRT
<213> ORGANISM: Artificial Sequence
<220> FEATURE:
<223> OTHER INFORMATION: Synthetic peptide

<400> SEQUENCE: 524

Gly Gly Gly Ser Val Gln
1               5

<210> SEQ ID NO 525
<211> LENGTH: 5
<212> TYPE: PRT
<213> ORGANISM: Artificial Sequence
<220> FEATURE:
<223> OTHER INFORMATION: Synthetic peptide
```

-continued

```
<400> SEQUENCE: 525

Gly Gly Ser Val Gln
1               5

<210> SEQ ID NO 526
<211> LENGTH: 4
<212> TYPE: PRT
<213> ORGANISM: Artificial Sequence
<220> FEATURE:
<223> OTHER INFORMATION: Synthetic peptide

<400> SEQUENCE: 526

Gly Ser Val Gln
1

<210> SEQ ID NO 527
<211> LENGTH: 3
<212> TYPE: PRT
<213> ORGANISM: Artificial Sequence
<220> FEATURE:
<223> OTHER INFORMATION: Synthetic peptide

<400> SEQUENCE: 527

Ser Val Gln
1

<210> SEQ ID NO 528
<211> LENGTH: 10
<212> TYPE: PRT
<213> ORGANISM: Artificial Sequence
<220> FEATURE:
<223> OTHER INFORMATION: Synthetic peptide

<400> SEQUENCE: 528

His Val Pro Gly Gly Gly Ser Val Gln Ile
1               5                   10

<210> SEQ ID NO 529
<211> LENGTH: 9
<212> TYPE: PRT
<213> ORGANISM: Artificial Sequence
<220> FEATURE:
<223> OTHER INFORMATION: Synthetic peptide

<400> SEQUENCE: 529

Val Pro Gly Gly Gly Ser Val Gln Ile
1               5

<210> SEQ ID NO 530
<211> LENGTH: 8
<212> TYPE: PRT
<213> ORGANISM: Artificial Sequence
<220> FEATURE:
<223> OTHER INFORMATION: Synthetic peptide

<400> SEQUENCE: 530

Pro Gly Gly Gly Ser Val Gln Ile
1               5

<210> SEQ ID NO 531
<211> LENGTH: 7
<212> TYPE: PRT
<213> ORGANISM: Artificial Sequence
<220> FEATURE:
<223> OTHER INFORMATION: Synthetic peptide
```

-continued

```
<400> SEQUENCE: 531

Gly Gly Gly Ser Val Gln Ile
1               5

<210> SEQ ID NO 532
<211> LENGTH: 6
<212> TYPE: PRT
<213> ORGANISM: Artificial Sequence
<220> FEATURE:
<223> OTHER INFORMATION: Synthetic peptide

<400> SEQUENCE: 532

Gly Gly Ser Val Gln Ile
1               5

<210> SEQ ID NO 533
<211> LENGTH: 5
<212> TYPE: PRT
<213> ORGANISM: Artificial Sequence
<220> FEATURE:
<223> OTHER INFORMATION: Synthetic peptide

<400> SEQUENCE: 533

Gly Ser Val Gln Ile
1               5

<210> SEQ ID NO 534
<211> LENGTH: 4
<212> TYPE: PRT
<213> ORGANISM: Artificial Sequence
<220> FEATURE:
<223> OTHER INFORMATION: Synthetic peptide

<400> SEQUENCE: 534

Ser Val Gln Ile
1

<210> SEQ ID NO 535
<211> LENGTH: 10
<212> TYPE: PRT
<213> ORGANISM: Artificial Sequence
<220> FEATURE:
<223> OTHER INFORMATION: Synthetic peptide

<400> SEQUENCE: 535

Gly Gly Ser Val Gln Ile Val Tyr Lys Ser
1               5                   10

<210> SEQ ID NO 536
<211> LENGTH: 9
<212> TYPE: PRT
<213> ORGANISM: Artificial Sequence
<220> FEATURE:
<223> OTHER INFORMATION: Synthetic peptide

<400> SEQUENCE: 536

Gly Ser Val Gln Ile Val Tyr Lys Ser
1               5

<210> SEQ ID NO 537
<211> LENGTH: 8
<212> TYPE: PRT
<213> ORGANISM: Artificial Sequence
<220> FEATURE:
<223> OTHER INFORMATION: Synthetic peptide

<400> SEQUENCE: 537
```

-continued

```
Ser Val Gln Ile Val Tyr Lys Ser
1               5

<210> SEQ ID NO 538
<211> LENGTH: 7
<212> TYPE: PRT
<213> ORGANISM: Artificial Sequence
<220> FEATURE:
<223> OTHER INFORMATION: Synthetic peptide

<400> SEQUENCE: 538

Val Gln Ile Val Tyr Lys Ser
1               5

<210> SEQ ID NO 539
<211> LENGTH: 6
<212> TYPE: PRT
<213> ORGANISM: Artificial Sequence
<220> FEATURE:
<223> OTHER INFORMATION: Synthetic peptide

<400> SEQUENCE: 539

Gln Ile Val Tyr Lys Ser
1               5

<210> SEQ ID NO 540
<211> LENGTH: 5
<212> TYPE: PRT
<213> ORGANISM: Artificial Sequence
<220> FEATURE:
<223> OTHER INFORMATION: Synthetic peptide

<400> SEQUENCE: 540

Ile Val Tyr Lys Ser
1               5

<210> SEQ ID NO 541
<211> LENGTH: 4
<212> TYPE: PRT
<213> ORGANISM: Artificial Sequence
<220> FEATURE:
<223> OTHER INFORMATION: Synthetic peptide

<400> SEQUENCE: 541

Val Tyr Lys Ser
1

<210> SEQ ID NO 542
<211> LENGTH: 3
<212> TYPE: PRT
<213> ORGANISM: Artificial Sequence
<220> FEATURE:
<223> OTHER INFORMATION: Synthetic peptide

<400> SEQUENCE: 542

Tyr Lys Ser
1

<210> SEQ ID NO 543
<211> LENGTH: 10
<212> TYPE: PRT
<213> ORGANISM: Artificial Sequence
<220> FEATURE:
<223> OTHER INFORMATION: Synthetic peptide

<400> SEQUENCE: 543
```

```
Gly Ser Val Gln Ile Val Tyr Lys Ser Val
1               5                   10
```

<210> SEQ ID NO 544
<211> LENGTH: 9
<212> TYPE: PRT
<213> ORGANISM: Artificial Sequence
<220> FEATURE:
<223> OTHER INFORMATION: Synthetic peptide

<400> SEQUENCE: 544

```
Ser Val Gln Ile Val Tyr Lys Ser Val
1               5
```

<210> SEQ ID NO 545
<211> LENGTH: 8
<212> TYPE: PRT
<213> ORGANISM: Artificial Sequence
<220> FEATURE:
<223> OTHER INFORMATION: Synthetic peptide

<400> SEQUENCE: 545

```
Val Gln Ile Val Tyr Lys Ser Val
1               5
```

<210> SEQ ID NO 546
<211> LENGTH: 7
<212> TYPE: PRT
<213> ORGANISM: Artificial Sequence
<220> FEATURE:
<223> OTHER INFORMATION: Synthetic peptide

<400> SEQUENCE: 546

```
Gln Ile Val Tyr Lys Ser Val
1               5
```

<210> SEQ ID NO 547
<211> LENGTH: 6
<212> TYPE: PRT
<213> ORGANISM: Artificial Sequence
<220> FEATURE:
<223> OTHER INFORMATION: Synthetic peptide

<400> SEQUENCE: 547

```
Ile Val Tyr Lys Ser Val
1               5
```

<210> SEQ ID NO 548
<211> LENGTH: 5
<212> TYPE: PRT
<213> ORGANISM: Artificial Sequence
<220> FEATURE:
<223> OTHER INFORMATION: Synthetic peptide

<400> SEQUENCE: 548

```
Val Tyr Lys Ser Val
1               5
```

<210> SEQ ID NO 549
<211> LENGTH: 4
<212> TYPE: PRT
<213> ORGANISM: Artificial Sequence
<220> FEATURE:
<223> OTHER INFORMATION: Synthetic peptide

<400> SEQUENCE: 549

```
Tyr Lys Ser Val
```

1

<210> SEQ ID NO 550
<211> LENGTH: 10
<212> TYPE: PRT
<213> ORGANISM: Artificial Sequence
<220> FEATURE:
<223> OTHER INFORMATION: Synthetic peptide

<400> SEQUENCE: 550

Ser Val Gln Ile Val Tyr Lys Ser Val Asp
1               5                   10

<210> SEQ ID NO 551
<211> LENGTH: 9
<212> TYPE: PRT
<213> ORGANISM: Artificial Sequence
<220> FEATURE:
<223> OTHER INFORMATION: Synthetic peptide

<400> SEQUENCE: 551

Val Gln Ile Val Tyr Lys Ser Val Asp
1               5

<210> SEQ ID NO 552
<211> LENGTH: 8
<212> TYPE: PRT
<213> ORGANISM: Artificial Sequence
<220> FEATURE:
<223> OTHER INFORMATION: Synthetic peptide

<400> SEQUENCE: 552

Gln Ile Val Tyr Lys Ser Val Asp
1               5

<210> SEQ ID NO 553
<211> LENGTH: 7
<212> TYPE: PRT
<213> ORGANISM: Artificial Sequence
<220> FEATURE:
<223> OTHER INFORMATION: Synthetic peptide

<400> SEQUENCE: 553

Ile Val Tyr Lys Ser Val Asp
1               5

<210> SEQ ID NO 554
<211> LENGTH: 6
<212> TYPE: PRT
<213> ORGANISM: Artificial Sequence
<220> FEATURE:
<223> OTHER INFORMATION: Synthetic peptide

<400> SEQUENCE: 554

Val Tyr Lys Ser Val Asp
1               5

<210> SEQ ID NO 555
<211> LENGTH: 5
<212> TYPE: PRT
<213> ORGANISM: Artificial Sequence
<220> FEATURE:
<223> OTHER INFORMATION: Synthetic peptide

<400> SEQUENCE: 555

Tyr Lys Ser Val Asp
1               5

-continued

```
<210> SEQ ID NO 556
<211> LENGTH: 4
<212> TYPE: PRT
<213> ORGANISM: Artificial Sequence
<220> FEATURE:
<223> OTHER INFORMATION: Synthetic peptide

<400> SEQUENCE: 556

Lys Ser Val Asp
1

<210> SEQ ID NO 557
<211> LENGTH: 3
<212> TYPE: PRT
<213> ORGANISM: Artificial Sequence
<220> FEATURE:
<223> OTHER INFORMATION: Synthetic peptide

<400> SEQUENCE: 557

Ser Val Asp
1

<210> SEQ ID NO 558
<211> LENGTH: 10
<212> TYPE: PRT
<213> ORGANISM: Artificial Sequence
<220> FEATURE:
<223> OTHER INFORMATION: Synthetic peptide

<400> SEQUENCE: 558

Val Gln Ile Val Tyr Lys Ser Val Asp Leu
1               5                   10

<210> SEQ ID NO 559
<211> LENGTH: 9
<212> TYPE: PRT
<213> ORGANISM: Artificial Sequence
<220> FEATURE:
<223> OTHER INFORMATION: Synthetic peptide

<400> SEQUENCE: 559

Gln Ile Val Tyr Lys Ser Val Asp Leu
1               5

<210> SEQ ID NO 560
<211> LENGTH: 8
<212> TYPE: PRT
<213> ORGANISM: Artificial Sequence
<220> FEATURE:
<223> OTHER INFORMATION: Synthetic peptide

<400> SEQUENCE: 560

Ile Val Tyr Lys Ser Val Asp Leu
1               5

<210> SEQ ID NO 561
<211> LENGTH: 7
<212> TYPE: PRT
<213> ORGANISM: Artificial Sequence
<220> FEATURE:
<223> OTHER INFORMATION: Synthetic peptide

<400> SEQUENCE: 561

Val Tyr Lys Ser Val Asp Leu
1               5
```

-continued

<210> SEQ ID NO 562
<211> LENGTH: 6
<212> TYPE: PRT
<213> ORGANISM: Artificial Sequence
<220> FEATURE:
<223> OTHER INFORMATION: Synthetic peptide

<400> SEQUENCE: 562

Tyr Lys Ser Val Asp Leu
1               5

<210> SEQ ID NO 563
<211> LENGTH: 5
<212> TYPE: PRT
<213> ORGANISM: Artificial Sequence
<220> FEATURE:
<223> OTHER INFORMATION: Synthetic peptide

<400> SEQUENCE: 563

Lys Ser Val Asp Leu
1               5

<210> SEQ ID NO 564
<211> LENGTH: 4
<212> TYPE: PRT
<213> ORGANISM: Artificial Sequence
<220> FEATURE:
<223> OTHER INFORMATION: Synthetic peptide

<400> SEQUENCE: 564

Ser Val Asp Leu
1

<210> SEQ ID NO 565
<211> LENGTH: 10
<212> TYPE: PRT
<213> ORGANISM: Artificial Sequence
<220> FEATURE:
<223> OTHER INFORMATION: Synthetic peptide

<400> SEQUENCE: 565

Gln Ile Val Tyr Lys Ser Val Asp Leu Ser
1               5                   10

<210> SEQ ID NO 566
<211> LENGTH: 9
<212> TYPE: PRT
<213> ORGANISM: Artificial Sequence
<220> FEATURE:
<223> OTHER INFORMATION: Synthetic peptide

<400> SEQUENCE: 566

Ile Val Tyr Lys Ser Val Asp Leu Ser
1               5

<210> SEQ ID NO 567
<211> LENGTH: 8
<212> TYPE: PRT
<213> ORGANISM: Artificial Sequence
<220> FEATURE:
<223> OTHER INFORMATION: Synthetic peptide

<400> SEQUENCE: 567

Val Tyr Lys Ser Val Asp Leu Ser
1               5

-continued

```
<210> SEQ ID NO 568
<211> LENGTH: 7
<212> TYPE: PRT
<213> ORGANISM: Artificial Sequence
<220> FEATURE:
<223> OTHER INFORMATION: Synthetic peptide

<400> SEQUENCE: 568

Tyr Lys Ser Val Asp Leu Ser
1               5

<210> SEQ ID NO 569
<211> LENGTH: 6
<212> TYPE: PRT
<213> ORGANISM: Artificial Sequence
<220> FEATURE:
<223> OTHER INFORMATION: Synthetic peptide

<400> SEQUENCE: 569

Lys Ser Val Asp Leu Ser
1               5

<210> SEQ ID NO 570
<211> LENGTH: 5
<212> TYPE: PRT
<213> ORGANISM: Artificial Sequence
<220> FEATURE:
<223> OTHER INFORMATION: Synthetic peptide

<400> SEQUENCE: 570

Ser Val Asp Leu Ser
1               5

<210> SEQ ID NO 571
<211> LENGTH: 10
<212> TYPE: PRT
<213> ORGANISM: Artificial Sequence
<220> FEATURE:
<223> OTHER INFORMATION: Synthetic peptide

<400> SEQUENCE: 571

Ile Val Tyr Lys Ser Val Asp Leu Ser Lys
1               5                   10

<210> SEQ ID NO 572
<211> LENGTH: 9
<212> TYPE: PRT
<213> ORGANISM: Artificial Sequence
<220> FEATURE:
<223> OTHER INFORMATION: Synthetic peptide

<400> SEQUENCE: 572

Val Tyr Lys Ser Val Asp Leu Ser Lys
1               5

<210> SEQ ID NO 573
<211> LENGTH: 8
<212> TYPE: PRT
<213> ORGANISM: Artificial Sequence
<220> FEATURE:
<223> OTHER INFORMATION: Synthetic peptide

<400> SEQUENCE: 573

Tyr Lys Ser Val Asp Leu Ser Lys
1               5

<210> SEQ ID NO 574
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 574

Lys Ser Val Asp Leu Ser Lys
1               5

<210> SEQ ID NO 575
<211> LENGTH: 10
<212> TYPE: PRT
<213> ORGANISM: Artificial Sequence
<220> FEATURE:
<223> OTHER INFORMATION: Synthetic peptide

<400> SEQUENCE: 575

Val Tyr Lys Ser Val Asp Leu Ser Lys Val
1               5                   10

<210> SEQ ID NO 576
<211> LENGTH: 9
<212> TYPE: PRT
<213> ORGANISM: Artificial Sequence
<220> FEATURE:
<223> OTHER INFORMATION: Synthetic peptide

<400> SEQUENCE: 576

Tyr Lys Ser Val Asp Leu Ser Lys Val
1               5

<210> SEQ ID NO 577
<211> LENGTH: 8
<212> TYPE: PRT
<213> ORGANISM: Artificial Sequence
<220> FEATURE:
<223> OTHER INFORMATION: Synthetic peptide

<400> SEQUENCE: 577

Lys Ser Val Asp Leu Ser Lys Val
1               5

<210> SEQ ID NO 578
<211> LENGTH: 7
<212> TYPE: PRT
<213> ORGANISM: Artificial Sequence
<220> FEATURE:
<223> OTHER INFORMATION: Synthetic peptide

<400> SEQUENCE: 578

Ser Val Asp Leu Ser Lys Val
1               5

<210> SEQ ID NO 579
<211> LENGTH: 10
<212> TYPE: PRT
<213> ORGANISM: Artificial Sequence
<220> FEATURE:
<223> OTHER INFORMATION: Synthetic peptide

<400> SEQUENCE: 579

Tyr Lys Ser Val Asp Leu Ser Lys Val Thr
1               5                   10

<210> SEQ ID NO 580
<211> LENGTH: 9
```

-continued

```
<212> TYPE: PRT
<213> ORGANISM: Artificial Sequence
<220> FEATURE:
<223> OTHER INFORMATION: Synthetic peptide

<400> SEQUENCE: 580

Lys Ser Val Asp Leu Ser Lys Val Thr
1               5

<210> SEQ ID NO 581
<211> LENGTH: 8
<212> TYPE: PRT
<213> ORGANISM: Artificial Sequence
<220> FEATURE:
<223> OTHER INFORMATION: Synthetic peptide

<400> SEQUENCE: 581

Ser Val Asp Leu Ser Lys Val Thr
1               5

<210> SEQ ID NO 582
<211> LENGTH: 6
<212> TYPE: PRT
<213> ORGANISM: Artificial Sequence
<220> FEATURE:
<223> OTHER INFORMATION: Synthetic peptide

<400> SEQUENCE: 582

Asp Leu Ser Lys Val Thr
1               5

<210> SEQ ID NO 583
<211> LENGTH: 5
<212> TYPE: PRT
<213> ORGANISM: Artificial Sequence
<220> FEATURE:
<223> OTHER INFORMATION: Synthetic peptide

<400> SEQUENCE: 583

Leu Ser Lys Val Thr
1               5

<210> SEQ ID NO 584
<211> LENGTH: 4
<212> TYPE: PRT
<213> ORGANISM: Artificial Sequence
<220> FEATURE:
<223> OTHER INFORMATION: Synthetic peptide

<400> SEQUENCE: 584

Ser Lys Val Thr
1

<210> SEQ ID NO 585
<211> LENGTH: 3
<212> TYPE: PRT
<213> ORGANISM: Artificial Sequence
<220> FEATURE:
<223> OTHER INFORMATION: Synthetic peptide

<400> SEQUENCE: 585

Lys Val Thr
1

<210> SEQ ID NO 586
<211> LENGTH: 10
<212> TYPE: PRT
```

-continued

```
<213> ORGANISM: Artificial Sequence
<220> FEATURE:
<223> OTHER INFORMATION: Synthetic peptide

<400> SEQUENCE: 586

His Gly Ala Glu Ile Val Tyr Lys Ser Val
1               5                   10

<210> SEQ ID NO 587
<211> LENGTH: 9
<212> TYPE: PRT
<213> ORGANISM: Artificial Sequence
<220> FEATURE:
<223> OTHER INFORMATION: Synthetic peptide

<400> SEQUENCE: 587

Gly Ala Glu Ile Val Tyr Lys Ser Val
1               5

<210> SEQ ID NO 588
<211> LENGTH: 8
<212> TYPE: PRT
<213> ORGANISM: Artificial Sequence
<220> FEATURE:
<223> OTHER INFORMATION: Synthetic peptide

<400> SEQUENCE: 588

Ala Glu Ile Val Tyr Lys Ser Val
1               5

<210> SEQ ID NO 589
<211> LENGTH: 10
<212> TYPE: PRT
<213> ORGANISM: Artificial Sequence
<220> FEATURE:
<223> OTHER INFORMATION: Synthetic peptide

<400> SEQUENCE: 589

Gly Ala Glu Ile Val Tyr Lys Ser Val Val
1               5                   10

<210> SEQ ID NO 590
<211> LENGTH: 9
<212> TYPE: PRT
<213> ORGANISM: Artificial Sequence
<220> FEATURE:
<223> OTHER INFORMATION: Synthetic peptide

<400> SEQUENCE: 590

Ala Glu Ile Val Tyr Lys Ser Val Val
1               5

<210> SEQ ID NO 591
<211> LENGTH: 8
<212> TYPE: PRT
<213> ORGANISM: Artificial Sequence
<220> FEATURE:
<223> OTHER INFORMATION: Synthetic peptide

<400> SEQUENCE: 591

Glu Ile Val Tyr Lys Ser Val Val
1               5

<210> SEQ ID NO 592
<211> LENGTH: 7
<212> TYPE: PRT
<213> ORGANISM: Artificial Sequence
```

```
<220> FEATURE:
<223> OTHER INFORMATION: Synthetic peptide

<400> SEQUENCE: 592

Ile Val Tyr Lys Ser Val Val
1               5

<210> SEQ ID NO 593
<211> LENGTH: 6
<212> TYPE: PRT
<213> ORGANISM: Artificial Sequence
<220> FEATURE:
<223> OTHER INFORMATION: Synthetic peptide

<400> SEQUENCE: 593

Val Tyr Lys Ser Val Val
1               5

<210> SEQ ID NO 594
<211> LENGTH: 5
<212> TYPE: PRT
<213> ORGANISM: Artificial Sequence
<220> FEATURE:
<223> OTHER INFORMATION: Synthetic peptide

<400> SEQUENCE: 594

Tyr Lys Ser Val Val
1               5

<210> SEQ ID NO 595
<211> LENGTH: 4
<212> TYPE: PRT
<213> ORGANISM: Artificial Sequence
<220> FEATURE:
<223> OTHER INFORMATION: Synthetic peptide

<400> SEQUENCE: 595

Lys Ser Val Val
1

<210> SEQ ID NO 596
<211> LENGTH: 3
<212> TYPE: PRT
<213> ORGANISM: Artificial Sequence
<220> FEATURE:
<223> OTHER INFORMATION: Synthetic peptide

<400> SEQUENCE: 596

Ser Val Val
1

<210> SEQ ID NO 597
<211> LENGTH: 10
<212> TYPE: PRT
<213> ORGANISM: Artificial Sequence
<220> FEATURE:
<223> OTHER INFORMATION: Synthetic peptide

<400> SEQUENCE: 597

Ala Glu Ile Val Tyr Lys Ser Val Val Ser
1               5                   10

<210> SEQ ID NO 598
<211> LENGTH: 9
<212> TYPE: PRT
<213> ORGANISM: Artificial Sequence
<220> FEATURE:
```

<223> OTHER INFORMATION: Synthetic peptide

<400> SEQUENCE: 598

Glu Ile Val Tyr Lys Ser Val Val Ser
1               5

<210> SEQ ID NO 599
<211> LENGTH: 8
<212> TYPE: PRT
<213> ORGANISM: Artificial Sequence
<220> FEATURE:
<223> OTHER INFORMATION: Synthetic peptide

<400> SEQUENCE: 599

Ile Val Tyr Lys Ser Val Val Ser
1               5

<210> SEQ ID NO 600
<211> LENGTH: 7
<212> TYPE: PRT
<213> ORGANISM: Artificial Sequence
<220> FEATURE:
<223> OTHER INFORMATION: Synthetic peptide

<400> SEQUENCE: 600

Val Tyr Lys Ser Val Val Ser
1               5

<210> SEQ ID NO 601
<211> LENGTH: 6
<212> TYPE: PRT
<213> ORGANISM: Artificial Sequence
<220> FEATURE:
<223> OTHER INFORMATION: Synthetic peptide

<400> SEQUENCE: 601

Tyr Lys Ser Val Val Ser
1               5

<210> SEQ ID NO 602
<211> LENGTH: 5
<212> TYPE: PRT
<213> ORGANISM: Artificial Sequence
<220> FEATURE:
<223> OTHER INFORMATION: Synthetic peptide

<400> SEQUENCE: 602

Lys Ser Val Val Ser
1               5

<210> SEQ ID NO 603
<211> LENGTH: 4
<212> TYPE: PRT
<213> ORGANISM: Artificial Sequence
<220> FEATURE:
<223> OTHER INFORMATION: Synthetic peptide

<400> SEQUENCE: 603

Ser Val Val Ser
1

<210> SEQ ID NO 604
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 604

Glu Ile Val Tyr Lys Ser Val Val Ser Gly
1               5                   10

<210> SEQ ID NO 605
<211> LENGTH: 9
<212> TYPE: PRT
<213> ORGANISM: Artificial Sequence
<220> FEATURE:
<223> OTHER INFORMATION: Synthetic peptide

<400> SEQUENCE: 605

Ile Val Tyr Lys Ser Val Val Ser Gly
1               5

<210> SEQ ID NO 606
<211> LENGTH: 8
<212> TYPE: PRT
<213> ORGANISM: Artificial Sequence
<220> FEATURE:
<223> OTHER INFORMATION: Synthetic peptide

<400> SEQUENCE: 606

Val Tyr Lys Ser Val Val Ser Gly
1               5

<210> SEQ ID NO 607
<211> LENGTH: 7
<212> TYPE: PRT
<213> ORGANISM: Artificial Sequence
<220> FEATURE:
<223> OTHER INFORMATION: Synthetic peptide

<400> SEQUENCE: 607

Tyr Lys Ser Val Val Ser Gly
1               5

<210> SEQ ID NO 608
<211> LENGTH: 6
<212> TYPE: PRT
<213> ORGANISM: Artificial Sequence
<220> FEATURE:
<223> OTHER INFORMATION: Synthetic peptide

<400> SEQUENCE: 608

Lys Ser Val Val Ser Gly
1               5

<210> SEQ ID NO 609
<211> LENGTH: 5
<212> TYPE: PRT
<213> ORGANISM: Artificial Sequence
<220> FEATURE:
<223> OTHER INFORMATION: Synthetic peptide

<400> SEQUENCE: 609

Ser Val Val Ser Gly
1               5

<210> SEQ ID NO 610
<211> LENGTH: 4
<212> TYPE: PRT
<213> ORGANISM: Artificial Sequence
<220> FEATURE:
<223> OTHER INFORMATION: Synthetic peptide
```

-continued

```
<400> SEQUENCE: 610

Val Val Ser Gly
1

<210> SEQ ID NO 611
<211> LENGTH: 3
<212> TYPE: PRT
<213> ORGANISM: Artificial Sequence
<220> FEATURE:
<223> OTHER INFORMATION: Synthetic peptide

<400> SEQUENCE: 611

Val Ser Gly
1

<210> SEQ ID NO 612
<211> LENGTH: 10
<212> TYPE: PRT
<213> ORGANISM: Artificial Sequence
<220> FEATURE:
<223> OTHER INFORMATION: Synthetic peptide

<400> SEQUENCE: 612

Ile Val Tyr Lys Ser Val Val Ser Gly Asp
1               5                   10

<210> SEQ ID NO 613
<211> LENGTH: 9
<212> TYPE: PRT
<213> ORGANISM: Artificial Sequence
<220> FEATURE:
<223> OTHER INFORMATION: Synthetic peptide

<400> SEQUENCE: 613

Val Tyr Lys Ser Val Val Ser Gly Asp
1               5

<210> SEQ ID NO 614
<211> LENGTH: 8
<212> TYPE: PRT
<213> ORGANISM: Artificial Sequence
<220> FEATURE:
<223> OTHER INFORMATION: Synthetic peptide

<400> SEQUENCE: 614

Tyr Lys Ser Val Val Ser Gly Asp
1               5

<210> SEQ ID NO 615
<211> LENGTH: 7
<212> TYPE: PRT
<213> ORGANISM: Artificial Sequence
<220> FEATURE:
<223> OTHER INFORMATION: Synthetic peptide

<400> SEQUENCE: 615

Lys Ser Val Val Ser Gly Asp
1               5

<210> SEQ ID NO 616
<211> LENGTH: 6
<212> TYPE: PRT
<213> ORGANISM: Artificial Sequence
<220> FEATURE:
<223> OTHER INFORMATION: Synthetic peptide

<400> SEQUENCE: 616
```

Ser Val Val Ser Gly Asp
1               5

<210> SEQ ID NO 617
<211> LENGTH: 5
<212> TYPE: PRT
<213> ORGANISM: Artificial Sequence
<220> FEATURE:
<223> OTHER INFORMATION: Synthetic peptide

<400> SEQUENCE: 617

Val Val Ser Gly Asp
1               5

<210> SEQ ID NO 618
<211> LENGTH: 10
<212> TYPE: PRT
<213> ORGANISM: Artificial Sequence
<220> FEATURE:
<223> OTHER INFORMATION: Synthetic peptide

<400> SEQUENCE: 618

Val Tyr Lys Ser Val Val Ser Gly Asp Thr
1               5                   10

<210> SEQ ID NO 619
<211> LENGTH: 9
<212> TYPE: PRT
<213> ORGANISM: Artificial Sequence
<220> FEATURE:
<223> OTHER INFORMATION: Synthetic peptide

<400> SEQUENCE: 619

Tyr Lys Ser Val Val Ser Gly Asp Thr
1               5

<210> SEQ ID NO 620
<211> LENGTH: 8
<212> TYPE: PRT
<213> ORGANISM: Artificial Sequence
<220> FEATURE:
<223> OTHER INFORMATION: Synthetic peptide

<400> SEQUENCE: 620

Lys Ser Val Val Ser Gly Asp Thr
1               5

<210> SEQ ID NO 621
<211> LENGTH: 7
<212> TYPE: PRT
<213> ORGANISM: Artificial Sequence
<220> FEATURE:
<223> OTHER INFORMATION: Synthetic peptide

<400> SEQUENCE: 621

Ser Val Val Ser Gly Asp Thr
1               5

<210> SEQ ID NO 622
<211> LENGTH: 10
<212> TYPE: PRT
<213> ORGANISM: Artificial Sequence
<220> FEATURE:
<223> OTHER INFORMATION: Synthetic peptide

<400> SEQUENCE: 622

```
Tyr Lys Ser Val Val Ser Gly Asp Thr Ser
1               5                   10

<210> SEQ ID NO 623
<211> LENGTH: 9
<212> TYPE: PRT
<213> ORGANISM: Artificial Sequence
<220> FEATURE:
<223> OTHER INFORMATION: Synthetic peptide

<400> SEQUENCE: 623

Lys Ser Val Val Ser Gly Asp Thr Ser
1               5

<210> SEQ ID NO 624
<211> LENGTH: 8
<212> TYPE: PRT
<213> ORGANISM: Artificial Sequence
<220> FEATURE:
<223> OTHER INFORMATION: Synthetic peptide

<400> SEQUENCE: 624

Ser Val Val Ser Gly Asp Thr Ser
1               5

<210> SEQ ID NO 625
<211> LENGTH: 10
<212> TYPE: PRT
<213> ORGANISM: Artificial Sequence
<220> FEATURE:
<223> OTHER INFORMATION: Synthetic peptide

<400> SEQUENCE: 625

Tyr Lys Ser Val Val Ser Gly Asp Thr Ser
1               5                   10

<210> SEQ ID NO 626
<211> LENGTH: 9
<212> TYPE: PRT
<213> ORGANISM: Artificial Sequence
<220> FEATURE:
<223> OTHER INFORMATION: Synthetic peptide

<400> SEQUENCE: 626

Lys Ser Val Val Ser Gly Asp Thr Ser
1               5

<210> SEQ ID NO 627
<211> LENGTH: 8
<212> TYPE: PRT
<213> ORGANISM: Artificial Sequence
<220> FEATURE:
<223> OTHER INFORMATION: Synthetic peptide

<400> SEQUENCE: 627

Ser Val Val Ser Gly Asp Thr Ser
1               5

<210> SEQ ID NO 628
<211> LENGTH: 7
<212> TYPE: PRT
<213> ORGANISM: Artificial Sequence
<220> FEATURE:
<223> OTHER INFORMATION: Synthetic peptide

<400> SEQUENCE: 628

Val Val Ser Gly Asp Thr Ser
```

-continued

```
1               5

<210> SEQ ID NO 629
<211> LENGTH: 10
<212> TYPE: PRT
<213> ORGANISM: Artificial Sequence
<220> FEATURE:
<223> OTHER INFORMATION: Synthetic peptide

<400> SEQUENCE: 629

Lys Ser Val Val Ser Gly Asp Thr Ser Pro
1               5                   10

<210> SEQ ID NO 630
<211> LENGTH: 9
<212> TYPE: PRT
<213> ORGANISM: Artificial Sequence
<220> FEATURE:
<223> OTHER INFORMATION: Synthetic peptide

<400> SEQUENCE: 630

Ser Val Val Ser Gly Asp Thr Ser Pro
1               5

<210> SEQ ID NO 631
<211> LENGTH: 10
<212> TYPE: PRT
<213> ORGANISM: Artificial Sequence
<220> FEATURE:
<223> OTHER INFORMATION: Synthetic peptide

<400> SEQUENCE: 631

Ser Val Val Ser Gly Asp Thr Ser Pro Arg
1               5                   10

<210> SEQ ID NO 632
<211> LENGTH: 10
<212> TYPE: PRT
<213> ORGANISM: Artificial Sequence
<220> FEATURE:
<223> OTHER INFORMATION: Synthetic peptide

<400> SEQUENCE: 632

Asp His Gly Ala Glu Ile Val Tyr Lys Pro
1               5                   10

<210> SEQ ID NO 633
<211> LENGTH: 9
<212> TYPE: PRT
<213> ORGANISM: Artificial Sequence
<220> FEATURE:
<223> OTHER INFORMATION: Synthetic peptide

<400> SEQUENCE: 633

His Gly Ala Glu Ile Val Tyr Lys Pro
1               5

<210> SEQ ID NO 634
<211> LENGTH: 8
<212> TYPE: PRT
<213> ORGANISM: Artificial Sequence
<220> FEATURE:
<223> OTHER INFORMATION: Synthetic peptide

<400> SEQUENCE: 634

Gly Ala Glu Ile Val Tyr Lys Pro
1               5
```

```
<210> SEQ ID NO 635
<211> LENGTH: 7
<212> TYPE: PRT
<213> ORGANISM: Artificial Sequence
<220> FEATURE:
<223> OTHER INFORMATION: Synthetic peptide

<400> SEQUENCE: 635

Ala Glu Ile Val Tyr Lys Pro
1               5

<210> SEQ ID NO 636
<211> LENGTH: 10
<212> TYPE: PRT
<213> ORGANISM: Artificial Sequence
<220> FEATURE:
<223> OTHER INFORMATION: Synthetic peptide

<400> SEQUENCE: 636

His Gly Ala Glu Ile Val Tyr Lys Pro Val
1               5                   10

<210> SEQ ID NO 637
<211> LENGTH: 9
<212> TYPE: PRT
<213> ORGANISM: Artificial Sequence
<220> FEATURE:
<223> OTHER INFORMATION: Synthetic peptide

<400> SEQUENCE: 637

Gly Ala Glu Ile Val Tyr Lys Pro Val
1               5

<210> SEQ ID NO 638
<211> LENGTH: 8
<212> TYPE: PRT
<213> ORGANISM: Artificial Sequence
<220> FEATURE:
<223> OTHER INFORMATION: Synthetic peptide

<400> SEQUENCE: 638

Ala Glu Ile Val Tyr Lys Pro Val
1               5

<210> SEQ ID NO 639
<211> LENGTH: 10
<212> TYPE: PRT
<213> ORGANISM: Artificial Sequence
<220> FEATURE:
<223> OTHER INFORMATION: Synthetic peptide

<400> SEQUENCE: 639

Gly Ala Glu Ile Val Tyr Lys Pro Val Val
1               5                   10

<210> SEQ ID NO 640
<211> LENGTH: 9
<212> TYPE: PRT
<213> ORGANISM: Artificial Sequence
<220> FEATURE:
<223> OTHER INFORMATION: Synthetic peptide

<400> SEQUENCE: 640

Ala Glu Ile Val Tyr Lys Pro Val Val
1               5
```

```
<210> SEQ ID NO 641
<211> LENGTH: 8
<212> TYPE: PRT
<213> ORGANISM: Artificial Sequence
<220> FEATURE:
<223> OTHER INFORMATION: Synthetic peptide

<400> SEQUENCE: 641

Glu Ile Val Tyr Lys Pro Val Val
1               5

<210> SEQ ID NO 642
<211> LENGTH: 7
<212> TYPE: PRT
<213> ORGANISM: Artificial Sequence
<220> FEATURE:
<223> OTHER INFORMATION: Synthetic peptide

<400> SEQUENCE: 642

Ile Val Tyr Lys Pro Val Val
1               5

<210> SEQ ID NO 643
<211> LENGTH: 6
<212> TYPE: PRT
<213> ORGANISM: Artificial Sequence
<220> FEATURE:
<223> OTHER INFORMATION: Synthetic peptide

<400> SEQUENCE: 643

Val Tyr Lys Pro Val Val
1               5

<210> SEQ ID NO 644
<211> LENGTH: 5
<212> TYPE: PRT
<213> ORGANISM: Artificial Sequence
<220> FEATURE:
<223> OTHER INFORMATION: Synthetic peptide

<400> SEQUENCE: 644

Tyr Lys Pro Val Val
1               5

<210> SEQ ID NO 645
<211> LENGTH: 4
<212> TYPE: PRT
<213> ORGANISM: Artificial Sequence
<220> FEATURE:
<223> OTHER INFORMATION: Synthetic peptide

<400> SEQUENCE: 645

Lys Pro Val Val
1

<210> SEQ ID NO 646
<211> LENGTH: 10
<212> TYPE: PRT
<213> ORGANISM: Artificial Sequence
<220> FEATURE:
<223> OTHER INFORMATION: Synthetic peptide

<400> SEQUENCE: 646

Ala Glu Ile Val Tyr Lys Pro Val Val Ser
1               5                   10
```

-continued

```
<210> SEQ ID NO 647
<211> LENGTH: 9
<212> TYPE: PRT
<213> ORGANISM: Artificial Sequence
<220> FEATURE:
<223> OTHER INFORMATION: Synthetic peptide

<400> SEQUENCE: 647

Glu Ile Val Tyr Lys Pro Val Val Ser
1               5

<210> SEQ ID NO 648
<211> LENGTH: 8
<212> TYPE: PRT
<213> ORGANISM: Artificial Sequence
<220> FEATURE:
<223> OTHER INFORMATION: Synthetic peptide

<400> SEQUENCE: 648

Ile Val Tyr Lys Pro Val Val Ser
1               5

<210> SEQ ID NO 649
<211> LENGTH: 7
<212> TYPE: PRT
<213> ORGANISM: Artificial Sequence
<220> FEATURE:
<223> OTHER INFORMATION: Synthetic peptide

<400> SEQUENCE: 649

Val Tyr Lys Pro Val Val Ser
1               5

<210> SEQ ID NO 650
<211> LENGTH: 6
<212> TYPE: PRT
<213> ORGANISM: Artificial Sequence
<220> FEATURE:
<223> OTHER INFORMATION: Synthetic peptide

<400> SEQUENCE: 650

Tyr Lys Pro Val Val Ser
1               5

<210> SEQ ID NO 651
<211> LENGTH: 5
<212> TYPE: PRT
<213> ORGANISM: Artificial Sequence
<220> FEATURE:
<223> OTHER INFORMATION: Synthetic peptide

<400> SEQUENCE: 651

Lys Pro Val Val Ser
1               5

<210> SEQ ID NO 652
<211> LENGTH: 10
<212> TYPE: PRT
<213> ORGANISM: Artificial Sequence
<220> FEATURE:
<223> OTHER INFORMATION: Synthetic peptide

<400> SEQUENCE: 652

Glu Ile Val Tyr Lys Pro Val Val Ser Gly
1               5                   10

<210> SEQ ID NO 653
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 653

Ile Val Tyr Lys Pro Val Val Ser Gly
1               5

<210> SEQ ID NO 654
<211> LENGTH: 8
<212> TYPE: PRT
<213> ORGANISM: Artificial Sequence
<220> FEATURE:
<223> OTHER INFORMATION: Synthetic peptide

<400> SEQUENCE: 654

Val Tyr Lys Pro Val Val Ser Gly
1               5

<210> SEQ ID NO 655
<211> LENGTH: 7
<212> TYPE: PRT
<213> ORGANISM: Artificial Sequence
<220> FEATURE:
<223> OTHER INFORMATION: Synthetic peptide

<400> SEQUENCE: 655

Tyr Lys Pro Val Val Ser Gly
1               5

<210> SEQ ID NO 656
<211> LENGTH: 6
<212> TYPE: PRT
<213> ORGANISM: Artificial Sequence
<220> FEATURE:
<223> OTHER INFORMATION: Synthetic peptide

<400> SEQUENCE: 656

Lys Pro Val Val Ser Gly
1               5

<210> SEQ ID NO 657
<211> LENGTH: 10
<212> TYPE: PRT
<213> ORGANISM: Artificial Sequence
<220> FEATURE:
<223> OTHER INFORMATION: Synthetic peptide

<400> SEQUENCE: 657

Ile Val Tyr Lys Pro Val Val Ser Gly Asp
1               5                   10

<210> SEQ ID NO 658
<211> LENGTH: 9
<212> TYPE: PRT
<213> ORGANISM: Artificial Sequence
<220> FEATURE:
<223> OTHER INFORMATION: Synthetic peptide

<400> SEQUENCE: 658

Val Tyr Lys Pro Val Val Ser Gly Asp
1               5

<210> SEQ ID NO 659
<211> LENGTH: 8
```

-continued

<212> TYPE: PRT
<213> ORGANISM: Artificial Sequence
<220> FEATURE:
<223> OTHER INFORMATION: Synthetic peptide

<400> SEQUENCE: 659

Tyr Lys Pro Val Val Ser Gly Asp
1               5

<210> SEQ ID NO 660
<211> LENGTH: 7
<212> TYPE: PRT
<213> ORGANISM: Artificial Sequence
<220> FEATURE:
<223> OTHER INFORMATION: Synthetic peptide

<400> SEQUENCE: 660

Lys Pro Val Val Ser Gly Asp
1               5

<210> SEQ ID NO 661
<211> LENGTH: 10
<212> TYPE: PRT
<213> ORGANISM: Artificial Sequence
<220> FEATURE:
<223> OTHER INFORMATION: Synthetic peptide

<400> SEQUENCE: 661

Val Tyr Lys Pro Val Val Ser Gly Asp Thr
1               5                   10

<210> SEQ ID NO 662
<211> LENGTH: 9
<212> TYPE: PRT
<213> ORGANISM: Artificial Sequence
<220> FEATURE:
<223> OTHER INFORMATION: Synthetic peptide

<400> SEQUENCE: 662

Tyr Lys Pro Val Val Ser Gly Asp Thr
1               5

<210> SEQ ID NO 663
<211> LENGTH: 8
<212> TYPE: PRT
<213> ORGANISM: Artificial Sequence
<220> FEATURE:
<223> OTHER INFORMATION: Synthetic peptide

<400> SEQUENCE: 663

Lys Pro Val Val Ser Gly Asp Thr
1               5

<210> SEQ ID NO 664
<211> LENGTH: 10
<212> TYPE: PRT
<213> ORGANISM: Artificial Sequence
<220> FEATURE:
<223> OTHER INFORMATION: Synthetic peptide

<400> SEQUENCE: 664

Tyr Lys Pro Val Val Ser Gly Asp Thr Ser
1               5                   10

<210> SEQ ID NO 665
<211> LENGTH: 9
<212> TYPE: PRT

```
<213> ORGANISM: Artificial Sequence
<220> FEATURE:
<223> OTHER INFORMATION: Synthetic peptide

<400> SEQUENCE: 665

Lys Pro Val Val Ser Gly Asp Thr Ser
1               5

<210> SEQ ID NO 666
<211> LENGTH: 8
<212> TYPE: PRT
<213> ORGANISM: Artificial Sequence
<220> FEATURE:
<223> OTHER INFORMATION: Synthetic peptide

<400> SEQUENCE: 666

Pro Val Val Ser Gly Asp Thr Ser
1               5

<210> SEQ ID NO 667
<211> LENGTH: 7
<212> TYPE: PRT
<213> ORGANISM: Artificial Sequence
<220> FEATURE:
<223> OTHER INFORMATION: Synthetic peptide

<400> SEQUENCE: 667

Val Val Ser Gly Asp Thr Ser
1               5

<210> SEQ ID NO 668
<211> LENGTH: 10
<212> TYPE: PRT
<213> ORGANISM: Artificial Sequence
<220> FEATURE:
<223> OTHER INFORMATION: Synthetic peptide

<400> SEQUENCE: 668

Lys Pro Val Val Ser Gly Asp Thr Ser Pro
1               5                   10

<210> SEQ ID NO 669
<211> LENGTH: 4
<212> TYPE: PRT
<213> ORGANISM: Artificial Sequence
<220> FEATURE:
<223> OTHER INFORMATION: Synthetic peptide

<400> SEQUENCE: 669

Cys Asn Ile Lys
1

<210> SEQ ID NO 670
<211> LENGTH: 5
<212> TYPE: PRT
<213> ORGANISM: Artificial Sequence
<220> FEATURE:
<223> OTHER INFORMATION: Synthetic peptide

<400> SEQUENCE: 670

Cys Asn Ile Lys His
1               5

<210> SEQ ID NO 671
<211> LENGTH: 6
<212> TYPE: PRT
<213> ORGANISM: Artificial Sequence
```

-continued

```
<220> FEATURE:
<223> OTHER INFORMATION: Synthetic peptide

<400> SEQUENCE: 671

Cys Asn Ile Lys His Val
1               5

<210> SEQ ID NO 672
<211> LENGTH: 9
<212> TYPE: PRT
<213> ORGANISM: Artificial Sequence
<220> FEATURE:
<223> OTHER INFORMATION: Synthetic peptide

<400> SEQUENCE: 672

Cys Asn Ile Lys His Val Pro Gly Gly
1               5

<210> SEQ ID NO 673
<211> LENGTH: 10
<212> TYPE: PRT
<213> ORGANISM: Artificial Sequence
<220> FEATURE:
<223> OTHER INFORMATION: Synthetic peptide

<400> SEQUENCE: 673

Cys Asn Ile Lys His Val Pro Gly Gly Gly
1               5                   10

<210> SEQ ID NO 674
<211> LENGTH: 11
<212> TYPE: PRT
<213> ORGANISM: Artificial Sequence
<220> FEATURE:
<223> OTHER INFORMATION: Synthetic peptide

<400> SEQUENCE: 674

Cys Asn Ile Lys His Val Pro Gly Gly Gly Ser
1               5                   10

<210> SEQ ID NO 675
<211> LENGTH: 10
<212> TYPE: PRT
<213> ORGANISM: Artificial Sequence
<220> FEATURE:
<223> OTHER INFORMATION: Synthetic peptide

<400> SEQUENCE: 675

Glu Asn Leu Lys His Gln Pro Gly Gly Gly
1               5                   10

<210> SEQ ID NO 676
<211> LENGTH: 9
<212> TYPE: PRT
<213> ORGANISM: Artificial Sequence
<220> FEATURE:
<223> OTHER INFORMATION: Synthetic peptide

<400> SEQUENCE: 676

Asn Leu Lys His Gln Pro Gly Gly Gly
1               5

<210> SEQ ID NO 677
<211> LENGTH: 8
<212> TYPE: PRT
<213> ORGANISM: Artificial Sequence
<220> FEATURE:
```

-continued

```
<223> OTHER INFORMATION: Synthetic peptide

<400> SEQUENCE: 677

Leu Lys His Gln Pro Gly Gly Gly
1               5

<210> SEQ ID NO 678
<211> LENGTH: 7
<212> TYPE: PRT
<213> ORGANISM: Artificial Sequence
<220> FEATURE:
<223> OTHER INFORMATION: Synthetic peptide

<400> SEQUENCE: 678

Lys His Gln Pro Gly Gly Gly
1               5

<210> SEQ ID NO 679
<211> LENGTH: 6
<212> TYPE: PRT
<213> ORGANISM: Artificial Sequence
<220> FEATURE:
<223> OTHER INFORMATION: Synthetic peptide

<400> SEQUENCE: 679

His Gln Pro Gly Gly Gly
1               5

<210> SEQ ID NO 680
<211> LENGTH: 5
<212> TYPE: PRT
<213> ORGANISM: Artificial Sequence
<220> FEATURE:
<223> OTHER INFORMATION: Synthetic peptide

<400> SEQUENCE: 680

Gln Pro Gly Gly Gly
1               5

<210> SEQ ID NO 681
<211> LENGTH: 10
<212> TYPE: PRT
<213> ORGANISM: Artificial Sequence
<220> FEATURE:
<223> OTHER INFORMATION: Synthetic peptide

<400> SEQUENCE: 681

Thr Glu Asn Leu Lys His Gln Pro Gly Gly
1               5                   10

<210> SEQ ID NO 682
<211> LENGTH: 9
<212> TYPE: PRT
<213> ORGANISM: Artificial Sequence
<220> FEATURE:
<223> OTHER INFORMATION: Synthetic peptide

<400> SEQUENCE: 682

Glu Asn Leu Lys His Gln Pro Gly Gly
1               5

<210> SEQ ID NO 683
<211> LENGTH: 8
<212> TYPE: PRT
<213> ORGANISM: Artificial Sequence
<220> FEATURE:
<223> OTHER INFORMATION: Synthetic peptide
```

<400> SEQUENCE: 683

Asn Leu Lys His Gln Pro Gly Gly
1               5

<210> SEQ ID NO 684
<211> LENGTH: 7
<212> TYPE: PRT
<213> ORGANISM: Artificial Sequence
<220> FEATURE:
<223> OTHER INFORMATION: Synthetic peptide

<400> SEQUENCE: 684

Leu Lys His Gln Pro Gly Gly
1               5

<210> SEQ ID NO 685
<211> LENGTH: 6
<212> TYPE: PRT
<213> ORGANISM: Artificial Sequence
<220> FEATURE:
<223> OTHER INFORMATION: Synthetic peptide

<400> SEQUENCE: 685

Lys His Gln Pro Gly Gly
1               5

<210> SEQ ID NO 686
<211> LENGTH: 5
<212> TYPE: PRT
<213> ORGANISM: Artificial Sequence
<220> FEATURE:
<223> OTHER INFORMATION: Synthetic peptide

<400> SEQUENCE: 686

His Gln Pro Gly Gly
1               5

<210> SEQ ID NO 687
<211> LENGTH: 4
<212> TYPE: PRT
<213> ORGANISM: Artificial Sequence
<220> FEATURE:
<223> OTHER INFORMATION: Synthetic peptide

<400> SEQUENCE: 687

Gln Pro Gly Gly
1

<210> SEQ ID NO 688
<211> LENGTH: 9
<212> TYPE: PRT
<213> ORGANISM: Artificial Sequence
<220> FEATURE:
<223> OTHER INFORMATION: Synthetic peptide

<400> SEQUENCE: 688

Thr Glu Asn Leu Lys His Gln Pro Gly
1               5

<210> SEQ ID NO 689
<211> LENGTH: 8
<212> TYPE: PRT
<213> ORGANISM: Artificial Sequence
<220> FEATURE:
<223> OTHER INFORMATION: Synthetic peptide -continued

```
<400> SEQUENCE: 689

Glu Asn Leu Lys His Gln Pro Gly
1               5

<210> SEQ ID NO 690
<211> LENGTH: 7
<212> TYPE: PRT
<213> ORGANISM: Artificial Sequence
<220> FEATURE:
<223> OTHER INFORMATION: Synthetic peptide

<400> SEQUENCE: 690

Asn Leu Lys His Gln Pro Gly
1               5

<210> SEQ ID NO 691
<211> LENGTH: 6
<212> TYPE: PRT
<213> ORGANISM: Artificial Sequence
<220> FEATURE:
<223> OTHER INFORMATION: Synthetic peptide

<400> SEQUENCE: 691

Leu Lys His Gln Pro Gly
1               5

<210> SEQ ID NO 692
<211> LENGTH: 5
<212> TYPE: PRT
<213> ORGANISM: Artificial Sequence
<220> FEATURE:
<223> OTHER INFORMATION: Synthetic peptide

<400> SEQUENCE: 692

Lys His Gln Pro Gly
1               5

<210> SEQ ID NO 693
<211> LENGTH: 4
<212> TYPE: PRT
<213> ORGANISM: Artificial Sequence
<220> FEATURE:
<223> OTHER INFORMATION: Synthetic peptide

<400> SEQUENCE: 693

His Gln Pro Gly
1

<210> SEQ ID NO 694
<211> LENGTH: 3
<212> TYPE: PRT
<213> ORGANISM: Artificial Sequence
<220> FEATURE:
<223> OTHER INFORMATION: Synthetic peptide

<400> SEQUENCE: 694

Gln Pro Gly
1

<210> SEQ ID NO 695
<211> LENGTH: 8
<212> TYPE: PRT
<213> ORGANISM: Artificial Sequence
<220> FEATURE:
<223> OTHER INFORMATION: Synthetic peptide

<400> SEQUENCE: 695
```

```
Thr Glu Asn Leu Lys His Gln Pro
1               5

<210> SEQ ID NO 696
<211> LENGTH: 7
<212> TYPE: PRT
<213> ORGANISM: Artificial Sequence
<220> FEATURE:
<223> OTHER INFORMATION: Synthetic peptide

<400> SEQUENCE: 696

Glu Asn Leu Lys His Gln Pro
1               5

<210> SEQ ID NO 697
<211> LENGTH: 6
<212> TYPE: PRT
<213> ORGANISM: Artificial Sequence
<220> FEATURE:
<223> OTHER INFORMATION: Synthetic peptide

<400> SEQUENCE: 697

Asn Leu Lys His Gln Pro
1               5

<210> SEQ ID NO 698
<211> LENGTH: 5
<212> TYPE: PRT
<213> ORGANISM: Artificial Sequence
<220> FEATURE:
<223> OTHER INFORMATION: Synthetic peptide

<400> SEQUENCE: 698

Leu Lys His Gln Pro
1               5

<210> SEQ ID NO 699
<211> LENGTH: 4
<212> TYPE: PRT
<213> ORGANISM: Artificial Sequence
<220> FEATURE:
<223> OTHER INFORMATION: Synthetic peptide

<400> SEQUENCE: 699

Lys His Gln Pro
1

<210> SEQ ID NO 700
<211> LENGTH: 3
<212> TYPE: PRT
<213> ORGANISM: Artificial Sequence
<220> FEATURE:
<223> OTHER INFORMATION: Synthetic peptide

<400> SEQUENCE: 700

His Gln Pro
1

<210> SEQ ID NO 701
<211> LENGTH: 7
<212> TYPE: PRT
<213> ORGANISM: Artificial Sequence
<220> FEATURE:
<223> OTHER INFORMATION: Synthetic peptide

<400> SEQUENCE: 701
```

-continued

```
Thr Glu Asn Leu Lys His Gln
1               5

<210> SEQ ID NO 702
<211> LENGTH: 6
<212> TYPE: PRT
<213> ORGANISM: Artificial Sequence
<220> FEATURE:
<223> OTHER INFORMATION: Synthetic peptide

<400> SEQUENCE: 702

Glu Asn Leu Lys His Gln
1               5

<210> SEQ ID NO 703
<211> LENGTH: 5
<212> TYPE: PRT
<213> ORGANISM: Artificial Sequence
<220> FEATURE:
<223> OTHER INFORMATION: Synthetic peptide

<400> SEQUENCE: 703

Asn Leu Lys His Gln
1               5

<210> SEQ ID NO 704
<211> LENGTH: 4
<212> TYPE: PRT
<213> ORGANISM: Artificial Sequence
<220> FEATURE:
<223> OTHER INFORMATION: Synthetic peptide

<400> SEQUENCE: 704

Leu Lys His Gln
1

<210> SEQ ID NO 705
<211> LENGTH: 3
<212> TYPE: PRT
<213> ORGANISM: Artificial Sequence
<220> FEATURE:
<223> OTHER INFORMATION: Synthetic peptide

<400> SEQUENCE: 705

Lys His Gln
1

<210> SEQ ID NO 706
<211> LENGTH: 6
<212> TYPE: PRT
<213> ORGANISM: Artificial Sequence
<220> FEATURE:
<223> OTHER INFORMATION: Synthetic peptide

<400> SEQUENCE: 706

Thr Glu Asn Leu Lys His
1               5

<210> SEQ ID NO 707
<211> LENGTH: 5
<212> TYPE: PRT
<213> ORGANISM: Artificial Sequence
<220> FEATURE:
<223> OTHER INFORMATION: Synthetic peptide

<400> SEQUENCE: 707

Glu Asn Leu Lys His
```

-continued

```
1                 5

<210> SEQ ID NO 708
<211> LENGTH: 4
<212> TYPE: PRT
<213> ORGANISM: Artificial Sequence
<220> FEATURE:
<223> OTHER INFORMATION: Synthetic peptide

<400> SEQUENCE: 708

Asn Leu Lys His
1

<210> SEQ ID NO 709
<211> LENGTH: 3
<212> TYPE: PRT
<213> ORGANISM: Artificial Sequence
<220> FEATURE:
<223> OTHER INFORMATION: Synthetic peptide

<400> SEQUENCE: 709

Leu Lys His
1

<210> SEQ ID NO 710
<211> LENGTH: 5
<212> TYPE: PRT
<213> ORGANISM: Artificial Sequence
<220> FEATURE:
<223> OTHER INFORMATION: Synthetic peptide

<400> SEQUENCE: 710

Thr Glu Asn Leu Lys
1                 5

<210> SEQ ID NO 711
<211> LENGTH: 4
<212> TYPE: PRT
<213> ORGANISM: Artificial Sequence
<220> FEATURE:
<223> OTHER INFORMATION: Synthetic peptide

<400> SEQUENCE: 711

Glu Asn Leu Lys
1

<210> SEQ ID NO 712
<211> LENGTH: 3
<212> TYPE: PRT
<213> ORGANISM: Artificial Sequence
<220> FEATURE:
<223> OTHER INFORMATION: Synthetic peptide

<400> SEQUENCE: 712

Asn Leu Lys
1

<210> SEQ ID NO 713
<211> LENGTH: 4
<212> TYPE: PRT
<213> ORGANISM: Artificial Sequence
<220> FEATURE:
<223> OTHER INFORMATION: Synthetic peptide

<400> SEQUENCE: 713

Thr Glu Asn Leu
1
```

```
<210> SEQ ID NO 714
<211> LENGTH: 3
<212> TYPE: PRT
<213> ORGANISM: Artificial Sequence
<220> FEATURE:
<223> OTHER INFORMATION: Synthetic peptide

<400> SEQUENCE: 714

Glu Asn Leu
1

<210> SEQ ID NO 715
<211> LENGTH: 3
<212> TYPE: PRT
<213> ORGANISM: Artificial Sequence
<220> FEATURE:
<223> OTHER INFORMATION: Synthetic peptide

<400> SEQUENCE: 715

Thr Glu Asn
1

<210> SEQ ID NO 716
<211> LENGTH: 11
<212> TYPE: PRT
<213> ORGANISM: Artificial Sequence
<220> FEATURE:
<223> OTHER INFORMATION: Synthetic peptide

<400> SEQUENCE: 716

Lys Asp Asn Ile Lys His Val Pro Gly Gly Gly
1               5                   10

<210> SEQ ID NO 717
<211> LENGTH: 4
<212> TYPE: PRT
<213> ORGANISM: Artificial Sequence
<220> FEATURE:
<223> OTHER INFORMATION: Synthetic peptide

<400> SEQUENCE: 717

Lys Asp Asn Ile
1

<210> SEQ ID NO 718
<211> LENGTH: 3
<212> TYPE: PRT
<213> ORGANISM: Artificial Sequence
<220> FEATURE:
<223> OTHER INFORMATION: Synthetic peptide

<400> SEQUENCE: 718

Lys Asp Asn
1

<210> SEQ ID NO 719
<211> LENGTH: 7
<212> TYPE: PRT
<213> ORGANISM: Artificial Sequence
<220> FEATURE:
<223> OTHER INFORMATION: Synthetic peptide

<400> SEQUENCE: 719

Ile Lys His Val Gly Gly Gly
1               5
```

<210> SEQ ID NO 720
<211> LENGTH: 6
<212> TYPE: PRT
<213> ORGANISM: Artificial Sequence
<220> FEATURE:
<223> OTHER INFORMATION: Synthetic peptide

<400> SEQUENCE: 720

Ile Lys His Val Gly Gly
1               5

<210> SEQ ID NO 721
<211> LENGTH: 5
<212> TYPE: PRT
<213> ORGANISM: Artificial Sequence
<220> FEATURE:
<223> OTHER INFORMATION: Synthetic peptide

<400> SEQUENCE: 721

Ile Lys His Val Gly
1               5

<210> SEQ ID NO 722
<211> LENGTH: 6
<212> TYPE: PRT
<213> ORGANISM: Artificial Sequence
<220> FEATURE:
<223> OTHER INFORMATION: Synthetic peptide

<400> SEQUENCE: 722

Lys His Val Gly Gly Gly
1               5

<210> SEQ ID NO 723
<211> LENGTH: 5
<212> TYPE: PRT
<213> ORGANISM: Artificial Sequence
<220> FEATURE:
<223> OTHER INFORMATION: Synthetic peptide

<400> SEQUENCE: 723

Lys His Val Gly Gly
1               5

<210> SEQ ID NO 724
<211> LENGTH: 4
<212> TYPE: PRT
<213> ORGANISM: Artificial Sequence
<220> FEATURE:
<223> OTHER INFORMATION: Synthetic peptide

<400> SEQUENCE: 724

Lys His Val Gly
1

<210> SEQ ID NO 725
<211> LENGTH: 11
<212> TYPE: PRT
<213> ORGANISM: Artificial Sequence
<220> FEATURE:
<223> OTHER INFORMATION: Synthetic peptide

<400> SEQUENCE: 725

Leu Gly Asn Ile His His Lys Pro Gly Gly Gly
1               5                   10

```
<210> SEQ ID NO 726
<211> LENGTH: 10
<212> TYPE: PRT
<213> ORGANISM: Artificial Sequence
<220> FEATURE:
<223> OTHER INFORMATION: Synthetic peptide

<400> SEQUENCE: 726

Gly Asn Ile His His Lys Pro Gly Gly Gly
1               5                   10

<210> SEQ ID NO 727
<211> LENGTH: 9
<212> TYPE: PRT
<213> ORGANISM: Artificial Sequence
<220> FEATURE:
<223> OTHER INFORMATION: Synthetic peptide

<400> SEQUENCE: 727

Asn Ile His His Lys Pro Gly Gly Gly
1               5

<210> SEQ ID NO 728
<211> LENGTH: 8
<212> TYPE: PRT
<213> ORGANISM: Artificial Sequence
<220> FEATURE:
<223> OTHER INFORMATION: Synthetic peptide

<400> SEQUENCE: 728

Ile His His Lys Pro Gly Gly Gly
1               5

<210> SEQ ID NO 729
<211> LENGTH: 7
<212> TYPE: PRT
<213> ORGANISM: Artificial Sequence
<220> FEATURE:
<223> OTHER INFORMATION: Synthetic peptide

<400> SEQUENCE: 729

His His Lys Pro Gly Gly Gly
1               5

<210> SEQ ID NO 730
<211> LENGTH: 5
<212> TYPE: PRT
<213> ORGANISM: Artificial Sequence
<220> FEATURE:
<223> OTHER INFORMATION: Synthetic peptide

<400> SEQUENCE: 730

Lys Pro Gly Gly Gly
1               5

<210> SEQ ID NO 731
<211> LENGTH: 10
<212> TYPE: PRT
<213> ORGANISM: Artificial Sequence
<220> FEATURE:
<223> OTHER INFORMATION: Synthetic peptide

<400> SEQUENCE: 731

Leu Gly Asn Ile His His Lys Pro Gly Gly
1               5                   10

<210> SEQ ID NO 732
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 732

Gly Asn Ile His His Lys Pro Gly Gly
1               5

<210> SEQ ID NO 733
<211> LENGTH: 8
<212> TYPE: PRT
<213> ORGANISM: Artificial Sequence
<220> FEATURE:
<223> OTHER INFORMATION: Synthetic peptide

<400> SEQUENCE: 733

Asn Ile His His Lys Pro Gly Gly
1               5

<210> SEQ ID NO 734
<211> LENGTH: 7
<212> TYPE: PRT
<213> ORGANISM: Artificial Sequence
<220> FEATURE:
<223> OTHER INFORMATION: Synthetic peptide

<400> SEQUENCE: 734

Ile His His Lys Pro Gly Gly
1               5

<210> SEQ ID NO 735
<211> LENGTH: 6
<212> TYPE: PRT
<213> ORGANISM: Artificial Sequence
<220> FEATURE:
<223> OTHER INFORMATION: Synthetic peptide

<400> SEQUENCE: 735

His His Lys Pro Gly Gly
1               5

<210> SEQ ID NO 736
<211> LENGTH: 4
<212> TYPE: PRT
<213> ORGANISM: Artificial Sequence
<220> FEATURE:
<223> OTHER INFORMATION: Synthetic peptide

<400> SEQUENCE: 736

Lys Pro Gly Gly
1

<210> SEQ ID NO 737
<211> LENGTH: 9
<212> TYPE: PRT
<213> ORGANISM: Artificial Sequence
<220> FEATURE:
<223> OTHER INFORMATION: Synthetic peptide

<400> SEQUENCE: 737

Leu Gly Asn Ile His His Lys Pro Gly
1               5

<210> SEQ ID NO 738
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 738

Gly Asn Ile His His Lys Pro Gly
1               5

<210> SEQ ID NO 739
<211> LENGTH: 7
<212> TYPE: PRT
<213> ORGANISM: Artificial Sequence
<220> FEATURE:
<223> OTHER INFORMATION: Synthetic peptide

<400> SEQUENCE: 739

Asn Ile His His Lys Pro Gly
1               5

<210> SEQ ID NO 740
<211> LENGTH: 6
<212> TYPE: PRT
<213> ORGANISM: Artificial Sequence
<220> FEATURE:
<223> OTHER INFORMATION: Synthetic peptide

<400> SEQUENCE: 740

Ile His His Lys Pro Gly
1               5

<210> SEQ ID NO 741
<211> LENGTH: 5
<212> TYPE: PRT
<213> ORGANISM: Artificial Sequence
<220> FEATURE:
<223> OTHER INFORMATION: Synthetic peptide

<400> SEQUENCE: 741

His His Lys Pro Gly
1               5

<210> SEQ ID NO 742
<211> LENGTH: 4
<212> TYPE: PRT
<213> ORGANISM: Artificial Sequence
<220> FEATURE:
<223> OTHER INFORMATION: Synthetic peptide

<400> SEQUENCE: 742

His Lys Pro Gly
1

<210> SEQ ID NO 743
<211> LENGTH: 3
<212> TYPE: PRT
<213> ORGANISM: Artificial Sequence
<220> FEATURE:
<223> OTHER INFORMATION: Synthetic peptide

<400> SEQUENCE: 743

Lys Pro Gly
1

<210> SEQ ID NO 744
<211> LENGTH: 8
<212> TYPE: PRT
```

-continued

```
<213> ORGANISM: Artificial Sequence
<220> FEATURE:
<223> OTHER INFORMATION: Synthetic peptide

<400> SEQUENCE: 744

Leu Gly Asn Ile His His Lys Pro
1               5

<210> SEQ ID NO 745
<211> LENGTH: 7
<212> TYPE: PRT
<213> ORGANISM: Artificial Sequence
<220> FEATURE:
<223> OTHER INFORMATION: Synthetic peptide

<400> SEQUENCE: 745

Gly Asn Ile His His Lys Pro
1               5

<210> SEQ ID NO 746
<211> LENGTH: 6
<212> TYPE: PRT
<213> ORGANISM: Artificial Sequence
<220> FEATURE:
<223> OTHER INFORMATION: Synthetic peptide

<400> SEQUENCE: 746

Asn Ile His His Lys Pro
1               5

<210> SEQ ID NO 747
<211> LENGTH: 5
<212> TYPE: PRT
<213> ORGANISM: Artificial Sequence
<220> FEATURE:
<223> OTHER INFORMATION: Synthetic peptide

<400> SEQUENCE: 747

Ile His His Lys Pro
1               5

<210> SEQ ID NO 748
<211> LENGTH: 4
<212> TYPE: PRT
<213> ORGANISM: Artificial Sequence
<220> FEATURE:
<223> OTHER INFORMATION: Synthetic peptide

<400> SEQUENCE: 748

His His Lys Pro
1

<210> SEQ ID NO 749
<211> LENGTH: 3
<212> TYPE: PRT
<213> ORGANISM: Artificial Sequence
<220> FEATURE:
<223> OTHER INFORMATION: Synthetic peptide

<400> SEQUENCE: 749

His Lys Pro
1

<210> SEQ ID NO 750
<211> LENGTH: 7
<212> TYPE: PRT
<213> ORGANISM: Artificial Sequence
```

-continued

```
<220> FEATURE:
<223> OTHER INFORMATION: Synthetic peptide

<400> SEQUENCE: 750

Leu Gly Asn Ile His His Lys
1               5

<210> SEQ ID NO 751
<211> LENGTH: 6
<212> TYPE: PRT
<213> ORGANISM: Artificial Sequence
<220> FEATURE:
<223> OTHER INFORMATION: Synthetic peptide

<400> SEQUENCE: 751

Gly Asn Ile His His Lys
1               5

<210> SEQ ID NO 752
<211> LENGTH: 5
<212> TYPE: PRT
<213> ORGANISM: Artificial Sequence
<220> FEATURE:
<223> OTHER INFORMATION: Synthetic peptide

<400> SEQUENCE: 752

Asn Ile His His Lys
1               5

<210> SEQ ID NO 753
<211> LENGTH: 4
<212> TYPE: PRT
<213> ORGANISM: Artificial Sequence
<220> FEATURE:
<223> OTHER INFORMATION: Synthetic peptide

<400> SEQUENCE: 753

Ile His His Lys
1

<210> SEQ ID NO 754
<211> LENGTH: 3
<212> TYPE: PRT
<213> ORGANISM: Artificial Sequence
<220> FEATURE:
<223> OTHER INFORMATION: Synthetic peptide

<400> SEQUENCE: 754

His His Lys
1

<210> SEQ ID NO 755
<211> LENGTH: 6
<212> TYPE: PRT
<213> ORGANISM: Artificial Sequence
<220> FEATURE:
<223> OTHER INFORMATION: Synthetic peptide

<400> SEQUENCE: 755

Leu Gly Asn Ile His His
1               5

<210> SEQ ID NO 756
<211> LENGTH: 5
<212> TYPE: PRT
<213> ORGANISM: Artificial Sequence
<220> FEATURE:
```

-continued

<223> OTHER INFORMATION: Synthetic peptide

<400> SEQUENCE: 756

Gly Asn Ile His His
1               5

<210> SEQ ID NO 757
<211> LENGTH: 4
<212> TYPE: PRT
<213> ORGANISM: Artificial Sequence
<220> FEATURE:
<223> OTHER INFORMATION: Synthetic peptide

<400> SEQUENCE: 757

Asn Ile His His
1

<210> SEQ ID NO 758
<211> LENGTH: 3
<212> TYPE: PRT
<213> ORGANISM: Artificial Sequence
<220> FEATURE:
<223> OTHER INFORMATION: Synthetic peptide

<400> SEQUENCE: 758

Ile His His
1

<210> SEQ ID NO 759
<211> LENGTH: 5
<212> TYPE: PRT
<213> ORGANISM: Artificial Sequence
<220> FEATURE:
<223> OTHER INFORMATION: Synthetic peptide

<400> SEQUENCE: 759

Leu Gly Asn Ile His
1               5

<210> SEQ ID NO 760
<211> LENGTH: 4
<212> TYPE: PRT
<213> ORGANISM: Artificial Sequence
<220> FEATURE:
<223> OTHER INFORMATION: Synthetic peptide

<400> SEQUENCE: 760

Gly Asn Ile His
1

<210> SEQ ID NO 761
<211> LENGTH: 3
<212> TYPE: PRT
<213> ORGANISM: Artificial Sequence
<220> FEATURE:
<223> OTHER INFORMATION: Synthetic peptide

<400> SEQUENCE: 761

Asn Ile His
1

<210> SEQ ID NO 762
<211> LENGTH: 4
<212> TYPE: PRT
<213> ORGANISM: Artificial Sequence
<220> FEATURE:
<223> OTHER INFORMATION: Synthetic peptide -continued

<400> SEQUENCE: 762

Leu Gly Asn Ile
1

<210> SEQ ID NO 763
<211> LENGTH: 3
<212> TYPE: PRT
<213> ORGANISM: Artificial Sequence
<220> FEATURE:
<223> OTHER INFORMATION: Synthetic peptide

<400> SEQUENCE: 763

Gly Asn Ile
1

<210> SEQ ID NO 764
<211> LENGTH: 3
<212> TYPE: PRT
<213> ORGANISM: Artificial Sequence
<220> FEATURE:
<223> OTHER INFORMATION: Synthetic peptide

<400> SEQUENCE: 764

Leu Gly Asn
1

<210> SEQ ID NO 765
<211> LENGTH: 11
<212> TYPE: PRT
<213> ORGANISM: Artificial Sequence
<220> FEATURE:
<223> OTHER INFORMATION: Synthetic peptide

<400> SEQUENCE: 765

Leu Asp Asn Ile Thr His Val Pro Gly Gly Gly
1               5                   10

<210> SEQ ID NO 766
<211> LENGTH: 10
<212> TYPE: PRT
<213> ORGANISM: Artificial Sequence
<220> FEATURE:
<223> OTHER INFORMATION: Synthetic peptide

<400> SEQUENCE: 766

Asp Asn Ile Thr His Val Pro Gly Gly Gly
1               5                   10

<210> SEQ ID NO 767
<211> LENGTH: 9
<212> TYPE: PRT
<213> ORGANISM: Artificial Sequence
<220> FEATURE:
<223> OTHER INFORMATION: Synthetic peptide

<400> SEQUENCE: 767

Asn Ile Thr His Val Pro Gly Gly Gly
1               5

<210> SEQ ID NO 768
<211> LENGTH: 8
<212> TYPE: PRT
<213> ORGANISM: Artificial Sequence
<220> FEATURE:
<223> OTHER INFORMATION: Synthetic peptide -continued

```
<400> SEQUENCE: 768

Ile Thr His Val Pro Gly Gly Gly
1               5

<210> SEQ ID NO 769
<211> LENGTH: 7
<212> TYPE: PRT
<213> ORGANISM: Artificial Sequence
<220> FEATURE:
<223> OTHER INFORMATION: Synthetic peptide

<400> SEQUENCE: 769

Thr His Val Pro Gly Gly Gly
1               5

<210> SEQ ID NO 770
<211> LENGTH: 10
<212> TYPE: PRT
<213> ORGANISM: Artificial Sequence
<220> FEATURE:
<223> OTHER INFORMATION: Synthetic peptide

<400> SEQUENCE: 770

Leu Asp Asn Ile Thr His Val Pro Gly Gly
1               5                   10

<210> SEQ ID NO 771
<211> LENGTH: 9
<212> TYPE: PRT
<213> ORGANISM: Artificial Sequence
<220> FEATURE:
<223> OTHER INFORMATION: Synthetic peptide

<400> SEQUENCE: 771

Asp Asn Ile Thr His Val Pro Gly Gly
1               5

<210> SEQ ID NO 772
<211> LENGTH: 8
<212> TYPE: PRT
<213> ORGANISM: Artificial Sequence
<220> FEATURE:
<223> OTHER INFORMATION: Synthetic peptide

<400> SEQUENCE: 772

Asn Ile Thr His Val Pro Gly Gly
1               5

<210> SEQ ID NO 773
<211> LENGTH: 7
<212> TYPE: PRT
<213> ORGANISM: Artificial Sequence
<220> FEATURE:
<223> OTHER INFORMATION: Synthetic peptide

<400> SEQUENCE: 773

Ile Thr His Val Pro Gly Gly
1               5

<210> SEQ ID NO 774
<211> LENGTH: 6
<212> TYPE: PRT
<213> ORGANISM: Artificial Sequence
<220> FEATURE:
<223> OTHER INFORMATION: Synthetic peptide

<400> SEQUENCE: 774
```

-continued

```
Thr His Val Pro Gly Gly
1               5

<210> SEQ ID NO 775
<211> LENGTH: 9
<212> TYPE: PRT
<213> ORGANISM: Artificial Sequence
<220> FEATURE:
<223> OTHER INFORMATION: Synthetic peptide

<400> SEQUENCE: 775

Leu Asp Asn Ile Thr His Val Pro Gly
1               5

<210> SEQ ID NO 776
<211> LENGTH: 8
<212> TYPE: PRT
<213> ORGANISM: Artificial Sequence
<220> FEATURE:
<223> OTHER INFORMATION: Synthetic peptide

<400> SEQUENCE: 776

Asp Asn Ile Thr His Val Pro Gly
1               5

<210> SEQ ID NO 777
<211> LENGTH: 7
<212> TYPE: PRT
<213> ORGANISM: Artificial Sequence
<220> FEATURE:
<223> OTHER INFORMATION: Synthetic peptide

<400> SEQUENCE: 777

Asn Ile Thr His Val Pro Gly
1               5

<210> SEQ ID NO 778
<211> LENGTH: 6
<212> TYPE: PRT
<213> ORGANISM: Artificial Sequence
<220> FEATURE:
<223> OTHER INFORMATION: Synthetic peptide

<400> SEQUENCE: 778

Ile Thr His Val Pro Gly
1               5

<210> SEQ ID NO 779
<211> LENGTH: 5
<212> TYPE: PRT
<213> ORGANISM: Artificial Sequence
<220> FEATURE:
<223> OTHER INFORMATION: Synthetic peptide

<400> SEQUENCE: 779

Thr His Val Pro Gly
1               5

<210> SEQ ID NO 780
<211> LENGTH: 8
<212> TYPE: PRT
<213> ORGANISM: Artificial Sequence
<220> FEATURE:
<223> OTHER INFORMATION: Synthetic peptide

<400> SEQUENCE: 780
```

```
Leu Asp Asn Ile Thr His Val Pro
1               5

<210> SEQ ID NO 781
<211> LENGTH: 7
<212> TYPE: PRT
<213> ORGANISM: Artificial Sequence
<220> FEATURE:
<223> OTHER INFORMATION: Synthetic peptide

<400> SEQUENCE: 781

Asp Asn Ile Thr His Val Pro
1               5

<210> SEQ ID NO 782
<211> LENGTH: 6
<212> TYPE: PRT
<213> ORGANISM: Artificial Sequence
<220> FEATURE:
<223> OTHER INFORMATION: Synthetic peptide

<400> SEQUENCE: 782

Asn Ile Thr His Val Pro
1               5

<210> SEQ ID NO 783
<211> LENGTH: 5
<212> TYPE: PRT
<213> ORGANISM: Artificial Sequence
<220> FEATURE:
<223> OTHER INFORMATION: Synthetic peptide

<400> SEQUENCE: 783

Ile Thr His Val Pro
1               5

<210> SEQ ID NO 784
<211> LENGTH: 4
<212> TYPE: PRT
<213> ORGANISM: Artificial Sequence
<220> FEATURE:
<223> OTHER INFORMATION: Synthetic peptide

<400> SEQUENCE: 784

Thr His Val Pro
1

<210> SEQ ID NO 785
<211> LENGTH: 7
<212> TYPE: PRT
<213> ORGANISM: Artificial Sequence
<220> FEATURE:
<223> OTHER INFORMATION: Synthetic peptide

<400> SEQUENCE: 785

Leu Asp Asn Ile Thr His Val
1               5

<210> SEQ ID NO 786
<211> LENGTH: 6
<212> TYPE: PRT
<213> ORGANISM: Artificial Sequence
<220> FEATURE:
<223> OTHER INFORMATION: Synthetic peptide

<400> SEQUENCE: 786

Asp Asn Ile Thr His Val
```

-continued

```
1               5

<210> SEQ ID NO 787
<211> LENGTH: 5
<212> TYPE: PRT
<213> ORGANISM: Artificial Sequence
<220> FEATURE:
<223> OTHER INFORMATION: Synthetic peptide

<400> SEQUENCE: 787

Asn Ile Thr His Val
1               5

<210> SEQ ID NO 788
<211> LENGTH: 4
<212> TYPE: PRT
<213> ORGANISM: Artificial Sequence
<220> FEATURE:
<223> OTHER INFORMATION: Synthetic peptide

<400> SEQUENCE: 788

Ile Thr His Val
1

<210> SEQ ID NO 789
<211> LENGTH: 3
<212> TYPE: PRT
<213> ORGANISM: Artificial Sequence
<220> FEATURE:
<223> OTHER INFORMATION: Synthetic peptide

<400> SEQUENCE: 789

Thr His Val
1

<210> SEQ ID NO 790
<211> LENGTH: 6
<212> TYPE: PRT
<213> ORGANISM: Artificial Sequence
<220> FEATURE:
<223> OTHER INFORMATION: Synthetic peptide

<400> SEQUENCE: 790

Leu Asp Asn Ile Thr His
1               5

<210> SEQ ID NO 791
<211> LENGTH: 5
<212> TYPE: PRT
<213> ORGANISM: Artificial Sequence
<220> FEATURE:
<223> OTHER INFORMATION: Synthetic peptide

<400> SEQUENCE: 791

Asp Asn Ile Thr His
1               5

<210> SEQ ID NO 792
<211> LENGTH: 4
<212> TYPE: PRT
<213> ORGANISM: Artificial Sequence
<220> FEATURE:
<223> OTHER INFORMATION: Synthetic peptide

<400> SEQUENCE: 792

Asn Ile Thr His
1
```

```
<210> SEQ ID NO 793
<211> LENGTH: 3
<212> TYPE: PRT
<213> ORGANISM: Artificial Sequence
<220> FEATURE:
<223> OTHER INFORMATION: Synthetic peptide

<400> SEQUENCE: 793

Ile Thr His
1

<210> SEQ ID NO 794
<211> LENGTH: 5
<212> TYPE: PRT
<213> ORGANISM: Artificial Sequence
<220> FEATURE:
<223> OTHER INFORMATION: Synthetic peptide

<400> SEQUENCE: 794

Leu Asp Asn Ile Thr
1               5

<210> SEQ ID NO 795
<211> LENGTH: 4
<212> TYPE: PRT
<213> ORGANISM: Artificial Sequence
<220> FEATURE:
<223> OTHER INFORMATION: Synthetic peptide

<400> SEQUENCE: 795

Asp Asn Ile Thr
1

<210> SEQ ID NO 796
<211> LENGTH: 3
<212> TYPE: PRT
<213> ORGANISM: Artificial Sequence
<220> FEATURE:
<223> OTHER INFORMATION: Synthetic peptide

<400> SEQUENCE: 796

Asn Ile Thr
1

<210> SEQ ID NO 797
<211> LENGTH: 4
<212> TYPE: PRT
<213> ORGANISM: Artificial Sequence
<220> FEATURE:
<223> OTHER INFORMATION: Synthetic peptide

<400> SEQUENCE: 797

Leu Asp Asn Ile
1

<210> SEQ ID NO 798
<211> LENGTH: 3
<212> TYPE: PRT
<213> ORGANISM: Artificial Sequence
<220> FEATURE:
<223> OTHER INFORMATION: Synthetic peptide

<400> SEQUENCE: 798

Leu Asp Asn
1
```

-continued

<210> SEQ ID NO 799
<211> LENGTH: 10
<212> TYPE: PRT
<213> ORGANISM: Artificial Sequence
<220> FEATURE:
<223> OTHER INFORMATION: Synthetic peptide

<400> SEQUENCE: 799

Lys Asn Val Lys Ser Lys Ile Gly Ser Thr
1               5                   10

<210> SEQ ID NO 800
<211> LENGTH: 9
<212> TYPE: PRT
<213> ORGANISM: Artificial Sequence
<220> FEATURE:
<223> OTHER INFORMATION: Synthetic peptide

<400> SEQUENCE: 800

Asn Val Lys Ser Lys Ile Gly Ser Thr
1               5

<210> SEQ ID NO 801
<211> LENGTH: 8
<212> TYPE: PRT
<213> ORGANISM: Artificial Sequence
<220> FEATURE:
<223> OTHER INFORMATION: Synthetic peptide

<400> SEQUENCE: 801

Val Lys Ser Lys Ile Gly Ser Thr
1               5

<210> SEQ ID NO 802
<211> LENGTH: 7
<212> TYPE: PRT
<213> ORGANISM: Artificial Sequence
<220> FEATURE:
<223> OTHER INFORMATION: Synthetic peptide

<400> SEQUENCE: 802

Lys Ser Lys Ile Gly Ser Thr
1               5

<210> SEQ ID NO 803
<211> LENGTH: 6
<212> TYPE: PRT
<213> ORGANISM: Artificial Sequence
<220> FEATURE:
<223> OTHER INFORMATION: Synthetic peptide

<400> SEQUENCE: 803

Ser Lys Ile Gly Ser Thr
1               5

<210> SEQ ID NO 804
<211> LENGTH: 5
<212> TYPE: PRT
<213> ORGANISM: Artificial Sequence
<220> FEATURE:
<223> OTHER INFORMATION: Synthetic peptide

<400> SEQUENCE: 804

Lys Ile Gly Ser Thr
1               5

-continued

```
<210> SEQ ID NO 805
<211> LENGTH: 4
<212> TYPE: PRT
<213> ORGANISM: Artificial Sequence
<220> FEATURE:
<223> OTHER INFORMATION: Synthetic peptide

<400> SEQUENCE: 805

Ile Gly Ser Thr
1

<210> SEQ ID NO 806
<211> LENGTH: 3
<212> TYPE: PRT
<213> ORGANISM: Artificial Sequence
<220> FEATURE:
<223> OTHER INFORMATION: Synthetic peptide

<400> SEQUENCE: 806

Gly Ser Thr
1

<210> SEQ ID NO 807
<211> LENGTH: 10
<212> TYPE: PRT
<213> ORGANISM: Artificial Sequence
<220> FEATURE:
<223> OTHER INFORMATION: Synthetic peptide

<400> SEQUENCE: 807

Asn Val Lys Ser Lys Ile Gly Ser Thr Glu
1               5                   10

<210> SEQ ID NO 808
<211> LENGTH: 9
<212> TYPE: PRT
<213> ORGANISM: Artificial Sequence
<220> FEATURE:
<223> OTHER INFORMATION: Synthetic peptide

<400> SEQUENCE: 808

Val Lys Ser Lys Ile Gly Ser Thr Glu
1               5

<210> SEQ ID NO 809
<211> LENGTH: 8
<212> TYPE: PRT
<213> ORGANISM: Artificial Sequence
<220> FEATURE:
<223> OTHER INFORMATION: Synthetic peptide

<400> SEQUENCE: 809

Lys Ser Lys Ile Gly Ser Thr Glu
1               5

<210> SEQ ID NO 810
<211> LENGTH: 7
<212> TYPE: PRT
<213> ORGANISM: Artificial Sequence
<220> FEATURE:
<223> OTHER INFORMATION: Synthetic peptide

<400> SEQUENCE: 810

Ser Lys Ile Gly Ser Thr Glu
1               5

<210> SEQ ID NO 811
```

-continued

```
<211> LENGTH: 6
<212> TYPE: PRT
<213> ORGANISM: Artificial Sequence
<220> FEATURE:
<223> OTHER INFORMATION: Synthetic peptide

<400> SEQUENCE: 811

Lys Ile Gly Ser Thr Glu
1               5

<210> SEQ ID NO 812
<211> LENGTH: 5
<212> TYPE: PRT
<213> ORGANISM: Artificial Sequence
<220> FEATURE:
<223> OTHER INFORMATION: Synthetic peptide

<400> SEQUENCE: 812

Ile Gly Ser Thr Glu
1               5

<210> SEQ ID NO 813
<211> LENGTH: 4
<212> TYPE: PRT
<213> ORGANISM: Artificial Sequence
<220> FEATURE:
<223> OTHER INFORMATION: Synthetic peptide

<400> SEQUENCE: 813

Gly Ser Thr Glu
1

<210> SEQ ID NO 814
<211> LENGTH: 3
<212> TYPE: PRT
<213> ORGANISM: Artificial Sequence
<220> FEATURE:
<223> OTHER INFORMATION: Synthetic peptide

<400> SEQUENCE: 814

Ser Thr Glu
1

<210> SEQ ID NO 815
<211> LENGTH: 10
<212> TYPE: PRT
<213> ORGANISM: Artificial Sequence
<220> FEATURE:
<223> OTHER INFORMATION: Synthetic peptide

<400> SEQUENCE: 815

Val Lys Ser Lys Ile Gly Ser Thr Glu Asn
1               5                   10

<210> SEQ ID NO 816
<211> LENGTH: 9
<212> TYPE: PRT
<213> ORGANISM: Artificial Sequence
<220> FEATURE:
<223> OTHER INFORMATION: Synthetic peptide

<400> SEQUENCE: 816

Lys Ser Lys Ile Gly Ser Thr Glu Asn
1               5

<210> SEQ ID NO 817
<211> LENGTH: 8
```

-continued

```
<212> TYPE: PRT
<213> ORGANISM: Artificial Sequence
<220> FEATURE:
<223> OTHER INFORMATION: Synthetic peptide

<400> SEQUENCE: 817

Ser Lys Ile Gly Ser Thr Glu Asn
1               5

<210> SEQ ID NO 818
<211> LENGTH: 7
<212> TYPE: PRT
<213> ORGANISM: Artificial Sequence
<220> FEATURE:
<223> OTHER INFORMATION: Synthetic peptide

<400> SEQUENCE: 818

Lys Ile Gly Ser Thr Glu Asn
1               5

<210> SEQ ID NO 819
<211> LENGTH: 6
<212> TYPE: PRT
<213> ORGANISM: Artificial Sequence
<220> FEATURE:
<223> OTHER INFORMATION: Synthetic peptide

<400> SEQUENCE: 819

Ile Gly Ser Thr Glu Asn
1               5

<210> SEQ ID NO 820
<211> LENGTH: 5
<212> TYPE: PRT
<213> ORGANISM: Artificial Sequence
<220> FEATURE:
<223> OTHER INFORMATION: Synthetic peptide

<400> SEQUENCE: 820

Gly Ser Thr Glu Asn
1               5

<210> SEQ ID NO 821
<211> LENGTH: 4
<212> TYPE: PRT
<213> ORGANISM: Artificial Sequence
<220> FEATURE:
<223> OTHER INFORMATION: Synthetic peptide

<400> SEQUENCE: 821

Ser Thr Glu Asn
1

<210> SEQ ID NO 822
<211> LENGTH: 10
<212> TYPE: PRT
<213> ORGANISM: Artificial Sequence
<220> FEATURE:
<223> OTHER INFORMATION: Synthetic peptide

<400> SEQUENCE: 822

Lys Ser Lys Ile Gly Ser Thr Glu Asn Leu
1               5                   10

<210> SEQ ID NO 823
<211> LENGTH: 9
<212> TYPE: PRT
```

-continued

```
<213> ORGANISM: Artificial Sequence
<220> FEATURE:
<223> OTHER INFORMATION: Synthetic peptide

<400> SEQUENCE: 823

Ser Lys Ile Gly Ser Thr Glu Asn Leu
1               5

<210> SEQ ID NO 824
<211> LENGTH: 8
<212> TYPE: PRT
<213> ORGANISM: Artificial Sequence
<220> FEATURE:
<223> OTHER INFORMATION: Synthetic peptide

<400> SEQUENCE: 824

Lys Ile Gly Ser Thr Glu Asn Leu
1               5

<210> SEQ ID NO 825
<211> LENGTH: 7
<212> TYPE: PRT
<213> ORGANISM: Artificial Sequence
<220> FEATURE:
<223> OTHER INFORMATION: Synthetic peptide

<400> SEQUENCE: 825

Ile Gly Ser Thr Glu Asn Leu
1               5

<210> SEQ ID NO 826
<211> LENGTH: 6
<212> TYPE: PRT
<213> ORGANISM: Artificial Sequence
<220> FEATURE:
<223> OTHER INFORMATION: Synthetic peptide

<400> SEQUENCE: 826

Gly Ser Thr Glu Asn Leu
1               5

<210> SEQ ID NO 827
<211> LENGTH: 5
<212> TYPE: PRT
<213> ORGANISM: Artificial Sequence
<220> FEATURE:
<223> OTHER INFORMATION: Synthetic peptide

<400> SEQUENCE: 827

Ser Thr Glu Asn Leu
1               5

<210> SEQ ID NO 828
<211> LENGTH: 10
<212> TYPE: PRT
<213> ORGANISM: Artificial Sequence
<220> FEATURE:
<223> OTHER INFORMATION: Synthetic peptide

<400> SEQUENCE: 828

Ser Lys Ile Gly Ser Thr Glu Asn Leu Lys
1               5                   10

<210> SEQ ID NO 829
<211> LENGTH: 9
<212> TYPE: PRT
<213> ORGANISM: Artificial Sequence
```

-continued

```
<220> FEATURE:
<223> OTHER INFORMATION: Synthetic peptide

<400> SEQUENCE: 829

Lys Ile Gly Ser Thr Glu Asn Leu Lys
1               5

<210> SEQ ID NO 830
<211> LENGTH: 8
<212> TYPE: PRT
<213> ORGANISM: Artificial Sequence
<220> FEATURE:
<223> OTHER INFORMATION: Synthetic peptide

<400> SEQUENCE: 830

Ile Gly Ser Thr Glu Asn Leu Lys
1               5

<210> SEQ ID NO 831
<211> LENGTH: 7
<212> TYPE: PRT
<213> ORGANISM: Artificial Sequence
<220> FEATURE:
<223> OTHER INFORMATION: Synthetic peptide

<400> SEQUENCE: 831

Gly Ser Thr Glu Asn Leu Lys
1               5

<210> SEQ ID NO 832
<211> LENGTH: 6
<212> TYPE: PRT
<213> ORGANISM: Artificial Sequence
<220> FEATURE:
<223> OTHER INFORMATION: Synthetic peptide

<400> SEQUENCE: 832

Ser Thr Glu Asn Leu Lys
1               5

<210> SEQ ID NO 833
<211> LENGTH: 10
<212> TYPE: PRT
<213> ORGANISM: Artificial Sequence
<220> FEATURE:
<223> OTHER INFORMATION: Synthetic peptide

<400> SEQUENCE: 833

Lys Ile Gly Ser Thr Glu Asn Leu Lys His
1               5                   10

<210> SEQ ID NO 834
<211> LENGTH: 9
<212> TYPE: PRT
<213> ORGANISM: Artificial Sequence
<220> FEATURE:
<223> OTHER INFORMATION: Synthetic peptide

<400> SEQUENCE: 834

Ile Gly Ser Thr Glu Asn Leu Lys His
1               5

<210> SEQ ID NO 835
<211> LENGTH: 8
<212> TYPE: PRT
<213> ORGANISM: Artificial Sequence
<220> FEATURE:
```

-continued

```
<223> OTHER INFORMATION: Synthetic peptide

<400> SEQUENCE: 835

Gly Ser Thr Glu Asn Leu Lys His
1               5

<210> SEQ ID NO 836
<211> LENGTH: 7
<212> TYPE: PRT
<213> ORGANISM: Artificial Sequence
<220> FEATURE:
<223> OTHER INFORMATION: Synthetic peptide

<400> SEQUENCE: 836

Ser Thr Glu Asn Leu Lys His
1               5

<210> SEQ ID NO 837
<211> LENGTH: 10
<212> TYPE: PRT
<213> ORGANISM: Artificial Sequence
<220> FEATURE:
<223> OTHER INFORMATION: Synthetic peptide

<400> SEQUENCE: 837

Ile Gly Ser Thr Glu Asn Leu Lys His Gln
1               5                   10

<210> SEQ ID NO 838
<211> LENGTH: 9
<212> TYPE: PRT
<213> ORGANISM: Artificial Sequence
<220> FEATURE:
<223> OTHER INFORMATION: Synthetic peptide

<400> SEQUENCE: 838

Gly Ser Thr Glu Asn Leu Lys His Gln
1               5

<210> SEQ ID NO 839
<211> LENGTH: 8
<212> TYPE: PRT
<213> ORGANISM: Artificial Sequence
<220> FEATURE:
<223> OTHER INFORMATION: Synthetic peptide

<400> SEQUENCE: 839

Ser Thr Glu Asn Leu Lys His Gln
1               5

<210> SEQ ID NO 840
<211> LENGTH: 10
<212> TYPE: PRT
<213> ORGANISM: Artificial Sequence
<220> FEATURE:
<223> OTHER INFORMATION: Synthetic peptide

<400> SEQUENCE: 840

Gly Ser Thr Glu Asn Leu Lys His Gln Pro
1               5                   10

<210> SEQ ID NO 841
<211> LENGTH: 9
<212> TYPE: PRT
<213> ORGANISM: Artificial Sequence
<220> FEATURE:
<223> OTHER INFORMATION: Synthetic peptide
```

<400> SEQUENCE: 841

Ser Thr Glu Asn Leu Lys His Gln Pro
1               5

<210> SEQ ID NO 842
<211> LENGTH: 10
<212> TYPE: PRT
<213> ORGANISM: Artificial Sequence
<220> FEATURE:
<223> OTHER INFORMATION: Synthetic peptide

<400> SEQUENCE: 842

Ser Thr Glu Asn Leu Lys His Gln Pro Gly
1               5                   10

<210> SEQ ID NO 843
<211> LENGTH: 10
<212> TYPE: PRT
<213> ORGANISM: Artificial Sequence
<220> FEATURE:
<223> OTHER INFORMATION: Synthetic peptide

<400> SEQUENCE: 843

Ser Asn Val Gln Ser Lys Cys Gly Ser Lys
1               5                   10

<210> SEQ ID NO 844
<211> LENGTH: 9
<212> TYPE: PRT
<213> ORGANISM: Artificial Sequence
<220> FEATURE:
<223> OTHER INFORMATION: Synthetic peptide

<400> SEQUENCE: 844

Asn Val Gln Ser Lys Cys Gly Ser Lys
1               5

<210> SEQ ID NO 845
<211> LENGTH: 8
<212> TYPE: PRT
<213> ORGANISM: Artificial Sequence
<220> FEATURE:
<223> OTHER INFORMATION: Synthetic peptide

<400> SEQUENCE: 845

Val Gln Ser Lys Cys Gly Ser Lys
1               5

<210> SEQ ID NO 846
<211> LENGTH: 7
<212> TYPE: PRT
<213> ORGANISM: Artificial Sequence
<220> FEATURE:
<223> OTHER INFORMATION: Synthetic peptide

<400> SEQUENCE: 846

Gln Ser Lys Cys Gly Ser Lys
1               5

<210> SEQ ID NO 847
<211> LENGTH: 6
<212> TYPE: PRT
<213> ORGANISM: Artificial Sequence
<220> FEATURE:
<223> OTHER INFORMATION: Synthetic peptide -continued

<400> SEQUENCE: 847

Ser Lys Cys Gly Ser Lys
1               5

<210> SEQ ID NO 848
<211> LENGTH: 5
<212> TYPE: PRT
<213> ORGANISM: Artificial Sequence
<220> FEATURE:
<223> OTHER INFORMATION: Synthetic peptide

<400> SEQUENCE: 848

Lys Cys Gly Ser Lys
1               5

<210> SEQ ID NO 849
<211> LENGTH: 4
<212> TYPE: PRT
<213> ORGANISM: Artificial Sequence
<220> FEATURE:
<223> OTHER INFORMATION: Synthetic peptide

<400> SEQUENCE: 849

Cys Gly Ser Lys
1

<210> SEQ ID NO 850
<211> LENGTH: 3
<212> TYPE: PRT
<213> ORGANISM: Artificial Sequence
<220> FEATURE:
<223> OTHER INFORMATION: Synthetic peptide

<400> SEQUENCE: 850

Gly Ser Lys
1

<210> SEQ ID NO 851
<211> LENGTH: 10
<212> TYPE: PRT
<213> ORGANISM: Artificial Sequence
<220> FEATURE:
<223> OTHER INFORMATION: Synthetic peptide

<400> SEQUENCE: 851

Asn Val Gln Ser Lys Cys Gly Ser Lys Asp
1               5                   10

<210> SEQ ID NO 852
<211> LENGTH: 9
<212> TYPE: PRT
<213> ORGANISM: Artificial Sequence
<220> FEATURE:
<223> OTHER INFORMATION: Synthetic peptide

<400> SEQUENCE: 852

Val Gln Ser Lys Cys Gly Ser Lys Asp
1               5

<210> SEQ ID NO 853
<211> LENGTH: 8
<212> TYPE: PRT
<213> ORGANISM: Artificial Sequence
<220> FEATURE:
<223> OTHER INFORMATION: Synthetic peptide

<400> SEQUENCE: 853

```
Gln Ser Lys Cys Gly Ser Lys Asp
1               5

<210> SEQ ID NO 854
<211> LENGTH: 7
<212> TYPE: PRT
<213> ORGANISM: Artificial Sequence
<220> FEATURE:
<223> OTHER INFORMATION: Synthetic peptide

<400> SEQUENCE: 854

Ser Lys Cys Gly Ser Lys Asp
1               5

<210> SEQ ID NO 855
<211> LENGTH: 6
<212> TYPE: PRT
<213> ORGANISM: Artificial Sequence
<220> FEATURE:
<223> OTHER INFORMATION: Synthetic peptide

<400> SEQUENCE: 855

Lys Cys Gly Ser Lys Asp
1               5

<210> SEQ ID NO 856
<211> LENGTH: 5
<212> TYPE: PRT
<213> ORGANISM: Artificial Sequence
<220> FEATURE:
<223> OTHER INFORMATION: Synthetic peptide

<400> SEQUENCE: 856

Cys Gly Ser Lys Asp
1               5

<210> SEQ ID NO 857
<211> LENGTH: 4
<212> TYPE: PRT
<213> ORGANISM: Artificial Sequence
<220> FEATURE:
<223> OTHER INFORMATION: Synthetic peptide

<400> SEQUENCE: 857

Gly Ser Lys Asp
1

<210> SEQ ID NO 858
<211> LENGTH: 3
<212> TYPE: PRT
<213> ORGANISM: Artificial Sequence
<220> FEATURE:
<223> OTHER INFORMATION: Synthetic peptide

<400> SEQUENCE: 858

Ser Lys Asp
1

<210> SEQ ID NO 859
<211> LENGTH: 10
<212> TYPE: PRT
<213> ORGANISM: Artificial Sequence
<220> FEATURE:
<223> OTHER INFORMATION: Synthetic peptide

<400> SEQUENCE: 859
```

```
Val Gln Ser Lys Cys Gly Ser Lys Asp Asn
1               5                   10

<210> SEQ ID NO 860
<211> LENGTH: 9
<212> TYPE: PRT
<213> ORGANISM: Artificial Sequence
<220> FEATURE:
<223> OTHER INFORMATION: Synthetic peptide

<400> SEQUENCE: 860

Gln Ser Lys Cys Gly Ser Lys Asp Asn
1               5

<210> SEQ ID NO 861
<211> LENGTH: 8
<212> TYPE: PRT
<213> ORGANISM: Artificial Sequence
<220> FEATURE:
<223> OTHER INFORMATION: Synthetic peptide

<400> SEQUENCE: 861

Ser Lys Cys Gly Ser Lys Asp Asn
1               5

<210> SEQ ID NO 862
<211> LENGTH: 7
<212> TYPE: PRT
<213> ORGANISM: Artificial Sequence
<220> FEATURE:
<223> OTHER INFORMATION: Synthetic peptide

<400> SEQUENCE: 862

Lys Cys Gly Ser Lys Asp Asn
1               5

<210> SEQ ID NO 863
<211> LENGTH: 6
<212> TYPE: PRT
<213> ORGANISM: Artificial Sequence
<220> FEATURE:
<223> OTHER INFORMATION: Synthetic peptide

<400> SEQUENCE: 863

Cys Gly Ser Lys Asp Asn
1               5

<210> SEQ ID NO 864
<211> LENGTH: 5
<212> TYPE: PRT
<213> ORGANISM: Artificial Sequence
<220> FEATURE:
<223> OTHER INFORMATION: Synthetic peptide

<400> SEQUENCE: 864

Gly Ser Lys Asp Asn
1               5

<210> SEQ ID NO 865
<211> LENGTH: 4
<212> TYPE: PRT
<213> ORGANISM: Artificial Sequence
<220> FEATURE:
<223> OTHER INFORMATION: Synthetic peptide

<400> SEQUENCE: 865

Ser Lys Asp Asn
```

-continued

1

```
<210> SEQ ID NO 866
<211> LENGTH: 10
<212> TYPE: PRT
<213> ORGANISM: Artificial Sequence
<220> FEATURE:
<223> OTHER INFORMATION: Synthetic peptide

<400> SEQUENCE: 866

Gln Ser Lys Cys Gly Ser Lys Asp Asn Ile
1               5                   10

<210> SEQ ID NO 867
<211> LENGTH: 9
<212> TYPE: PRT
<213> ORGANISM: Artificial Sequence
<220> FEATURE:
<223> OTHER INFORMATION: Synthetic peptide

<400> SEQUENCE: 867

Ser Lys Cys Gly Ser Lys Asp Asn Ile
1               5

<210> SEQ ID NO 868
<211> LENGTH: 8
<212> TYPE: PRT
<213> ORGANISM: Artificial Sequence
<220> FEATURE:
<223> OTHER INFORMATION: Synthetic peptide

<400> SEQUENCE: 868

Lys Cys Gly Ser Lys Asp Asn Ile
1               5

<210> SEQ ID NO 869
<211> LENGTH: 7
<212> TYPE: PRT
<213> ORGANISM: Artificial Sequence
<220> FEATURE:
<223> OTHER INFORMATION: Synthetic peptide

<400> SEQUENCE: 869

Cys Gly Ser Lys Asp Asn Ile
1               5

<210> SEQ ID NO 870
<211> LENGTH: 6
<212> TYPE: PRT
<213> ORGANISM: Artificial Sequence
<220> FEATURE:
<223> OTHER INFORMATION: Synthetic peptide

<400> SEQUENCE: 870

Gly Ser Lys Asp Asn Ile
1               5

<210> SEQ ID NO 871
<211> LENGTH: 5
<212> TYPE: PRT
<213> ORGANISM: Artificial Sequence
<220> FEATURE:
<223> OTHER INFORMATION: Synthetic peptide

<400> SEQUENCE: 871

Ser Lys Asp Asn Ile
1               5
```

-continued

```
<210> SEQ ID NO 872
<211> LENGTH: 10
<212> TYPE: PRT
<213> ORGANISM: Artificial Sequence
<220> FEATURE:
<223> OTHER INFORMATION: Synthetic peptide

<400> SEQUENCE: 872

Ser Lys Val Thr Ser Lys Cys Gly Ser Leu
1               5                   10

<210> SEQ ID NO 873
<211> LENGTH: 9
<212> TYPE: PRT
<213> ORGANISM: Artificial Sequence
<220> FEATURE:
<223> OTHER INFORMATION: Synthetic peptide

<400> SEQUENCE: 873

Lys Val Thr Ser Lys Cys Gly Ser Leu
1               5

<210> SEQ ID NO 874
<211> LENGTH: 8
<212> TYPE: PRT
<213> ORGANISM: Artificial Sequence
<220> FEATURE:
<223> OTHER INFORMATION: Synthetic peptide

<400> SEQUENCE: 874

Val Thr Ser Lys Cys Gly Ser Leu
1               5

<210> SEQ ID NO 875
<211> LENGTH: 7
<212> TYPE: PRT
<213> ORGANISM: Artificial Sequence
<220> FEATURE:
<223> OTHER INFORMATION: Synthetic peptide

<400> SEQUENCE: 875

Thr Ser Lys Cys Gly Ser Leu
1               5

<210> SEQ ID NO 876
<211> LENGTH: 6
<212> TYPE: PRT
<213> ORGANISM: Artificial Sequence
<220> FEATURE:
<223> OTHER INFORMATION: Synthetic peptide

<400> SEQUENCE: 876

Ser Lys Cys Gly Ser Leu
1               5

<210> SEQ ID NO 877
<211> LENGTH: 5
<212> TYPE: PRT
<213> ORGANISM: Artificial Sequence
<220> FEATURE:
<223> OTHER INFORMATION: Synthetic peptide

<400> SEQUENCE: 877

Lys Cys Gly Ser Leu
1               5
```

-continued

```
<210> SEQ ID NO 878
<211> LENGTH: 4
<212> TYPE: PRT
<213> ORGANISM: Artificial Sequence
<220> FEATURE:
<223> OTHER INFORMATION: Synthetic peptide

<400> SEQUENCE: 878

Cys Gly Ser Leu
1

<210> SEQ ID NO 879
<211> LENGTH: 3
<212> TYPE: PRT
<213> ORGANISM: Artificial Sequence
<220> FEATURE:
<223> OTHER INFORMATION: Synthetic peptide

<400> SEQUENCE: 879

Gly Ser Leu
1

<210> SEQ ID NO 880
<211> LENGTH: 10
<212> TYPE: PRT
<213> ORGANISM: Artificial Sequence
<220> FEATURE:
<223> OTHER INFORMATION: Synthetic peptide

<400> SEQUENCE: 880

Lys Val Thr Ser Lys Cys Gly Ser Leu Gly
1               5                   10

<210> SEQ ID NO 881
<211> LENGTH: 9
<212> TYPE: PRT
<213> ORGANISM: Artificial Sequence
<220> FEATURE:
<223> OTHER INFORMATION: Synthetic peptide

<400> SEQUENCE: 881

Val Thr Ser Lys Cys Gly Ser Leu Gly
1               5

<210> SEQ ID NO 882
<211> LENGTH: 8
<212> TYPE: PRT
<213> ORGANISM: Artificial Sequence
<220> FEATURE:
<223> OTHER INFORMATION: Synthetic peptide

<400> SEQUENCE: 882

Thr Ser Lys Cys Gly Ser Leu Gly
1               5

<210> SEQ ID NO 883
<211> LENGTH: 7
<212> TYPE: PRT
<213> ORGANISM: Artificial Sequence
<220> FEATURE:
<223> OTHER INFORMATION: Synthetic peptide

<400> SEQUENCE: 883

Ser Lys Cys Gly Ser Leu Gly
1               5
```

-continued

```
<210> SEQ ID NO 884
<211> LENGTH: 6
<212> TYPE: PRT
<213> ORGANISM: Artificial Sequence
<220> FEATURE:
<223> OTHER INFORMATION: Synthetic peptide

<400> SEQUENCE: 884

Lys Cys Gly Ser Leu Gly
1               5

<210> SEQ ID NO 885
<211> LENGTH: 5
<212> TYPE: PRT
<213> ORGANISM: Artificial Sequence
<220> FEATURE:
<223> OTHER INFORMATION: Synthetic peptide

<400> SEQUENCE: 885

Cys Gly Ser Leu Gly
1               5

<210> SEQ ID NO 886
<211> LENGTH: 4
<212> TYPE: PRT
<213> ORGANISM: Artificial Sequence
<220> FEATURE:
<223> OTHER INFORMATION: Synthetic peptide

<400> SEQUENCE: 886

Gly Ser Leu Gly
1

<210> SEQ ID NO 887
<211> LENGTH: 3
<212> TYPE: PRT
<213> ORGANISM: Artificial Sequence
<220> FEATURE:
<223> OTHER INFORMATION: Synthetic peptide

<400> SEQUENCE: 887

Ser Leu Gly
1

<210> SEQ ID NO 888
<211> LENGTH: 10
<212> TYPE: PRT
<213> ORGANISM: Artificial Sequence
<220> FEATURE:
<223> OTHER INFORMATION: Synthetic peptide

<400> SEQUENCE: 888

Val Thr Ser Lys Cys Gly Ser Leu Gly Asn
1               5                   10

<210> SEQ ID NO 889
<211> LENGTH: 9
<212> TYPE: PRT
<213> ORGANISM: Artificial Sequence
<220> FEATURE:
<223> OTHER INFORMATION: Synthetic peptide

<400> SEQUENCE: 889

Thr Ser Lys Cys Gly Ser Leu Gly Asn
1               5

<210> SEQ ID NO 890
```

-continued

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 890

Ser Lys Cys Gly Ser Leu Gly Asn
1               5

<210> SEQ ID NO 891
<211> LENGTH: 7
<212> TYPE: PRT
<213> ORGANISM: Artificial Sequence
<220> FEATURE:
<223> OTHER INFORMATION: Synthetic peptide

<400> SEQUENCE: 891

Lys Cys Gly Ser Leu Gly Asn
1               5

<210> SEQ ID NO 892
<211> LENGTH: 6
<212> TYPE: PRT
<213> ORGANISM: Artificial Sequence
<220> FEATURE:
<223> OTHER INFORMATION: Synthetic peptide

<400> SEQUENCE: 892

Cys Gly Ser Leu Gly Asn
1               5

<210> SEQ ID NO 893
<211> LENGTH: 5
<212> TYPE: PRT
<213> ORGANISM: Artificial Sequence
<220> FEATURE:
<223> OTHER INFORMATION: Synthetic peptide

<400> SEQUENCE: 893

Gly Ser Leu Gly Asn
1               5

<210> SEQ ID NO 894
<211> LENGTH: 4
<212> TYPE: PRT
<213> ORGANISM: Artificial Sequence
<220> FEATURE:
<223> OTHER INFORMATION: Synthetic peptide

<400> SEQUENCE: 894

Ser Leu Gly Asn
1

<210> SEQ ID NO 895
<211> LENGTH: 10
<212> TYPE: PRT
<213> ORGANISM: Artificial Sequence
<220> FEATURE:
<223> OTHER INFORMATION: Synthetic peptide

<400> SEQUENCE: 895

Thr Ser Lys Cys Gly Ser Leu Gly Asn Ile
1               5                   10

<210> SEQ ID NO 896
<211> LENGTH: 9
```

-continued

```
<212> TYPE: PRT
<213> ORGANISM: Artificial Sequence
<220> FEATURE:
<223> OTHER INFORMATION: Synthetic peptide

<400> SEQUENCE: 896

Ser Lys Cys Gly Ser Leu Gly Asn Ile
1               5

<210> SEQ ID NO 897
<211> LENGTH: 8
<212> TYPE: PRT
<213> ORGANISM: Artificial Sequence
<220> FEATURE:
<223> OTHER INFORMATION: Synthetic peptide

<400> SEQUENCE: 897

Lys Cys Gly Ser Leu Gly Asn Ile
1               5

<210> SEQ ID NO 898
<211> LENGTH: 7
<212> TYPE: PRT
<213> ORGANISM: Artificial Sequence
<220> FEATURE:
<223> OTHER INFORMATION: Synthetic peptide

<400> SEQUENCE: 898

Cys Gly Ser Leu Gly Asn Ile
1               5

<210> SEQ ID NO 899
<211> LENGTH: 6
<212> TYPE: PRT
<213> ORGANISM: Artificial Sequence
<220> FEATURE:
<223> OTHER INFORMATION: Synthetic peptide

<400> SEQUENCE: 899

Gly Ser Leu Gly Asn Ile
1               5

<210> SEQ ID NO 900
<211> LENGTH: 5
<212> TYPE: PRT
<213> ORGANISM: Artificial Sequence
<220> FEATURE:
<223> OTHER INFORMATION: Synthetic peptide

<400> SEQUENCE: 900

Ser Leu Gly Asn Ile
1               5

<210> SEQ ID NO 901
<211> LENGTH: 10
<212> TYPE: PRT
<213> ORGANISM: Artificial Sequence
<220> FEATURE:
<223> OTHER INFORMATION: Synthetic peptide

<400> SEQUENCE: 901

Ser Lys Cys Gly Ser Leu Gly Asn Ile His
1               5                   10

<210> SEQ ID NO 902
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 902

Lys Cys Gly Ser Leu Gly Asn Ile His
1               5

<210> SEQ ID NO 903
<211> LENGTH: 8
<212> TYPE: PRT
<213> ORGANISM: Artificial Sequence
<220> FEATURE:
<223> OTHER INFORMATION: Synthetic peptide

<400> SEQUENCE: 903

Cys Gly Ser Leu Gly Asn Ile His
1               5

<210> SEQ ID NO 904
<211> LENGTH: 7
<212> TYPE: PRT
<213> ORGANISM: Artificial Sequence
<220> FEATURE:
<223> OTHER INFORMATION: Synthetic peptide

<400> SEQUENCE: 904

Gly Ser Leu Gly Asn Ile His
1               5

<210> SEQ ID NO 905
<211> LENGTH: 6
<212> TYPE: PRT
<213> ORGANISM: Artificial Sequence
<220> FEATURE:
<223> OTHER INFORMATION: Synthetic peptide

<400> SEQUENCE: 905

Ser Leu Gly Asn Ile His
1               5

<210> SEQ ID NO 906
<211> LENGTH: 10
<212> TYPE: PRT
<213> ORGANISM: Artificial Sequence
<220> FEATURE:
<223> OTHER INFORMATION: Synthetic peptide

<400> SEQUENCE: 906

Lys Cys Gly Ser Leu Gly Asn Ile His His
1               5                   10

<210> SEQ ID NO 907
<211> LENGTH: 9
<212> TYPE: PRT
<213> ORGANISM: Artificial Sequence
<220> FEATURE:
<223> OTHER INFORMATION: Synthetic peptide

<400> SEQUENCE: 907

Cys Gly Ser Leu Gly Asn Ile His His
1               5

<210> SEQ ID NO 908
<211> LENGTH: 8
<212> TYPE: PRT
<213> ORGANISM: Artificial Sequence
```

-continued

```
<220> FEATURE:
<223> OTHER INFORMATION: Synthetic peptide

<400> SEQUENCE: 908

Gly Ser Leu Gly Asn Ile His His
1               5

<210> SEQ ID NO 909
<211> LENGTH: 7
<212> TYPE: PRT
<213> ORGANISM: Artificial Sequence
<220> FEATURE:
<223> OTHER INFORMATION: Synthetic peptide

<400> SEQUENCE: 909

Ser Leu Gly Asn Ile His His
1               5

<210> SEQ ID NO 910
<211> LENGTH: 10
<212> TYPE: PRT
<213> ORGANISM: Artificial Sequence
<220> FEATURE:
<223> OTHER INFORMATION: Synthetic peptide

<400> SEQUENCE: 910

Cys Gly Ser Leu Gly Asn Ile His His Lys
1               5                   10

<210> SEQ ID NO 911
<211> LENGTH: 9
<212> TYPE: PRT
<213> ORGANISM: Artificial Sequence
<220> FEATURE:
<223> OTHER INFORMATION: Synthetic peptide

<400> SEQUENCE: 911

Gly Ser Leu Gly Asn Ile His His Lys
1               5

<210> SEQ ID NO 912
<211> LENGTH: 8
<212> TYPE: PRT
<213> ORGANISM: Artificial Sequence
<220> FEATURE:
<223> OTHER INFORMATION: Synthetic peptide

<400> SEQUENCE: 912

Ser Leu Gly Asn Ile His His Lys
1               5

<210> SEQ ID NO 913
<211> LENGTH: 10
<212> TYPE: PRT
<213> ORGANISM: Artificial Sequence
<220> FEATURE:
<223> OTHER INFORMATION: Synthetic peptide

<400> SEQUENCE: 913

Gly Ser Leu Gly Asn Ile His His Lys Pro
1               5                   10

<210> SEQ ID NO 914
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 914

Ser Leu Gly Asn Ile His His Lys Pro
1               5

<210> SEQ ID NO 915
<211> LENGTH: 10
<212> TYPE: PRT
<213> ORGANISM: Artificial Sequence
<220> FEATURE:
<223> OTHER INFORMATION: Synthetic peptide

<400> SEQUENCE: 915

Ser Leu Gly Asn Ile His His Lys Pro Gly
1               5                   10

<210> SEQ ID NO 916
<211> LENGTH: 10
<212> TYPE: PRT
<213> ORGANISM: Artificial Sequence
<220> FEATURE:
<223> OTHER INFORMATION: Synthetic peptide

<400> SEQUENCE: 916

Asp Arg Val Gln Ser Lys Ile Gly Ser Leu
1               5                   10

<210> SEQ ID NO 917
<211> LENGTH: 9
<212> TYPE: PRT
<213> ORGANISM: Artificial Sequence
<220> FEATURE:
<223> OTHER INFORMATION: Synthetic peptide

<400> SEQUENCE: 917

Arg Val Gln Ser Lys Ile Gly Ser Leu
1               5

<210> SEQ ID NO 918
<211> LENGTH: 8
<212> TYPE: PRT
<213> ORGANISM: Artificial Sequence
<220> FEATURE:
<223> OTHER INFORMATION: Synthetic peptide

<400> SEQUENCE: 918

Val Gln Ser Lys Ile Gly Ser Leu
1               5

<210> SEQ ID NO 919
<211> LENGTH: 7
<212> TYPE: PRT
<213> ORGANISM: Artificial Sequence
<220> FEATURE:
<223> OTHER INFORMATION: Synthetic peptide

<400> SEQUENCE: 919

Gln Ser Lys Ile Gly Ser Leu
1               5

<210> SEQ ID NO 920
<211> LENGTH: 6
<212> TYPE: PRT
<213> ORGANISM: Artificial Sequence
<220> FEATURE:
<223> OTHER INFORMATION: Synthetic peptide
```

<400> SEQUENCE: 920

Ser Lys Ile Gly Ser Leu
1               5

<210> SEQ ID NO 921
<211> LENGTH: 5
<212> TYPE: PRT
<213> ORGANISM: Artificial Sequence
<220> FEATURE:
<223> OTHER INFORMATION: Synthetic peptide

<400> SEQUENCE: 921

Lys Ile Gly Ser Leu
1               5

<210> SEQ ID NO 922
<211> LENGTH: 4
<212> TYPE: PRT
<213> ORGANISM: Artificial Sequence
<220> FEATURE:
<223> OTHER INFORMATION: Synthetic peptide

<400> SEQUENCE: 922

Ile Gly Ser Leu
1

<210> SEQ ID NO 923
<211> LENGTH: 10
<212> TYPE: PRT
<213> ORGANISM: Artificial Sequence
<220> FEATURE:
<223> OTHER INFORMATION: Synthetic peptide

<400> SEQUENCE: 923

Arg Val Gln Ser Lys Ile Gly Ser Leu Asp
1               5                   10

<210> SEQ ID NO 924
<211> LENGTH: 9
<212> TYPE: PRT
<213> ORGANISM: Artificial Sequence
<220> FEATURE:
<223> OTHER INFORMATION: Synthetic peptide

<400> SEQUENCE: 924

Val Gln Ser Lys Ile Gly Ser Leu Asp
1               5

<210> SEQ ID NO 925
<211> LENGTH: 8
<212> TYPE: PRT
<213> ORGANISM: Artificial Sequence
<220> FEATURE:
<223> OTHER INFORMATION: Synthetic peptide

<400> SEQUENCE: 925

Gln Ser Lys Ile Gly Ser Leu Asp
1               5

<210> SEQ ID NO 926
<211> LENGTH: 7
<212> TYPE: PRT
<213> ORGANISM: Artificial Sequence
<220> FEATURE:
<223> OTHER INFORMATION: Synthetic peptide -continued

```
<400> SEQUENCE: 926

Ser Lys Ile Gly Ser Leu Asp
1               5

<210> SEQ ID NO 927
<211> LENGTH: 6
<212> TYPE: PRT
<213> ORGANISM: Artificial Sequence
<220> FEATURE:
<223> OTHER INFORMATION: Synthetic peptide

<400> SEQUENCE: 927

Lys Ile Gly Ser Leu Asp
1               5

<210> SEQ ID NO 928
<211> LENGTH: 5
<212> TYPE: PRT
<213> ORGANISM: Artificial Sequence
<220> FEATURE:
<223> OTHER INFORMATION: Synthetic peptide

<400> SEQUENCE: 928

Ile Gly Ser Leu Asp
1               5

<210> SEQ ID NO 929
<211> LENGTH: 4
<212> TYPE: PRT
<213> ORGANISM: Artificial Sequence
<220> FEATURE:
<223> OTHER INFORMATION: Synthetic peptide

<400> SEQUENCE: 929

Gly Ser Leu Asp
1

<210> SEQ ID NO 930
<211> LENGTH: 3
<212> TYPE: PRT
<213> ORGANISM: Artificial Sequence
<220> FEATURE:
<223> OTHER INFORMATION: Synthetic peptide

<400> SEQUENCE: 930

Ser Leu Asp
1

<210> SEQ ID NO 931
<211> LENGTH: 10
<212> TYPE: PRT
<213> ORGANISM: Artificial Sequence
<220> FEATURE:
<223> OTHER INFORMATION: Synthetic peptide

<400> SEQUENCE: 931

Val Gln Ser Lys Ile Gly Ser Leu Asp Asn
1               5                   10

<210> SEQ ID NO 932
<211> LENGTH: 9
<212> TYPE: PRT
<213> ORGANISM: Artificial Sequence
<220> FEATURE:
<223> OTHER INFORMATION: Synthetic peptide

<400> SEQUENCE: 932
```

Gln Ser Lys Ile Gly Ser Leu Asp Asn
1               5

<210> SEQ ID NO 933
<211> LENGTH: 8
<212> TYPE: PRT
<213> ORGANISM: Artificial Sequence
<220> FEATURE:
<223> OTHER INFORMATION: Synthetic peptide

<400> SEQUENCE: 933

Ser Lys Ile Gly Ser Leu Asp Asn
1               5

<210> SEQ ID NO 934
<211> LENGTH: 7
<212> TYPE: PRT
<213> ORGANISM: Artificial Sequence
<220> FEATURE:
<223> OTHER INFORMATION: Synthetic peptide

<400> SEQUENCE: 934

Lys Ile Gly Ser Leu Asp Asn
1               5

<210> SEQ ID NO 935
<211> LENGTH: 6
<212> TYPE: PRT
<213> ORGANISM: Artificial Sequence
<220> FEATURE:
<223> OTHER INFORMATION: Synthetic peptide

<400> SEQUENCE: 935

Ile Gly Ser Leu Asp Asn
1               5

<210> SEQ ID NO 936
<211> LENGTH: 5
<212> TYPE: PRT
<213> ORGANISM: Artificial Sequence
<220> FEATURE:
<223> OTHER INFORMATION: Synthetic peptide

<400> SEQUENCE: 936

Gly Ser Leu Asp Asn
1               5

<210> SEQ ID NO 937
<211> LENGTH: 4
<212> TYPE: PRT
<213> ORGANISM: Artificial Sequence
<220> FEATURE:
<223> OTHER INFORMATION: Synthetic peptide

<400> SEQUENCE: 937

Ser Leu Asp Asn
1

<210> SEQ ID NO 938
<211> LENGTH: 10
<212> TYPE: PRT
<213> ORGANISM: Artificial Sequence
<220> FEATURE:
<223> OTHER INFORMATION: Synthetic peptide

<400> SEQUENCE: 938

```
Gln Ser Lys Ile Gly Ser Leu Asp Asn Ile
1               5                   10

<210> SEQ ID NO 939
<211> LENGTH: 9
<212> TYPE: PRT
<213> ORGANISM: Artificial Sequence
<220> FEATURE:
<223> OTHER INFORMATION: Synthetic peptide

<400> SEQUENCE: 939

Ser Lys Ile Gly Ser Leu Asp Asn Ile
1               5

<210> SEQ ID NO 940
<211> LENGTH: 8
<212> TYPE: PRT
<213> ORGANISM: Artificial Sequence
<220> FEATURE:
<223> OTHER INFORMATION: Synthetic peptide

<400> SEQUENCE: 940

Lys Ile Gly Ser Leu Asp Asn Ile
1               5

<210> SEQ ID NO 941
<211> LENGTH: 7
<212> TYPE: PRT
<213> ORGANISM: Artificial Sequence
<220> FEATURE:
<223> OTHER INFORMATION: Synthetic peptide

<400> SEQUENCE: 941

Ile Gly Ser Leu Asp Asn Ile
1               5

<210> SEQ ID NO 942
<211> LENGTH: 6
<212> TYPE: PRT
<213> ORGANISM: Artificial Sequence
<220> FEATURE:
<223> OTHER INFORMATION: Synthetic peptide

<400> SEQUENCE: 942

Gly Ser Leu Asp Asn Ile
1               5

<210> SEQ ID NO 943
<211> LENGTH: 10
<212> TYPE: PRT
<213> ORGANISM: Artificial Sequence
<220> FEATURE:
<223> OTHER INFORMATION: Synthetic peptide

<400> SEQUENCE: 943

Ser Lys Ile Gly Ser Leu Asp Asn Ile Thr
1               5                   10

<210> SEQ ID NO 944
<211> LENGTH: 9
<212> TYPE: PRT
<213> ORGANISM: Artificial Sequence
<220> FEATURE:
<223> OTHER INFORMATION: Synthetic peptide

<400> SEQUENCE: 944

Lys Ile Gly Ser Leu Asp Asn Ile Thr
```

```
1               5

<210> SEQ ID NO 945
<211> LENGTH: 8
<212> TYPE: PRT
<213> ORGANISM: Artificial Sequence
<220> FEATURE:
<223> OTHER INFORMATION: Synthetic peptide

<400> SEQUENCE: 945

Ile Gly Ser Leu Asp Asn Ile Thr
1               5

<210> SEQ ID NO 946
<211> LENGTH: 7
<212> TYPE: PRT
<213> ORGANISM: Artificial Sequence
<220> FEATURE:
<223> OTHER INFORMATION: Synthetic peptide

<400> SEQUENCE: 946

Gly Ser Leu Asp Asn Ile Thr
1               5

<210> SEQ ID NO 947
<211> LENGTH: 6
<212> TYPE: PRT
<213> ORGANISM: Artificial Sequence
<220> FEATURE:
<223> OTHER INFORMATION: Synthetic peptide

<400> SEQUENCE: 947

Ser Leu Asp Asn Ile Thr
1               5

<210> SEQ ID NO 948
<211> LENGTH: 10
<212> TYPE: PRT
<213> ORGANISM: Artificial Sequence
<220> FEATURE:
<223> OTHER INFORMATION: Synthetic peptide

<400> SEQUENCE: 948

Lys Ile Gly Ser Leu Asp Asn Ile Thr His
1               5                   10

<210> SEQ ID NO 949
<211> LENGTH: 9
<212> TYPE: PRT
<213> ORGANISM: Artificial Sequence
<220> FEATURE:
<223> OTHER INFORMATION: Synthetic peptide

<400> SEQUENCE: 949

Ile Gly Ser Leu Asp Asn Ile Thr His
1               5

<210> SEQ ID NO 950
<211> LENGTH: 8
<212> TYPE: PRT
<213> ORGANISM: Artificial Sequence
<220> FEATURE:
<223> OTHER INFORMATION: Synthetic peptide

<400> SEQUENCE: 950

Gly Ser Leu Asp Asn Ile Thr His
1               5
```

```
<210> SEQ ID NO 951
<211> LENGTH: 7
<212> TYPE: PRT
<213> ORGANISM: Artificial Sequence
<220> FEATURE:
<223> OTHER INFORMATION: Synthetic peptide

<400> SEQUENCE: 951

Ser Leu Asp Asn Ile Thr His
1               5

<210> SEQ ID NO 952
<211> LENGTH: 10
<212> TYPE: PRT
<213> ORGANISM: Artificial Sequence
<220> FEATURE:
<223> OTHER INFORMATION: Synthetic peptide

<400> SEQUENCE: 952

Ile Gly Ser Leu Asp Asn Ile Thr His Val
1               5                   10

<210> SEQ ID NO 953
<211> LENGTH: 9
<212> TYPE: PRT
<213> ORGANISM: Artificial Sequence
<220> FEATURE:
<223> OTHER INFORMATION: Synthetic peptide

<400> SEQUENCE: 953

Gly Ser Leu Asp Asn Ile Thr His Val
1               5

<210> SEQ ID NO 954
<211> LENGTH: 8
<212> TYPE: PRT
<213> ORGANISM: Artificial Sequence
<220> FEATURE:
<223> OTHER INFORMATION: Synthetic peptide

<400> SEQUENCE: 954

Ser Leu Asp Asn Ile Thr His Val
1               5

<210> SEQ ID NO 955
<211> LENGTH: 10
<212> TYPE: PRT
<213> ORGANISM: Artificial Sequence
<220> FEATURE:
<223> OTHER INFORMATION: Synthetic peptide

<400> SEQUENCE: 955

Gly Ser Leu Asp Asn Ile Thr His Val Pro
1               5                   10

<210> SEQ ID NO 956
<211> LENGTH: 9
<212> TYPE: PRT
<213> ORGANISM: Artificial Sequence
<220> FEATURE:
<223> OTHER INFORMATION: Synthetic peptide

<400> SEQUENCE: 956

Ser Leu Asp Asn Ile Thr His Val Pro
1               5
```

-continued

```
<210> SEQ ID NO 957
<211> LENGTH: 10
<212> TYPE: PRT
<213> ORGANISM: Artificial Sequence
<220> FEATURE:
<223> OTHER INFORMATION: Synthetic peptide

<400> SEQUENCE: 957

Ser Leu Asp Asn Ile Thr His Val Pro Gly
1               5                   10

<210> SEQ ID NO 958
<211> LENGTH: 8
<212> TYPE: PRT
<213> ORGANISM: Artificial Sequence
<220> FEATURE:
<223> OTHER INFORMATION: Synthetic peptide

<400> SEQUENCE: 958

Pro Asp Leu Lys Asn Val Lys Ser
1               5

<210> SEQ ID NO 959
<211> LENGTH: 8
<212> TYPE: PRT
<213> ORGANISM: Artificial Sequence
<220> FEATURE:
<223> OTHER INFORMATION: Synthetic peptide

<400> SEQUENCE: 959

Asp Leu Lys Asn Val Lys Ser Lys
1               5

<210> SEQ ID NO 960
<211> LENGTH: 8
<212> TYPE: PRT
<213> ORGANISM: Artificial Sequence
<220> FEATURE:
<223> OTHER INFORMATION: Synthetic peptide

<400> SEQUENCE: 960

Leu Lys Asn Val Lys Ser Lys Ile
1               5

<210> SEQ ID NO 961
<211> LENGTH: 8
<212> TYPE: PRT
<213> ORGANISM: Artificial Sequence
<220> FEATURE:
<223> OTHER INFORMATION: Synthetic peptide

<400> SEQUENCE: 961

Lys Asn Val Lys Ser Lys Ile Gly
1               5

<210> SEQ ID NO 962
<211> LENGTH: 8
<212> TYPE: PRT
<213> ORGANISM: Artificial Sequence
<220> FEATURE:
<223> OTHER INFORMATION: Synthetic peptide

<400> SEQUENCE: 962

Asn Val Lys Ser Lys Ile Gly Ser
1               5
```

-continued

```
<210> SEQ ID NO 963
<211> LENGTH: 8
<212> TYPE: PRT
<213> ORGANISM: Artificial Sequence
<220> FEATURE:
<223> OTHER INFORMATION: Synthetic peptide

<400> SEQUENCE: 963

Asp Leu Ser Asn Val Gln Ser Lys
1               5

<210> SEQ ID NO 964
<211> LENGTH: 8
<212> TYPE: PRT
<213> ORGANISM: Artificial Sequence
<220> FEATURE:
<223> OTHER INFORMATION: Synthetic peptide

<400> SEQUENCE: 964

Leu Ser Asn Val Gln Ser Lys Cys
1               5

<210> SEQ ID NO 965
<211> LENGTH: 8
<212> TYPE: PRT
<213> ORGANISM: Artificial Sequence
<220> FEATURE:
<223> OTHER INFORMATION: Synthetic peptide

<400> SEQUENCE: 965

Ser Asn Val Gln Ser Lys Cys Gly
1               5

<210> SEQ ID NO 966
<211> LENGTH: 8
<212> TYPE: PRT
<213> ORGANISM: Artificial Sequence
<220> FEATURE:
<223> OTHER INFORMATION: Synthetic peptide

<400> SEQUENCE: 966

Asn Val Gln Ser Lys Cys Gly Ser
1               5

<210> SEQ ID NO 967
<211> LENGTH: 8
<212> TYPE: PRT
<213> ORGANISM: Artificial Sequence
<220> FEATURE:
<223> OTHER INFORMATION: Synthetic peptide

<400> SEQUENCE: 967

Val Asp Leu Ser Lys Val Thr Ser
1               5

<210> SEQ ID NO 968
<211> LENGTH: 8
<212> TYPE: PRT
<213> ORGANISM: Artificial Sequence
<220> FEATURE:
<223> OTHER INFORMATION: Synthetic peptide

<400> SEQUENCE: 968

Asp Leu Ser Lys Val Thr Ser Lys
1               5

<210> SEQ ID NO 969
```

-continued

```
<211> LENGTH: 8
<212> TYPE: PRT
<213> ORGANISM: Artificial Sequence
<220> FEATURE:
<223> OTHER INFORMATION: Synthetic peptide

<400> SEQUENCE: 969

Leu Ser Lys Val Thr Ser Lys Cys
1               5

<210> SEQ ID NO 970
<211> LENGTH: 8
<212> TYPE: PRT
<213> ORGANISM: Artificial Sequence
<220> FEATURE:
<223> OTHER INFORMATION: Synthetic peptide

<400> SEQUENCE: 970

Ser Lys Val Thr Ser Lys Cys Gly
1               5

<210> SEQ ID NO 971
<211> LENGTH: 8
<212> TYPE: PRT
<213> ORGANISM: Artificial Sequence
<220> FEATURE:
<223> OTHER INFORMATION: Synthetic peptide

<400> SEQUENCE: 971

Lys Val Thr Ser Lys Cys Gly Ser
1               5

<210> SEQ ID NO 972
<211> LENGTH: 8
<212> TYPE: PRT
<213> ORGANISM: Artificial Sequence
<220> FEATURE:
<223> OTHER INFORMATION: Synthetic peptide

<400> SEQUENCE: 972

Leu Asp Phe Lys Asp Arg Val Gln
1               5

<210> SEQ ID NO 973
<211> LENGTH: 8
<212> TYPE: PRT
<213> ORGANISM: Artificial Sequence
<220> FEATURE:
<223> OTHER INFORMATION: Synthetic peptide

<400> SEQUENCE: 973

Asp Phe Lys Asp Arg Val Gln Ser
1               5

<210> SEQ ID NO 974
<211> LENGTH: 8
<212> TYPE: PRT
<213> ORGANISM: Artificial Sequence
<220> FEATURE:
<223> OTHER INFORMATION: Synthetic peptide

<400> SEQUENCE: 974

Phe Lys Asp Arg Val Gln Ser Lys
1               5

<210> SEQ ID NO 975
<211> LENGTH: 8
```

```
<212> TYPE: PRT
<213> ORGANISM: Artificial Sequence
<220> FEATURE:
<223> OTHER INFORMATION: Synthetic peptide

<400> SEQUENCE: 975

Lys Asp Arg Val Gln Ser Lys Ile
1               5

<210> SEQ ID NO 976
<211> LENGTH: 8
<212> TYPE: PRT
<213> ORGANISM: Artificial Sequence
<220> FEATURE:
<223> OTHER INFORMATION: Synthetic peptide

<400> SEQUENCE: 976

Asp Arg Val Gln Ser Lys Ile Gly
1               5

<210> SEQ ID NO 977
<211> LENGTH: 8
<212> TYPE: PRT
<213> ORGANISM: Artificial Sequence
<220> FEATURE:
<223> OTHER INFORMATION: Synthetic peptide

<400> SEQUENCE: 977

Arg Val Gln Ser Lys Ile Gly Ser
1               5

<210> SEQ ID NO 978
<211> LENGTH: 11
<212> TYPE: PRT
<213> ORGANISM: Artificial Sequence
<220> FEATURE:
<223> OTHER INFORMATION: Synthetic peptide

<400> SEQUENCE: 978

Ser Lys Ile Gly Ser Thr Glu Asn Leu Lys His
1               5                   10

<210> SEQ ID NO 979
<211> LENGTH: 11
<212> TYPE: PRT
<213> ORGANISM: Artificial Sequence
<220> FEATURE:
<223> OTHER INFORMATION: Synthetic peptide

<400> SEQUENCE: 979

Ser Lys Ile Gly Ser Thr Glu Asn Ile Lys His
1               5                   10

<210> SEQ ID NO 980
<211> LENGTH: 11
<212> TYPE: PRT
<213> ORGANISM: Artificial Sequence
<220> FEATURE:
<223> OTHER INFORMATION: Synthetic peptide

<400> SEQUENCE: 980

Ser Lys Ile Gly Ser Lys Asp Asn Leu Lys His
1               5                   10

<210> SEQ ID NO 981
<211> LENGTH: 11
<212> TYPE: PRT
```

-continued

<213> ORGANISM: Artificial Sequence
<220> FEATURE:
<223> OTHER INFORMATION: Synthetic peptide

<400> SEQUENCE: 981

Ser Lys Ile Gly Ser Lys Glu Asn Ile Lys His
1               5                   10

<210> SEQ ID NO 982
<211> LENGTH: 11
<212> TYPE: PRT
<213> ORGANISM: Artificial Sequence
<220> FEATURE:
<223> OTHER INFORMATION: Synthetic peptide

<400> SEQUENCE: 982

Ser Lys Ile Gly Ser Leu Glu Asn Leu Lys His
1               5                   10

<210> SEQ ID NO 983
<211> LENGTH: 11
<212> TYPE: PRT
<213> ORGANISM: Artificial Sequence
<220> FEATURE:
<223> OTHER INFORMATION: Synthetic peptide

<400> SEQUENCE: 983

Ser Lys Ile Gly Ser Leu Glu Asn Ile Lys His
1               5                   10

<210> SEQ ID NO 984
<211> LENGTH: 11
<212> TYPE: PRT
<213> ORGANISM: Artificial Sequence
<220> FEATURE:
<223> OTHER INFORMATION: Synthetic peptide

<400> SEQUENCE: 984

Ser Lys Ile Gly Ser Thr Asp Asn Leu Lys His
1               5                   10

<210> SEQ ID NO 985
<211> LENGTH: 11
<212> TYPE: PRT
<213> ORGANISM: Artificial Sequence
<220> FEATURE:
<223> OTHER INFORMATION: Synthetic peptide

<400> SEQUENCE: 985

Ser Lys Ile Gly Ser Thr Asp Asn Ile Lys His
1               5                   10

<210> SEQ ID NO 986
<211> LENGTH: 11
<212> TYPE: PRT
<213> ORGANISM: Artificial Sequence
<220> FEATURE:
<223> OTHER INFORMATION: Synthetic peptide

<400> SEQUENCE: 986

Ser Lys Ile Gly Ser Lys Asp Asn Ile Lys His
1               5                   10

<210> SEQ ID NO 987
<211> LENGTH: 11
<212> TYPE: PRT
<213> ORGANISM: Artificial Sequence -continued

```
<220> FEATURE:
<223> OTHER INFORMATION: Synthetic peptide

<400> SEQUENCE: 987

Ser Lys Ile Gly Ser Leu Asp Asn Leu Lys His
1               5                   10

<210> SEQ ID NO 988
<211> LENGTH: 11
<212> TYPE: PRT
<213> ORGANISM: Artificial Sequence
<220> FEATURE:
<223> OTHER INFORMATION: Synthetic peptide

<400> SEQUENCE: 988

Ser Lys Ile Gly Ser Leu Asp Asn Ile Lys His
1               5                   10

<210> SEQ ID NO 989
<211> LENGTH: 11
<212> TYPE: PRT
<213> ORGANISM: Artificial Sequence
<220> FEATURE:
<223> OTHER INFORMATION: Synthetic peptide

<400> SEQUENCE: 989

Ser Lys Ile Gly Ser Thr Gly Asn Leu Lys His
1               5                   10

<210> SEQ ID NO 990
<211> LENGTH: 11
<212> TYPE: PRT
<213> ORGANISM: Artificial Sequence
<220> FEATURE:
<223> OTHER INFORMATION: Synthetic peptide

<400> SEQUENCE: 990

Ser Lys Ile Gly Ser Thr Gly Asn Ile Lys His
1               5                   10

<210> SEQ ID NO 991
<211> LENGTH: 11
<212> TYPE: PRT
<213> ORGANISM: Artificial Sequence
<220> FEATURE:
<223> OTHER INFORMATION: Synthetic peptide

<400> SEQUENCE: 991

Ser Lys Ile Gly Ser Lys Gly Asn Leu Lys His
1               5                   10

<210> SEQ ID NO 992
<211> LENGTH: 11
<212> TYPE: PRT
<213> ORGANISM: Artificial Sequence
<220> FEATURE:
<223> OTHER INFORMATION: Synthetic peptide

<400> SEQUENCE: 992

Ser Lys Ile Gly Ser Lys Gly Asn Ile Lys His
1               5                   10

<210> SEQ ID NO 993
<211> LENGTH: 11
<212> TYPE: PRT
<213> ORGANISM: Artificial Sequence
<220> FEATURE:
```

-continued

```
<223> OTHER INFORMATION: Synthetic peptide

<400> SEQUENCE: 993

Ser Lys Ile Gly Ser Leu Gly Asn Leu Lys His
1               5                   10

<210> SEQ ID NO 994
<211> LENGTH: 11
<212> TYPE: PRT
<213> ORGANISM: Artificial Sequence
<220> FEATURE:
<223> OTHER INFORMATION: Synthetic peptide

<400> SEQUENCE: 994

Ser Lys Ile Gly Ser Leu Gly Asn Ile Lys His
1               5                   10

<210> SEQ ID NO 995
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is I or C
<220> FEATURE:
<221> NAME/KEY: MISC_FEATURE
<222> LOCATION: (3)..(3)
<223> OTHER INFORMATION: Xaa is G
<220> FEATURE:
<221> NAME/KEY: MISC_FEATURE
<222> LOCATION: (5)..(5)
<223> OTHER INFORMATION: Xaa is T or K or L
<220> FEATURE:
<221> NAME/KEY: MISC_FEATURE
<222> LOCATION: (6)..(6)
<223> OTHER INFORMATION: Xaa is E or D or G
<220> FEATURE:
<221> NAME/KEY: MISC_FEATURE
<222> LOCATION: (8)..(8)
<223> OTHER INFORMATION: Xaa is L or I
<220> FEATURE:
<221> NAME/KEY: MISC_FEATURE
<222> LOCATION: (9)..(9)
<223> OTHER INFORMATION: Xaa is K or H or T

<400> SEQUENCE: 995

Lys Xaa Xaa Ser Xaa Xaa Asn Xaa Xaa His
1               5                   10

<210> SEQ ID NO 996
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa can be Q or E
<220> FEATURE:
<221> NAME/KEY: MISC_FEATURE
<222> LOCATION: (6)..(6)
<223> OTHER INFORMATION: Xaa can be S or P

<400> SEQUENCE: 996

Xaa Ile Val Tyr Lys Xaa
1               5
```

```
<210> SEQ ID NO 997
<211> LENGTH: 6
<212> TYPE: PRT
<213> ORGANISM: Artificial Sequence
<220> FEATURE:
<223> OTHER INFORMATION: Synthetic peptide

<400> SEQUENCE: 997

Gln Ile Val Tyr Lys Ser
1               5

<210> SEQ ID NO 998
<211> LENGTH: 6
<212> TYPE: PRT
<213> ORGANISM: Artificial Sequence
<220> FEATURE:
<223> OTHER INFORMATION: Synthetic peptide

<400> SEQUENCE: 998

Glu Ile Val Tyr Lys Ser
1               5

<210> SEQ ID NO 999
<211> LENGTH: 6
<212> TYPE: PRT
<213> ORGANISM: Artificial Sequence
<220> FEATURE:
<223> OTHER INFORMATION: Synthetic peptide

<400> SEQUENCE: 999

Glu Ile Val Tyr Lys Pro
1               5

<210> SEQ ID NO 1000
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1000

Cys Asn Ile Lys His Val Pro Gly
1               5

<210> SEQ ID NO 1001

<400> SEQUENCE: 1001

000

<210> SEQ ID NO 1002
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1002

Val His His Gln Lys Leu Val Phe Phe Ala
1               5                   10

<210> SEQ ID NO 1003
<211> LENGTH: 9
<212> TYPE: PRT
<213> ORGANISM: Artificial Sequence
<220> FEATURE:
<223> OTHER INFORMATION: Synthetic peptide
```

```
<400> SEQUENCE: 1003

Val His His Gln Lys Leu Val Phe Phe
1               5

<210> SEQ ID NO 1004
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1004

Val His His Gln Lys Leu Val Phe
1               5

<210> SEQ ID NO 1005
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1005

Val His His Gln Lys Leu Val
1               5

<210> SEQ ID NO 1006
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1006

Val His His Gln Lys Leu
1               5

<210> SEQ ID NO 1007
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1007

His His Gln Lys Leu Val Phe Phe Ala Glu
1               5                   10

<210> SEQ ID NO 1008
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1008

His His Gln Lys Leu Val Phe Phe Ala
1               5

<210> SEQ ID NO 1009
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1009
```

-continued

His His Gln Lys Leu Val Phe Phe
1               5

<210> SEQ ID NO 1010
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1010

His His Gln Lys Leu Val Phe
1               5

<210> SEQ ID NO 1011
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1011

His His Gln Lys Leu Val
1               5

<210> SEQ ID NO 1012
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1012

His His Gln Lys Leu
1               5

<210> SEQ ID NO 1013
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1013

His Gln Lys Leu Val Phe Phe Ala Glu Asp
1               5                   10

<210> SEQ ID NO 1014
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1014

His Gln Lys Leu Val Phe Phe Ala Glu
1               5

<210> SEQ ID NO 1015
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1015

```
His Gln Lys Leu Val Phe Phe Ala
1               5

<210> SEQ ID NO 1016
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1016

His Gln Lys Leu Val Phe Phe
1               5

<210> SEQ ID NO 1017
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1017

His Gln Lys Leu Val Phe
1               5

<210> SEQ ID NO 1018
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1018

His Gln Lys Leu Val
1               5

<210> SEQ ID NO 1019
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1019

His Gln Lys Leu
1

<210> SEQ ID NO 1020
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1020

Gln Lys Leu Val Phe Phe Ala Glu Asp Val
1               5                   10

<210> SEQ ID NO 1021
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1021

Gln Lys Leu Val Phe Phe Ala Glu Asp
```

```
1               5

<210> SEQ ID NO 1022
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1022

Gln Lys Leu Val Phe Phe Ala Glu
1               5

<210> SEQ ID NO 1023
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1023

Gln Lys Leu Val Phe Phe Ala
1               5

<210> SEQ ID NO 1024
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1024

Gln Lys Leu Val Phe Phe
1               5

<210> SEQ ID NO 1025
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1025

Gln Lys Leu Val Phe
1               5

<210> SEQ ID NO 1026
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1026

Gln Lys Leu Val
1

<210> SEQ ID NO 1027
<211> LENGTH: 3
<212> TYPE: PRT
<213> ORGANISM: Artificial Sequence
<220> FEATURE:
<223> OTHER INFORMATION: Synthetic peptide

<400> SEQUENCE: 1027

Gln Lys Leu
1
```

```
<210> SEQ ID NO 1028
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1028

Lys Leu Val Phe Phe Ala Glu Asp Val Gly
1               5                   10

<210> SEQ ID NO 1029
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1029

Lys Leu Val Phe Phe Ala Glu Asp Val
1               5

<210> SEQ ID NO 1030
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1030

Lys Leu Val Phe Phe Ala Glu Asp
1               5

<210> SEQ ID NO 1031
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1031

Lys Leu Val Phe Phe Ala Glu
1               5

<210> SEQ ID NO 1032
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1032

Lys Leu Val Phe Phe Ala
1               5

<210> SEQ ID NO 1033
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1033

Lys Leu Val Phe Phe
1               5
```

-continued

```
<210> SEQ ID NO 1034
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1034

Lys Leu Val Phe
1

<210> SEQ ID NO 1035
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1035

Lys Leu Val Phe
1

<210> SEQ ID NO 1036
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1036

Leu Val Phe Phe Ala Glu Asp Val Gly
1               5

<210> SEQ ID NO 1037
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1037

Leu Val Phe Phe Ala Glu Asp Val
1               5

<210> SEQ ID NO 1038
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1038

Leu Val Phe Phe Ala Glu Asp
1               5

<210> SEQ ID NO 1039
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1039

Leu Val Phe Phe Ala Glu
1               5
```

```
<210> SEQ ID NO 1040
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1040

Leu Val Phe Phe Ala
1               5

<210> SEQ ID NO 1041
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1041

Leu Val Phe Phe
1

<210> SEQ ID NO 1042
<211> LENGTH: 3
<212> TYPE: PRT
<213> ORGANISM: Artificial Sequence
<220> FEATURE:
<223> OTHER INFORMATION: Synthetic peptide

<400> SEQUENCE: 1042

Leu Val Phe
1

<210> SEQ ID NO 1043
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1043

Val Phe Phe Ala Glu Asp Val Gly
1               5

<210> SEQ ID NO 1044
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1044

Val Phe Phe Ala Glu Asp Val
1               5

<210> SEQ ID NO 1045
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1045

Val Phe Phe Ala Glu Asp
1               5

<210> SEQ ID NO 1046
```

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1046

Val Phe Phe Ala Glu
1               5

<210> SEQ ID NO 1047
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1047

Val Phe Phe Ala
1

<210> SEQ ID NO 1048
<211> LENGTH: 3
<212> TYPE: PRT
<213> ORGANISM: Artificial Sequence
<220> FEATURE:
<223> OTHER INFORMATION: Synthetic peptide

<400> SEQUENCE: 1048

Val Phe Phe
1

<210> SEQ ID NO 1049
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1049

Phe Phe Ala Glu Asp Val Gly
1               5

<210> SEQ ID NO 1050
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1050

Phe Phe Ala Glu Asp Val
1               5

<210> SEQ ID NO 1051
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1051

Phe Phe Ala Glu Asp
1               5

<210> SEQ ID NO 1052
<211> LENGTH: 4
```

-continued

```
<212> TYPE: PRT
<213> ORGANISM: Artificial Sequence
<220> FEATURE:
<223> OTHER INFORMATION: Synthetic peptide

<400> SEQUENCE: 1052

Phe Phe Ala Glu
1

<210> SEQ ID NO 1053
<211> LENGTH: 3
<212> TYPE: PRT
<213> ORGANISM: Artificial Sequence
<220> FEATURE:
<223> OTHER INFORMATION: Synthetic peptide

<400> SEQUENCE: 1053

Phe Phe Ala
1

<210> SEQ ID NO 1054
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1054

Phe Ala Glu Asp Val Gly
1               5

<210> SEQ ID NO 1055
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1055

Phe Ala Glu Asp Val
1               5

<210> SEQ ID NO 1056
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1056

Phe Ala Glu Asp
1

<210> SEQ ID NO 1057
<211> LENGTH: 3
<212> TYPE: PRT
<213> ORGANISM: Artificial Sequence
<220> FEATURE:
<223> OTHER INFORMATION: Synthetic peptide

<400> SEQUENCE: 1057

Phe Ala Glu
1

<210> SEQ ID NO 1058
<211> LENGTH: 30
<212> TYPE: PRT
```

```
<213> ORGANISM: Artificial Sequence
<220> FEATURE:
<223> OTHER INFORMATION: Synthetic peptide

<400> SEQUENCE: 1058

Asp Ala Glu Phe Arg His Asp Arg Arg Asp Pro Asp Asn Glu Ala Tyr
1               5                   10                  15

Glu Arg Arg Glu Asn Leu Lys His Gln Pro Gly Gly Gly Cys
            20                  25                  30

<210> SEQ ID NO 1059
<211> LENGTH: 30
<212> TYPE: PRT
<213> ORGANISM: Artificial Sequence
<220> FEATURE:
<223> OTHER INFORMATION: Synthetic peptide

<400> SEQUENCE: 1059

Asp Ala Glu Phe Arg His Asp Arg Arg Glu Asn Leu Lys His Gln Pro
1               5                   10                  15

Gly Arg Arg Asp Pro Asp Asn Glu Ala Tyr Glu Gly Gly Cys
            20                  25                  30

<210> SEQ ID NO 1060
<211> LENGTH: 29
<212> TYPE: PRT
<213> ORGANISM: Artificial Sequence
<220> FEATURE:
<223> OTHER INFORMATION: Synthetic peptide

<400> SEQUENCE: 1060

Asp Ala Glu Phe Arg His Asp Arg Arg Pro Asp Asn Glu Ala Tyr Glu
1               5                   10                  15

Arg Arg Glu Asn Leu Lys His Gln Pro Gly Gly Gly Cys
            20                  25

<210> SEQ ID NO 1061
<211> LENGTH: 29
<212> TYPE: PRT
<213> ORGANISM: Artificial Sequence
<220> FEATURE:
<223> OTHER INFORMATION: Synthetic peptide

<400> SEQUENCE: 1061

Asp Ala Glu Phe Arg His Asp Arg Arg Glu Asn Leu Lys His Gln Pro
1               5                   10                  15

Gly Arg Arg Pro Asp Asn Glu Ala Tyr Glu Gly Gly Cys
            20                  25

<210> SEQ ID NO 1062
<211> LENGTH: 33
<212> TYPE: PRT
<213> ORGANISM: Artificial Sequence
<220> FEATURE:
<223> OTHER INFORMATION: linker

<400> SEQUENCE: 1062

Asp Ala Glu Phe Arg His Asp Arg Arg Ser Lys Ile Gly Ser Lys Asp
1               5                   10                  15

Asn Ile Lys His Arg Arg Asp Pro Asp Asn Glu Ala Tyr Glu Gly Gly
            20                  25                  30

Cys
```

```
<210> SEQ ID NO 1063
<211> LENGTH: 33
<212> TYPE: PRT
<213> ORGANISM: Artificial Sequence
<220> FEATURE:
<223> OTHER INFORMATION: linker

<400> SEQUENCE: 1063

Asp Ala Glu Phe Arg His Asp Arg Arg Asp Pro Asp Asn Glu Ala Tyr
1               5                   10                  15

Glu Arg Arg Ser Lys Ile Gly Ser Lys Asp Asn Ile Lys His Gly Gly
            20                  25                  30

Cys

<210> SEQ ID NO 1064
<211> LENGTH: 4
<212> TYPE: PRT
<213> ORGANISM: Artificial Sequence
<220> FEATURE:
<223> OTHER INFORMATION: Linker

<400> SEQUENCE: 1064

Gly Gly Gly Ser
1

<210> SEQ ID NO 1065
<211> LENGTH: 5
<212> TYPE: PRT
<213> ORGANISM: Artificial Sequence
<220> FEATURE:
<223> OTHER INFORMATION: Linker

<400> SEQUENCE: 1065

Gly Gly Gly Gly Ser
1               5
```

MULTIEPITOPE VACCINE FOR THE TREATMENT OF ALZHEIMER'S DISEASE

RELATED APPLICATIONS

This application claims the benefit of U.S. Provisional Patent Application No. 63/062,919, filed Aug. 7, 2021, which is incorporated by reference herein in its entirety.

SEQUENCE LISTING STATEMENT

A computer readable form of the Sequence Listing is filed with this application by electronic submission and is incorporated into this application by reference in its entirety. The Sequence Listing is contained in the ASCII text file created on Aug. 6, 2021, having the file name "20-1085-WO_Sequence-Listing_ST25.txt" and is 191 kb in size.

FIELD

The disclosure relates to the technical fields of immunology and medicine, and in particular to the treatment of Alzheimer's disease and other diseases of protein misfolding.

BACKGROUND

Alzheimer's disease (AD) is a progressive disease resulting in senile dementia. Broadly speaking, the disease falls into two categories: late onset, which occurs in old age (65+ years) and early onset, which develops well before the senile period, i.e., between 35 and 60 years. In both types of disease, the pathology is the same, but the abnormalities tend to be more severe and widespread in cases beginning at an earlier age. The disease is characterized by at least two types of lesions in the brain, neurofibrillary tangles and senile plaques. Neurofibrillary tangles are intracellular deposits of microtubule associated tau protein consisting of two filaments twisted about each other in pairs. Senile plaques (i.e., amyloid plaques) are areas of disorganized neuropil up to 150 μm across with extracellular amyloid deposits at the center which are visible by microscopic analysis of sections of brain tissue. The accumulation of amyloid plaques within the central nervous system is also associated with Down's syndrome and other cognitive disorders, Cerebral amyloid angiopathy (CAA), and the ocular disease Age-Related Macular Degeneration.

A principal constituent of the plaques is a peptide termed Aβ or β-amyloid peptide. Aβ peptide is a 4-kDa internal fragment of 38-43 amino acids of a larger transmembrane glycoprotein named amyloid precursor protein (APP). As a result of proteolytic processing of APP by different secretase enzymes, Aβ is primarily found in both a short form, 40 amino acids in length, and a long form, ranging from 42-43 amino acids in length. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The cognitive and physical symptoms associated with this type of neural deterioration characterize Alzheimer's disease.

Another protein reported to occur at increased levels in Alzheimer's patients relative to the general population is tau, the principal constituent of neurofibrillary tangles, which together with amyloid plaques are a hallmark characteristic of Alzheimer's disease. Tau tangles constitute abnormal fibrils measuring 10 nm in diameter occurring in pairs wound in a helical fashion with a regular periodicity of 80 nm. The tau within neurofibrillary tangles is abnormally phosphorylated (hyperphosphorylated) with phosphate groups attached to specific sites on the molecule. Severe involvement of neurofibrillary tangles is seen in the layer II neurons of the entorhinal cortex, the CA1 and subicular regions of the hippocampus, the amygdala, and the deeper layers (layers III, V, and superficial VI) of the neocortex in Alzheimer's disease. Tau pathologies are known to correlate to cognitive decline.

Alpha-synuclein, a protein found in neurons and other cells, is a major component of pathology that characterizes several neurodegenerative disorders including Parkinson's disease, dementia with Lewy bodies, and multiple system atrophy, which collectively are termed synucleinopathies. The understanding of the normal physiological function of alpha-synuclein is limited, but evidence indicates that soluble forms of the protein may interact with other proteins and certain intracellular membranes. In synucleinopathies, the alpha-synuclein protein appears to be abnormally aggregated intracellularly, which contributes to disease pathology. There is increasing evidence that certain aggregated forms of alpha-synuclein can be transmitted from neuron to neuron, resulting in a propagation of pathology that causes neuronal dysfunction and loss. Alpha-synuclein (SNCA) misfolding and aggregation can often be accompanied by β-amyloid deposition in some neurodegenerative diseases, and alpha-synuclein and tau aggregates coexist in several neurodegenerative disorders, including Alzheimer's disease and Parkinson's disease.

Accordingly, there exists the need for new therapies and reagents for the prevention or treatment of Alzheimer's disease, in particular, therapies and reagents capable of causing an immune response to the Aβ, Tau and alpha-synuclein present in patients.

SUMMARY

In some embodiments, disclosure is directed to a polypeptide including a first peptide comprising 3-10 amino acids from residues 1-10 or 12-25 of SEQ ID NO:01, a second peptide including 3-13 amino acids from residues 244-400 of SEQ ID NO:02, and a third peptide comprising 3-10 amino acids from residues 81-140 of SEQ ID NO:58. In certain embodiments, the polypeptide further comprises a fourth peptide selected from one of: (a) a peptide comprising 3-10 amino acids from residues 1-10 or 12-25 of SEQ ID NO:01; (b) a peptide comprising 3-13 amino acids from residues 244-400 of SEQ ID NO:02; and (c) a peptide comprising 3-10 amino acids from residues 81-140 of SEQ ID NO:58. In some embodiments, the first peptide, second peptide, third peptide, and fourth peptide are arranged in any order in the polypeptide. For example, the second peptide may be from the microtubule binding region (MTBR) of tau (residues 244-372 of SEQ ID NO:02). In addition, the first peptide may include an amino acid sequence of one of SEQ ID NOS: 3 to 38 or 1002-1057, the second peptide may include an amino acid sequence of one of SEQ ID NOS: 39 to 57, or 142 to 1000, the third peptide may include an amino acid sequence of one of SEQ ID NOS: 59-129, and the fourth peptide, if present, is one of any one of the amino acid sequences of SEQ ID NO: 3-38, 1002-1057, 39-57, 142 to 1000, and 59-129. For example, the first polypeptide may be DAEFRHD (SEQ ID NO:06), or EFRHDSG (SEQ ID NO:19), the second polypeptide may be 5-10 amino acids, for example QIVYKPV (SEQ ID NO:39), or NIKHVPG (SEQ ID NO:57), the third polypeptide may be PDNEAYE (SEQ ID NO:75), or DPDNEAY (SEQ ID NO:69), and the fourth polypeptide, if present, may be NIKHVP (SEQ ID NO:48), or QIVYKPV (SEQ ID NO:39).

In other embodiments, two or more of the first peptide, the second peptide, and the third peptide, and the fourth peptide, if present, may be linked by a cleavable linker, which may be an amino acid sequence. A cleavable peptide linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the cleavable peptide linker is 1 amino acid, 2 amino acids, 3 amino acids, 4 amino acids, 5 amino acids, 6 amino acids, 7 amino acids, 8 amino acids, 9 amino acids, or 10 amino acids. For example, the linker may be arginine-arginine (Arg-Arg), arginine-valine-arginine-arginine (Arg-Val-Arg-Arg (SEQ ID NO:138)), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; SEQ ID NO:139), Ala-Gly-Ala-Gly (SEQ ID NO:140), or Lys-Gly-Lys-Gly (SEQ ID NO:141). In particular embodiments, the polypeptide may be DAEFRHDRRPDNEAYERRQIVYKPVKKC (SEQ ID NO:130), DAEFRHDRRQIVYKPVRRPD-NEAYEKKC (SEQ ID NO:131), DAEFRHDRRPDNEAY-ERRNIKHVPGKKC(SEQ ID NO: 132), DAE-FRHDRRNIKHVPGRRPDNEAYEKKC (SEQ ID NO:133), DAEFRHDRRQIVYKPVRRPDNEAY-ERRNIKHVPGGC (SEQ ID NO:134), DAE-FRHDRRDPDNEAYRRNIKHVPGRRQIVYKPVGGC (SEQ ID NO:135), EFRHDSGRRQIVYKPVRRPDNEAY-ERRNIKHVPGGC (SEQ ID NO:136), EFRHDSGRRDPD-NEAYRRNIKHVPGRRQIVYKPVGGC (SEQ ID NO:137), DAEFRHDRRDPDNEAYER-RENLKHQPGGGC (SEQ ID NO:1058), DAEFRHDR-RENLKHQPGRRDPDNEAYEGGC (SEQ ID NO: 1059), DAEFRHDRRPDNEAYERRENLKHQPGGGC (SEQ ID NO:1060), DAEFRHDRRENLKHQPGRRPDNEAYEGGC (SEQ ID NO:1061), DAEFRHDRRSKIGSKD-NIKHRRDPDNEAYEGGC (SEQ ID NO:1062), or DAE-FRHDRRDPDNEAYERRSKIGSKDNIKHGGC (SEQ ID NO:1063).

In certain embodiments, the polypeptide further comprises a blocked amine at the N-terminus.

In further embodiments, the polypeptide may include a linker to a carrier at a C-terminal portion of the polypeptide, or at a N-terminal portion of the polypeptide. A linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the linker is 1 amino acid, 2 amino acids, 3 amino acids, 4 amino acids, 5 amino acids, 6 amino acids, 7 amino acids, 8 amino acids, 9 amino acids, or 10 amino acids. For example, the linker may include an amino acid sequence of GG, GGG, AA, AAA, KK, KKK, SS, SSS, GAGA (SEQ ID NO:139), AGAG (SEQ ID NO:140), and KGKG (SEQ ID NO:141). In addition, the linker to the carrier, if present at the C-terminus, may include a C-terminal cysteine (C). For example, the polypeptide may include the amino acid sequence of DAEFRHDRRPDNEAYERRQIVYKPVKKC (SEQ ID NO:130), wherein KK and C are independently optional and, if present, KK can be replaced with GG, AA, SS, GAGA (SEQ ID NO:139), AGAG (SEQ ID NO:140), or KGKG (SEQ ID NO:141). Alternatively, the linker to the carrier, if present at the N-terminus, may include a N-terminal cysteine (C). For example, the sequence may be represented as CXX-polypeptide, wherein XX and C are independently optional and, if present, XX can be GG, AA, KK, SS, GAGA (SEQ ID NO:139), AGAG (SEQ ID NO: 140), or KGKG (SEQ ID NO:141).

In other embodiments, the disclosure is directed to an immunotherapy composition including the polypeptides of the disclosure, wherein the polypeptide may be linked to a carrier. The carrier may include serum albumins, immuno-globulin molecules, thyroglobulin, ovalbumin, tetanus tox-oid (TT), diphtheria toxoid (DT), a genetically modified cross-reacting material (CRM) of diphtheria toxin, CRM197, meningococcal outer membrane protein complex (OMPC) and *H. influenzae* protein D (HiD), rEPA (*Pseudomonas aeruginosa* exotoxin A), KLH (keyhole lim-pet hemocyanin), and flagellin.

Still further, embodiments of the disclosure are directed to a pharmaceutical formulation includes the polypeptides or the immunotherapy compositions of the disclosure, and including at least one adjuvant. The adjuvant may be alu-minum hydroxide, aluminum phosphate, aluminum sulfate, 3 De-O-acylated monophosphoryl lipid A (MPL), QS-21, QS-18, QS-17, QS-7, TQL1055, Complete Freund's Adju-vant (CFA), Incomplete Freund's Adjuvant (IFA), oil in water emulsions (such as squalene or peanut oil), CpG, polyglutamic acid, polylysine, AddaVax™, MF59®, and combinations thereof. In addition, the formulation may include a liposomal formulation, a diluent, or a multiple antigen presenting system (MAP). The MAP may include one or more of a Lys-based dendritic scaffold, helper T-cell epitopes, immune stimulating lipophilic moieties, cell pen-etrating peptides, radical induced polymerization, self-as-sembling nanoparticles as antigen-presenting platforms and gold nanoparticles.

Still further, embodiments of the disclosure are directed to an immunotherapy composition including a first peptide sequence comprising 3-10 amino acid residues from the first ten or 12 to 25 N-terminal residues of SEQ ID NO:01 and a second peptide sequence comprising 3-13 amino acids from residues 244-400 of SEQ ID NO:02, and a third sequence comprising 3-10 amino acids from residues 81-140 of SEQ ID NO:58. The first peptide may include an amino acid sequence of one of SEQ ID NOS: 3 to 38 or SEQ ID NOS:1002 to 1057, and the second peptide may include an amino acid sequence of one of SEQ ID NOS: 39 to 57 or 142-1000, the third peptide sequence may include an amino acid sequence of one of SEQ ID NOS:59-129, and a fourth peptide sequence, if present, is one of any one of the amino acid sequences of SEQ ID NO: 3-38, 1002-1057, 39-57, 142-1000, and 59-129. Each of the first peptide and the second peptide, the third peptide, and the fourth peptide may include a linker to a carrier at a C-terminal portion of the polypeptide, or at a N-terminal portion of the polypeptide. When present, the linker may include an amino acid sequence selected from GG, GGG, AA, AAA, KK, KKK, SS, SSS, GAGA (SEQ ID NO:139), AGAG (SEQ ID NO:140), and KGKG (SEQ ID NO:141), and may include a C-terminal cysteine (C). In some embodiments, where the C-terminal residues in the immunogen are either IVYKPV (SEQ ID NO:194), VYKPV (SEQ ID NO: 195), YKPV (SEQ ID NO:196), KPV, or PV the linker is an amino acid linker that does not have a N-terminal glycine (e.g., GG, GAGA (SEQ ID NO:139)). The carrier may include serum albumins, immunoglobulin molecules, thyroglobulin, oval-bumin, tetanus toxoid (TT), diphtheria toxoid (DT), a genetically modified cross-reacting material (CRM) of diph-theria toxin, CRM197, meningococcal outer membrane pro-tein complex (OMPC) and *H. influenzae* protein D (HiD), rEPA (*Pseudomonas aeruginosa* exotoxin A), KLH (keyhole limpet hemocyanin), and flagellin.

In addition, the immunotherapy composition may include at least one pharmaceutically acceptable diluent and/or a multiple antigen presenting system (MAP). The MAP may include one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

The immunotherapy composition may be included in a pharmaceutical composition including the immunotherapy composition and at least one adjuvant such as aluminum hydroxide, aluminum phosphate, aluminum sulfate, 3 De-O-acylated monophosphoryl lipid A (MPL), QS-21, QS-18, QS-17, QS-7, TQL1055, Complete Freund's Adjuvant (CFA), Incomplete Freund's Adjuvant (IFA), oil in water emulsions (such as squalene or peanut oil), CpG, polyglu-tamic acid, polylysine, AddaVax™, MF59®, and combina-tions thereof.

Embodiments of the disclosure are also directed to nucleic acid sequences encoding the polypeptides and the immuno-therapy compositions of the disclosure. The nucleic acids may be included in a nucleic acid immunotherapy compo-sition including the nucleic acid and at least one adjuvant.

Still further, embodiments of the disclosure are directed to a methods for treating or effecting prophylaxis of Alzheim-er's disease in a subject, and methods for inhibiting or reducing aggregation of at least one of Aβ, tau, and alpha-synuclein in a subject having or at risk of developing Alzheimer's disease. The methods include administrating to the subject an immunotherapy composition, a nucleic acids immunotherapy composition, or a pharmaceutical formula-tion of the disclosure.

The methods of the disclosure may include repeating the administering at least a second time, at least a third time, at least a fourth time, at least a fifth time, or at least a sixth time, and may include repeating the administering at an interval of about 21 to about 28 days.

Still further, methods of the disclosure are directed to inducing an immune response in an animal. The methods include administering to the animal a polypeptide, an immu-notherapy composition, a pharmaceutical formulation or a nucleic acid immunotherapy composition of the disclosure in a regimen effective to generate an immune response including antibodies that specifically bind to Aβ, and/or tau, and/or alpha-synuclein. The immune response may include antibodies that specifically bind to the N-terminal region of Aβ and/or the microtubule region of tau, and/or the C-ter-minal region of alpha-synuclein.

In other embodiments, the disclosure is directed to an immunization kit including an immunotherapy composition of the disclosure and may include an adjuvant, wherein the immunotherapy composition may be in a first container and the adjuvant may be a second container.

Still further, the disclosure is directed to a kit including a nucleic acid immunotherapy composition of the disclosure and may include an adjuvant. The nucleic acid may be in a first container and the adjuvant may be in a second container.

Figure 1A:
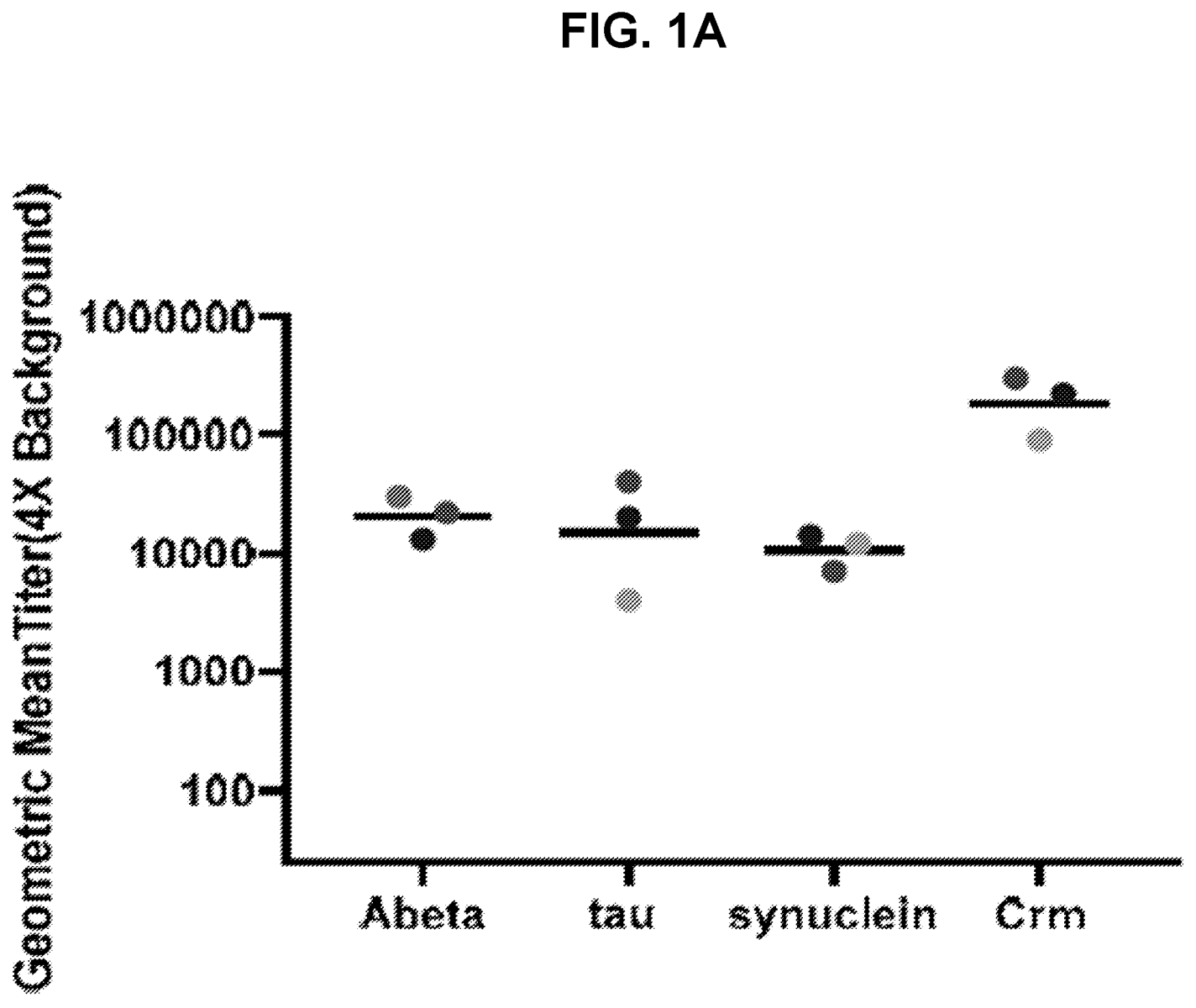
Figure 1B:
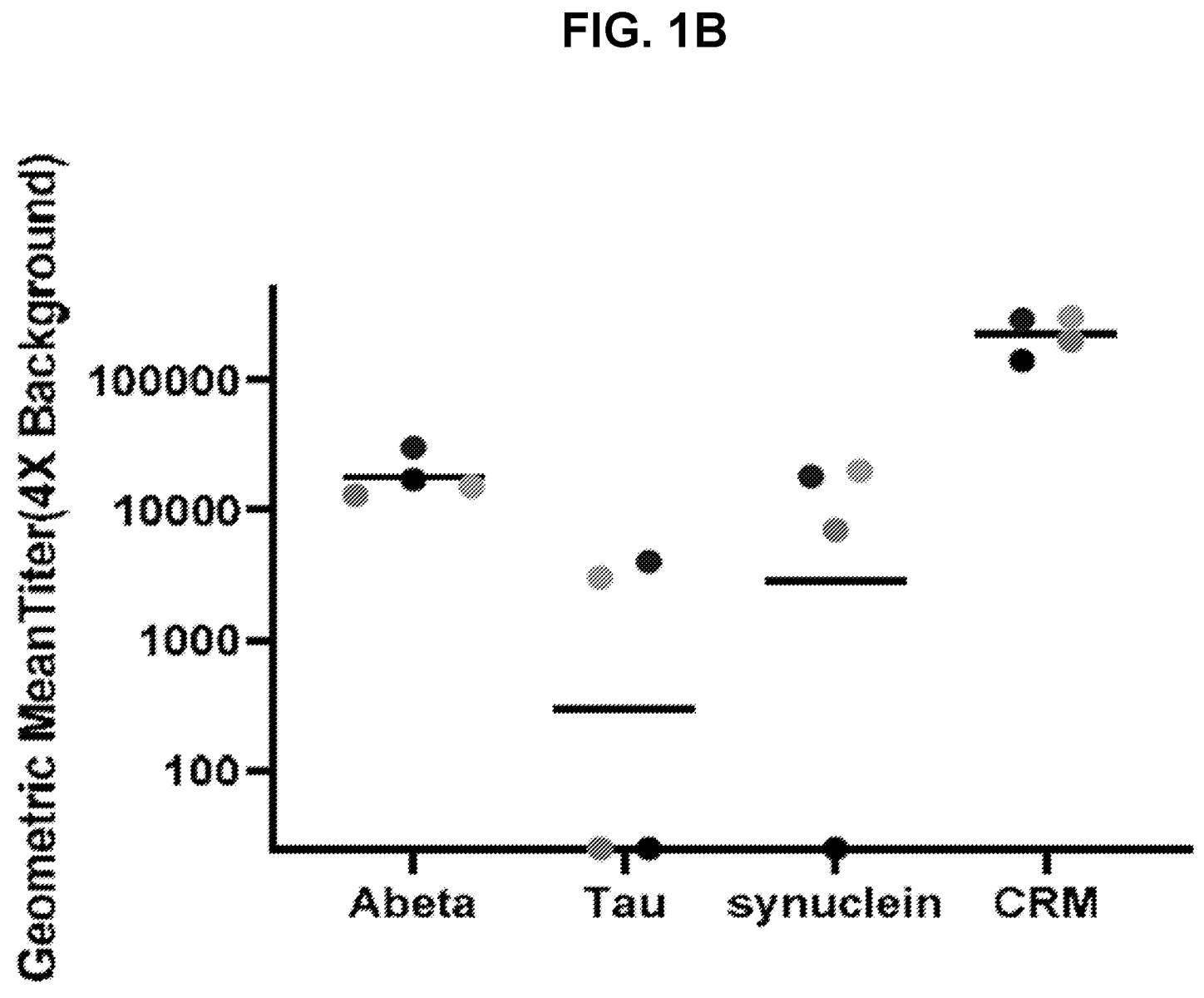
Figure 1C:
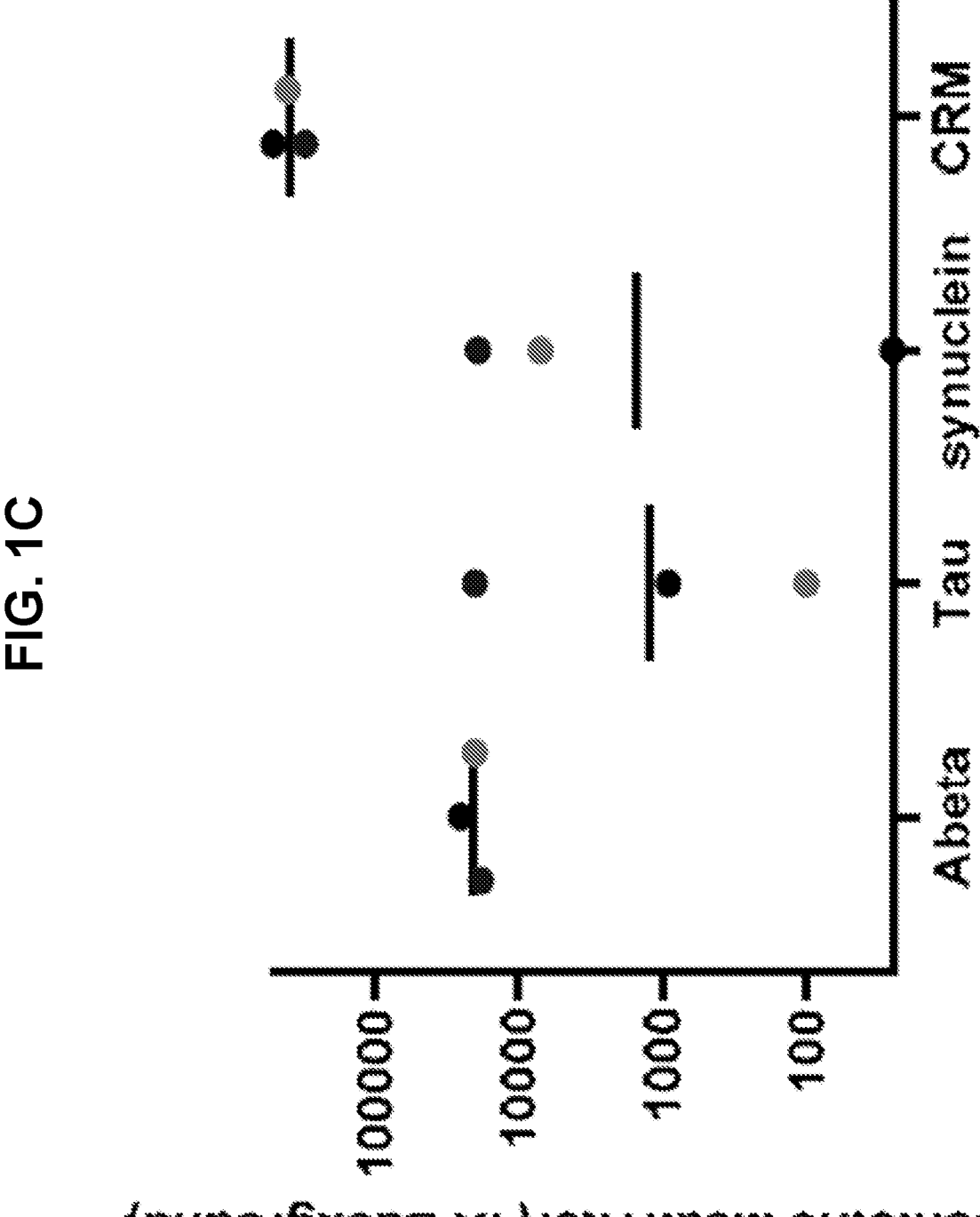
FIG. 1A shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 25 (DAEFRHDRRQI-VYKPVRRPDNEAYEKKC; SEQ ID NO:131) on day 0, week 3, and week 7, and serum was collected one week after each injection (i.e., week 1, week 4 and week 8).

FIG. 1B shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 27 (DAE-FRHDRRNIKHVPGRRPDNEAYEKKC; SEQ ID NO:133) on day 0, week 3, and week 7, and serum was collected one week after each injection (i.e., week 1, week 4 and week 8).

FIG. 1C shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 26 (DAEFRHDRRPD-NEAYERRNIKHVPGKKC; SEQ ID NO:132) on day 0, week 3, and week 7, and serum was collected one week after each injection (i.e., week 1, week 4 and week 8).

Figure 1D:
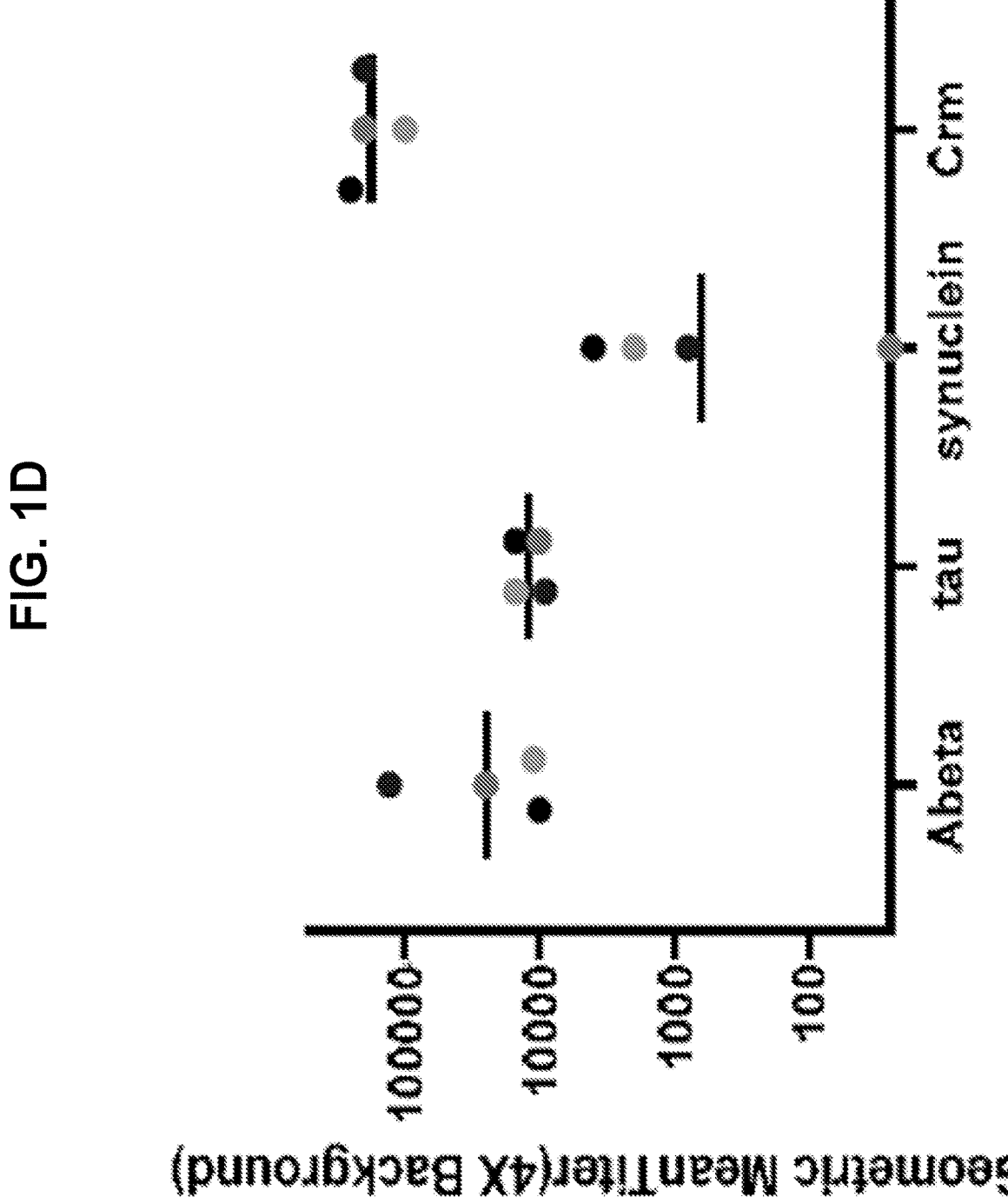

FIG. 1D shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 24 (DAEFRHDRRPD-NEAYERRQIVYKPVKKC; SEQ ID NO:130) on day 0, week 3, and week 7, and serum was collected one week after each injection (i.e., week 1, week 4 and week 8).

Figure 2A:
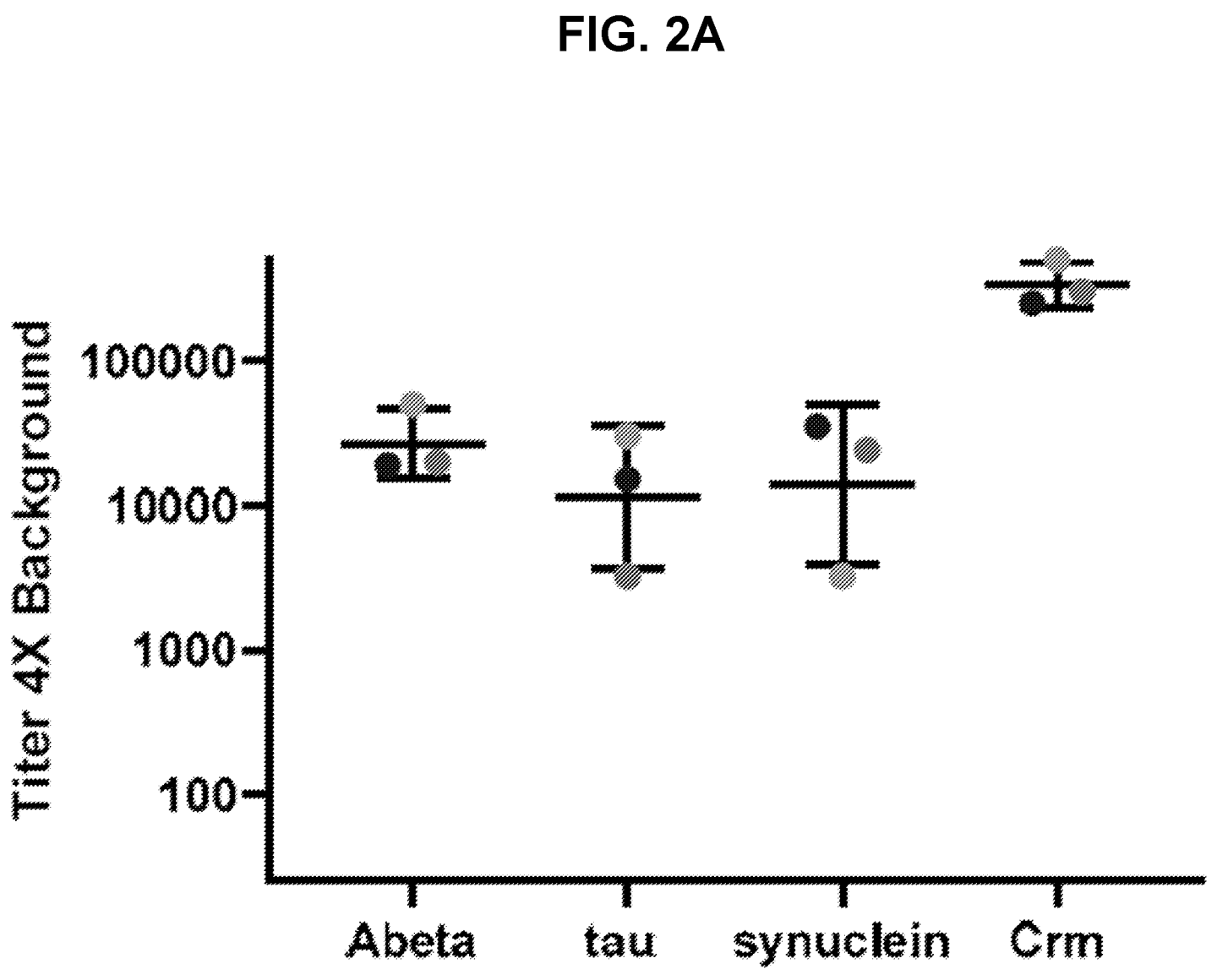

FIG. 2A shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 25 (DAEFRHDRRQI-VYKPVRRPDNEAYEKKC; SEQ ID NO:131) on day 0, week 3, week 7, and week 11, and serum was collected one week after each injection (i.e., week 1, week 4, week 8, and week 12).

Figure 2B:
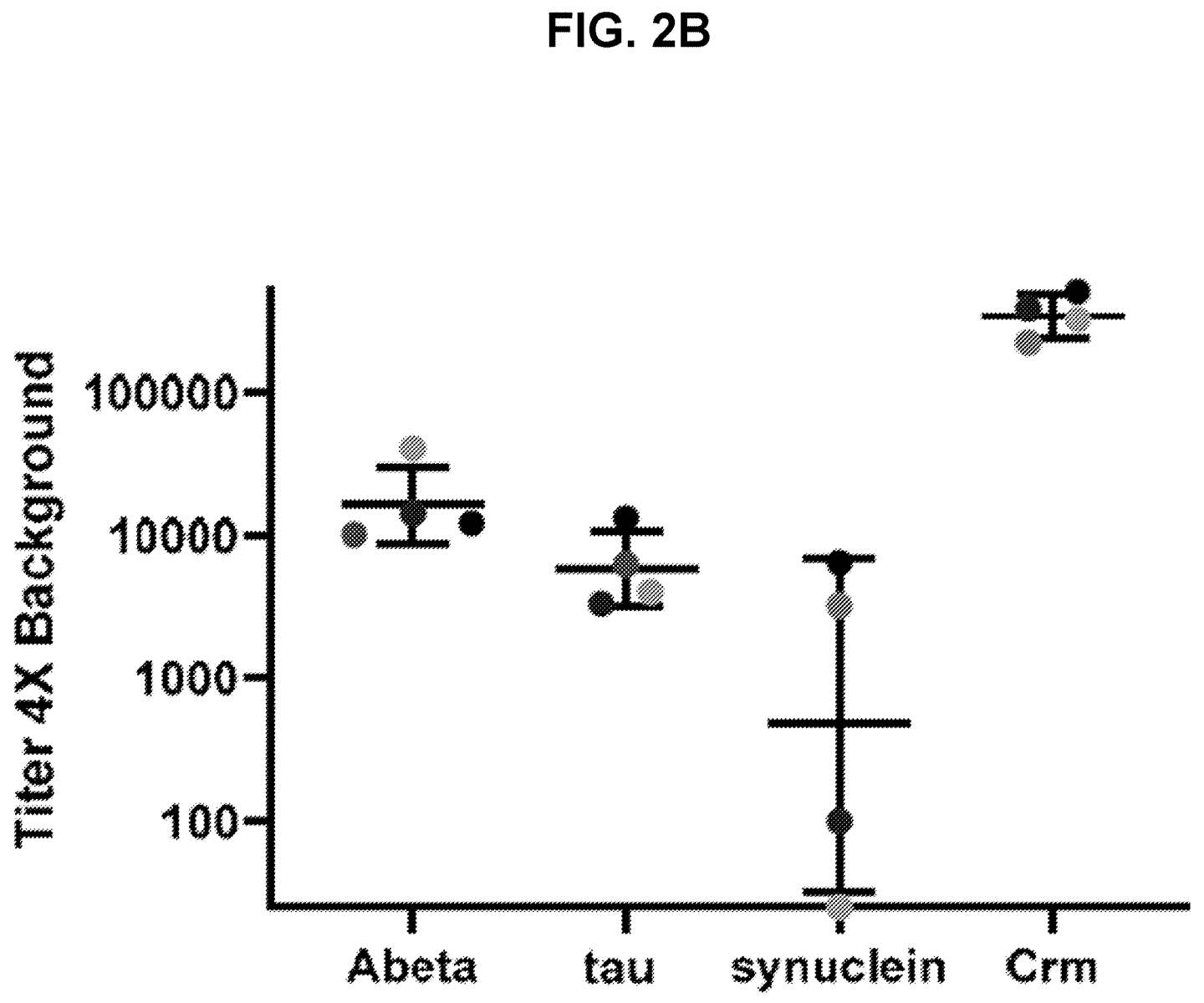

FIG. 2B shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 24 (DAEFRHDRRPD-NEAYERRQIVYKPVKKC; SEQ ID NO:130) on day 0, week 3, week 7, and week 11, and serum was collected one week after each injection (i.e., week 1, week 4, week 8, and week 12).

Figure 2C:
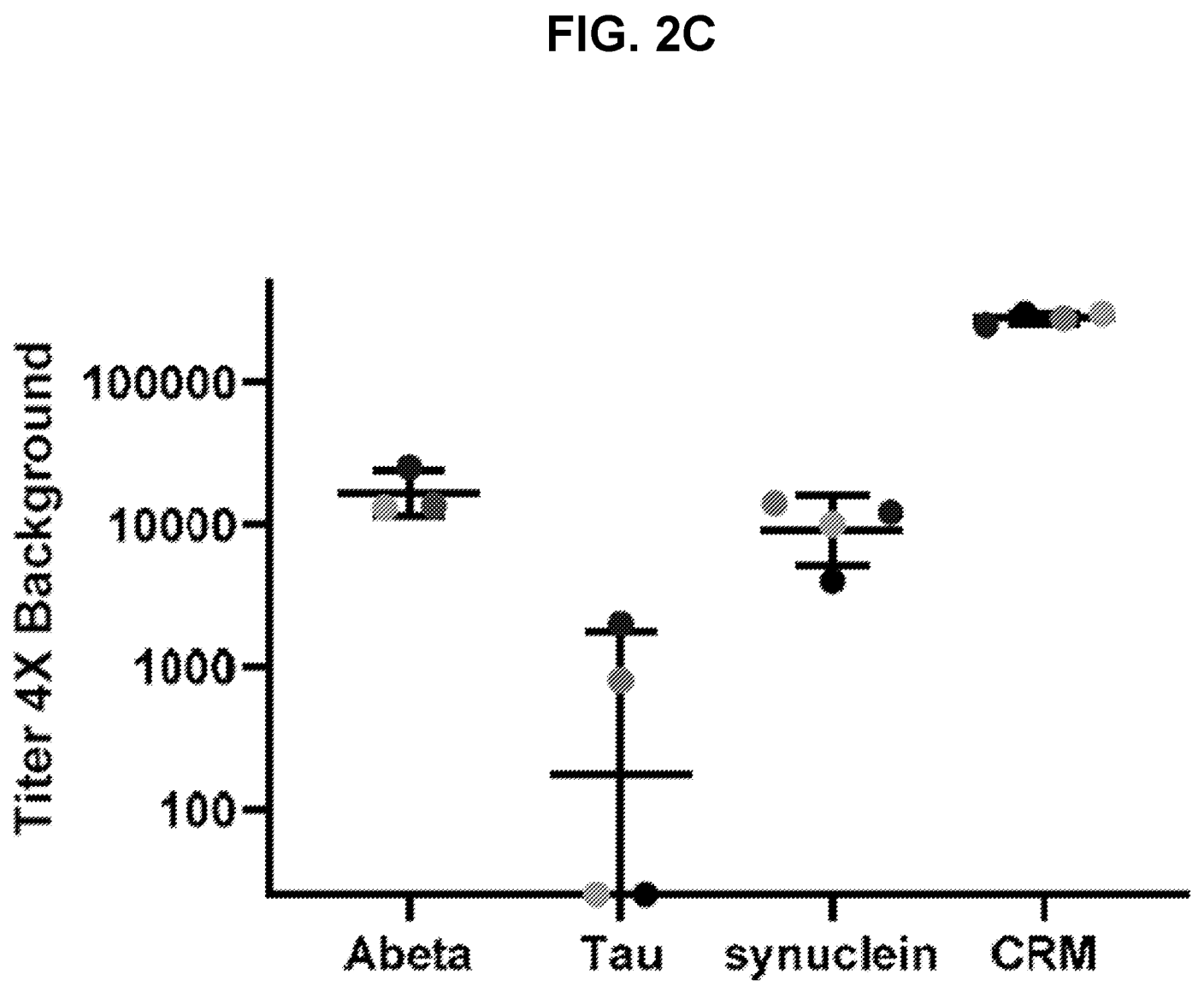

FIG. 2C shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 27 (DAE-FRHDRRNIKHVPGRRPDNEAYEKKC; SEQ ID NO:133) on day 0, week 3, week 7, and week 11, and serum was collected one week after each injection (i.e., week 1, week 4, week 8, and week 12).

Figure 2D:
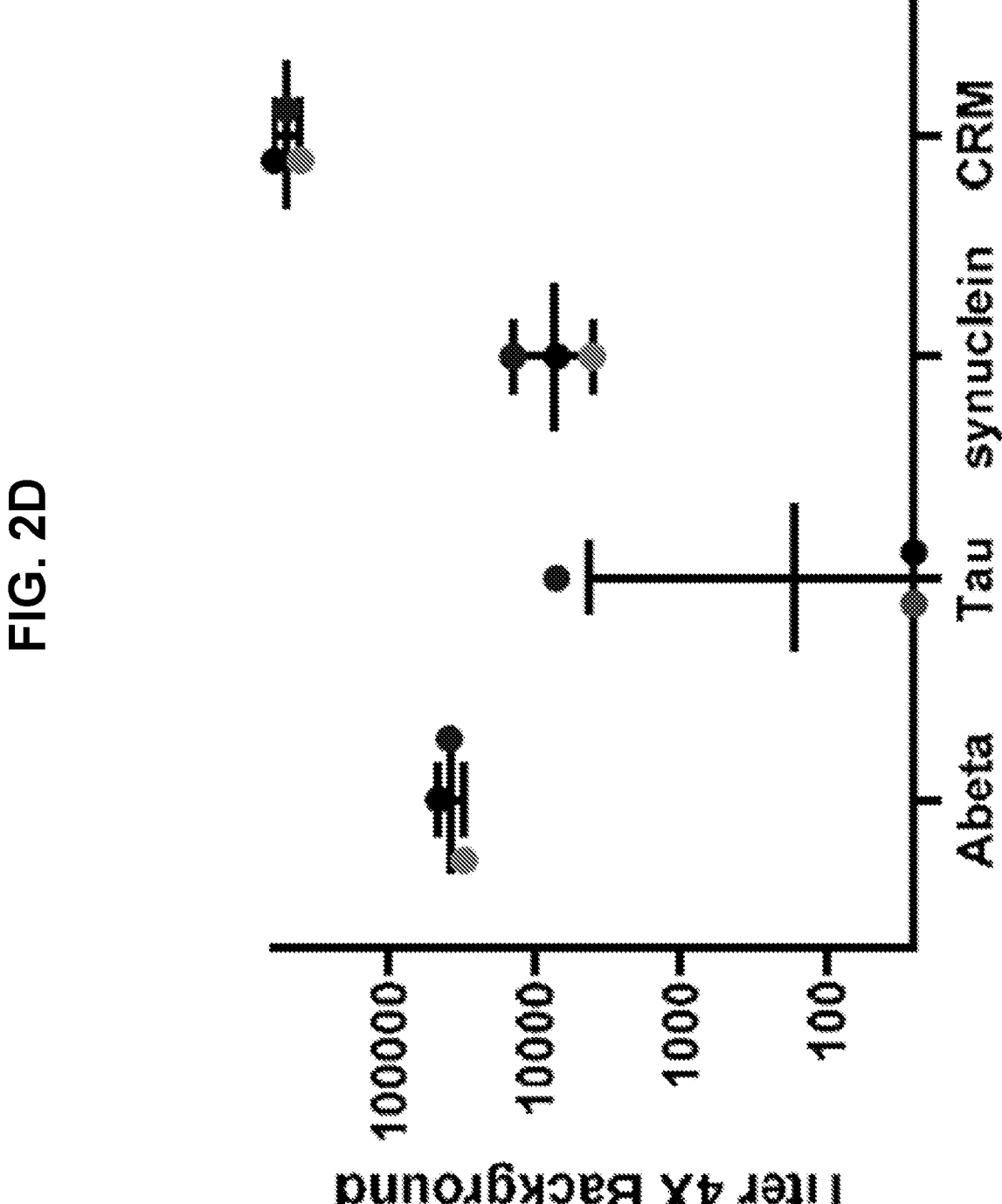

FIG. 2D shows the serum of guinea pigs vaccinated with a tri-peptide immunogen comprising an Aβ peptide, a Tau peptide and an alpha-synuclein peptide antigen produce titers to Aβ, Tau, and alpha-synuclein. Three guinea pigs were injected with Immunogen 26 (DAEFRHDRRPD-NEAYERRNIKHVPGKKC; SEQ ID NO:132) on day 0, week 3, week 7, and week 11, and serum was collected one week after each injection (i.e., week 1, week 4, week 8, and week 12).

Figure 3:
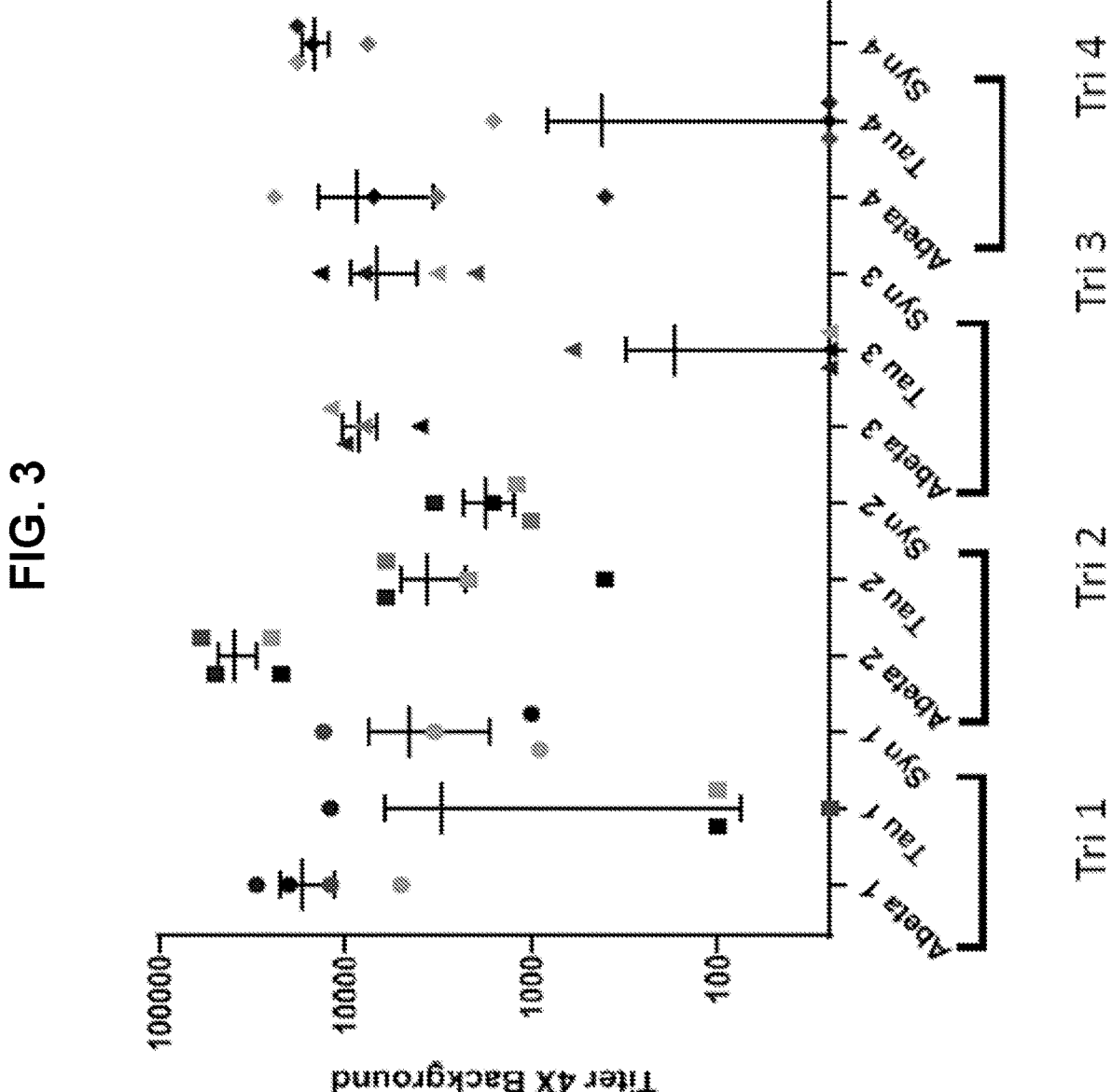

FIG. 3 shows that the serum of mice vaccinated with one of 4 tri-peptide immunogens each comprising an Aβ peptide, a Tau peptide and an alpha-synuclein peptide antigen produce titers to Aβ, Tau, and alpha-synuclein. Four Swiss webster mice per immunogen were injected on day 0 and day 10, and serum was collected on day 16. Tri 2 is DAEFRHDRRDPDNEAYERRENLKHQPGGGC (SEQ ID NO:1058), Tri 1 is DAEFRHDRRENLKHQPGRRDPD-NEAYEGGC (SEQ ID NO: 1059), Tri 4 is DAE-FRHDRRPDNEAYERRENLKHQPGGGC (SEQ ID NO:1060), Tri 3 is DAEFRHDRRENLKHQPGRRPD-NEAYEGGC (SEQ ID NO:1061) (also see Table 4).

DESCRIPTION

The disclosure provides peptide compositions and immunotherapy compositions comprising an amyloid-beta (Aβ) peptide, a tau peptide, and an alpha-synuclein peptide. The disclosure also provides methods of treating or effecting prophylaxis of Alzheimer's disease or other diseases with beta-amyloid deposition in a subject, including methods of clearing and preventing formation of deposits, inhibiting or reducing aggregation of Aβ and/or tau, and/or alpha-synuclein, blocking the binding and/or uptake of Aβ and/or tau and/or alpha-synuclein by neurons, inhibiting transmission of tau species between cells, and inhibiting propagation of pathology between brain regions in a subject having or at risk of developing Alzheimer's disease or other diseases containing tau and/or amyloid-beta accumulations. The methods include administering to such patients the compositions comprising an amyloid-beta (Aβ) peptide, a tau peptide, and an alpha-synuclein peptide.

A number of terms are defined below. As used herein, the singular forms "a," "an", and "the" include plural referents unless the context clearly dictates otherwise. For example, the term "a compound" or "at least one compound" can include a plurality of compounds, including mixtures thereof.

Unless otherwise apparent from the context, the term "about" encompasses insubstantial variations, such as values within a standard margin of error of measurement (e.g., SEM) of a stated value. For example the term "about" as used herein when referring to a measurable value such as a parameter, an amount, a temporal duration, can encompass variations of +/−10% or less, +/−5% or less, or +/−1% or less or less of and from the specified value. Designation of a range of values includes all integers within or defining the range, and all subranges defined by integers within the range. As used herein, statistical significance means $p \leq 0.05$.

Compositions or methods "comprising" or "including" one or more recited elements may include other elements not specifically recited. For example, a composition that "comprises" or "includes" a polypeptide sequence may contain the sequence alone or in combination with other sequences or ingredients.

An individual is at increased risk of a disease if the subject has at least one known risk-factor (e.g., age, genetic, biochemical, family history, and situational exposure) placing individuals with that risk factor at a statistically significant greater risk of developing the disease than individuals without the risk factor.

The term "patient" includes human and other mammalian subjects that receive either prophylactic or therapeutic treatment, including treatment naïve subjects. As used herein, the terms "subject" or "patient" refer to any single subject for which treatment is desired, including other mammalian subjects such as, humans, cattle, dogs, guinea pigs, rabbits, and so on. Also intended to be included as a subject are any subjects involved in clinical research trials not showing any clinical sign of disease, or subjects involved in epidemiological studies, or subjects used as controls.

The term "disease" refers to any abnormal condition that impairs physiological function. The term is used broadly to encompass any disorder, illness, abnormality, pathology, sickness, condition, or syndrome in which physiological function is impaired, irrespective of the nature of the etiology.

The term "symptom" refers to a subjective evidence of a disease, such as altered gait, as perceived by the subject. A "sign" refers to objective evidence of a disease as observed by a physician.

As used herein, the terms "treat" and "treatment" refer to the alleviation or amelioration of one or more symptoms or effects associated with the disease, prevention, inhibition or delay of the onset of one or more symptoms or effects of the disease, lessening of the severity or frequency of one or more symptoms or effects of the disease, and/or increasing or trending toward desired outcomes as described herein.

The terms "prevention", "prevent", or "preventing" as used herein refer to contacting (for example, administering) the peptide(s) or immunotherapy compositions of the present disclosure with a subject before the onset of a disease, with or without Aβ and/or tau pathology already present (primary and secondary prevention), thereby delaying the onset of clinical symptoms and/or alleviating symptoms of the disease after the onset of the disease, compared to when the subject is not contacted with the peptide or immunotherapy compositions, and does not refer to completely suppressing the onset of the disease. In some cases, prevention may occur for limited time after administration of the peptide or immunotherapy compositions of the present disclosure. In other cases, prevention may occur for the duration of a treatment regimen comprising administering the peptide or immunotherapy compositions of the present disclosure.

The terms "reduction", "reduce", or "reducing" as used herein refer to decreasing the amount of Aβ and/or tau and/or alpha-synuclein present in a subject or in tissue of the subject, or suppressing an increase in the amount of Aβ and/or tau and/or alpha-synuclein present in a subject or in tissue of the subject, which encompasses decreasing or suppressing an increase in (e.g., decreasing the rate of increase) the amount of Aβ and/or tau and/or alpha-synuclein present, accumulated, aggregated, or deposited in the subject or tissue in the subject. In certain embodiments, the decrease in or suppression of an increase in (e.g., decreasing the rate of increase) the amount of Aβ and/or tau and/or alpha-synuclein present, accumulated, aggregated, or deposited in the subject refers to an amount of Aβ and/or tau and/or alpha-synuclein present, accumulated, aggregated, or deposited in the central nervous system (CNS) of the subject. In certain embodiments, the decrease in or suppression of an increase in (e.g., decreasing the rate of increase) the amount of Aβ and/or tau and/or alpha-synuclein present, accumulated, aggregated, or deposited in the subject refers to an amount of Aβ and/or tau and/or alpha-synuclein present, accumulated, aggregated, or deposited in the periphery (e.g., peripheral circulatory system) of the subject. In certain embodiments, the decrease in or suppression of an increase in (e.g., decreasing the rate of increase) the amount of Aβ and/or tau and/or alpha-synuclein present, accumulated, aggregated, or deposited in the subject refers to an amount of Aβ and/or tau and/or alpha-synuclein present, accumulated, aggregated, or deposited in the brain of the subject. In some embodiments, the Aβ and/or tau and/or alpha-synuclein reduced is the pathological form(s) of the Aβ (e.g., extracellular plaque deposits of the β-amyloid peptide (Aβ), neuritic amyloid plaques), and/or tau (e.g., neurofibrillary tangles of tau, dystrophic neurites), and/or alpha-synuclein (e.g., fibular alpha-synuclein inclusions, oligomeric or fibrillar alpha-synuclein conglomerates, and protofibrillar intermediates of alpha-synuclein oligomers). In yet other embodiments, pathological indicators of neurodegenerative disease and/or synucleinopathies are decreased.

The terms "epitope" or "antigenic determinant" refers to a site on an antigen to which B and/or T cells respond, or to a site on an antigen to which an antibody binds. Epitopes can be formed both from contiguous amino acids or from noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, at least 4, at least 5, at least 6, at least 7, at least 8, at least 9, at least 10, at least 11, at least 12, or at least 13 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996).

An "immunogenic agent" or "immunogen" or "antigen" is capable of inducing an immunological response against itself or modified/processed versions of itself upon administration to an animal, optionally in conjunction with an adjuvant. The terms "immunogenic agent" or "immunogen" or "antigen" refer to a compound or composition comprising a peptide, polypeptide or protein which is "antigenic" or "immunogenic" when administered in an appropriate amount (an "immunogenically effective amount"), i.e., capable of inducing, eliciting, augmenting or boosting a cellular and/or humoral immune response and of being recognized by the products of that response (T cells, antibodies). An immunogen can be a peptide, or a combination of two or more same or different peptides, that includes at least 3, at least 4, at least 5, at least 6, at least 7, at least 8, at least 9, at least 10, at least 11, at least 12, or at least 13 amino acids in a liner or spatial conformation.

An immunogen may be effective when given alone or in combination, or linked to, or fused to, another substance (which can be administered at one time or over several intervals). An immunogenic agent or immunogen may include an antigenic peptide or polypeptide that is linked to a carrier as described herein.

A nucleic acid such as DNA or RNA that encodes an antigenic peptide, or polypeptide is referred to as a "DNA [or RNA] immunogen," as the encoded peptide or polypeptide is expressed in vivo after administration of the DNA or RNA. The peptide or polypeptide can be recombinantly expressed from a vaccine vector, which can be naked DNA or RNA that comprises the peptide or polypeptide coding sequence operably linked to a promoter, e.g., an expression vector or cassette as described herein.

The term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages. An adjuvant may be a natural compound, a modified version of or derivative of a natural compound, or a synthetic compound.

The terms "peptide" and "polypeptide" are used interchangeably herein and refer to a chain of two or more consecutive amino acids. If and when a distinction is made, context makes the meaning clear. For example, if two or more peptides described herein are joined to make a dimeric or multimeric peptide, polypeptide may be used to indicate "poly" or "more than one" peptide.

The term "pharmaceutically acceptable" means that the carrier, diluent, excipient, adjuvant, or auxiliary is compatible with the other ingredients of a pharmaceutical formulation and not substantially deleterious to the recipient thereof.

The terms "immunotherapy" or "immune response" refer to the development of a beneficial humoral (antibody mediated) and/or a cellular (mediated by antigen-specific T cells or their secretion products) response directed against an Aβ and/or tau peptide in a recipient. Such a response can be an active response induced by administration of immunogen (e.g. an Aβ peptide and/or tau peptide and/or alpha-synuclein peptide). A cellular immune response is elicited by the presentation of polypeptide epitopes in association with Class I or Class II MHC molecules to activate antigen-specific CD4$^+$ T helper cells and/or CD8$^+$ cytotoxic T cells. The response may also involve activation of monocytes, macrophages, NK cells, basophils, dendritic cells, astrocytes, microglia cells, eosinophils or other components of innate immunity. The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

Amyloid Beta (Aβ)

Aβ (also referred to herein as beta amyloid peptide or Abeta) peptide is about a 4-kDa internal fragment of 38-43 amino acids of APP (Aβ39, Aβ40, Aβ41, Aβ42, and Aβ43). Aβ40, for example, consists of residues 672-711 of APP and Aβ42 consists of residues 673-713 of APP. As a result of proteolytic processing of APP by different secretase enzymes in vivo or in situ, Aβ is found in both a "short form", 40 amino acids in length, and a "long form", ranging from 42-43 amino acids in length. Epitopes or antigenic determinants, as described herein, are located within the N-terminus of the Aβ peptide and include residues within amino acids 1-10 and 12-25 of Aβ, for example from residues 1-3, 1-4, 1-5, 1-6, 1-7, or 3-7 of Aβ42. Additional examples of epitopes or antigenic determinants include residues 2-4, 2-5, 2-6, 2-7, or 2-8 of Aβ, residues 3-5, 3-6, 3-7, 3-8, or 3-9 of Aβ, or residues 4-7, 4-8, 4-9, or 4-10 of Aβ42. Aβ residues 12-24, 12-23, 12-22, 13-25, 13-24, 13-23, 13-22, 14-25, 14-24, 14-23, 14-22, 15-25, 15-24, 15-23, or 15-22 of Aβ. For example, from residues 12-17, 12-18, 12-19, 12-20, 12-21, 13-17, 13-18, 13-19, 13-20, 13-21, 13-22, 14-17, 14-18, 14-19, 14-20, 14-21, 14-22, 14-23, 15-17, 15-18, 15-19, 15-20, 15-21, 15-22, 15-23, or 15-24 of Aβ42. Additional examples of epitopes or antigenic determinants include residues 16-18, 16-19, 16-20, 16-21, 16-22, 16-23, 16-24, 16-25, 17-19, 17-20, 17-21, 17-22, 17-23, 17-24 or 17-25 of Aβ42. Other examples of epitopes or antigenic determinants include residues 18-20, 18-21, 18-22, 18-23, 18-24, 18-25, 19-21, 19-22, 19-23, 19-24, 19-25, 20-22, 20-23, 20-24, 20-25, 21-23, 21-24 or 21-25 of Aβ42.

Aβ (Abeta) is the principal component of characteristic plaques of Alzheimer's disease. Aβ is generated by process- ing of a larger protein APP by two enzymes, termed beta and gamma secretases. Known mutations in APP associated with Alzheimer's disease occur proximate to the site of beta or gamma secretase, or within Aβ. Part of the hydrophobic transmembrane domain of APP is found at the carboxy end of Aβ, and may account for the ability of Aβ to aggregate into plaques, particularly in the case of the long form. Accumulation of amyloid plaques in the brain eventually leads to neuronal cell death. The physical symptoms asso- ciated with this type of neural deterioration characterize Alzheimer's disease.

Tau

Tau is a protein with a molecular weight of about 50,000 that is normally present in nerve axons or the like, and contributes to microtubular stability. The tau proteins (or τ proteins) are a group of six highly-soluble protein isoforms produced by alternative splicing from the gene MAPT (microtubule-associated protein tau). They have roles pri- marily in maintaining the stability of microtubules in axons and are abundant in the neurons of the central nervous system (CNS). They are less common elsewhere but are also expressed at very low levels in CNS astrocytes and oligo- dendrocytes. Pathologies and dementias of the nervous system such as Alzheimer's disease and Parkinson's disease are associated with tau proteins that have become hyper- phosphorylated insoluble aggregates called neurofibrillary tangles. Pathogenic tau species causes toxic effects through direct binding to cells and/or accumulation inside cells and/or initiation of misfolding processes (seeding) and is can be propagated from one cell to another via cell-to-cell transmission. Toxicity could also happen by neurofibrillary tangles (NFTs), which leads to cell death and cognitive decline. Other tauopathies include, for example, progressive supranuclear palsy, corticobasal syndrome, some frontotem- poral dementias, and chronic traumatic encephalopathy.

Alpha-Synuclein

Alpha-synuclein is a highly conserved protein that is abundant in neurons, especially presynaptic terminals. Aggregated alpha-synuclein proteins form brain lesions that are hallmarks of neurodegenerative synucleinopathies. Fur- thermore, misfolding and aggregation can often be accom- panied by β-amyloid deposition in some neurodegenerative diseases, and alpha-synuclein and tau aggregates coexist in several neurodegenerative disorders, including Alzheimer's disease and Parkinson's disease.

Aβ/Tau/Alpha-Synuclein Polypeptides of an Immunogen

An agent used for active immunization can induce in a patient an immune response and can serve as an immuno- therapy. Agents used for active immunization can be, for example, the same types of immunogens used for generating monoclonal antibodies in laboratory animals, and may include 3, 4, 5, 6, 7, 8, 9, 10, 11, 12, or 13 or more contiguous amino acids from a region of Aβ and/or tau peptide and/or alpha-synuclein peptide. In each of the embodiments of the peptides described herein, the peptides may comprise, consist, or consist essentially of the recited sequences.

In some embodiments of the disclosure, an Aβ/tau/alpha- synuclein immunogen can include an Aβ peptide comprising 3-10 amino acids from residues 1-10 or 12-25 of the N-terminal sequence of Aβ (SEQ ID NO:01) linked to a tau peptide comprising 3-13 amino acids from residues 244-400 of the long form of tau (SEQ ID NO:02), and an alpha- synuclein peptide comprising 3-10 amino acids from resi- dues 81-140 of SEQ ID NO:58. For example, the tau peptide may comprise 3-13 amino acids from the microtubule bind- ing region of tau (residues 344-372 of SEQ ID NO:02).

In some embodiments of the disclosure, the Aβ peptide can include 3-10 amino acids from residues 1-10 or 12-25 of DAEFRHDSGYEVHHQKLVFFAEDVGSNK- GAIIGLMVGGVVIA (SEQ ID NO:01). For example, the Aβ peptide is selected from the following:

```
                                        (SEQ ID NO: 03)
          DAEFRHDSGY (SEQ ID NO: 04)
          DAEFRHDSG, (SEQ ID NO: 05)
          DAEFRHDS, (SEQ ID NO: 06)
          DAEFRHD, (SEQ ID NO: 07)
          DAEFRH, (SEQ ID NO: 08)
          DAEFR, (SEQ ID NO: 09)
          DAEF, (SEQ ID NO: 10)
          DAE, (SEQ ID NO: 11)
          AEFRHDSGY, (SEQ ID NO: 12)
          AEFRHDSG, (SEQ ID NO: 13)
          AEFRHDS, (SEQ ID NO: 14)
          AEFRHD, (SEQ ID NO: 15)
          AEFRH, (SEQ ID NO: 16)
          AEFR, (SEQ ID NO: 17)
          AEF, (SEQ ID NO: 18)
          EFRHDSGY, (SEQ ID NO: 19)
          EFRHDSG, (SEQ ID NO: 20)
          EFRHDS, (SEQ ID NO: 21)
          EFRHD, (SEQ ID NO: 22)
          EFRH, (SEQ ID NO: 23)
          EFR, (SEQ ID NO: 24)
          FRHDSGY,
```

-continued (SEQ ID NO: 25)
FRHDSG, (SEQ ID NO: 26)
FRHDS, (SEQ ID NO: 27)
FRHD, (SEQ ID NO: 28)
FRH, (SEQ ID NO: 29)
RHDSGY, (SEQ ID NO: 30)
RHDSG, (SEQ ID NO: 31)
RHDS, (SEQ ID NO: 32)
RHD, (SEQ ID NO: 33)
HDSGY, (SEQ ID NO: 34)
HDSG, (SEQ ID NO: 35)
HDS, (SEQ ID NO: 36)
DSGY, (SEQ ID NO: 37)
DSG, (SEQ ID NO: 38)
SGY, (SEQ ID NO: 1002)
VHHQKLVFFA, (SEQ ID NO: 1003)
VHHQKLVFF, (SEQ ID NO: 1004)
VHHQKLVF, (SEQ ID NO: 1005)
VHHQKLV, (SEQ ID NO: 1006)
VHHQKL, (SEQ ID NO: 1007)
HHQKLVFFAE, (SEQ ID NO: 1008)
HHQKLVFFA, (SEQ ID NO: 1009)
HHQKLVFF, (SEQ ID NO: 1010)
HHQKLVF, (SEQ ID NO: 1011)
HHQKLV, (SEQ ID NO: 1012)
HHQKL, (SEQ ID NO: 1013)
HQKLVFFAED, (SEQ ID NO: 1014)
HQKLVFFAE, -continued (SEQ ID NO: 1015)
HQKLVFFA, (SEQ ID NO: 1016)
HQKLVFF, (SEQ ID NO: 1017)
HQKLVF, (SEQ ID NO: 1018)
HQKLV, (SEQ ID NO: 1019)
HQKL, (SEQ ID NO: 1020)
QKLVFFAEDV, (SEQ ID NO: 1021)
QKLVFFAED, (SEQ ID NO: 1022)
QKLVFFAE, (SEQ ID NO: 1023)
QKLVFFA, (SEQ ID NO: 1024)
QKLVFF, (SEQ ID NO: 1025)
QKLVF, (SEQ ID NO: 1026)
QKLV, (SEQ ID NO: 1027)
QKL, (SEQ ID NO: 1028)
KLVFFAEDVG, (SEQ ID NO: 1029)
KLVFFAEDV, (SEQ ID NO: 1030)
KLVFFAED, (SEQ ID NO: 1031)
KLVFFAE, (SEQ ID NO: 1032)
KLVFFA, (SEQ ID NO: 1033)
KLVFF, (SEQ ID NO: 1034)
KLVF, (SEQ ID NO: 1035)
KLV, (SEQ ID NO: 1036)
LVFFAEDVG, (SEQ ID NO: 1037)
LVFFAEDV, (SEQ ID NO: 1038)
LVFFAED, (SEQ ID NO: 1039)
LVFFAE, (SEQ ID NO: 1040)
LVFFA, (SEQ ID NO: 1041)
LVFF, -continued (SEQ ID NO: 1042)
LVF, (SEQ ID NO: 1043)
VFFAEDVG, (SEQ ID NO: 1044)
VFFAEDV, (SEQ ID NO: 1045)
VFFAED, (SEQ ID NO: 1046)
VFFAE, (SEQ ID NO: 1047)
VFFA, (SEQ ID NO: 1048)
VFF, (SEQ ID NO: 1049)
FFAEDVG, (SEQ ID NO: 1050)
FFAEDV, (SEQ ID NO: 1051)
FFAED, (SEQ ID NO: 1052)
FFAE, (SEQ ID NO: 1053)
FFA, (SEQ ID NO: 1054)
FAEDVG, (SEQ ID NO: 1055)
FAEDV, (SEQ ID NO: 1056)
FAED,
and (SEQ ID NO: 1057)
FAE.

In certain embodiments, the Aβ peptide is DAEFRHD (SEQ ID NO:06), DAEFR (SEQ ID NO:08) or EFRHD (SEQ ID NO:21).

The tau peptide can correspond to a peptide comprising 3-13 amino acids from residues 244-400 of SEQ ID NO:02. In some embodiments, the fragment is unphosphorylated. In some embodiments, the fragment is phosphorylated. In some embodiments, the tau peptide comprises an amino acid sequence represented by the consensus motif (Q/E)IVYK (S/P) (SEQ ID NO:996). In some embodiments, the tau peptide comprises an amino acid sequence represented by the consensus motif KXXSXXNX(K/H)H (SEQ ID NO: 995) where X is any amino acid. In some embodiments, the tau peptide is selected from SEQ ID NOS: 146-1000. In some embodiments, the tau peptide is selected from the following:

(SEQ ID NO: 39)
QIVYKPV, (SEQ ID NO: 40)
QIVYKP, (SEQ ID NO: 41)
QIVYKSV,

-continued (SEQ ID NO: 42)
EIVYKSV, (SEQ ID NO: 997)
QIVYKS, (SEQ ID NO: 43)
EIVYKSP, (SEQ ID NO: 998)
EIVYKS, (SEQ ID NO: 44)
EIVYKPV, (SEQ ID NO: 999)
EIVYKP, (SEQ ID NO: 45)
IVYKSPV, (SEQ ID NO: 46)
IVYK, (SEQ ID NO: 1000)
CNIKHVPG, (SEQ ID NO: 47)
CNIKHVP, (SEQ ID NO: 48)
NIKHVP, (SEQ ID NO: 49)
HVPGGG, (SEQ ID NO: 50)
HVPGG, (SEQ ID NO: 51)
HKPGGG, (SEQ ID NO: 52)
HKPGG, (SEQ ID NO: 53)
KHVPGGG, (SEQ ID NO: 54)
KHVPGG, (SEQ ID NO: 55)
HQPGGG, (SEQ ID NO: 56)
HQPGG, (SEQ ID NO: 57)
NIKHVPG,
and

SEQ ID NOS: 146-996.

The alpha-synuclein peptide can correspond to a peptide comprising 3-10 amino acids from residues 81-140 of SEQ ID NO:58. In some embodiments, alpha-synuclein is unphosphorylated. In some embodiments, alpha-synuclein is phosphorylated. In some compositions, the alpha-synuclein peptide is selected from the following:

(SEQ ID NO: 59)
VDPDNEAYEM, (SEQ ID NO: 60)
VDPDNEAYE, (SEQ ID NO: 61)
VDPDNEAY,

17

(SEQ ID NO: 62)
VDPDNEA, (SEQ ID NO: 63)
VDPDNE, (SEQ ID NO: 64)
VDPDN, (SEQ ID NO: 65)
VDPD, (SEQ ID NO: 66)
VDP, (SEQ ID NO: 67)
DPDNEAYEM, (SEQ ID NO: 68)
DPDNEAYE, (SEQ ID NO: 69)
DPDNEAY, (SEQ ID NO: 70)
DPDNEA, (SEQ ID NO: 71)
DPDNE, (SEQ ID NO: 72)
DPDN, (SEQ ID NO: 73)
DPD, (SEQ ID NO: 74)
PDNEAYEM, (SEQ ID NO: 75)
PDNEAYE, (SEQ ID NO: 76)
PDNEAY, (SEQ ID NO: 77)
PDNEA, (SEQ ID NO: 78)
PDNE, (SEQ ID NO: 79)
PDN, (SEQ ID NO: 80)
DNEAYEM, (SEQ ID NO: 81)
DNEAYE, (SEQ ID NO: 82)
DNEAY, (SEQ ID NO: 83)
DNEA, (SEQ ID NO: 84)
DNE, (SEQ ID NO: 85)
NEAYEM, (SEQ ID NO: 86)
NEAYE, (SEQ ID NO: 87)
NEAY, (SEQ ID NO: 88)
NEA,

18

(SEQ ID NO: 89)
EAYEM, (SEQ ID NO: 90)
EAYE, (SEQ ID NO: 91)
EAY, (SEQ ID NO: 92)
AYEM, (SEQ ID NO: 93)
AYE, (SEQ ID NO: 94)
YEM, (SEQ ID NO: 95)
ATGFVKKDQL, (SEQ ID NO: 96)
ATGFVKKDQ, (SEQ ID NO: 97)
ATGFVKKD, (SEQ ID NO: 98)
ATGFVKK, (SEQ ID NO: 99)
ATGFVK, (SEQ ID NO: 100)
ATGFV, (SEQ ID NO: 101)
ATGF, (SEQ ID NO: 102)
ATG, (SEQ ID NO: 103)
TGFVKKDQL, (SEQ ID NO: 104)
TGFVKKDQ, (SEQ ID NO: 105)
TGFVKKD, (SEQ ID NO: 106)
TGFVKK, (SEQ ID NO: 107)
TGFVK, (SEQ ID NO: 108)
TGFV, (SEQ ID NO: 109)
TGF, (SEQ ID NO: 110)
GFVKKDQL, (SEQ ID NO: 111)
GFVKKDQ, (SEQ ID NO: 112)
GFVKKD, (SEQ ID NO: 113)
GFVKK, (SEQ ID NO: 114)
GFVK, (SEQ ID NO: 115)
GFV,

19
-continued

FVKKDQL, (SEQ ID NO: 116)

FVKKDQ, (SEQ ID NO: 117)

FVKKD, (SEQ ID NO: 118)

FVKK, (SEQ ID NO: 119)

FVK, (SEQ ID NO: 120)

VKKDQL, (SEQ ID NO: 121)

VKKDQ, (SEQ ID NO: 122)

VKKD, (SEQ ID NO: 123)

VKK, (SEQ ID NO: 124)

KKDQL, (SEQ ID NO: 125)

KKDQ, (SEQ ID NO: 126)

KKD, (SEQ ID NO: 127)

KDQL, and (SEQ ID NO: 128)

KDQ. (SEQ ID NO: 129)

In each of these embodiments, the peptide may comprise, consist, or consist essentially of the recited sequences.

In some embodiments, the Aβ and/or tau and/or alpha-synuclein peptides are linked to form a multiple Aβ/tau/alpha-synuclein polypeptide. The Aβ, tau, and alpha-synuclein peptides can be linked by an intra-peptide linker. For example, a polypeptide linker located between the C-terminal of the first peptide and the N terminal of the second peptide. With or without the intra-peptide linker, the Aβ peptide and/or the tau peptide and/or the alpha-synuclein peptide may be positioned in a multiple Aβ/tau/alpha-synuclein polypeptide in any order. For example, the Aβ peptide may be positioned at the N-terminal portion of the multiple polypeptide and the alpha-synuclein peptide may be positioned at the C-terminal portion of the multiple polypeptide. Or, the tau peptide may be positioned at the N-terminal portion of the multiple polypeptide and the Aβ peptide may be positioned at the C-terminal portion of the multiple polypeptide side of the tau peptide. Reference to a first peptide or a second peptide or a third peptide or a fourth peptide herein is not intended to suggest an order of the Aβ and/or tau and/or alpha-synuclein peptides in the polypeptide of the immunogens.

In addition, the C-terminal portion of the Aβ peptide, the tau peptide, the alpha-synuclein, or the multiple Aβ/tau/alpha-synuclein polypeptide can include a linker for conjugating the peptides or the polypeptide to a carrier. Linkers that couple the peptides or multiple polypeptide to the carrier may include, for example, GG, GGG, KK, KKK, AA, AAA, SS, SSS, GAGA (SEQ ID NO:139), AGAG (SEQ ID NO:140), KGKG (SEQ ID NO:141), and the like between the peptides or dual polypeptide and the carrier and may further include a C-terminal or a N-terminal cysteine to provide a short peptide linker (e.g., G-G-C-, K-K-C-, A-A-C-, or S-S-C-). In some embodiments, where the C-terminal residues in the immunogen are either IVYKPV (SEQ ID NO:194), VYKPV (SEQ ID NO:195), YKPV (SEQ ID NO:196), KPV, or PV the linker is an amino acid linker that does not have a N-terminal glycine (e.g., GG, GAGA (SEQ ID NO:139), and KGKG (SEQ ID NO:141). In some embodiments, the linker comprises an amino acid sequence any one of AA, AAA, KK, KKK, SS, SSS, AGAG (SEQ ID NO:140), GG, GGG, GAGA (SEQ ID NO:139), and KGKG (SEQ ID NO:141). In some embodiments, any of the Aβ peptide, the tau peptide, the alpha-synuclein peptide and the multiple Aβ/tau/alpha-synuclein polypeptide may include a C-terminal cysteine without the spacer. In some embodiments, any of the Aβ peptide, the tau peptide, the alpha-synuclein peptide and the multiple Aβ/tau/alpha-synuclein polypeptide may include a N-terminal cysteine without the spacer.

When the Aβ, tau, and/or alpha-synuclein polypeptides are linked to form a multiple Aβ/tau/alpha-synuclein polypeptide, the linker may be a cleavable linker. As used herein, the term "cleavable linker" refers to any linker between the antigenic peptides that promotes or otherwise renders the Aβ peptide, the tau peptide, and/or the alpha-synuclein peptide more susceptible to separation from each other by cleavage (for example, by endopeptidases, proteases, low pH or any other means that may occur within or around the antigen-presenting cell) and, thereby, processing by the antigen-presenting cell, than equivalent peptides lacking such a cleavable linker. In some compositions, the cleavable linker is a protease-sensitive dipeptide or oligopeptide cleavable linker. In certain embodiments, the cleavable linker is sensitive to cleavage by a protease of the trypsin family of proteases. In some compositions, the cleavable linker comprises an amino acid sequence selected from the group consisting of arginine-arginine (Arg-Arg), arginine-valine-arginine-arginine (Arg-Val-Arg-Arg; SEQ ID NO:138), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; GAGA (SEQ ID NO:139)), Ala-Gly-Ala-Gly; AGAG (SEQ ID NO:140), and Lys-Gly-Lys-Gly; KGKG (SEQ ID NO:141). In some compositions, the cleavable linker is arginine-arginine (Arg-Arg).

In some embodiments of the disclosure, the multiple Aβ/tau/alpha-synuclein polypeptide comprises, consists or consists essentially of an amino acid sequence selected from SEQ ID NOs: 130-137 and SEQ ID NOs: 1058-1063.

In some embodiments, the multiple Aβ/tau/alpha-synuclein polypeptide is as follows:

[P1]-[CL1]-[P2]-[CL2]-[P3]-[L1]-[Cys]; Formula I:

[P1]-[CL1]-[P2]-[CL2]-[P3]-[CL3]-[P4]-[L1]-[Cys]; Formula II:

wherein, each of P1, P2, P3 and P4 may be independently selected from an Aβ peptide, a tau peptide and an alpha-synuclein peptide, provided that each of an Aβ peptide, a tau peptide and an alpha-synuclein peptide are selected. In embodiments, the P1 is an Aβ peptide, for example if the first peptide [P1] is an Aβ peptide then the second peptide [P2] is a tau peptide, and the third peptide [P3] is an alpha-synuclein peptide, or if [P1] is an Aβ peptide then [P2] is a tau Aβ peptide, and the fourth peptide [P4] is a tau peptide, or if [P1] is an Aβ peptide then [P2] is an alpha-synuclein peptide, and [P3] is a tau peptide, or if [P1] is an Aβ peptide then [P2] is an alpha-synuclein peptide, [P3] is a tau peptide, and [P4] is a tau peptide, and each of [CL1], [CL2], and [CL3] are cleavable linkers and [L1] is a linker, and [CL1], [CL2], [CL3], [L1], and [Cys] are optional.

Examples of the Aβ peptide include any one SEQ ID NOS 3-38 or 1002-1057.

Examples of the tau peptide include any one of SEQ ID NOS: 39-57, or 142-1000.

Examples of the alpha-synuclein peptide include any one of SEQ ID NOS: 59-129.

[CL1], [CL2], and [CL3] are optional, and when present, may be a cleavable linker. A cleavable linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the cleavable linker is 1 amino acid, 2 amino acids, 3 amino acids, 4 amino acids, 5 amino acids, 6 amino acids, 7 amino acids, 8 amino acids, 9 amino acids, or 10 amino acids. In some embodiments, the linker may be a cleavable linker having an amino acid sequence selected from the group consisting of arginine-arginine (Arg-Arg), arginine-valine-arginine-arginine (Arg-Val-Arg-Arg; SEQ ID NO:138), valine-citrulline (Val-Cit), valine-arginine (Val-Arg), valine-lysine (Val-Lys), valine-alanine (Val-Ala), phenylalanine-lysine (Phe-Lys), glycine-alanine-glycine-alanine (Gly-Ala-Gly-Ala; SEQ ID NO: 139), alanine-glycine-alanine-glycine (Ala-Gly-Ala-Gly; SEQ ID NO:140), and lysine-glycine-lysine-glycine (Lys-Gly-Lys-Gly; SEQ ID NO:141)).

[L1] is optional, and when present is a linker that couples the polypeptide to a carrier. A linker, if present, can be 1-10 amino acids in length. In some embodiments, the linker comprises between about 1-10 amino acids, about 1-9 amino acids, about 1-8 amino acids, about 1-7 amino acids, about 1-6 amino acids, about 1-5 amino acids, about 1-4 amino acids, about 1-3 amino acids, about 2 amino acids, or one (1) amino acid. In some embodiments, the linker is 1 amino acid, 2 amino acids, 3 amino acids, 4 amino acids, 5 amino acids, 6 amino acids, 7 amino acids, 8 amino acids, 9 amino acids, or 10 amino acids. In some embodiments, the amino acid composition of a linker can mimic the composition of linkers found in natural multidomain proteins, where certain amino acids are overrepresented, underrepresented or equirepresented in natural linkers as compared to their abundance in whole protein. For example, threonine (Thr), serine (Ser), proline (Pro), glycine (Gly), aspartic acid (Asp), lysine (Lys), glutamine (Gln), asparagine (Asn), arginine (Arg), phenylalanine (Phe), glutamic acid (Glu) and alanine (Ala) are overrepresented in natural linkers. In contrast, isoleucine (Ile), tyrosine (Tyr), tryptophan (Trp), and cysteine (Cys) are underrepresented. In general, overrepresented amino acids were polar uncharged or charged residues, which constitute approximately 50% of naturally encoded amino acids, and Pro, Thr, and Gln were the most preferable amino acids for natural linkers. In some embodiments, the amino acid composition of a linker can mimic the composition of linkers commonly found in recombinant proteins, which can generally by classified as flexible or rigid linkers. For example, flexible linkers found in recombinant proteins are generally composed of small, non-polar (e.g. Gly) or polar (e.g. Ser or Thr) amino acids whose small size provides flexibility and allows for mobility of the connecting functional domains. The incorporation of, e.g., Ser or Thr can maintain the stability of the linker in aqueous solutions by forming hydrogen bonds with the water molecules, and therefore can reduce interactions between the linker and the immunogens. In some embodiments, a linker comprises stretches of Gly and Ser residues ("GS" linker). An example of a widely used flexible linker is (Gly-Gly-Ser)n, (Gly-Gly-Gly-Ser)n (SEQ ID NO:1064) or (Gly-Gly-Gly-Gly-Ser)n (SEQ ID NO: 1065), where n=1-3. Adjusting the copy number "n" can optimize a linker to achieve sufficient separation of the functional immunogen domains to, e.g., maximize an immunogenic response. Many other flexible linkers have been designed for recombinant fusion proteins that can be used herein. In some embodiments, linkers can be rich in small or polar amino acids such as Gly and Ser but also contain additional amino acids such as Thr and Ala to maintain flexibility, as well as polar amino acids such as Lys and Glu to improve solubility. See, e.g., Chen, X. et al., "Fusion Protein Linkers: Property, Design and Functionality" Adv Drug Deliv Rev., 15; 65(10): 1357-1369 (203). In certain embodiments, when present, the linker can be an amino acid sequence selected from the group consisting of as GG, GGG, KK, KKK, AA, AAA, SS, SSS, G-A-G-A (SEQ ID NO: 139), A-G-A-G (SEQ ID NO:140), and K-G-K-G (SEQ ID NO: 142).

[Cys] is optional and can be helpful to conjugate the polypeptide to a carrier. When present, the Cys can be at the C-terminal portion of the polypeptide, or at the N-terminal portion of the polypeptide.

Examples of multiple Aβ/tau/alpha-synuclein polypeptide of the disclosure include the following:

TABLE 1

| Formula I: [P1]-[CL1]-[P2]-[CL2]-[P3]-[L1]-[Cys] | | | | | | | |
|---|---|---|---|---|---|---|---|
| Immunogen Lab ID (SEQ ID NO) | [P1] (SEQ ID NO) | [CL1] | [P2] (SEQ ID NO) | [CL2] | [P3] (SEQ ID NO) | [L1] | Cys |
| 24 (130) | DAEFRHD (06) | RR | PDNEAYE (75) | RR | QIVYKPV (39) | KK | C |
| 25 (131) | DAEFRHD (06) | RR | QIVYKPV (39) | RR | PDNEAYE (75) | KK | C |
| 26 (132) | DAEFRHD (06) | RR | PDNEAYE (75) | RR | NIKHVPG (57) | KK | C |
| 27 (133) | DAEFRHD (06) | RR | NIKHVPG (57) | RR | PDNEAYE (75) | KK | C |

TABLE 1-continued

| Formula I: [P1]-[CL1]-[P2]-[CL2]-[P3]-[L1]-[Cys] | | | | | | | | |
|---|---|---|---|---|---|---|---|---|
| Immunogen Lab ID (SEQ ID NO) | [P1] (SEQ ID NO) | [CL1] | [P2] (SEQ ID NO) | [CL2] | [P3] (SEQ ID NO) | [L1] | Cys | |
| Tri 2 (1058) | DAEFRHD (06) | RR | DPDNEAYE (68) | RR | ENLKHQPG (777) | GG | C | |
| Tri 1 (1059) | DAEFRHD (06) | RR | ENLKHQPG (777) | RR | DPDNEAYE (68) | GG | C | |
| Tri 4 (1060) | DAEFRHD (06) | RR | PDNEAYE (75) | RR | ENLKHQPG (777) | GG | C | |
| Tri 3 (1061) | DAEFRHD (06) | RR | ENLKHQPG (777) | RR | PDNEAYE (75) | GG | C | |
| Tri 5 (1062) | DAEFRHD (06) | RR | SKIGSKDNIKH (986) | RR | DPDNEAYE (68) | GG | C | |
| Tri 6 (1063) | DAEFRHD (06) | RR | DPDNEAYE (68) | RR | SKIGSKDNIKH (986) | GG | C | |

TABLE 2

| Formula II: [P1]-[CL1]-[P2]-[CL2]-[P3]-[CL3]-[P4]-[L1]-[Cys] | | | | | | | | | | |
|---|---|---|---|---|---|---|---|---|---|---|
| Immunogen Lab ID (SEQ ID NO) | [P1] (SEQ ID NO) | [CL1] | [P2] (SEQ ID NO) | [CL2] | [P3] (SEQ ID NO) | [CL3] | [P4] (SEQ ID NO) | [L1] | Cys |
| 14 (134) | DAEFRHD (06) | RR | QIVYKPV (39) | RR | PDNEAYE (75) | RR | NIKHVP (48) | GG | C |
| 15 (135) | DAEFRHD (06) | RR | DPDNEAY (69) | RR | NIKHVPG (57) | RR | QIVYKPV (39) | GG | C |
| 16 (136) | EFRHDSG (19) | RR | QIVYKPV (39) | RR | PDNEAYE (75) | RR | NIKHVP (48) | GG | C |
| 17 (137) | EFRHDSG (19) | RR | DPDNEAY (69) | RR | NIKHVPG (57) | RR | QIVYKPV (39) | GG | C |

Polypeptide Immunogens

The Aβ peptide, the tau peptide, the alpha-synuclein, and the multiple Aβ/tau/alpha-synuclein polypeptide are immunogens in accordance with the disclosure. In some embodiments, the peptides and the multiple Aβ/tau/alpha-synuclein polypeptide can be linked to a suitable carrier to help elicit an immune response. Accordingly, one or more the peptides and multiple Aβ/tau/alpha-synuclein polypeptides of the disclosure can be linked to a carrier. For example, each of the Aβ peptide, tau peptide, the alpha-synuclein peptide, and the Aβ/tau/alpha-synuclein polypeptide may be linked to the carrier with or without spacer amino acids (e.g., Gly-Gly, Gly-Gly-Gly, Ala-Ala, Ala-Ala-Ala, Lys-Lys, Lys-Lys-Lys, Ser-Ser, Ser-Ser-Ser, Gly-Ala-Gly-Ala (SEQ ID NO:139), Ala-Gly-Ala-Gly (SEQ ID NO:140), and Lys-Gly-Lys-Gly (SEQ ID NO:141)). In certain embodiments, the multiple Aβ/tau/alpha-synuclein polypeptide can be linked to a suitable carrier using a C-terminal cysteine to provide a linker between the peptide(s) and the carrier or the multiple Aβ/tau/alpha-synuclein polypeptide and the carrier. In certain embodiments, the multiple Aβ/tau/alpha-synuclein polypeptide can be linked to a suitable carrier using an N-terminal cysteine to provide a linker between the peptide(s) and the carrier. In some embodiments, where the C-terminal residues in the immunogen are IVYKPV (SEQ ID NO:194), VYKPV (SEQ ID NO:195), YKPV (SEQ ID NO:196), KPV, or PV the linker is an amino acid linker that does not have a N-terminal glycine (e.g., GG, GAGA (SEQ ID NO:139)).

Suitable carriers include, but are not limited to serum albumins, keyhole limpet hemocyanin, immunoglobulin molecules, thyroglobulin, ovalbumin, tetanus toxoid, or a toxoid from other pathogenic bacteria, such as diphtheria (e.g., CRM197), E. coli, cholera, or H. pylori, or an attenuated toxin derivative. T cell epitopes are also suitable carrier molecules. Some conjugates can be formed by linking peptide immunogens of the invention to an immunostimulatory polymer molecule (e.g., tripalmitoyl-S-glycerine cysteine (Pam3Cys), mannan (a mannose polymer), or glucan (a β 1-2 polymer)), cytokines (e.g., IL-1, IL-1 alpha and β peptides, IL-2, γ-INF, IL-10, GM-CSF), and chemokines (e.g., MIP1-α and β, and RANTES). Additional carriers include virus-like particles. In some compositions, immunogenic peptides can also be linked to carriers by chemical crosslinking. Techniques for linking an immunogen to a carrier include the formation of disulfide linkages using N-succinimidyl 3-(2-pyridylthio)propionate (SPDP), and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. In some embodiments, chemical crosslinking can comprise use of SBAP (succinimidyl 3-(bromoacetamido)propionate), which is a short (6.2 angstrom) cross-linker for amine-to-sulfhydryl conjugation via N-hydroxysuccinimide (NHS) ester and bromoacetyl reactive groups. A variety of such disulfide/amide-forming agents are described by Jansen et al., "Immunotoxins: Hybrid Molecules Combining High Specificity and Potent Cytotoxicity" *Immunological Reviews* 62:185-216 (February 1982). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt. Virus-like particles (VLPs), also called pseudovirions or virus-derived particles, represent subunit structures composed of multiple copies of a viral capsid and/or envelope protein capable of self-assembly into VLPs of defined spherical symmetry in vivo. (Powilleit, et al., (2007) *PLoS ONE* 2(5):e415.) Alternatively, peptide immunogens can be linked to at least one artificial T-cell epitope capable of binding a large proportion of MHC Class II molecules, such as the pan DR epitope ("PADRE"). Pan DR-binding peptides (PADREs described in U.S. Pat. No. 5,736,142, WO 95/07707, and Alexander, et al, *Immunity,* 1:751-761 (1994).

Active immunogens can be presented in multimeric form in which multiple copies of an immunogen (peptide of polypeptide) are presented on a carrier as a single covalent molecule. In some embodiments, the carrier includes various forms of the multiple Aβ/tau/alpha-synuclein polypeptide. For instance, the multiple Aβ/tau/alpha-synuclein polypeptide of the immunogen can include polypeptides that have the Aβ antigen, the tau antigen and alpha-synuclein antigen in different orders, or may be present with or without an intrapeptide linker and/or a linker to a carrier.

In some compositions, the immunogenic peptides can also be expressed as fusion proteins with carriers. In certain compositions, the immunogenic peptides can be linked at the amino terminus, the carboxyl terminus, or internally to the carrier. In some compositions, the carrier is CRM197. In some compositions, the carrier is diphtheria toxoid.

Nucleic Acids

The disclosure further provides nucleic acids encoding any of the amyloid-beta (Aβ) peptides, the tau peptides, and/or the alpha-synuclein peptides as disclosed herein. The nucleic acid immunotherapy compositions, as disclosed herein, comprise, consist of, or consist essentially of, a first nucleic acid sequence encoding an amyloid-beta (Aβ) peptide, a second nucleic acid sequence encoding a tau peptide, and/or a third nucleic acid sequence encoding an alpha-synuclein peptide as disclosed herein. For example, the Aβ peptide is a sequence that is 3-10 amino acid residues in length and from the first ten or 12 to 25 N-terminal residues of SEQ ID NO:01, and the tau peptide is a sequence that is 3-13 amino acids in length and from residues 244-400 of SEQ ID NO:02, and the alpha-synuclein peptide is a sequence that is 3-10 amino acids in length and from residues 81-140 of SEQ ID NO:58. Accordingly, a nucleic acid encoding any of SEQ ID NOS: 3-38 or 1002 to 1057 may be combined with a nucleic acid encoding any of SEQ ID NOS: 39-57, or 142-1000, and/or a nucleic acid encoding any of SEQ ID NOS: 59-129 to provide an immunogen and a component of pharmaceutical composition of the disclosure. Likewise, one or more nucleic acids encoding any of Aβ, tau and alpha-synuclein sequences may include the codons for an RR- N-terminal or -RR C-terminal dipeptide or polypeptide. In certain embodiments, the Aβ, tau and alpha-synuclein peptide sequences may be encoded by the same nucleic acid sequence or by separate nucleic acid sequences. In some embodiments, the nucleic acid sequences may also encode a linker to a carrier and/or a C-terminal cysteine as described herein. In addition, when a single nucleic acid sequence encodes both peptides, the sequence may also encode an intra-peptide linker as described herein. The nucleic acid compositions described herein (pharmaceutical compositions) can be used in methods for treating or effecting prophylaxis and/or prevention of Alzheimer's disease. In another embodiment, the nucleic acid immunotherapy compositions as disclosed herein provide compositions for reducing pathogenic forms of Aβ and/or tau and/or alpha-synuclein in the subject and/or in the tissue of the subject. In some embodiments, the Aβ and/or tau and/or alpha-synuclein reduced by the immunotherapy compositions is the pathological form(s) of the Aβ (e.g. extracellular plaque deposits of the β-amyloid peptide (Aβ); neuritic amyloid plaques), tau (e.g. flame-shaped neurofibrillary tangles of tau; neurofibrillary tangles of tau), and/or alpha-synuclein (e.g. oligomeric or fibrillar alpha-synuclein conglomerates and protofibrillar intermediates of alpha-synuclein oligomers). In yet other embodiment, pathological indicators of neurodegenerative disease and/or synucleinopathies are decreased by the nucleic acid immunotherapy compositions. In another embodiment, the nucleic acid immunotherapy compositions as disclosed herein provide compositions for reducing brain Aβ, brain tau and brain alpha-synuclein.

A nucleic acid such as DNA that encodes an immunogen and is used as a vaccine can be referred to as a "DNA immunogen" or "DNA vaccine" as the encoded polypeptides are expressed in vivo after administration of the DNA. DNA vaccines are intended to induce antibodies against the proteins of interest they encode in a subject by: integrating DNA encoding the proteins of interest into a vector (a plasmid or virus); administering the vector to the subject; and expressing the proteins of interest in the subject in which the vector has been administered to stimulate the immune system of the subject. A DNA vaccine remains in the body of the subject for a long time after the administration, and continues to slowly produce the encoded proteins. Thus, excessive immune responses can be avoided. DNA vaccines can also be modified using a genetic engineering techniques. Optionally, such nucleic acids further encode a signal peptide and can be expressed with the signal peptide linked to peptide. Coding sequences of nucleic acids can be operably linked with regulatory sequences to ensure expression of the coding sequences, such as a promoter, enhancer, ribosome binding site, transcription termination signal, and the like. The nucleic acids encoding Aβ, tau, and/or alpha-synuclein can occur in isolated form or can be cloned into one or more vectors. The nucleic acids can be synthesized by, for example, solid state synthesis or PCR of overlapping oligonucleotides. Nucleic acids encoding Aβ, tau, and/or alpha-synuclein peptides and polypeptides with and without linkers or cleavable linkers and with our without protein based carriers can be joined as one contiguous nucleic acid, e.g., within an expression vector.

DNA is more stable than RNA, but involves some potential safety risks such as induction of anti-DNA antibodies, thus in some embodiments, the nucleic acid can be RNA. RNA nucleic acid that encodes an immunogen and is used as a vaccine can be referred to as a "RNA immunogen" or "RNA vaccine" or "mRNA vaccine" as the encoded polypeptides are expressed in vivo after administration of the RNA. Ribonucleic acid (RNA) vaccines can safely direct a subject's cellular machinery to produce one or more polypeptide(s) of interest. In some embodiments, a RNA vaccine can be a non-replicating mRNA (messenger-RNA) or a virally derived, self-amplifying RNA. mRNA-based vaccines encode the antigens of interest and contain 5' and 3' untranslated regions (UTRs), whereas self-amplifying RNAs encode not only the antigens, but also the viral replication machinery that enables intracellular RNA amplification and abundant protein expression. In vitro transcribed mRNA can be produced from a linear DNA template using a T7, a T3 or an Sp6 phage RNA polymerase. The resulting product can contain an open reading frame that encodes the peptides of interest as disclosed herein, flanking 5'- and 3'-UTR sequences, a 5' cap and a poly(A) tail. In some embodiments, a RNA vaccine can comprise transamplifying RNA (for example, see Beissert et al., *Molecular Therapy* January 2020 28(1):119-128). In certain embodiments, RNA vaccines encode an Aβ peptide and a tau peptide as disclosed herein, and are capable of expressing the Aβ and a tau peptides, in particular if transferred into a cell such as an immature antigen presenting cell. RNA may also contain sequences which encode other polypeptide sequences such as immune stimulating elements. In some embodiments, the RNA of a RNA vaccine can be modified RNA. The term "modified" in the context of the RNA can include any modification of RNA which is not naturally present in RNA. For example, modified RNA can refer to RNA with a 5'-cap; however, RNA may comprise further modifications. A 5'-cap can be modified to possess the ability to stabilize RNA when attached thereto. In certain embodiments, a further modification may be an extension or truncation of the naturally occurring poly(A) tail or an alteration of the 5'- or 3'-untranslated regions (UTR). In some embodiments, the RNA e.g. or mRNA vaccine is formulated in an effective amount to produce an antigen specific immune response in a subject. For example, the RNA vaccine formulation is administered to a subject in order to stimulate the humoral and/or cellular immune system of the subject against the Aβ, tau and alpha synuclein antigens, and thus may further comprise one or more adjuvant(s), diluents, carriers, and/or excipients, and is applied to the subject in any suitable route in order to elicit a protective and/or therapeutic immune reaction against the Aβ, tau and alpha synuclein antigens.

Basic texts disclosing general methods of molecular biology, all of which are incorporated by reference, include: Sambrook, J et al., Molecular Cloning: A Laboratory Manual, 2nd Edition, Cold Spring Harbor Press, Cold Spring Harbor, N.Y., 1989; Ausubel, F M et al. Current Protocols in Molecular Biology, Vol. 2, Wiley-Interscience, New York, (current edition); Kriegler, Gene Transfer and Expression: A Laboratory Manual (1990); Glover, D M, ed, DNA Cloning: A Practical Approach, vol. I & II, IRL Press, 1985; Albers, B. et al., Molecular Biology of the Cell, 2nd Ed., Garland Publishing, Inc., New York, N.Y. (1989); Watson, J D et al., Recombinant DNA, 2nd Ed., Scientific American Books, New York, 1992; and Old, R W et al., Principles of Gene Manipulation: An Introduction to Genetic Engineering, 2nd Ed., University of California Press, Berkeley, Calif. (1981).

Techniques for the manipulation of nucleic acids, such as, e.g., generating mutations in sequences, sub-cloning, labeling probes, sequencing, hybridization and the like are well described in the scientific and patent literature. See, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Tijssen, ed. Elsevier, N.Y. (1993).

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immuno-electrophoresis, radioimmunoassays (RIAs), enzyme-linked immunosorbent assays (ELISAs), immunofluorescence assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

Pharmaceutical Compositions

Each of the peptides and immunogens described herein can be presented in a pharmaceutical composition that is administered with pharmaceutically acceptable adjuvants and pharmaceutically acceptable excipients. The adjuvant increases the titer of induced antibodies and/or the binding affinity of induced antibodies relative to the situation if the peptide were used alone. A variety of adjuvants can be used in combination with an immunogen of the disclosure to elicit an immune response. Some adjuvants augment the intrinsic response to an immunogen without causing conformational changes in the immunogen that affect the qualitative form of the response. An adjuvant may be a natural compound, a modified version of or derivative of a natural compound, or a synthetic compound.

Some adjuvants include aluminum salts, such as aluminum hydroxide and aluminum phosphate, 3 De-O-acylated monophosphoryl lipid A (MPL™) (see GB 2220211 (RIBI ImmunoChem Research Inc., Hamilton, Montana, now part of Corixa). As used herein, MPL refers to natural and synthetic versions of MPL. Examples of synthetic versions include PHAD®, 3D-PHAD® and 3D(6A)-PHAD® (Avanti Polar Lipids, Alabaster, Alabama).

QS-21 is a triterpene glycoside or saponin isolated from the bark of the *Quillaja saponaria* Molina tree found in South America (see Kensil et al., in Vaccine Design: The Subunit and Adjuvant Approach (eds. Powell & Newman, Plenum Press, NY, 1995)) QS-21 products include Stimulon® (Antigenics, Inc., New York, NY; now Agenus, Inc. Lexington, MA) and QS-21 Vaccine Adjuvant (Desert King, San Diego, CA). QS-21 has been disclosed, characterized, and evaluated in U.S. Pat. Nos. 5,057,540, and 8,034,348, the disclosures of which are herein incorporated by reference. Additionally, QS-21 has been evaluated in numerous clinical trials in various dosages. See, NCT00960531 (clinicaltrials.gov/ct2/show/study/NCT00960531), Hüll et al.,

*Curr Alzheimer Res.* 2017 July; 14(7): 696-708 (evaluated 50 mcg of QS-21 in with various doses of vaccine ACC-001); Gilman et al., "Clinical effects of Abeta immunization (AN1792) in patients with AD in an interrupted trial" *Neurology.* 2005 May 10; 64(9):1553-62; Wald et al., "Safety and immunogenicity of long HSV-2 peptides complexed with rhHsc70 in HSV-2 seropositive persons" Vaccine 2011; 29(47):8520-8529; and Cunningham et al., "Efficacy of the Herpes Zoster Subunit Vaccine in Adults 70 Years of Age or Older." *NEJM* 2016 Sep. 15; 375(11):1019-32. QS-21 is used in FDA approved vaccines including SHINGRIX. SHINGRIX contains 50 mcg of QS-21. In certain embodiments, the amount of QS-21 is from about 10 µg to about 500 µg.

TQL1055 is an analogue of QS-21 (Adjuvance Technologies, Lincoln, NE). The semi-synthetic TQL1055 has been characterized in comparison to QS-21 as having high purity, increased stability, decreased local tolerability, decreased systemic tolerability. TQL1055 has been disclosed, characterized, and evaluated in US20180327436 A1, WO2018191598 A1, WO2018200656 A1, and WO2019079160 A1, the disclosures of which are herein incorporated by reference. US20180327436 A1 teaches that 2.5 fold more TQ1055 was superior to 20 µg QS-21 but there was not an improvement over 50 µg TQ1055. However, unlike QS-21 there was no increase in either weight loss or hemolysis of RBC as the TQL1055 dose increased. WO2018200656 A1 teaches that with an optimal amount of TQ1055, one can lower the amount of antigen and achieve superior titers. In certain embodiments, the amount of TQL1055 is from about 10 µg to about 500 µg.

Other adjuvants are oil in water emulsions (such as squalene or peanut oil), optionally in combination with immune stimulants, such as monophosphoryl lipid A (see Stoute et al., *N. Engl. J. Med.* 336, 86-91 (1997)), pluronic polymers, and killed mycobacteria. Ribi adjuvants are oil-in-water emulsions. Ribi contains a metabolizable oil (squalene) emulsified with saline containing Tween 80. Ribi also contains refined mycobacterial products which act as immunostimulants and bacterial monophosphoryl lipid A. Other adjuvants can be CpG oligonucleotides (see WO 98/40100), cytokines (e.g., IL-1, IL-1 alpha and β peptides, IL-2, γ-INF, IL-10, GM-CSF), chemokines (e.g., MIP1-α and β, and RANTES), saponins, RNA, and/or TLR agonists (for example, TLR4 agonists such as MPL and synthetic MPL molecules), aminoalkyl glucosaminide phosphate and other TLR agonists. Adjuvants can be administered as a component of a therapeutic composition with an active agent or can be administered separately, before, concurrently with, or after administration of the therapeutic agent.

In various embodiments of the disclosure, the adjuvant is QS-21 (Stimulon™). In some compositions, the adjuvant is MPL. In certain embodiments, the amount of MPL is from about 10 µg to about 500 µg. In some compositions, the adjuvant is TQL1055. In certain embodiments, the amount of TQL1055 is from about 10 µg to about 500 µg. In some compositions, the adjuvant is QS21. In certain embodiments, the amount of QS21 is from about 10 µg to about 500 µg. In some compositions, the adjuvant is a combination of MPL and QS-21. In some compositions, the adjuvant is a combination of MPL and TQL1055. In some compositions, the adjuvant can be in a liposomal formulation.

In addition, some embodiments of the disclosure can comprise a multiple antigen presenting system (MAP). Multiple antigen-presenting peptide vaccine systems have been developed to avoid the adverse effects associated with conventional vaccines (i.e., live-attenuated, killed or inacti-vated pathogens), carrier proteins and cytotoxic adjuvants. Two main approaches have been used to develop multiple antigen presenting peptide vaccine systems: (1) the addition of functional components, e.g., T-cell epitopes, cell-penetrating peptides, and lipophilic moieties; and (2) synthetic approaches using size-defined nanomaterials, e.g., self-assembling peptides, non-peptidic dendrimers, and gold nanoparticles, as antigen-displaying platforms. Use of a multiple antigenic peptide (MAP) system can improve the sometimes poor immunogenicity of subunit peptide vaccines. In a MAP system, multiple copies of antigenic peptides are simultaneously bound to the a- and ε-amino groups of a non-immunogenic Lys-based dendritic scaffold, helping to confer stability from degradation, thus enhancing molecular recognition by immune cells, and induction of stronger immune responses compared with small antigenic peptides alone. In some compositions, the MAP comprises one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, the peptides of the disclosure can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively, peptide compositions can be in lyophilized form for constitution with a suitable vehicle, e.g., sterile pyrogen-free water, before use.

Peptides (and optionally a carrier fused to the peptide(s)) can also be administered in the form of a nucleic acid encoding the peptide(s) and expressed in situ in a subject. A nucleic acid segment encoding an immunogen is typically linked to regulatory elements, such as a promoter and enhancer that allow expression of the DNA segment in the intended target cells of a subject. For expression in blood cells, as is desirable for induction of an immune response, promoter and enhancer elements from, for example, light or heavy chain immunoglobulin genes or the CMV major intermediate early promoter and enhancer are suitable to direct expression. The linked regulatory elements and coding sequences are often cloned into a vector.

DNA and RNA can be delivered in naked form (i.e., without colloidal or encapsulating materials). Alternatively a number of viral vector systems can be used including retroviral systems (see, e.g., Boris-Lawrie and Teumin, *Cur. Opin. Genet. Develop.* 3(1):102-109 (1993)); adenoviral vectors (see, e.g., Bett et al, *J. Virol.* 67(10); 5911-21 (1993)); adeno-associated virus vectors (see, e.g., Zhou et al., *J. Exp. Med.* 179(6):1867-75 (1994)), viral vectors from the pox family including vaccinia virus and the avian pox viruses, viral vectors from the alpha virus genus such as those derived from Sindbis and Semliki Forest Viruses (see, e.g., Dubensky et al., *J Virol.* 70(1):508-519 (1996)), Venezuelan equine encephalitis virus (see U.S. Pat. No. 5,643, 576) and rhabdoviruses, such as vesicular stomatitis virus (see WO 96/34625) and papillomaviruses (WO 94/12629;

Ohe et al., *Human Gene Therapy* 6(3):325-333 (1995); and Xiao & Brandsma, *Nucleic Acids. Res.* 24(13):2620-2622 (1996)).

DNA and RNA encoding an immunogen, or a vector containing the same, can be packaged into liposomes, nanoparticles or lipoproteins complexes. Suitable other polymers, include, for example, protamine liposomes, polysaccharide particles, cationic nanoemulsion, cationic polymer, cationic polymer liposome, cationic lipid nanoparticles, cationic lipid, cholesterol nanoparticles, cationic lipid-cholesterol, PEG nanoparticle, or dendrimer nanoparticles. Additional suitable lipids and related analogs are described by U.S. Pat. Nos. 5,208,036, 5,264,618, 5,279,833, and 5,283,185, each of which are herein incorporated by reference in their entirety. Vectors and DNA encoding an immunogen can also be adsorbed to or associated with particulate carriers, examples of which include polymethyl methacrylate polymers and polylactides and poly(lactide-co-glycolides), (see, e.g., McGee et al., *J. Micro Encap.* March-April 1997; 14(2):197-210).

Pharmaceutically acceptable carrier compositions can also include additives, including, but not limited to, water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethyl starch sodium, pectin, methylcellulose, ethylcellulose, xanthan gum, gum arabic, casein, agar, polyethylene glycol, diglycerine, glycerine, propylene glycol, petrolatum, paraffin, stearyl alcohol, stearic acid, human serum albumin, mannitol, sorbitol, lactose, and surfactants acceptable as pharmaceutical additives.

Subjects Amenable to Treatment

The presence of Aβ plaques and/or neurofibrillary tangles has been found in several diseases including Alzheimer's disease, Down's syndrome, mild cognitive impairment, cerebral amyloid angiopathy, primary age-related tauopathy, postencephalitic parkinsonism, posttraumatic dementia or dementia pugilistica, Pick's disease, type C Niemann-Pick disease, supranuclear palsy, frontotemporal dementia, frontotemporal lobar degeneration, argyrophilic grain disease, globular glial tauopathy, amyotrophic lateral sclerosis/parkinsonism dementia complex of Guam, corticobasal degeneration (CBD), dementia with Lewy bodies, Lewy body variant of Alzheimer's disease (LBVAD), chronic traumatic encephalopathy (CTE), globular glial tauopathy (GGT), Parkinson's disease, progressive supranuclear palsy (PSP), dry age-related macular degeneration (AMD), and inclusion-body myositis.

The compositions and methods of the disclosure can be used in treatment or prophylaxis of any of these diseases. Because of the widespread association between neurological diseases and Aβ and/or tau and/or alpha-synuclein, the compositions and methods of the disclosure can be used in treatment or prophylaxis of any subject showing elevated levels of Aβ and/or tau and/or alpha-synuclein (e.g., in the CSF) compared with a mean value in individuals without neurological disease. The compositions and methods of the disclosure can also be used in treatment or prophylaxis of neurological disease in individuals having a mutation in Aβ and/or tau and/or alpha-synuclein associated with neurological disease. The methods are particularly suitable for treatment or prophylaxis of Alzheimer's disease.

Subjects amenable to treatment include individuals at risk of disease but not showing symptoms, as well as patients presently showing symptoms, including treatment naïve subjects that have not been previous treated for disease.

Subjects at risk of disease include those in an aging population, asymptomatic subjects with Aβ and/or tau and/or alpha-synuclein pathologies and having a known genetic risk of disease. Such individuals include those having relatives who have experienced this disease, and those whose risk is determined by analysis of genetic or biochemical markers. Genetic markers of risk include mutations in Aβ and/or tau and/or alpha-synuclein, as well as mutations in other genes associated with neurological disease. For example, the ApoE4 allele in heterozygous and even more so in homozygous form is associated with risk of Alzheimer's disease (AD). Other markers of risk of Alzheimer's disease include mutations in the APP gene, particularly mutations at position 717 and positions 670 and 671 referred to as the Hardy and Swedish mutations respectively, mutations in the presenilin genes, PS1 and PS2, a family history of Aβ, hypercholesterolemia or atherosclerosis. Individuals presently suffering from Alzheimer's disease can be recognized by PET imaging, from characteristic dementia, as well as the presence of risk factors described above. In addition, a number of diagnostic tests are available for identifying individuals who have AD. These include measurement of CSF or blood tau or phospho-tau and Aβ42 levels. Elevated tau or phospho-tau and decreased Aβ42 levels signify the presence of AD. Some mutations associated with Parkinson's disease, for example, Ala30Pro or Ala53Thr, or mutations in other genes associated with Parkinson's disease such as leucine-rich repeat kinase (LRRK2 or PARK8). Subjects can also be diagnosed with any of the neurological diseases mentioned above by the criteria of the DSM IV TR.

In asymptomatic subjects, treatment can begin at any age (e.g., 10, 20, 30, or more). Usually, however, it is not necessary to begin treatment until a subject reaches 20, 30, 40, 50, 60, 70, 80, or 90 years of age. Treatment typically entails multiple dosages over a period of time. Treatment can be monitored by assaying antibody levels over time. If the response falls, a booster dosage is indicated. In the case of potential Down's syndrome patients, treatment can begin antenatally by administering therapeutic agent to the mother or shortly after birth.

Methods of Treatments and Uses

The disclosure provides methods of inhibiting or reducing aggregation of Abeta and/or tau and/or alpha-synuclein in a subject having or at risk of developing a neurodegenerative disease (e.g., Alzheimer's disease). The methods include administering to the subject the compositions as disclosed herein. A therapeutically effective amount is a dosage that, when given for an effective period of time, achieves the desired immunological or clinical effect. Dosage regimens may be adjusted to provide the optimum therapeutic response. For example, several divided doses may be administered at set intervals (e.g., weekly, monthly) or the dose may be proportionally reduced as indicated by the exigencies of the therapeutic situation.

In prophylactic applications, the compositions described herein can be administered to a subject susceptible to, or otherwise at risk of a disease (e.g., Alzheimer's disease) in a regimen (dose, frequency and route of administration) effective to reduce the risk, lessen the severity, or delay the onset of at least one sign or symptom of the disease. In particular, the regimen is effective to inhibit or delay Aβ plaque formation and/or inhibit or delay tau or phospho-tau and paired filaments and/or alpha-synuclein synucleinopathies formed from it in the brain, and/or inhibit or delay its toxic effects and/or inhibit/or delay development of behavioral deficits. In therapeutic applications, the compositions described herein are administered to a subject suspected of, or a patient already suffering from a disease (e.g., Alzheimer's disease) in a regimen (dose, frequency and route of administration) effective to ameliorate or at least inhibit further deterioration of at least one sign or symptom of the disease. In particular, the regimen is preferably effective to reduce or at least inhibit further increase of levels of Aβ plaques and/or tau, phosphor-tau, or paired filaments formed from it, and/or alpha-synuclein synucleinopathies, and associated toxicities and/or behavioral deficits.

A regimen is considered therapeutically or prophylactically effective if an individual treated achieves an outcome more favorable than the mean outcome in a control population of comparable subjects not treated by methods of the invention, or if a more favorable outcome is demonstrated in treated subjects versus control subjects in a controlled clinical trial (e.g., a phase II, phase II/III or phase III trial) at the $p<0.05$ or 0.01 or even 0.001 level.

Effective doses of vary depending on many different factors, such as means of administration, target site, physiological state of the patient, whether the patient is an ApoE carrier, whether the patient is human or an animal, other medications administered, and whether treatment is prophylactic or therapeutic.

In some embodiments, the effective amount is a total dose of 25 μg to 1000 μg, or 50 μg to 1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times. In some embodiments, a RNA (e.g., mRNA) vaccine is administered to a subject by intradermal, intramuscular injection, or by intranasal administration.

In some embodiments, the amount of an agent for active immunotherapy varies from 1 to 1,000 micrograms (μg), or from 0.1-500 μg, or from 10 to 500 μg, or from 50 to 250 μg per patient and can be from 1-100 or 1-10 μg per injection for human administration. The timing of injections can vary significantly from once a day, to once a week, to once a month, to once a year, to once a decade. A typical regimen consists of an immunization followed by booster injections at time intervals, such as 6 week intervals or two months. Another regimen consists of an immunization followed by one or more booster injections 1, 2, 3, 4, 5, 6, 7, 8, 9, 10, 11, or 12 months later. Another regimen entails an injection every two months for life. Alternatively, booster injections can be on an irregular basis as indicated by monitoring of immune response. The frequency of administration may be once or more as long as the side effects are within a clinically acceptable range.

In some embodiments, the compositions or methods as disclosed herein comprise administering to a subject a nucleic acid vaccine comprising one or more DNA or RNA polynucleotides having an open reading frame encoding a first peptide and a second peptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350

μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid is administered to the subject by intradermal or intramuscular injection. In some embodiments, the nucleic acid is administered to the subject on day zero. In some embodiments, a second dose of the nucleic acid is administered to the subject on day seven, or fourteen, or twenty one.

The compositions described herein are preferably administered via a peripheral route (i.e., one in which the administered composition results in a robust immune response and/or the induced antibody population crosses the blood brain barrier to reach an intended site in the brain, spinal cord, or eye). For peripheral diseases, the induced antibodies leave the vasculature to reach the intended peripheral organs. Routes of administration include oral, subcutaneous, intranasal, intradermal, or intramuscular. Some routes for active immunization are subcutaneous and intramuscular. Intramuscular administration and subcutaneous administration can be made at a single site or multiple sites. Intramuscular injection is most typically performed in the arm or leg muscles. In some methods, agents are injected directly into a particular tissue where deposits have accumulated.

The number of dosages administered can be adjusted to result in a more robust immune response (for example, higher titers). For acute disorders or acute exacerbations of a chronic disorder, between 1 and 10 doses are often sufficient. Sometimes a single bolus dose, optionally in divided form, is sufficient for an acute disorder or acute exacerbation of a chronic disorder. For chronic disorders, a vaccine/immunotherapy as disclosed herein can be administered at regular intervals, e.g., weekly, fortnightly, monthly, quarterly, every six months for at least 1, 5 or 10 years, or the life of the patient.

An effective amount of a DNA or RNA encoded immunogen can be between about 1 nanogram and about 1 gram per kilogram of body weight of the recipient, or about between about 0.1 μg/kg and about 10 mg/kg, or about between about 1 μg/kg and about 1 mg/kg. Dosage forms suitable for internal administration preferably contain (for the latter dose range) from about 0.1 μg to 100 μg of active ingredient per unit. The active ingredient may vary from 0.5 to 95% by weight based on the total weight of the composition. Alternatively, an effective dose of dendritic cells loaded with the antigen is between about $10^4$ and $10^8$ cells. Those skilled in the art of immunotherapy will be able to adjust these doses without undue experimentation.

The nucleic acid compositions may be administered in a convenient manner, e.g., injection by a convenient and effective route. Routes can include, but are not limited to, intradermal "gene gun" delivery or intramuscular injection. The modified dendritic cells are administered by subcutaneous, intravenous or intramuscular routes. Other possible routes include oral administration, intrathecal, inhalation, transdermal application, or rectal administration.

Depending on the route of administration, the composition may be coated in a material to protect the compound from the action of enzymes, acids and other natural conditions which may inactivate the compound. Thus, it may be necessary to coat the composition with, or co-administer the composition with, a material to prevent its inactivation. For example, an enzyme inhibitors of nucleases or proteases (e.g., pancreatic trypsin inhibitor, diisopropylfluorophosphate and trasylol) or in an appropriate carrier such as liposomes (including water-in-oil-in-water emulsions) as well as conventional liposomes (Strejan et al., *J. Neuroimmunol* 7(1):27-41, 1984).

The immunotherapeutic compositions disclosed herein may also be used in combination with other treatments for diseases associated with the accumulation of Aβ and/or tau and/or alpha-synuclein, for example, anti-Aβ antibodies such as antibodies that specifically bind to any of the Aβ epitopes disclosed herein. For example, aducanumab or any of the antibodies disclosed in, for example, U.S. Patent Publication No. 20100202968 and U.S. Pat. No. 8,906,367, and/or anti-tau antibodies such as antibodies that specifically bind to any of the tau epitopes disclosed herein, ABBV-8E12, gosuranemab, zagotenemab, RG-6100, BIIB076 or any of the antibodies disclosed in WO2014/165271, U.S. Pat. No. 10,501,531, WO2017/191560, US2019/0330314, WO2017/191561, US2019/0330316, WO2017/191559, and WO2018/204546; and/or anti-alpha-synuclein antibodies such as antibodies that specifically bind to any of the alpha-synuclein epitopes disclosed herein, or antibodies and/or other alpha-synuclein binding compounds, such as, PRX002/RO7046015, PRX002/RG7935 (Prasinezumab), NPT200-11/UCB0599, NPT088, BIIB054 (Cinpanemab), ABBV-0805, MEDI-1341, NPT088, Lu AF82422. In some combination therapy methods, the patient receives passive immunotherapy prior to the active immunotherapy methods disclosed herein. In other methods, the patient receives passive and active immunotherapy during the same period of treatment. Alternatively, patients may receive active immunotherapy prior to passive immunotherapy. Combinations may also include small molecule therapies and non-immunogenic therapies such as RAZADYNE® (galantamine), EXELON® (rivastigmine), and ARICEPT® (donepezil) and other compositions that improve the function of nerve cells in the brain.

The compositions of the disclosure may be used in the manufacture of medicaments for the treatment regimens described herein.

Treatment Regimens

Desired outcomes of the methods of treatment as disclosed herein vary according to the disease and patient profile and are determinable to those skilled in the art. Desired outcomes include an improvement in the patient's health status. Generally, desired outcomes include measurable indices such as reduction or clearance of pathologic amyloid fibrils, decreased or inhibited amyloid aggregation and/or deposition of amyloid fibrils, reduction or clearance of Aβ plaque formation and/or inhibit or delay tau or phospho-tau and paired filaments and/or decreased alpha-synuclein synucleinopathies, and increased immune response to pathologic and/or aggregated amyloid fibrils. Desired outcomes also include amelioration of amyloid disease-specific symptoms. As used herein, relative terms such as "improve," "increase," or "reduce" indicate values relative to a control, such as a measurement in the same individual prior to initiation of treatment described herein, or a measurement in a control individual or group. A control individual is an individual afflicted with the same amyloid disease as the individual being treated, who is about the same age as the individual being treated (to ensure that the stages of the disease in the treated individual and the control individual are comparable), but who has not received treatment using the disclosed immunotherapy/vaccine formulations. Alternatively, a control individual is a healthy individual, who is about the same age as the individual being treated. Changes or improvements in response to therapy are generally statistically significant and described by a p-value less than or equal to 0.1, less than 0.05, less than 0.01, less than 0.005, or less than 0.001 may be regarded as significant.

Effective doses of the compositions as disclosed herein, for the treatment of a subject vary depending upon many different factors, including means of administration, target site, physiological state of the patient, whether the patient is human or an animal, other medications administered, if any, and whether treatment is prophylactic or therapeutic. Treatment dosages can be titrated to optimize safety and efficacy. The amount of immunogen can also depend on whether adjuvant is also administered, with higher dosages being required in the absence of adjuvant. The amount of an immunogen for administration sometimes varies from 1-500 μg per patient and more usually from 5-500 μg per injection for human administration. Occasionally, a higher dose of 1-2 mg per dosage is used. Typically, about 10, 20, 50 or 100 μg is used for each human dosage. The timing of dosages can vary significantly from once a day, to once a year, to once a decade. On any given day that a dosage of immunogen is given, the dosage is greater than 1 μg/patient and usually greater than 10 μg/patient if adjuvant is also administered, and greater than 10 μg/patient and usually greater than 100 μg/patient in the absence of adjuvant. A typical regimen consists of an immunization followed by booster dosage(s) at 6-week intervals. Another regimen consists of an immunization followed by booster dosage(s) 1, 2, 3, 4, 5, 6, 7, 8, 9, 10, 11, or 12 months later. Another regimen entails dosage(s) every two months for life. Alternatively, booster dosage(s) can be on an irregular basis as indicated by monitoring of immune response.

When administered in combination with a second treatment for Alzheimer's disease, such as, Razadyne® (galantamine), Exelon® (rivastigmine), and Aricept® (donepezil), the second treatment can be administered according the product label or as necessary in view of the treatment with the compositions of the disclosure.

Kits

The disclosure further provides kits (e.g., containers) comprising the compositions disclosed herein and related materials, such as instructions for use (e.g., package insert). The instructions for use may contain, for example, instructions for administration of the compositions and optionally one or more additional agents. The containers of peptide and/or nucleic acid compositions may be unit doses, bulk packages (e.g., multi-dose packages), or sub-unit doses.

Package insert refers to instructions customarily included in commercial packages of therapeutic products that contain information about the indications, usage, dosage, administration, contraindications and/or warnings concerning the use of such therapeutic products. Kits can also include a second container comprising a pharmaceutically acceptable buffer, such as bacteriostatic water for injection (BWFI), phosphate-buffered saline, Ringer's solution and dextrose solution. It can also include other materials desirable from a commercial and user standpoint, including other buffers, diluents, filters, needles, and syringes.

Uses

Each of the peptides, polypeptides, immunogens, and pharmaceutical compositions described herein may be for use in treating one or more of the diseases as described herein. In addition, each of the peptides, polypeptides, immunogens, and pharmaceutical compositions described herein may be for use in methods for treating one or more of the diseases as described herein. Each of the peptides, polypeptides, immunogens, and pharmaceutical compositions described herein may be used in a method for manufacturing a medicament for treating or use in treating one or more of the diseases as described herein.

The following are provided for exemplification purposes only and are not intended to limit the scope of the invention described in broad terms above.

All U.S. and international patent applications identified herein are incorporated by reference in their entirety.

EXAMPLES

Example 1: Animal Immunizations

Female Swiss Webster mice are injected subcutaneously at two sites with 100 μl (200 μl in total) of immunogen on day 0, 14, and 28. Immunogens are prepared by combining 25 μg of test immunogen and 25 μg of QS21 adjuvant in 200 μl phosphate buffered saline (PBS). Mice are bled at least on day 21 and 35 by nicking tails and collecting 50 μl of blood, followed by processing to serum. The immunogens tested include:

TABLE 3

| Immunogens comprising Aβ/tau/alpha-synuclein peptides | |
|---|---|
| Immunogen | Immunogen sequence (SEQ ID NO.) |
| 24 | DAEFRHDRRPDNEAYERRQIVYKPVKKC (SEQ ID NO: 130) |
| 25 | DAEFRHDRRQIVYKPVRRPDNEAYEKKC (SEQ ID NO: 131) |
| 26 | DAEFRHDRRPDNEAYERRNIKHVPGKKC (SEQ ID NO: 132) |
| 27 | DAEFRHDRRNIKHVPGRRPDNEAYEKKC (SEQ ID NO: 133) |
| 14 | DAEFRHDRRQIVYKPVRRPDNEAYERRN IKHVPGGC (SEQ ID NO: 134) |
| 15 | DAEFRHDRRDPDNEAYRRNIKHVPGRRQ IVYKPVGGC (SEQ ID NO: 135) |
| 16 | blocked amine-EFRHDSGRRQIVYK PVRRPDNEAYERRNIKHVPGGC (SEQ ID NO: 136) |
| 17 | blocked amine-EFRHDSGRRDPDNE AYRRNIKHVPGRRQIVYKPVGGC (SEQ ID NO: 137) |
| Tri 2 | DAEFRHDRRDPDNEAYERRENLKHQPGG GC (SEQ ID NO: 1058) |
| Tri 1 | DAEFRHDRRENLKHQPGRRDPDNEAYEG GC (SEQ ID NO: 1059) |
| Tri 4 | DAEFRHDRRPDNEAYERRENLKHQPGGG C (SEQ ID NO: 1060) |
| Tri 3 | DAEFRHDRRENLKHQPGRRPDNEAYEGG C (SEQ ID NO: 1061) |
| Tri 5 | DAEFRHDRRSKIGSKDNIKHRRDPDNEA YEGGC (SEQ ID NO: 1062) |
| Tri 6 | DAEFRHDRRDPDNEAYERRSKIGSKDNI KHGGC (SEQ ID NO: 1063) |

Immunogens comprise Aβ/tau/alpha-synuclein peptides, a C-terminal linker, and a C-terminal cysteine, and are coupled through the C-terminal cysteine to CRM-197 with a maleimide linkage.

Guinea pigs were injected intramuscularly with 50 μg of a test immunogen, 25 μg QS21 in 200 μl of Addavax on day 0, 21, 49 and 77. Bleeds were done starting 7 days post immunization. The immunogens tested are shown in Table 3. The immunogens peptides are coupled through the C-terminal cysteine to CRM-197 with a maleimide linkage.

Female Guinea Pigs were at least 5 weeks old at the start of the study having an approximate body weight of 350-500 g. Appropriate animal housing and research procedures for animal husbandry and care were conducted in an accredited facility in accordance with the guidelines of the U.S. Department of Agriculture's (USDA) and the Assessment and Accreditation of Laboratory Animal Care (AAALAC) International.

The immunogen concentration was 0.5 mg/ml. Prior to each administration of the test immunogen, approximately a 3 cm² area on each hind limb was shaved and wiped with ethanol for visualization of the injection site. Each animal received a test immunogen dose of 200 microliters (0.25 micrograms/microliter) divided into two separate sites each of 100 microliter per injection (i.e., animals received 50 μg of immunogen in 100 μl PBS+25 μg of QS21 in 100 μl MF59). A 25 G-27 G needle was inserted intramuscularly into the hind limb, approximately 0.25-0.5 cm deep, and injected at 100 microliters per site. Injection sites were rotated each administration between four separate sites per hind limb and separated by at least 2 cm.

Example 2: Measurement of Antibody Titers

Whole blood samples were collected into clot activator tubes via jugular vein at 250-350 microliters per collection at weeks 1, 4, 8 and 12 for Guinea pigs and 50 microliters per collection at weeks 1, 3, 7 and 11 by nicking tails for mice. The maximum volume of whole blood was collected into clot activator tubes via cardiac puncture at termination on the final collection week. All blood samples were allowed to clot at room temperature for greater than 30 minutes, centrifuged at ambient temperature (approximately 20-25° C.) at 3,000 RPM for 10-15 minutes, and serum supernatant was transferred individually into clean cryovials. Serum supernatant was stored frozen at −80° C. (±12° C.).

Aβ Titers (Mice)

2 μg/ml Aβ 1-28 monomers are coated at coated on to the plate 100 μl per well in PBS and incubated overnight at room temperature. Plates were blocked for 1 hour with 1% BSA in PBS. Plates were aspirated, and to row A 200 μl of 0.1% BSA in PBS Tween was added. In column 1, negative mouse serum was added at 1/100 while the rest of the row contained 1/100 test serums. Rows were serially diluted ½ down the plate giving dilution of 1/100 to 1/12800. Wells were incubated 2 hours at room temperature then were washed. A 1/5000 dilution of anti-mouse IgG HRP in 0.1% BSA in PBS Tween was prepared and then 100 μl added to the washed well. This incubated for 1 hour and was washed. OPD substrate was prepared using Thermo-Fisher OPD tablets at 1 tablet per 10 mL. Thermo-Fisher substrate buffer was added at 1/10, and each well had 100 μl added and was incubated for 15 minutes. 50 μl of 2N $H_2SO_4$ was added to stop the reaction and plates were read on a Molecular Devices Spectromax at 490 nM. Titer was defined as the dilution giving 50% maximum OD and were extrapolated if it fell between dilutions.

Tau Titers (Mice)

2 μg/ml recombinant WT Tau 4R2N was coated on to the plate using 100 μl per well in PBS and incubated overnight at room temperature. Plates were blocked for 1 hour with 1% BSA in PBS. Plates were aspirated and to row A 200 μl of 0.1% BSA in PBS Tween was added. In column 1, negative mouse serum was added at 1/100 while the rest of the row contained 1/100 test sera. Rows were serially diluted ½ down the plate giving dilution of 1/100 to 1/12800. Wells were incubated 2 hours at room temperature then were washed. A 1/5000 dilution of anti-mouse IgG HRP in 0.1% BSA in PBS Tween was prepared and then 100 µl added to the washed well. This reaction mixture was incubated for 1 hour and was washed. OPD substrate was prepared using Thermo-Fisher OPD tablets at 1 tablet per 10 mL. Thermo-Fisher substrate buffer was added at 1/10 and each well had 100 µl added and was incubated for 15 minutes. 50 µl of 2N $H_2SO_4$ was added to stop the reaction and plates were read at 490 nm on a Molecular Devices Spectromax. Titer was defined as the dilution giving 50% maximum OD measurement and was extrapolated if it fell between dilutions.

Alpha-Synuclein Titers (Mice)

2 µg/ml recombinant human alpha-synuclein was coated on to the plate 100 µl per well in PBS and incubated overnight at room temperature. Plates were blocked for 1 hour with 1% BSA in PBS. Plates were aspirated and to row A 200 µl of 0.1% BSA in PBS Tween was added. In column 1, negative mouse serum was added at 1/100 while the rest of the row contained 1/100 test serums. Rows were serially diluted ½ down the plate giving dilution of 1/100 to 1/12800. Wells incubated 2 hours at room temperature then were washed and a 1/5000 dilution of anti-mouse IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mL. Thermo-Fisher substrate buffer was added at 1/10 and each well had 100 µl added and was incubated for 15 minutes. 50 µl of 2N $H_2SO_4$ was added to stop the reaction and plates were read on a Molecular Devices Spectromax at 490 nm. Titer was defined as the dilution giving 50% maximum OD and was extrapolated if it fell between dilutions.

Aβ Titers (Guinea Pig)

2 µg/ml Aβ 1-28 monomers were coated onto the plate at 100 µl per well in PBS and incubated overnight at room temperature. Plates were blocked for 1 hour with 1% BSA in PBS. Plates were re-aspirated, and to row A 200 µL of 0.1% BSA in PBS Tween was added. In column 1, negative Guinea Pig serum was added at 1/100 while the rest of the rows contained 1/100 test serums. Rows were serially diluted ½ down the plate giving dilution of 1/100 to 1/12800. Wells incubated 2 hours at room temperature then were washed and a 1/5000 dilution of anti-Guinea Pig IgG HRP in 0.1% BSA in PBS Tween was prepared and then 100 µl added to the washed well. This incubated for 1 hour and was washed. OPD substrate was prepared using Thermo-Fisher OPD tablets at 1 tablet per 10 mL. Thermo-Fisher substrate buffer was added at 1/10 and each well had 100 µl added and was incubated for 15 minutes. 50 µl of 2N $H_2SO_4$ was added to stop the reaction and plates were read on a Molecular Devices Spectromax at 490 nm. Titer was defined as the dilution giving 50% maximum OD and was extrapolated if it fell between dilutions.

Tau Titers (Guinea Pig)

2 µg/ml recombinant wild-type Tau 4R2N was coated on to the plate at 100 µl per well in PBS and incubated overnight at room temperature. Plates were blocked for 1 hour with 1% BSA in PBS. Plates were aspirated, and to row A 200 µl of 0.1% BSA in PBS Tween was added. In column 1, negative Rabbit serum was added at 1/100 while the rest of the row contained 1/100 test serums. Rows were serially diluted ½ down the plate giving dilution of 1/100 to 1/12800. Wells were incubated 2 hours at room temperature then washed. A 1/5000 dilution of anti-rabbit IgG HRP in 0.1% BSA in PBS Tween was prepared and then 100 µl added to the washed well. This mixture was incubated for 1 hour and then washed. OPD substrate was prepared using Thermo-Fisher OPD tablets at 1 tablet per 10 mL. Thermo-Fisher substrate buffer was added at 1/10 (each well having 100 µl added) and was incubated for 15 minutes. 50 µl of 2N $H_2SO_4$ was added to stop the reaction and plates were read on a Molecular Devices Spectromax at 490 nm. Titer was defined as the dilution giving 50% maximum OD and was extrapolated if it fell between dilutions.

TABLE 4

Titers of mice vaccinated with one of 4 tri-peptide immunogens.

| | Aβ titer | Tau titer | AS titer |
|---|---|---|---|
| Tri 1 immunogen: DAEFRHDRRENLKHQPGRRDPDNEAYEGGC (SEQ ID NO: 1059) | | | |
| Mouse 1 | 20000 | 100 | 1000 |
| Mouse 2 | 12000 | 25 | 13000 |
| Mouse 3 | 5000 | 100 | 900 |
| Mouse 4 | 30000 | 12000 | 3300 |
| Tri 2 immunogen: DAEFRHDRRDPDNEAYERRENLKHQPGGGC (SEQ ID NO: 1058) | | | |
| Mouse 1 | 22000 | 400 | 1600 |
| Mouse 2 | 60000 | 6000 | 1000 |
| Mouse 3 | 25000 | 2200 | 1200 |
| Mouse 4 | 50000 | 6000 | 3300 |
| Tri 3 immunogen: DAEFRHDRRENLKHQPGRRPDNEAYEGGC (SEQ ID NO: 1061) | | | |
| Mouse 1 | 4000 | 25 | 13500 |
| Mouse 2 | 8000 | 600 | 2000 |
| Mouse 3 | 12000 | 25 | 3200 |
| Mouse 4 | 10000 | 25 | 8000 |
| Tri 4 immunogen: DAEFRHDRRPDNEAYERRENLKHQPGGGC (SEQ ID NO: 1060) | | | |
| Mouse 1 | 7000 | 25 | 15000 |
| Mouse 2 | 3200 | 25 | 7500 |
| Mouse 3 | 24000 | 1600 | 18000 |
| Mouse 4 | 400 | 25 | 18000 |

Alpha-Synuclein Titers (Guinea Pig)

2 µg/ml recombinant human alpha synuclein was coated on to the plate at 100 µl per well in PBS and incubated overnight at room temperature. Plates were blocked for 1 hour with 1% BSA in PBS. Plates were re-aspirated, and to row A 200 µl of 0.1% BSA in PBS Tween was added. In column 1, negative Guinea pig serum was added at 1/100, while the rest of the row contained 1/100 test sera. Rows were serially diluted ½ down the plate giving dilution of 1/100 to 1/12800. Wells were incubated 2 hours at room temperature then washed. A 1/5000 dilution of anti-Guinea Pig IgG HRP in 0.1% BSA in PBS Tween was prepared and then 100 µl added to the washed well. This mixture was incubated for 1 hour and then washed. OPD substrate was prepared using Thermo-Fisher OPD tablets at 1 tablet per 10 mL. Thermo-Fisher substrate buffer was added at 1/10 (each well having 100 µl added) and the mixture was incubated for 15 minutes. 50 µl of 2N $H_2SO_4$ was added to stop the reaction and plates were read on a Molecular Devices Spectromax at 490 nm. Titer was defined as the dilution giving 50% maximum OD and was extrapolated if it fell between dilutions.

Example 3: Staining of Alzheimer's Brain Tissue with Sera from Animals Immunized with Immunogens as Disclosed Herein Autopsy blocks of fresh frozen human brain tissue (~0.5 g) were embedded in optimal cutting temperature compound (OCT compound) and cut using a cryostat to generate 10 µm sections. The sections were placed into a solution of glucose oxidase and beta D-glucose, in the presence of sodium azide, to block endogenous peroxidase. Once tissue sections were prepared, the staining with the specified animal sera from animals immunized with a vaccine as disclosed herein was carried out at two dilutions (1:300 and 1:1500), using a species appropriate secondary antibody and a DAKO DAB Detection Kit as per the manufacturer's instructions. The staining was processed using an automated Leica Bond Stainer. The results indicate whether sera from animals immunized with a vaccine as disclosed herein comprise antibodies specific to Aβ, tau, and/or alpha-synuclein in human brain tissue of Alzheimer's patients.

Example 4: Serum from Vaccinated Animals Blocks Soluble Aβ Aggregates from Binding to Neurons E18 primary rat hippocampal neurons are cultured as described previously (Zago, et al. "Neutralization of Soluble, Synaptotoxic Amyloid β Species by Antibodies Is Epitope Specific," *J Neurosci.* 2012 Feb. 22; 32(8): 2696-2702). Soluble Aβ aggregate was pre-incubated with or without animal vaccine serum on culture DIV14-21 to block soluble Aβ aggregate from neuritic binding. Animal serum was isolated from animals vaccinated with immunogen peptides as shown in Table 3. Fresh unlabeled, biotinylated or (9:1) soluble Aβ was prepared one day prior and incubated overnight at 4° C. Each diluted serum sample (1:1000, 1:300, and 1:100) and soluble Aβ solution was prepared at 2x the final concentration in one-half of final treatment volume using NeuroBasal-no phenol red (NB-NPR) medium. This was combined with one-half final volume of 2x soluble Aβ and with one-half final volume of 2x diluted animal vaccine serum to make up a 1x final concentration in total final treatment volume, which was mixed well and then pre-incubated for 30 minutes at 37° C. E18 neurons were rinsed with NB-NPR at 150 μL/well before adding binding treatment. Animal serum from vaccinated animals/AD treatment was added to E18 neurons at 60 μL/well, and then incubated for 30 minutes at 37° C. under normal incubator conditions (5% $CO_2$; 9% $O_2$). Cells were rinsed twice using 150 μL/well of NB-NPR, and then fixed in 4% paraformaldehyde in 1xDPBS for 20 minutes. Cells were permeabilized using 0.1 TX-100 for 5 minutes, and blocked using 10% normal goat serum (NGS) for 1 hour at room temperature (RT). Cells were incubated with MAP2 & NeuN primary antibodies in 100 μL/well, 1xDPBS containing 1% BSA+1% NGS overnight at 4° C. The next day, cells were rinsed twice in 150 μL/well 1xDPBS for 5 minutes each wash. Secondary antibodies were added for 1 hour at RT in 100 μL/well 1xDPBS+1% BSA+1% NGS. High-content imaging (HCI) analysis was performed to quantify soluble aggregate Aβ neuritic binding using Operetta HCI CLS instrument (Perkin Elmer; modified Neurite Outgrowth algorithm: 40x $H_2O$ objective; 40 fields per well; (n=3) per condition; data shown as mean (+/−) SD); MAP2 & NeuN (Abcam) neuronal markers used to each trace neurite tree and count cell body number per optical field; Neuritic Aβ soluble aggregate spots detected using streptavidin-488 or polyclonal Aβ antibody (Thermo; Millipore); and data reported as Aβ soluble aggregate spots/neuron (or as Integrated Intensity)).

Approximately 80-150 neurons were observed per well for each condition tested. The results indicate whether animal serum from animals vaccinated with the immunogen peptides as disclosed herein comprise antibodies specific to Aβ that can block soluble Aβ aggregates from binding to neurons.

Example 5: Serum from Vaccinated Animals Stains Aβ Plaques and/or Tau Pathologies and/or Synucleinopathies in Human Brain Tissue Fresh frozen human brain tissues from autopsied Alzheimer's disease donors or non-diseased controls was embedded in OCT, and cut in a cryostat to generate 10 μm frozen sections. The tissue sections were incubated in a solution of glucose oxidase and beta D-glucose, in the presence of sodium azide, to block endogenous peroxidase. The staining with sera from vaccinated animals (animals were vaccinated with the immunogen peptides as disclosed in Table 3) or control animals were then carried out at 1:1000 dilution, in an automated Leica Bond Rx Stainer (Leica Biosystems). Antibody binding was detected using the Bond Polymer Refine Detection Kit (DS9800, Leica Biosystems), which is based on an anti-mouse polymer detection, DAB visualization and hematoxylin nuclear counter-staining. After cover-slipping, the stained tissue slides were digitally imaged with a Hamamatsu NanoZoomer 2.0HT slide scanner (Hamamatsu Corporation) with an NDP.scan, 2.5.85 software. The digitized images were viewed and analyzed using the NDP.view, 2.7.43.0 software.

Results demonstrate Aβ plaques and/or tau neurofibrillary tangles, and/or alpha-synuclein based synucleinopathies were identified based on their typical histopathological characteristics. Such pathologies were absent from tissues incubated with control animal serum. Non-diseased tissue had no such pathological staining after incubation with the sera from animals vaccinated with the immunogen peptides as disclosed herein. The immunogens disclosed herein produce Aβ antibody titers capable of causing phagocytosis of Aβ, and the synuclein titers are able to prevent the internalization of synuclein soluble aggregates into cells.

Although various specific embodiments of the present invention have been described herein, it is to be understood that the invention is not limited to those precise embodiments and that various changes or modifications can be affected therein by one skilled in the art without departing from the scope and spirit of the invention.

```
SEQUENCES
Abeta (Aβ) 1-42

SEQ ID NO: 01

DAEFRHDSGYEVHHQKLVFFAEDVGSNKGAIIGLMVGGVVIA

TAU (UNIPROTKB-P10636 (Homo sapiens)
>P10636-8 (Isoform Tau-F)

SEQ ID NO: 02

10        20        30        40        50
MAEPRQEFEV MEDHAGTYGL GDRKDQGGYT MHQDQEGDTD AGLKESPLQT 60        70        80        90        100
PTEDGSEEPG SETSDAKSTP TAEDVTAPLV DEGAPGKQAA AQPHTEIPEG 110       120       130       140       150
TTAEEAGIGD TPSLEDEAAG HVTQARMVSK SKDGTGSDDK KAKGADGKTK
```

```
                            -continued
        160        170        180        190        200
IATPRGAAPP GQKGQANATR IPAKTPPAPK TPPSSGEPPK SGDRSGYSSP 210        220        230        240        250
GSPGTPGSRS RTPSLPTPPT REPKKVAVVR TPPKSPSSAK SRLQTAPVPM 260        270        280        290        300
PDLKNVKSKI GSTENLKHQP GGGKVQIINK KLDLSNVQSK CGSKDNIKHV 310        320        330        340        350
PGGGSVQIVY KPVDLSKVTS KCGSLGNIHH KPGGGQVEVK SEKLDFKDRV 360        370        380        390        400
QSKIGSLDNI THVPGGGNKK IETHKLTFRE NAKAKTDHGA EIVYKSPVVS 410        420        430        440
GDTSPRHLSN VSSTGSIDMV DSPQLATLAD EVSASLAKQG L A-beta immunogens:
```

(SEQ ID NO: 03)

DAEFRHDSGY (SEQ ID NO: 04)

DAEFRHDSG (SEQ ID NO: 05)

DAEFRHDS (SEQ ID NO: 06)

DAEFRHD (SEQ ID NO: 07)

DAEFRH (SEQ ID NO: 08)

DAEFR (SEQ ID NO: 09)

DAEF (SEQ ID NO: 10)

DAE (SEQ ID NO: 11)

AEFRHDSGY (SEQ ID NO: 12)

AEFRHDSG (SEQ ID NO: 13)

AEFRHDS (SEQ ID NO: 14)

AEFRHD (SEQ ID NO: 15)

AEFRH (SEQ ID NO: 16)

AEFR (SEQ ID NO: 17)

AEF (SEQ ID NO: 18)

EFRHDSGY (SEQ ID NO: 19)

EFRHDSG (SEQ ID NO: 20)

EFRHDS (SEQ ID NO: 21)

EFRHD (SEQ ID NO: 22)

EFRH (SEQ ID NO: 23)

EFR

-continued

```
                                          (SEQ ID NO: 24)
FRHDSGY (SEQ ID NO: 25)
FRHDSG (SEQ ID NO: 26)
FRHDS (SEQ ID NO: 27)
FRHD (SEQ ID NO: 28)
FRH (SEQ ID NO: 29)
RHDSGY (SEQ ID NO: 30)
RHDSG (SEQ ID NO: 31)
RHDS (SEQ ID NO: 32)
RHD (SEQ ID NO: 33)
HDSGY (SEQ ID NO: 34)
HDSG (SEQ ID NO: 35)
HDS (SEQ ID NO: 36)
DSGY (SEQ ID NO: 37)
DSG (SEQ ID NO: 38)
SGY (SEQ ID NO: 1002)
VHHQKLVFFA (SEQ ID NO: 1003)
VHHQKLVFF (SEQ ID NO: 1004)
VHHQKLVF (SEQ ID NO: 1005)
VHHQKLV (SEQ ID NO: 1006)
VHHQKL (SEQ ID NO: 1007)
HHQKLVFFAE (SEQ ID NO: 1008)
HHQKLVFFA (SEQ ID NO: 1009)
HHQKLVFF (SEQ ID NO: 1010)
HHQKLVF (SEQ ID NO: 1011)
HHQKLV (SEQ ID NO: 1012)
HHQKL (SEQ ID NO: 1013)
HQKLVFFAED
```

-continued

```
                                    (SEQ ID NO: 1014)
HQKLVFFAE (SEQ ID NO: 1015)
HQKLVFFA (SEQ ID NO: 1016)
HQKLVFF (SEQ ID NO: 1017)
HQKLVF (SEQ ID NO: 1018)
HQKLV (SEQ ID NO: 1019)
HQKL (SEQ ID NO: 1020)
QKLVFFAEDV (SEQ ID NO: 1021)
QKLVFFAED (SEQ ID NO: 1022)
QKLVFFAE (SEQ ID NO: 1023)
QKLVFFA (SEQ ID NO: 1024)
QKLVFF (SEQ ID NO: 1025)
QKLVF (SEQ ID NO: 1026)
QKLV (SEQ ID NO: 1027)
QKL (SEQ ID NO: 1028)
KLVFFAEDVG (SEQ ID NO: 1029)
KLVFFAEDV (SEQ ID NO: 1030)
KLVFFAED (SEQ ID NO: 1031)
KLVFFAE (SEQ ID NO: 1032)
KLVFFA (SEQ ID NO: 1033)
KLVFF (SEQ ID NO: 1034)
KLVF (SEQ ID NO: 1035)
KLV (SEQ ID NO: 1036)
LVFFAEDVG (SEQ ID NO: 1037)
LVFFAEDV (SEQ ID NO: 1038)
LVFFAED (SEQ ID NO: 1039)
LVFFAE (SEQ ID NO: 1040)
LVFFA
```

-continued

```
                                        (SEQ ID NO: 1041)
LVFF (SEQ ID NO: 1042)
LVF (SEQ ID NO: 1043)
VFFAEDVG (SEQ ID NO: 1044)
VFFAEDV (SEQ ID NO: 1045)
VFFAED (SEQ ID NO: 1046)
VFFAE (SEQ ID NO: 1047)
VFFA (SEQ ID NO: 1048)
VFF (SEQ ID NO: 1049)
FFAEDVG (SEQ ID NO: 1050)
FFAEDV (SEQ ID NO: 1051)
FFAED (SEQ ID NO: 1052)
FFAE (SEQ ID NO: 1053)
FFA (SEQ ID NO: 1054)
FAEDVG (SEQ ID NO: 1055)
FAEDV (SEQ ID NO: 1056)
FAED (SEQ ID NO: 1057)
FAE

Tau immunogens:
                                         (SEQ ID NO: 39)
QIVYKPV (SEQ ID NO: 40)
QIVYKP (SEQ ID NO: 41)
QIVYKSV (SEQ ID NO: 42)
EIVYKSV (SEQ ID NO: 997)
QIVYKS (SEQ ID NO: 43)
EIVYKSP (SEQ ID NO: 998)
EIVYKS (SEQ ID NO: 44)
EIVYKPV (SEQ ID NO: 999)
EIVYKP
```

-continued (SEQ ID NO: 45)
IVYKSPV (SEQ ID NO: 46)
IVYK (SEQ ID NO: 1000)
CNIKHVPG (SEQ ID NO: 47)
CNIKHVP (SEQ ID NO: 48)
NIKHVP (SEQ ID NO: 49)
HVPGGG (SEQ ID NO: 50)
HVPGG (SEQ ID NO: 51)
HKPGGG (SEQ ID NO: 52)
HKPGG (SEQ ID NO: 53)
KHVPGGG (SEQ ID NO: 54)
KHVPGG (SEQ ID NO: 55)
HQPGGG (SEQ ID NO: 56)
HQPGG (SEQ ID NO: 57)
NIKHVPG (SEQ ID NO: 146)
VQIINK (SEQ ID NO: 147)
VQIINKK (SEQ ID NO: 148)
VQIINKKL (SEQ ID NO: 149)
QIINK (SEQ ID NO: 150)
QIINKK (SEQ ID NO: 151)
QIINKKL (SEQ ID NO: 152)
EAAGHVTQC (SEQ ID NO: 153)
EAAGHVTQAR (SEQ ID NO: 154)
AAGHVTQAC (SEQ ID NO: 155)
AGHVTQARC (SEQ ID NO: 156)
AGHVTQAR (SEQ ID NO: 157)
GYTMHQD (SEQ ID NO: 158)
QGGYTMHC -continued (SEQ ID NO: 159)
QGGYTMHQD (SEQ ID NO: 160)
GGYTMHQC (SEQ ID NO: 161)
VPGGGSVQIV (SEQ ID NO: 162)
PGGGSVQIV (SEQ ID NO: 163)
GGGSVQIV (SEQ ID NO: 164)
GGSVQIV (SEQ ID NO: 165)
GSVQIV (SEQ ID NO: 166)
SVQIV (SEQ ID NO: 167)
VQIV (SEQ ID NO: 168)
QIV (SEQ ID NO: 169)
PGGGSVQIVY (SEQ ID NO: 170)
GGGSVQIVY (SEQ ID NO: 171)
GGSVQIVY (SEQ ID NO: 172)
GSVQIVY (SEQ ID NO: 173)
SVQIVY (SEQ ID NO: 174)
VQIVY (SEQ ID NO: 175)
QIVY (SEQ ID NO: 176)
IVY (SEQ ID NO: 177)
GGGSVQIVYK (SEQ ID NO: 178)
GGSVQIVYK (SEQ ID NO: 179)
GSVQIVYK (SEQ ID NO: 180)
SVQIVYK (SEQ ID NO: 181)
VQIVYK (SEQ ID NO: 182)
QIVYK (SEQ ID NO: 183)
VYK (SEQ ID NO: 184)
GGSVQIVYKP (SEQ ID NO: 185)
GSVQIVYKP -continued

```
                                      (SEQ ID NO: 186)
SVQIVYKP (SEQ ID NO: 187)
VQIVYKP (SEQ ID NO: 188)
IVYKP (SEQ ID NO: 189)
VYKP (SEQ ID NO: 190)
YKP (SEQ ID NO: 191)
GSVQIVYKPV (SEQ ID NO: 192)
SVQIVYKPV (SEQ ID NO: 193)
VQIVYKPV (SEQ ID NO: 194)
IVYKPV (SEQ ID NO: 195)
VYKPV (SEQ ID NO: 196)
YKPV (SEQ ID NO: 197)
KPV (SEQ ID NO: 198)
SVQIVYKPVD (SEQ ID NO: 199)
VQIVYKPVD (SEQ ID NO: 200)
QIVYKPVD (SEQ ID NO: 201)
IVYKPVD (SEQ ID NO: 203)
VYKPVD (SEQ ID NO: 204)
YKPVD (SEQ ID NO: 205)
KPVD (SEQ ID NO: 206)
PVD (SEQ ID NO: 207)
VQIVYKPVDL (SEQ ID NO: 208)
QIVYKPVDL (SEQ ID NO: 209)
IVYKPVDL (SEQ ID NO: 210)
VYKPVDL (SEQ ID NO: 211)
YKPVDL (SEQ ID NO: 212)
KPVDL (SEQ ID NO: 213)
PVDL
```

-continued (SEQ ID NO: 214)
VDL (SEQ ID NO: 215)
QIVYKPVDLS (SEQ ID NO: 216)
IVYKPVDLS (SEQ ID NO: 217)
VYKPVDLS (SEQ ID NO: 218)
YKPVDLS (SEQ ID NO: 219)
KPVDLS (SEQ ID NO: 220)
PVDLS (SEQ ID NO: 221)
VDLS (SEQ ID NO: 222)
DLS (SEQ ID NO: 223)
IVYKPVDLSK (SEQ ID NO: 224)
VYKPVDLSK (SEQ ID NO: 225)
YKPVDLSK (SEQ ID NO: 226)
KPVDLSK (SEQ ID NO: 227)
PVDLSK (SEQ ID NO: 228)
VDLSK (SEQ ID NO: 229)
DLSK (SEQ ID NO: 230)
LSK (SEQ ID NO: 231)
VYKPVDLSKV (SEQ ID NO: 232)
YKPVDLSKV (SEQ ID NO: 233)
KPVDLSKV (SEQ ID NO: 234)
PVDLSKV (SEQ ID NO: 235)
VDLSKV (SEQ ID NO: 236)
DLSKV (SEQ ID NO: 237)
LSKV (SEQ ID NO: 238)
SKV (SEQ ID NO: 239)
YKPVDLSKVT (SEQ ID NO: 240)
KPVDLSKVT -continued (SEQ ID NO: 241)
PVDLSKVT (SEQ ID NO: 242)
VDLSKVT (SEQ ID NO: 243)
AKTDHGAEIV (SEQ ID NO: 244)
KTDHGAEIV (SEQ ID NO: 245)
TDHGAEIV (SEQ ID NO: 246)
DHGAEIV (SEQ ID NO: 247)
HGAEIV (SEQ ID NO: 248)
GAEIV (SEQ ID NO: 249)
AEIV (SEQ ID NO: 250)
EIV (SEQ ID NO: 251)
KTDHGAEIVY (SEQ ID NO: 252)
TDHGAEIVY (SEQ ID NO: 253)
DHGAEIVY (SEQ ID NO: 254)
HGAEIVY (SEQ ID NO: 255)
GAEIVY (SEQ ID NO: 256)
AEIVY (SEQ ID NO: 257)
EIVY (SEQ ID NO: 258)
IVY (SEQ ID NO: 259)
TDHGAEIVYK (SEQ ID NO: 260)
DHGAEIVYK (SEQ ID NO: 261)
HGAEIVYK (SEQ ID NO: 262)
GAEIVYK (SEQ ID NO: 263)
AEIVYK (SEQ ID NO: 264)
EIVYK (SEQ ID NO: 265)
IVYK (SEQ ID NO: 266)
DHGAEIVYKS (SEQ ID NO: 267)
HGAEIVYKS -continued (SEQ ID NO: 268)
GAEIVYKS (SEQ ID NO: 269)
AEIVYKS (SEQ ID NO: 270)
EIVYKS (SEQ ID NO: 271)
IVYKS (SEQ ID NO: 272)
VYKS (SEQ ID NO: 273)
YKS (SEQ ID NO: 274)
HGAEIVYKSP (SEQ ID NO: 275)
GAEIVYKSP (SEQ ID NO: 276)
AEIVYKSP (SEQ ID NO: 277)
EIVYKSP (SEQ ID NO: 278)
IVYKSP (SEQ ID NO: 279)
VYKSP (SEQ ID NO: 280)
YKSP (SEQ ID NO: 281)
KSP (SEQ ID NO: 282)
GAEIVYKSPV (SEQ ID NO: 283)
AEIVYKSPV (SEQ ID NO: 284)
EIVYKSPV (SEQ ID NO: 285)
IVYKSPV (SEQ ID NO: 286)
VYKSPV (SEQ ID NO: 287)
YKSPV (SEQ ID NO: 288)
KSPV (SEQ ID NO: 289)
SPV (SEQ ID NO: 290)
AEIVYKSPVV (SEQ ID NO: 291)
EIVYKSPVV (SEQ ID NO: 292)
IVYKSPVV (SEQ ID NO: 293)
VYKSPVV (SEQ ID NO: 294)
YKSPVV -continued

```
                                            (SEQ ID NO: 295)
KSPVV (SEQ ID NO: 296)
SPVV (SEQ ID NO: 297)
PVV (SEQ ID NO: 298)
EIVYKSPVVS (SEQ ID NO: 299)
IVYKSPVVS (SEQ ID NO: 300)
VYKSPVVS (SEQ ID NO: 301)
YKSPVVS (SEQ ID NO: 302)
KSPVVS (SEQ ID NO: 303)
SPVVS (SEQ ID NO: 304)
PVVS (SEQ ID NO: 305)
VVS (SEQ ID NO: 306)
IVYKSPVVSG (SEQ ID NO: 307)
VYKSPVVSG (SEQ ID NO: 308)
YKSPVVSG (SEQ ID NO: 309)
KSPVVSG (SEQ ID NO: 310)
SPVVSG (SEQ ID NO: 311)
PVVSG (SEQ ID NO: 312)
VVSG (SEQ ID NO: 313)
VSG (SEQ ID NO: 314)
VYKSPVVSGD (SEQ ID NO: 315)
YKSPVVSGD (SEQ ID NO: 316)
KSPVVSGD (SEQ ID NO: 317)
SPVVSGD (SEQ ID NO: 318)
PVVSGD (SEQ ID NO: 319)
VVSGD (SEQ ID NO: 320)
VSGD (SEQ ID NO: 321)
SGD
```

-continued

```
                                            (SEQ ID NO: 322)
YKSPVVSGDT (SEQ ID NO: 323)
KSPVVSGDT (SEQ ID NO: 324)
SPVVSGDT (SEQ ID NO: 325)
PVVSGDT (SEQ ID NO: 326)
VVSGDT (SEQ ID NO: 327)
VSGDT (SEQ ID NO: 328)
SGDT (SEQ ID NO: 329)
GDT (SEQ ID NO: 330)
KSPVVSGDTS (SEQ ID NO: 331)
SPVVSGDTS (SEQ ID NO: 332)
PVVSGDTS (SEQ ID NO: 333)
VVSGDTS (SEQ ID NO: 334)
VSGDTS (SEQ ID NO: 335)
SGDTS (SEQ ID NO: 336)
GDTS (SEQ ID NO: 337)
DTS (SEQ ID NO: 338)
SPVVSGDTSP (SEQ ID NO: 339)
PVVSGDTSP (SEQ ID NO: 340)
VVSGDTSP (SEQ ID NO: 341)
VSGDTSP (SEQ ID NO: 342)
SGDTSP (SEQ ID NO: 343)
GDTSP (SEQ ID NO: 344)
DTSP (SEQ ID NO: 345)
TSP (SEQ ID NO: 346)
PVVSGDTSPR (SEQ ID NO: 347)
VVSGDTSPR (SEQ ID NO: 348)
VSGDTSPR
```

-continued

```
                                        (SEQ ID NO: 349)
SGDTSPR (SEQ ID NO: 350)
GDTSPR (SEQ ID NO: 351)
DTSPR (SEQ ID NO: 352)
TSPR (SEQ ID NO: 353)
SPR (SEQ ID NO: 354)
HQPGGGKVQI (SEQ ID NO: 355)
QPGGGKVQI (SEQ ID NO: 356)
PGGGKVQI (SEQ ID NO: 357)
GGGKVQI (SEQ ID NO: 358)
GGKVQI (SEQ ID NO: 359)
GKVQI (SEQ ID NO: 360)
KVQI (SEQ ID NO: 361)
VQI (SEQ ID NO: 362)
QPGGGKVQII (SEQ ID NO: 363)
PGGGKVQII (SEQ ID NO: 365)
GGGKVQII (SEQ ID NO: 366)
GGKVQII (SEQ ID NO: 367)
GKVQII (SEQ ID NO: 368)
KVQII (SEQ ID NO: 369)
VQII (SEQ ID NO: 370)
QII (SEQ ID NO: 371)
PGGGKVQIIN (SEQ ID NO: 372)
GGGKVQIIN (SEQ ID NO: 373)
GGKVQIIN (SEQ ID NO: 374)
GKVQIIN (SEQ ID NO: 375)
KVQIIN (SEQ ID NO: 376)
VQIIN
```

-continued

```
                                     (SEQ ID NO: 377)
QIIN (SEQ ID NO: 378)
IIN (SEQ ID NO: 379)
GGGKVQIINK (SEQ ID NO: 380)
GGKVQIINK (SEQ ID NO: 381)
GKVQIINK (SEQ ID NO: 382)
KVQIINK (SEQ ID NO: 383)
IINK (SEQ ID NO: 384)
INK (SEQ ID NO: 385)
GGKVQIINKK (SEQ ID NO: 386)
GKVQIINKK (SEQ ID NO: 387)
KVQIINKK (SEQ ID NO: 388)
IINKK (SEQ ID NO: 389)
INKK (SEQ ID NO: 390)
NKK (SEQ ID NO: 391)
GKVQIINKKL (SEQ ID NO: 392)
KVQIINKKL (SEQ ID NO: 393)
IINKKL (SEQ ID NO: 394)
INKKL (SEQ ID NO: 395)
NKKL (SEQ ID NO: 396)
KKL (SEQ ID NO: 397)
KVQIINKKLD (SEQ ID NO: 398)
VQIINKKLD (SEQ ID NO: 399)
QIINKKLD (SEQ ID NO: 400)
IINKKLD (SEQ ID NO: 401)
INKKLD (SEQ ID NO: 402)
NKKLD (SEQ ID NO: 403)
KKLD
```

-continued (SEQ ID NO: 404)
KLD (SEQ ID NO: 405)
VQIINKKLDL (SEQ ID NO: 406)
QIINKKLDL (SEQ ID NO: 407)
IINKKLDL (SEQ ID NO: 408)
INKKLDL (SEQ ID NO: 409)
NKKLDL (SEQ ID NO: 410)
KKLDL (SEQ ID NO: 411)
KLDL (SEQ ID NO: 412)
LDL (SEQ ID NO: 413)
QIINKKLDLS (SEQ ID NO: 414)
IINKKLDLS (SEQ ID NO: 415)
INKKLDLS (SEQ ID NO: 416)
NKKLDLS (SEQ ID NO: 417)
KKLDLS (SEQ ID NO: 418)
KLDLS (SEQ ID NO: 419)
LDLS (SEQ ID NO: 420)
IINKKLDLSN (SEQ ID NO: 421)
INKKLDLSN (SEQ ID NO: 422)
NKKLDLSN (SEQ ID NO: 423)
KKLDLSN (SEQ ID NO: 424)
KLDLSN (SEQ ID NO: 425)
LDLSN (SEQ ID NO: 426)
DLSN (SEQ ID NO: 427)
LSN (SEQ ID NO: 428)
INKKLDLSNV (SEQ ID NO: 429)
NKKLDLSNV (SEQ ID NO: 430)
KKLDLSNV -continued

```
                                        (SEQ ID NO: 431)
KLDLSNV (SEQ ID NO: 432)
LDLSNV (SEQ ID NO: 433)
DLSNV (SEQ ID NO: 434)
LSNV (SEQ ID NO: 435)
SNV (SEQ ID NO: 436)
NKKLDLSNVQ (SEQ ID NO: 437)
KKLDLSNVQ (SEQ ID NO: 438)
KLDLSNVQ (SEQ ID NO: 439)
LDLSNVQ (SEQ ID NO: 440)
DLSNVQ (SEQ ID NO: 441)
LSNVQ (SEQ ID NO: 442)
SNVQ (SEQ ID NO: 443)
NVQ (SEQ ID NO: 444)
KKLDLSNVQS (SEQ ID NO: 445)
KLDLSNVQS (SEQ ID NO: 446)
LDLSNVQS (SEQ ID NO: 447)
DLSNVQS (SEQ ID NO: 448)
LSNVQS (SEQ ID NO: 449)
SNVQS (SEQ ID NO: 450)
NVQS (SEQ ID NO: 451)
VQS (SEQ ID NO: 452)
SKCGSKDNIK (SEQ ID NO: 453)
KCGSKDNIK (SEQ ID NO: 454)
CGSKDNIK (SEQ ID NO: 455)
GSKDNIK (SEQ ID NO: 456)
SKDNIK (SEQ ID NO: 457)
KDNIK
```

-continued (SEQ ID NO: 458)
DNIK (SEQ ID NO: 459)
NIK (SEQ ID NO: 460)
KCGSKDNIKH (SEQ ID NO: 461)
CGSKDNIKH (SEQ ID NO: 462)
GSKDNIKH (SEQ ID NO: 463)
SKDNIKH (SEQ ID NO: 464)
KDNIKH (SEQ ID NO: 465)
DNIKH (SEQ ID NO: 466)
NIKH (SEQ ID NO: 467)
IKH (SEQ ID NO: 468)
CGSKDNIKHV (SEQ ID NO: 469)
GSKDNIKHV (SEQ ID NO: 470)
SKDNIKHV (SEQ ID NO: 471)
KDNIKHV (SEQ ID NO: 472)
DNIKHV (SEQ ID NO: 473)
NIKHV (SEQ ID NO: 474)
IKHV (SEQ ID NO: 475)
KHV (SEQ ID NO: 476)
GSKDNIKHVP (SEQ ID NO: 477)
SKDNIKHVP (SEQ ID NO: 478)
KDNIKHVP (SEQ ID NO: 479)
DNIKHVP (SEQ ID NO: 480)
IKHVP (SEQ ID NO: 481)
KHVP (SEQ ID NO: 482)
HVP (SEQ ID NO: 483)
SKDNIKHVPG (SEQ ID NO: 484)
KDNIKHVPG -continued

```
                                        (SEQ ID NO: 485)
DNIKHVPG (SEQ ID NO: 486)
NIKHVPG (SEQ ID NO: 487)
IKHVPG (SEQ ID NO: 488)
KHVPG (SEQ ID NO: 489)
HVPG (SEQ ID NO: 490)
VPG (SEQ ID NO: 491)
KDNIKHVPGG (SEQ ID NO: 492)
DNIKHVPGG (SEQ ID NO: 493)
NIKHVPGG (SEQ ID NO: 494)
IKHVPGG (SEQ ID NO: 495)
KHVPGG (SEQ ID NO: 496)
VPGG (SEQ ID NO: 497)
PGG (SEQ ID NO: 498)
DNIKHVPGGG (SEQ ID NO: 499)
NIKHVPGGG (SEQ ID NO: 500)
IKHVPGGG (SEQ ID NO: 501)
VPGGG (SEQ ID NO: 502)
PGGG (SEQ ID NO: 503)
GGG (SEQ ID NO: 504)
NIKHVPGGGS (SEQ ID NO: 505)
IKHVPGGGS (SEQ ID NO: 506)
KHVPGGGS (SEQ ID NO: 507)
HVPGGGS (SEQ ID NO: 508)
VPGGGS (SEQ ID NO: 509)
PGGGS (SEQ ID NO: 510)
GGGS (SEQ ID NO: 511)
GGS
```

-continued (SEQ ID NO: 512)
IKHVPGGGSV (SEQ ID NO: 513)
KHVPGGGSV (SEQ ID NO: 514)
HVPGGGSV (SEQ ID NO: 515)
VPGGGSV (SEQ ID NO: 516)
PGGGSV (SEQ ID NO: 517)
GGGSV (SEQ ID NO: 518)
GGSV (SEQ ID NO: 519)
GSV (SEQ ID NO: 520)
KHVPGGGSVQ (SEQ ID NO: 521)
HVPGGGSVQ (SEQ ID NO: 522)
VPGGGSVQ (SEQ ID NO: 523)
PGGGSVQ (SEQ ID NO: 524)
GGGSVQ (SEQ ID NO: 525)
GGSVQ (SEQ ID NO: 526)
GSVQ (SEQ ID NO: 527)
SVQ (SEQ ID NO: 528)
HVPGGGSVQI (SEQ ID NO: 529)
VPGGGSVQI (SEQ ID NO: 530)
PGGGSVQI (SEQ ID NO: 531)
GGGSVQI (SEQ ID NO: 532)
GGSVQI (SEQ ID NO: 533)
GSVQI (SEQ ID NO: 534)
SVQI (SEQ ID NO: 535)
GGSVQIVYKS (SEQ ID NO: 536)
GSVQIVYKS (SEQ ID NO: 537)
SVQIVYKS (SEQ ID NO: 538)
VQIVYKS -continued

```
                                         (SEQ ID NO: 539)
QIVYKS (SEQ ID NO: 540)
IVYKS (SEQ ID NO: 541)
VYKS (SEQ ID NO: 542)
YKS (SEQ ID NO: 543)
GSVQIVYKSV (SEQ ID NO: 544)
SVQIVYKSV (SEQ ID NO: 545)
VQIVYKSV (SEQ ID NO: 546)
QIVYKSV (SEQ ID NO: 547)
IVYKSV (SEQ ID NO: 548)
VYKSV (SEQ ID NO: 549)
YKSV (SEQ ID NO: 550)
SVQIVYKSVD (SEQ ID NO: 551)
VQIVYKSVD (SEQ ID NO: 552)
QIVYKSVD (SEQ ID NO: 553)
IVYKSVD (SEQ ID NO: 554)
VYKSVD (SEQ ID NO: 555)
YKSVD (SEQ ID NO: 556)
KSVD (SEQ ID NO: 557)
SVD (SEQ ID NO: 558)
VQIVYKSVDL (SEQ ID NO: 559)
QIVYKSVDL (SEQ ID NO: 560)
IVYKSVDL (SEQ ID NO: 561)
VYKSVDL (SEQ ID NO: 562)
YKSVDL (SEQ ID NO: 563)
KSVDL (SEQ ID NO: 564)
SVDL (SEQ ID NO: 565)
QIVYKSVDLS
```

-continued

```
                                    (SEQ ID NO: 566)
IVYKSVDLS (SEQ ID NO: 567)
VYKSVDLS (SEQ ID NO: 568)
YKSVDLS (SEQ ID NO: 569)
KSVDLS (SEQ ID NO: 570)
SVDLS (SEQ ID NO: 571)
IVYKSVDLSK (SEQ ID NO: 572)
VYKSVDLSK (SEQ ID NO: 573)
YKSVDLSK (SEQ ID NO: 574)
KSVDLSK (SEQ ID NO: 364)
SVDLSK (SEQ ID NO: 575)
VYKSVDLSKV (SEQ ID NO: 576)
YKSVDLSKV (SEQ ID NO: 577)
KSVDLSKV (SEQ ID NO: 578)
SVDLSKV (SEQ ID NO: 579)
YKSVDLSKVT (SEQ ID NO: 580)
KSVDLSKVT (SEQ ID NO: 581)
SVDLSKVT (SEQ ID NO: 582)
DLSKVT (SEQ ID NO: 583)
LSKVT (SEQ ID NO: 584)
SKVT (SEQ ID NO: 585)
KVT (SEQ ID NO: 586)
HGAEIVYKSV (SEQ ID NO: 587)
GAEIVYKSV (SEQ ID NO: 588)
AEIVYKSV (SEQ ID NO: 589)
GAEIVYKSVV (SEQ ID NO: 590)
AEIVYKSVV (SEQ ID NO: 591)
EIVYKSVV
```

-continued (SEQ ID NO: 592)
IVYKSVV (SEQ ID NO: 593)
VYKSVV (SEQ ID NO: 594)
YKSVV (SEQ ID NO: 595)
KSVV (SEQ ID NO: 596)
SVV (SEQ ID NO: 597)
AEIVYKSVVS (SEQ ID NO: 598)
EIVYKSVVS (SEQ ID NO: 599)
IVYKSVVS (SEQ ID NO: 600)
VYKSVVS (SEQ ID NO: 601)
YKSVVS (SEQ ID NO: 602)
KSVVS (SEQ ID NO: 603)
SVVS (SEQ ID NO: 604)
EIVYKSVVSG (SEQ ID NO: 605)
IVYKSVVSG (SEQ ID NO: 606)
VYKSVVSG (SEQ ID NO: 607)
YKSVVSG (SEQ ID NO: 608)
KSVVSG (SEQ ID NO: 609)
SVVSG (SEQ ID NO: 610)
VVSG (SEQ ID NO: 611)
VSG (SEQ ID NO: 612)
IVYKSVVSGD (SEQ ID NO: 613)
VYKSVVSGD (SEQ ID NO: 614)
YKSVVSGD (SEQ ID NO: 615)
KSVVSGD (SEQ ID NO: 616)
SVVSGD (SEQ ID NO: 617)
VVSGD (SEQ ID NO: 618)
VYKSVVSGDT -continued

```
                                      (SEQ ID NO: 619)
YKSVVSGDT (SEQ ID NO: 620)
KSVVSGDT (SEQ ID NO: 621)
SVVSGDT (SEQ ID NO: 622)
YKSVVSGDTS (SEQ ID NO: 623)
KSVVSGDTS (SEQ ID NO: 624)
SVVSGDTS (SEQ ID NO: 625)
YKSVVSGDTS (SEQ ID NO: 626)
KSVVSGDTS (SEQ ID NO: 627)
SVVSGDTS (SEQ ID NO: 628)
VVSGDTS (SEQ ID NO: 629)
KSVVSGDTSP (SEQ ID NO: 630)
SVVSGDTSP (SEQ ID NO: 631)
SVVSGDTSPR (SEQ ID NO: 632)
DHGAEIVYKP (SEQ ID NO: 633)
HGAEIVYKP (SEQ ID NO: 634)
GAEIVYKP (SEQ ID NO: 635)
AEIVYKP (SEQ ID NO: 636)
HGAEIVYKPV (SEQ ID NO: 637)
GAEIVYKPV (SEQ ID NO: 638)
AEIVYKPV (SEQ ID NO: 639)
GAEIVYKPVV (SEQ ID NO: 640)
AEIVYKPVV (SEQ ID NO: 641)
EIVYKPVV (SEQ ID NO: 642)
IVYKPVV (SEQ ID NO: 643)
VYKPVV (SEQ ID NO: 644)
YKPVV (SEQ ID NO: 645)
KPVV
```

-continued (SEQ ID NO: 646)
AEIVYKPVVS (SEQ ID NO: 647)
EIVYKPVVS (SEQ ID NO: 648)
IVYKPVVS (SEQ ID NO: 649)
VYKPVVS (SEQ ID NO: 650)
YKPVVS (SEQ ID NO: 651)
KPVVS (SEQ ID NO: 652)
EIVYKPVVSG (SEQ ID NO: 653)
IVYKPVVSG (SEQ ID NO: 654)
VYKPVVSG (SEQ ID NO: 655)
YKPVVSG (SEQ ID NO: 656)
KPVVSG (SEQ ID NO: 657)
IVYKPVVSGD (SEQ ID NO: 658)
VYKPVVSGD (SEQ ID NO: 659)
YKPVVSGD (SEQ ID NO: 660)
KPVVSGD (SEQ ID NO: 661)
VYKPVVSGDT (SEQ ID NO: 662)
YKPVVSGDT (SEQ ID NO: 663)
KPVVSGDT (SEQ ID NO: 664)
YKPVVSGDTS (SEQ ID NO: 665)
KPVVSGDTS (SEQ ID NO: 666)
PVVSGDTS (SEQ ID NO: 667)
VVSGDTS (SEQ ID NO: 668)
KPVVSGDTSP (SEQ ID NO: 669)
CNIK (SEQ ID NO: 670)
CNIKH (SEQ ID NO: 671)
CNIKHV (SEQ ID NO: 672)
CNIKHVPGG -continued

```
                                      (SEQ ID NO: 673)
CNIKHVPGGG (SEQ ID NO: 674)
CNIKHVPGGGS (SEQ ID NO: 675)
ENLKHQPGGG (SEQ ID NO: 676)
NLKHQPGGG (SEQ ID NO: 677)
LKHQPGGG (SEQ ID NO: 678)
KHQPGGG (SEQ ID NO: 679)
HQPGGG (SEQ ID NO: 680)
QPGGG (SEQ ID NO: 681)
TENLKHQPGG (SEQ ID NO: 682)
ENLKHQPGG (SEQ ID NO: 683)
NLKHQPGG (SEQ ID NO: 684)
LKHQPGG (SEQ ID NO: 685)
KHQPGG (SEQ ID NO: 686)
HQPGG (SEQ ID NO: 687)
QPGG (SEQ ID NO: 688)
TENLKHQPG (SEQ ID NO: 689)
ENLKHQPG (SEQ ID NO: 690)
NLKHQPG (SEQ ID NO: 691)
LKHQPG (SEQ ID NO: 692)
KHQPG (SEQ ID NO: 693)
HQPG (SEQ ID NO: 694)
QPG (SEQ ID NO: 695)
TENLKHQP (SEQ ID NO: 696)
ENLKHQP (SEQ ID NO: 697)
NLKHQP (SEQ ID NO: 698)
LKHQP (SEQ ID NO: 699)
KHQP
```

-continued (SEQ ID NO: 700)
HQP (SEQ ID NO: 701)
TENLKHQ (SEQ ID NO: 702)
ENLKHQ (SEQ ID NO: 703)
NLKHQ (SEQ ID NO: 704)
LKHQ (SEQ ID NO: 705)
KHQ (SEQ ID NO: 706)
TENLKH (SEQ ID NO: 707)
ENLKH (SEQ ID NO: 708)
NLKH (SEQ ID NO: 709)
LKH (SEQ ID NO: 710)
TENLK (SEQ ID NO: 711)
ENLK (SEQ ID NO: 712)
NLK (SEQ ID NO: 713)
TENL (SEQ ID NO: 714)
ENL (SEQ ID NO: 715)
TEN (SEQ ID NO: 716)
KDNIKHVPGGG (SEQ ID NO: 717)
KDNI (SEQ ID NO: 718)
KDN (SEQ ID NO: 719)
IKHVGGG (SEQ ID NO: 720)
IKHVGG (SEQ ID NO: 721)
IKHVG (SEQ ID NO: 722)
KHVGGG (SEQ ID NO: 723)
KHVGG (SEQ ID NO: 724)
KHVG (SEQ ID NO: 725)
LGNIHHKPGGG (SEQ ID NO: 726)
GNIHHKPGGG -continued (SEQ ID NO: 727)
NIHHKPGGG (SEQ ID NO: 728)
IHHKPGGG (SEQ ID NO: 729)
HHKPGGG (SEQ ID NO: 730)
KPGGG (SEQ ID NO: 731)
LGNIHHKPGG (SEQ ID NO: 732)
GNIHHKPGG (SEQ ID NO: 733)
NIHHKPGG (SEQ ID NO: 734)
IHHKPGG (SEQ ID NO: 735)
HHKPGG (SEQ ID NO: 736)
KPGG (SEQ ID NO: 737)
LGNIHHKPG (SEQ ID NO: 738)
GNIHHKPG (SEQ ID NO: 739)
NIHHKPG (SEQ ID NO: 740)
IHHKPG (SEQ ID NO: 741)
HHKPG (SEQ ID NO: 742)
HKPG (SEQ ID NO: 743)
KPG (SEQ ID NO: 744)
LGNIHHKP (SEQ ID NO: 745)
GNIHHKP (SEQ ID NO: 746)
NIHHKP (SEQ ID NO: 747)
IHHKP (SEQ ID NO: 748)
HHKP (SEQ ID NO: 749)
HKP (SEQ ID NO: 750)
LGNIHHK (SEQ ID NO: 751)
GNIHHK (SEQ ID NO: 752)
NIHHK (SEQ ID NO: 753)
IHHK -continued

```
                                              (SEQ ID NO: 754)
HHK (SEQ ID NO: 755)
LGNIHH (SEQ ID NO: 756)
GNIHH (SEQ ID NO: 757)
NIHH (SEQ ID NO: 758)
IHH (SEQ ID NO: 759)
LGNIH (SEQ ID NO: 760)
GNIH (SEQ ID NO: 761)
NIH (SEQ ID NO: 762)
LGNI (SEQ ID NO: 763)
GNI (SEQ ID NO: 764)
LGN (SEQ ID NO: 765)
LDNITHVPGGG (SEQ ID NO: 766)
DNITHVPGGG (SEQ ID NO: 767)
NITHVPGGG (SEQ ID NO: 768)
ITHVPGGG (SEQ ID NO: 769)
THVPGGG (SEQ ID NO: 770)
LDNITHVPGG (SEQ ID NO: 771)
DNITHVPGG (SEQ ID NO: 772)
NITHVPGG (SEQ ID NO: 773)
ITHVPGG (SEQ ID NO: 774)
THVPGG (SEQ ID NO: 775)
LDNITHVPG (SEQ ID NO: 776)
DNITHVPG (SEQ ID NO: 777)
NITHVPG (SEQ ID NO: 778)
ITHVPG (SEQ ID NO: 779)
THVPG (SEQ ID NO: 780)
LDNITHVP
```

-continued

```
                                        (SEQ ID NO: 781)
DNITHVP (SEQ ID NO: 782)
NITHVP (SEQ ID NO: 783)
ITHVP (SEQ ID NO: 784)
THVP (SEQ ID NO: 785)
LDNITHV (SEQ ID NO: 786)
DNITHV (SEQ ID NO: 787)
NITHV (SEQ ID NO: 788)
ITHV (SEQ ID NO: 789)
THV (SEQ ID NO: 790)
LDNITH (SEQ ID NO: 791)
DNITH (SEQ ID NO: 792)
NITH (SEQ ID NO: 793)
ITH (SEQ ID NO: 794)
LDNIT (SEQ ID NO: 795)
DNIT (SEQ ID NO: 796)
NIT (SEQ ID NO: 797)
LDNI (SEQ ID NO: 798)
LDN (SEQ ID NO: 799)
KNVKSKIGST (SEQ ID NO: 800)
NVKSKIGST (SEQ ID NO: 801)
VKSKIGST (SEQ ID NO: 802)
KSKIGST (SEQ ID NO: 803)
SKIGST (SEQ ID NO: 804)
KIGST (SEQ ID NO: 805)
IGST (SEQ ID NO: 806)
GST (SEQ ID NO: 807)
NVKSKIGSTE
```

-continued (SEQ ID NO: 808)
VKSKIGSTE (SEQ ID NO: 809)
KSKIGSTE (SEQ ID NO: 810)
SKIGSTE (SEQ ID NO: 811)
KIGSTE (SEQ ID NO: 812)
IGSTE (SEQ ID NO: 813)
GSTE (SEQ ID NO: 814)
STE (SEQ ID NO: 815)
VKSKIGSTEN (SEQ ID NO: 816)
KSKIGSTEN (SEQ ID NO: 817)
SKIGSTEN (SEQ ID NO: 818)
KIGSTEN (SEQ ID NO: 819)
IGSTEN (SEQ ID NO: 820)
GSTEN (SEQ ID NO: 821)
STEN (SEQ ID NO: 822)
KSKIGSTENL (SEQ ID NO: 823)
SKIGSTENL (SEQ ID NO: 824)
KIGSTENL (SEQ ID NO: 825)
IGSTENL (SEQ ID NO: 826)
GSTENL (SEQ ID NO: 827)
STENL (SEQ ID NO: 828)
SKIGSTENLK (SEQ ID NO: 829)
KIGSTENLK (SEQ ID NO: 830)
IGSTENLK (SEQ ID NO: 831)
GSTENLK (SEQ ID NO: 832)
STENLK (SEQ ID NO: 833)
KIGSTENLKH (SEQ ID NO: 834)
IGSTENLKH -continued

```
                                        (SEQ ID NO: 835)
GSTENLKH (SEQ ID NO: 836)
STENLKH (SEQ ID NO: 837)
IGSTENLKHQ (SEQ ID NO: 838)
GSTENLKHQ (SEQ ID NO: 839)
STENLKHQ (SEQ ID NO: 840)
GSTENLKHQP (SEQ ID NO: 841)
STENLKHQP (SEQ ID NO: 842)
STENLKHQPG (SEQ ID NO: 843)
SNVQSKCGSK (SEQ ID NO: 844)
NVQSKCGSK (SEQ ID NO: 845)
VQSKCGSK (SEQ ID NO: 846)
QSKCGSK (SEQ ID NO: 847)
SKCGSK (SEQ ID NO: 848)
KCGSK (SEQ ID NO: 849)
CGSK (SEQ ID NO: 850)
GSK (SEQ ID NO: 851)
NVQSKCGSKD (SEQ ID NO: 852)
VQSKCGSKD (SEQ ID NO: 853)
QSKCGSKD (SEQ ID NO: 854)
SKCGSKD (SEQ ID NO: 855)
KCGSKD (SEQ ID NO: 856)
CGSKD (SEQ ID NO: 857)
GSKD (SEQ ID NO: 858)
SKD (SEQ ID NO: 859)
VQSKCGSKDN (SEQ ID NO: 860)
QSKCGSKDN (SEQ ID NO: 861)
SKCGSKDN
```

-continued

```
                                                            (SEQ ID NO: 862)
KCGSKDN (SEQ ID NO: 863)
CGSKDN (SEQ ID NO: 864)
GSKDN (SEQ ID NO: 865)
SKDN (SEQ ID NO: 866)
QSKCGSKDNI (SEQ ID NO: 867)
SKCGSKDNI (SEQ ID NO: 868)
KCGSKDNI (SEQ ID NO: 869)
CGSKDNI (SEQ ID NO: 870)
GSKDNI (SEQ ID NO: 871)
SKDNI (SEQ ID NO: 872)
SKVTSKCGSL (SEQ ID NO: 873)
KVTSKCGSL (SEQ ID NO: 874)
VTSKCGSL (SEQ ID NO: 875)
TSKCGSL (SEQ ID NO: 876)
SKCGSL (SEQ ID NO: 877)
KCGSL (SEQ ID NO: 878)
CGSL (SEQ ID NO: 879)
GSL (SEQ ID NO: 880)
KVTSKCGSLG (SEQ ID NO: 881)
VTSKCGSLG (SEQ ID NO: 882)
TSKCGSLG (SEQ ID NO: 883)
SKCGSLG (SEQ ID NO: 884)
KCGSLG (SEQ ID NO: 885)
CGSLG (SEQ ID NO: 886)
GSLG (SEQ ID NO: 887)
SLG (SEQ ID NO: 888)
VTSKCGSLGN
```

-continued (SEQ ID NO: 889)
TSKCGSLGN (SEQ ID NO: 890)
SKCGSLGN (SEQ ID NO: 891)
KCGSLGN (SEQ ID NO: 892)
CGSLGN (SEQ ID NO: 893)
GSLGN (SEQ ID NO: 894)
SLGN (SEQ ID NO: 895)
TSKCGSLGNI (SEQ ID NO: 896)
SKCGSLGNI (SEQ ID NO: 897)
KCGSLGNI (SEQ ID NO: 898)
CGSLGNI (SEQ ID NO: 899)
GSLGNI (SEQ ID NO: 900)
SLGNI (SEQ ID NO: 901)
SKCGSLGNIH (SEQ ID NO: 902)
KCGSLGNIH (SEQ ID NO: 903)
CGSLGNIH (SEQ ID NO: 904)
GSLGNIH (SEQ ID NO: 905)
SLGNIH (SEQ ID NO: 906)
KCGSLGNIHH (SEQ ID NO: 907)
CGSLGNIHH (SEQ ID NO: 908)
GSLGNIHH (SEQ ID NO: 909)
SLGNIHH (SEQ ID NO: 910)
CGSLGNIHHK (SEQ ID NO: 911)
GSLGNIHHK (SEQ ID NO: 912)
SLGNIHHK (SEQ ID NO: 913)
GSLGNIHHKP (SEQ ID NO: 914)
SLGNIHHKP (SEQ ID NO: 915)
SLGNIHHKPG -continued (SEQ ID NO: 916)
DRVQSKIGSL (SEQ ID NO: 917)
RVQSKIGSL (SEQ ID NO: 918)
VQSKIGSL (SEQ ID NO: 919)
QSKIGSL (SEQ ID NO: 920)
SKIGSL (SEQ ID NO: 921)
KIGSL (SEQ ID NO: 922)
IGSL (SEQ ID NO: 923)
RVQSKIGSLD (SEQ ID NO: 924)
VQSKIGSLD (SEQ ID NO: 925)
QSKIGSLD (SEQ ID NO: 926)
SKIGSLD (SEQ ID NO: 927)
KIGSLD (SEQ ID NO: 928)
IGSLD (SEQ ID NO: 929)
GSLD (SEQ ID NO: 930)
SLD (SEQ ID NO: 931)
VQSKIGSLDN (SEQ ID NO: 932)
QSKIGSLDN (SEQ ID NO: 933)
SKIGSLDN (SEQ ID NO: 934)
KIGSLDN (SEQ ID NO: 935)
IGSLDN (SEQ ID NO: 936)
GSLDN (SEQ ID NO: 937)
SLDN (SEQ ID NO: 938)
QSKIGSLDNI (SEQ ID NO: 939)
SKIGSLDNI (SEQ ID NO: 940)
KIGSLDNI (SEQ ID NO: 941)
IGSLDNI (SEQ ID NO: 942)
GSLDNI -continued

```
                                      (SEQ ID NO: 943)
SKIGSLDNIT (SEQ ID NO: 944)
KIGSLDNIT (SEQ ID NO: 945)
IGSLDNIT (SEQ ID NO: 946)
GSLDNIT (SEQ ID NO: 947)
SLDNIT (SEQ ID NO: 948)
KIGSLDNITH (SEQ ID NO: 949)
IGSLDNITH (SEQ ID NO: 950)
GSLDNITH (SEQ ID NO: 951)
SLDNITH (SEQ ID NO: 952)
IGSLDNITHV (SEQ ID NO: 953)
GSLDNITHV (SEQ ID NO: 954)
SLDNITHV (SEQ ID NO: 955)
GSLDNITHVP (SEQ ID NO: 956)
SLDNITHVP (SEQ ID NO: 957)
SLDNITHVPG (SEQ ID NO: 958)
PDLKNVKS (SEQ ID NO: 959)
DLKNVKSK (SEQ ID NO: 960)
LKNVKSKI (SEQ ID NO: 961)
KNVKSKIG (SEQ ID NO: 962)
NVKSKIGS (SEQ ID NO: 963)
DLSNVQSK (SEQ ID NO: 964)
LSNVQSKC (SEQ ID NO: 965)
SNVQSKCG (SEQ ID NO: 966)
NVQSKCGS (SEQ ID NO: 967)
VDLSKVTS (SEQ ID NO: 968)
DLSKVTSK (SEQ ID NO: 969)
LSKVTSKC
```

-continued (SEQ ID NO: 970)
SKVTSKCG (SEQ ID NO: 971)
KVTSKCGS (SEQ ID NO: 972)
LDFKDRVQ (SEQ ID NO: 973)
DFKDRVQS (SEQ ID NO: 974)
FKDRVQSK (SEQ ID NO: 975)
KDRVQSKI (SEQ ID NO: 976)
DRVQSKIG (SEQ ID NO: 977)
RVQSKIGS (SEQ ID NO: 978)
SKIGSTENLKH (SEQ ID NO: 979)
SKIGSTENIKH (SEQ ID NO: 980)
SKIGSKDNLKH (SEQ ID NO: 981)
SKIGSKENIKH (SEQ ID NO: 982)
SKIGSLENLKH (SEQ ID NO: 983)
SKIGSLENIKH (SEQ ID NO: 984)
SKIGSTDNLKH (SEQ ID NO: 985)
SKIGSTDNIKH (SEQ ID NO: 986)
SKIGSKDNIKH (SEQ ID NO: 987)
SKIGSLDNLKH (SEQ ID NO: 988)
SKIGSLDNIKH (SEQ ID NO: 989)
SKIGSTGNLKH (SEQ ID NO: 990)
SKIGSTGNIKH (SEQ ID NO: 991)
SKIGSKGNLKH (SEQ ID NO: 992)
SKIGSKGNIKH (SEQ ID NO: 993)
SKIGSLGNLKH (SEQ ID NO: 994)
SKIGSLGNIKH (SEQ ID NO: 995)
Lys Xaa$_1$ Xaa$_2$ Ser Xaa$_3$ Xaa$_4$ Asn Xaa$_5$ Xaa$_6$ His,
wherein
Xaa$_1$ is I or C;
Xaa$_2$ is G;
Xaa$_3$ is T, K or L;

Xaa₄ is E, D or G;
Xaa₅ is L or I;
Xaa₆ is K, H or T.

(SEQ ID NO: 996)

(Q/E)IVYK(S/P)

alpha-synuclein isoform NACP140 [Homo sapiens]
NCBI Reference Sequence: NP_000336.1

(SEQ ID NO: 58)

1    MDVFMKGLSK AKEGVVAAAE KTKQGVAEAA GKTKEGVLYV GSKTKEGVVH GVATVAEKTK

61    EQVTNVGGAV VTGVTAVAQK TVEGAGSIAA ATGFVKKDQL GKNEEGAPQE GILEDMPVDP

121    DNEAYEMPSE EGYQDYEPEA (SEQ ID NO: 59)

VDPDNEAYEM (SEQ ID NO: 60)

VDPDNEAYE (SEQ ID NO: 61)

VDPDNEAY (SEQ ID NO: 62)

VDPDNEA (SEQ ID NO: 63)

VDPDNE (SEQ ID NO: 64)

VDPDN (SEQ ID NO: 65)

VDPD (SEQ ID NO: 66)

VDP (SEQ ID NO: 67)

DPDNEAYEM (SEQ ID NO: 68)

DPDNEAYE (SEQ ID NO: 69)

DPDNEAY (SEQ ID NO: 70)

DPDNEA (SEQ ID NO: 71)

DPDNE (SEQ ID NO: 72)

DPDN (SEQ ID NO: 73)

DPD (SEQ ID NO: 74)

PDNEAYEM (SEQ ID NO: 75)

PDNEAYE (SEQ ID NO: 76)

PDNEAY (SEQ ID NO: 77)

PDNEA (SEQ ID NO: 78)

PDNE (SEQ ID NO: 79)

PDN (SEQ ID NO: 80)

DNEAYEM

-continued

```
                                          (SEQ ID NO: 81)
DNEAYE (SEQ ID NO: 82)
DNEAY (SEQ ID NO: 83)
DNEA (SEQ ID NO: 84)
DNE (SEQ ID NO: 85)
NEAYEM (SEQ ID NO: 86)
NEAYE (SEQ ID NO: 87)
NEAY (SEQ ID NO: 88)
NEA (SEQ ID NO: 89)
EAYEM (SEQ ID NO: 90)
EAYE (SEQ ID NO: 91)
EAY (SEQ ID NO: 92)
AYEM (SEQ ID NO: 93)
AYE (SEQ ID NO: 94)
YEM (SEQ ID NO: 95)
ATGFVKKDQL (SEQ ID NO: 96)
ATGFVKKDQ (SEQ ID NO: 97)
ATGFVKKD (SEQ ID NO: 98)
ATGFVKK (SEQ ID NO: 99)
ATGFVK (SEQ ID NO: 100)
ATGFV (SEQ ID NO: 101)
ATGF (SEQ ID NO: 102)
ATG (SEQ ID NO: 103)
TGFVKKDQL (SEQ ID NO: 104)
TGFVKKDQ (SEQ ID NO: 105)
TGFVKKD (SEQ ID NO: 106)
TGFVKK (SEQ ID NO: 107)
TGFVK
```

-continued (SEQ ID NO: 108)
TGFV (SEQ ID NO: 109)
TGF (SEQ ID NO: 110)
GFVKKDQL (SEQ ID NO: 111)
GFVKKDQ (SEQ ID NO: 112)
GFVKKD (SEQ ID NO: 113)
GFVKK (SEQ ID NO: 114)
GFVK (SEQ ID NO: 115)
GFV (SEQ ID NO: 116)
FVKKDQL (SEQ ID NO: 117)
FVKKDQ (SEQ ID NO: 118)
FVKKD (SEQ ID NO: 119)
FVKK (SEQ ID NO: 120)
FVK (SEQ ID NO: 121)
VKKDQL (SEQ ID NO: 122)
VKKDQ (SEQ ID NO: 123)
VKKD (SEQ ID NO: 124)
VKK (SEQ ID NO: 125)
KKDQL (SEQ ID NO: 126)
KKDQ (SEQ ID NO: 127)
KKD (SEQ ID NO: 128)
KDQL (SEQ ID NO: 129)
KDQ (SEQ ID NO: 130)
DAEFRHDRRPDNEAYERRQIVYKPVKKC (SEQ ID NO: 131)
DAEFRHDRRQIVYKPVRRPDNEAYEKKC (SEQ ID NO: 132)
DAEFRHDRRPDNEAYERRNIKHVPGKKC (SEQ ID NO: 133)
DAEFRHDRRNIKHVPGRRPDNEAYEKKC (SEQ ID NO: 134)
DAEFRHDRRQIVYKPVRRPDNEAYERRNIKHVPGGC -continued

```
                                                    (SEQ ID NO: 135)
DAEFRHDRRDPDNEAYRRNIKHVPGRRQIVYKPVGGC (SEQ ID NO: 136)
EFRHDSGRRQIVYKPVRRPDNEAYERRNIKHVPGGC (SEQ ID NO: 137)
EFRHDSGRRDPDNEAYRRNIKHVPGRRQIVYKPVGGC (SEQ ID NO: 1058)
DAEFRHDRRDPDNEAYERRENLKHQPGGGC (SEQ ID NO: 1059)
DAEFRHDRRENLKHQPGRRDPDNEAYEGGC (SEQ ID NO: 1060)
DAEFRHDRRPDNEAYERRENLKHQPGGGC (SEQ ID NO: 1061)
DAEFRHDRRENLKHQPGRRPDNEAYEGGC (SEQ ID NO: 1062)
DAEFRHDRRSKIGSKDNIKHRRDPDNEAYEGGC (SEQ ID NO: 1063)
DAEFRHDRRDPDNEAYERRSKIGSKDNIKHGGC (RVRR; SEQ ID NO: 138)
Arg-Val-Arg-Arg (GAGA; SEQ ID NO: 139)
Gly-Ala-Gly-Ala (AGAG; SEQ ID NO: 140)
Ala-Gly-Ala-Gly (KGKG; SEQ ID NO: 141)
Lys-Gly-Lys-Gly (SEQ ID NO: 142)
AEFRHDSGC (SEQ ID NO: 143)
DAEFRHDC (SEQ ID NO: 144)
CPDNEAYE (SEQ ID NO: 145)
DPDNEAYC (SEQ ID NO: 1064)
GGGS (SEQ ID NO: 1065)
GGGGS
```

---

The invention claimed is:

1. A polypeptide comprising an amino acid sequence of:
DAEFRHDRRPDNEAYERRQIVYKPVKKC (SEQ ID NO:130);
DAEFRHDRRQIVYKPVRRPDNEAYEKKC (SEQ ID NO:131);
DAEFRHDRRPDNEAYERRNIKHVPGKKC (SEQ ID NO:132);
DAEFRHDRRNIKHVPGRRPDNEAYEKKC (SEQ ID NO: 133);
DAEFRHDRRQIVYKPVRRPDNEAY-ERRNIKHVPGGC (SEQ ID NO:134);
DAEFRHDRRDPDNEAYRRNIKHVPGRRQI-VYKPVGGC (SEQ ID NO:135);
EFRHDSGRRQIVYKPVRRPDNEAY-ERRNIKHVPGGC (SEQ ID NO: 136);
EFRHDSGRRDPDNEAYRRNIKHVPGRRQI-VYKPVGGC (SEQ ID NO:137);
DAEFRHDRRDPDNEAYERRENLKHQPGGGC (SEQ ID NO:1058);
DAEFRHDRRENLKHQPGRRDPDNEAYEGGC (SEQ ID NO:1059);
DAEFRHDRRPDNEAYERRENLKHOPGGGC (SEQ ID NO:1060);
DAEFRHDRRENLKHQPGRRPDNEAYEGGC (SEQ ID NO:1061);
DAEFRHDRRSKIGSKDNIKHRRDPDNEAYEGGC (SEQ ID NO:1062); or

DAEFRHDRRDPDNEAYERRSKIGSKDNIKHGGC (SEQ ID NO:1063).

2. The polypeptide of claim 1, wherein the polypeptide further comprises a blocked amine at the N-terminus.

3. The polypeptide of claim 1, wherein the polypeptide is EFRHDSGRRQIVYKPVRRPDNEAYERRNIKHVPGGC (SEQ ID NO:136), and further comprises a blocked amine at the N-terminus.

4. The polypeptide of claim 1, wherein the polypeptide is EFRHDSGRRDPDNEAYRRNIKHVPGRRQI-VYKPVGGC (SEQ ID NO:137), and further comprising a blocked amine at the N-terminus.

5. An immunotherapy composition, comprising the polypeptide of claim 1, wherein the polypeptide is linked to a carrier.

6. The immunotherapy composition of claim 5, wherein the carrier comprises serum albumins, immunoglobulin molecules, thyroglobulin, ovalbumin, tetanus toxoid (TT), diphtheria toxoid (DT), a genetically modified cross-reacting material (CRM) of diphtheria toxin, CRM197, meningococcal outer membrane protein complex (OMPC) and *H. influenzae* protein D (HiD), rEPA (*Pseudomonas aeruginosa* exotoxin A), KLH (keyhole limpet hemocyanin), and flagellin.

7. The immunotherapy composition of claim 6, wherein the carrier is CRM197.

8. The immunotherapy composition of claim 6, wherein the carrier is diphtheria toxoid.

9. A pharmaceutical composition comprising the immunotherapy composition of claim 5 and an adjuvant.

10. The pharmaceutical composition of claim 9, wherein the adjuvant is selected from the group consisting of aluminum hydroxide, aluminum phosphate, aluminum sulfate, 3 De-O-acylated monophosphoryl lipid A (MPL), QS-21, TQL1055, QS-18, QS-17, QS-7, Complete Freund's Adjuvant (CFA), Incomplete Freund's Adjuvant (IFA), oil in water emulsions (such as squalene or peanut oil), CpG, polyglutamic acid, polylysine, AddaVax™, MF59®, and combinations thereof.

11. The pharmaceutical composition of claim 10, wherein the adjuvant is QS-21 or TQL1055.

12. The pharmaceutical composition of claim 10, wherein the adjuvant is MPL.

13. The pharmaceutical composition of claim 10, wherein the adjuvant is a combination of MPL and QS-21 or a combination of MPL and TQL1055.

14. A method of treating or effecting prophylaxis of Alzheimer's disease in a subject, comprising administrating to the subject the immunotherapy composition of claim 5.

15. The method of claim 14, further comprising repeating the administering at least a second time, at least a third time, at least a fourth time, at least a fifth time, or at least a sixth time.

16. The method of claim 15, further comprising repeating the administering at an interval of about 21 to about 28 days.

17. A method of inhibiting or reducing aggregation of at least one of Aβ, tau, and alpha-synuclein in a subject having or at risk of developing Alzheimer's disease, comprising, administering to the subject the immunotherapy composition of claim 5.

18. A method of inducing an immune response in an animal, comprising administering to the animal the immunotherapy composition of claim 5 in a regimen effective to generate an immune response comprising antibodies that specifically bind to Aβ, tau, and/or alpha-synuclein.

19. The method of claim 18, wherein the immune response comprises antibodies that specifically bind to Aβ, antibodies that specifically bind to tau, and antibodies that specifically bind to alpha-synuclein.

20. The method of claim 18, wherein the inducing the immune response comprises antibodies that specifically bind to the N-terminal region of AB, the microtubule region of tau, and/or the C-terminal region of alpha-synuclein.

21. An immunization kit comprising the immunotherapy composition of claim 5.

22. The kit of claim 21, further comprising an adjuvant.

23. The kit of claim 22, wherein the immunotherapy composition is in a first container and the adjuvant is in a second container.

24. A pharmaceutical formulation comprising (a) the polypeptide of claim 1 and (b) an adjuvant.

25. The pharmaceutical formulation of claim 24, wherein the adjuvant is selected from the group consisting of aluminum hydroxide, aluminum phosphate, aluminum sulfate, 3 De-O-acylated monophosphoryl lipid A (MPL), QS-21, TQL1055, QS-18, QS-17, QS-7, Complete Freund's Adjuvant (CFA), Incomplete Freund's Adjuvant (IFA), oil in water emulsions (such as squalene or peanut oil), CpG, polyglutamic acid, polylysine, AddaVax™, MF59®, and combinations thereof.

26. The pharmaceutical formulation of claim 25, wherein the adjuvant is QS-21 or TQL1055.

27. The pharmaceutical formulation of claim 25, wherein the adjuvant is MPL.

28. The pharmaceutical formulation of claim 25, wherein the adjuvant is a combination of MPL and QS-21 or a combination of MPL and TQL1055.

29. The pharmaceutical formulation of claim 24, wherein the adjuvant comprises a liposomal formulation.

30. The pharmaceutical formulation of claim 24, wherein the composition comprises at least one pharmaceutically acceptable diluent.

31. The pharmaceutical formulation of claim 24, comprising a multiple antigen presenting system (MAP).

32. The pharmaceutical formulation of claim 31, wherein the MAP comprises one or more of a Lys-based dendritic scaffold, helper T-cell epitopes, immune stimulating lipophilic moieties, cell penetrating peptides, radical induced polymerization, self-assembling nanoparticles as antigen-presenting platforms and gold nanoparticles.

33. A nucleic acid comprising a nucleic acid sequence encoding a polypeptide of claim 1.

34. A nucleic acid immunotherapy composition comprising the nucleic acid of claim 33 and at least one adjuvant.

35. A method of treating or effecting prophylaxis of Alzheimer's disease in a subject, comprising administrating to the subject the nucleic acid immunotherapy composition of claim 34.

36. A method of inhibiting or reducing aggregation of at least one of Aβ, tau, and alpha-synuclein in a subject having or at risk of developing Alzheimer's disease, comprising administering to the subject the nucleic acid immunotherapy composition of claim 34.

37. A kit comprising the nucleic acid immunotherapy composition of claim 34.

38. The kit of claim 37, further comprising an adjuvant.

39. The kit of claim 38, wherein the nucleic acid is in a first container and the adjuvant is in a second container.

* * * * *